US012642888B2

(12) United States Patent
Szereszewski et al.

(10) Patent No.: US 12,642,888 B2
(45) Date of Patent: Jun. 2, 2026

(54) DERMAL FILLERS

(71) Applicant: Spiderwort Inc., Ottawa (CA)

(72) Inventors: Kama Szereszewski, Ottawa (CA); Ryan Hickey, Ottawa (CA); Andrew E. Pelling, Ottawa (CA); Maxime Leblanc Latour, Gatineau (CA); Mark Stroobach, Ottawa (CA); Pavel Milman, Ottawa (CA); Christopher Odding, Gatineau (CA); Paula Cristina de Sousa Faria Tischer, Parana (BR)

(73) Assignee: Spiderwort Inc., Ottawa (CA)

( * ) Notice: Subject to any disclaimer, the term of this patent is extended or adjusted under 35 U.S.C. 154(b) by 694 days.

(21) Appl. No.: 17/927,432

(22) PCT Filed: Jun. 8, 2021

(86) PCT No.: PCT/CA2021/050783
§ 371 (c)(1),
(2) Date: Nov. 23, 2022

(87) PCT Pub. No.: WO2021/248236
PCT Pub. Date: Dec. 16, 2021

(65) Prior Publication Data
US 2023/0414835 A1     Dec. 28, 2023

Related U.S. Application Data

(60) Provisional application No. 63/036,126, filed on Jun. 8, 2020.

(51) Int. Cl.
*A61K 36/00* (2006.01)
*A61L 27/36* (2006.01)

(52) U.S. Cl.
CPC ....... *A61L 27/3683* (2013.01); *A61L 27/3637* (2013.01); *A61L 2400/06* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 5,166,187 A | 11/1992 | Collombel et al. | |
| 2013/0224278 A1 | 8/2013 | Czaja et al. | |
| 2013/0344036 A1 | 12/2013 | Yliperttula et al. | |
| 2014/0377368 A1 | 12/2014 | Kiehm et al. | |
| 2019/0060520 A1* | 2/2019 | Pelling .................. | A61L 27/507 |
| 2021/0154371 A1 | 5/2021 | Allen et al. | |

FOREIGN PATENT DOCUMENTS

| | | |
|---|---|---|
| AU | 2013222371 A1 | 8/2014 |
| CA | 2815276 A1 | 5/2012 |
| CA | 3014256 A1 | 8/2017 |
| CA | 3110904 A1 | 2/2020 |
| CN | 101404977 B | 9/2012 |
| CN | 103224565 A | 7/2013 |
| CN | 107583109 A | 1/2018 |
| CN | 109152863 A | 1/2019 |
| EP | 2633032 B1 | 2/2015 |
| WO | 2008107384 A1 | 9/2008 |
| WO | 2012056109 A2 | 5/2012 |
| WO | 2013126635 A1 | 8/2013 |
| WO | 2017136950 A1 | 8/2017 |
| WO | 2017160862 A1 | 9/2017 |
| WO | 2020041612 A1 | 2/2020 |
| WO | 2020214964 A1 | 10/2020 |
| WO | 2020264385 A1 | 12/2020 |

OTHER PUBLICATIONS

Modulevsky DJ, et al. (2016) Biocompatibility of Subcutaneously Implanted Plant-Derived Cellulose Biomaterials. PLoS One 11(6): e0157894. https://doi.org/10.1371/journal.pone.0157894; Published: Jun. 21, 2016.
European Patent Office, Extended European Search Report for EP Application No. 21822411.1 mailed May 17, 2024.
Modulevsky, D. J. et al. Apple derived cellulose scaffolds for 3D mammalian cell culture. PLoS One 2014 (May 1, 2014), vol. 9 (5), pp. e97835 1-10.
Nicholas Miliaras, Apple Does 3D Cell Culture, ASCB, Sep. 10, 2014, available at : https://www.ascb.org/science-news/apple-does-3d-cell-culture/.
Modulevsky, D., et al., "Open Source Biomaterials for Regenerative Medicine." O'Reilly, BioCoder 8, pp. 17-28 (Jul. 2015).
Modulevsky, D., et al., "DIY Open Source Biomaterials" O'Reilly, BioCoder 8, pp. 43-57 (Jul. 2015).
Andrew Pelling, "Putting Cells Where They Don't Belong, "14th Annual Chemical Biophysics Symposium (CBP), Toronto, Canada Apr. 10-12, 2015, Abstract of Oral Presentation, session III, Fri 7:50 pm.

* cited by examiner

*Primary Examiner* — Russell G Fiebig
(74) *Attorney, Agent, or Firm* — Lisa Mueller; Casimir Jones SC

(57) ABSTRACT

Provided herein are dermal fillers including decellularized plant or fungal tissue from which cellular materials and nucleic acids of the tissue are removed; as well as methods and uses thereof for cosmetic and/or reconstructive applications. Also provided are methods for preparing such dermal fillers, and dermal filler kits.

31 Claims, 79 Drawing Sheets

A

B

| Saline | HA | Collagen |

A

B

A

B

A

B

C

A

B

A

B

A                  B                  C

DERMAL FILLERS

CROSS-REFERENCE TO RELATED APPLICATIONS

This application is a national stage application of PCT/CA2021/050783, filed Jun. 8, 2021, which claims the benefit of and priority to U.S. Provisional Patent Application No. 63/036,126 filed Jun. 8, 2020, each of which are hereby incorporated by reference in their entirety.

FIELD OF INVENTION

The present invention relates generally to dermal fillers. More specifically, the present invention relates to dermal fillers comprising decellularized plant or fungal tissue.

BACKGROUND

A variety of dermal filler products have been developed for injection underneath the skin, primarily for cosmetic applications. The location of the injection may vary depending on the particular cosmetic application; superficial wrinkles are treated with intradermal injections, whereas volume augmentation procedures often involve injections into the deep dermis. In general, injections into the subcutaneous fat are typically avoided.

Dermal filler products may be generally separated into two distinct categories: temporary and permanent. Temporary dermal fillers are often composed of hydrogels such as collagen or hyaluronic acid, which slowly resorb into the body over time. On the other hand, the only FDA-approved permanent dermal filler at present is BellaFill™. Bellafill™ is composed of 80% (v/v) 3.5% Bovine Collagen I (w/v) and 20% (v/v) 30-40 µm poly(methyl methacrylate) (PMMA) microspheres. The microspheres are hard, non-resorbable particles composed of a petrochemical polymer. The intent of the microspheres is to fill up physical space within a tissue, and provide a permanent support structure for cells to grow onto as well as deposit natural extracellular matrix proteins which gradually replace the resorbing bovine collagen. Bellafill™ has become a popular choice for patients, as it is long lasting and typically only requires 1-2 treatments with little to no follow up.

Unfortunately, permanent dermal fillers in the field often include a synthetic material that may be permanently left behind in the body, which may carry certain risks such as potential allergic reactions, potential for granulomas and/or foreign body responses.

Alternative, additional, and/or improved dermal fillers, methods and uses thereof, and methods for the production thereof, are desirable.

SUMMARY OF INVENTION

Provided herein are dermal fillers comprising decellularized plant or fungal tissue from which cellular materials and nucleic acids of the tissue are removed; as well as methods and uses thereof for cosmetic and/or reconstructive applications. Also provided are methods for preparing such dermal fillers, and dermal filler kits.

As described herein, the present inventors have now developed dermal filler products comprising decellularized plant or fungal tissue. Data provided herein indicates dermal fillers had good biocompatibility, and were substantially non-resorbable. Methods for preparing such dermal filler products are described, which may allow for control over size and various other beneficial properties, including the avoidance of small undesirable particles below 20 µm in size. Preparations are developed having good syringability/injectability through small gauge needles, as well as preparations compatible with carrier fluids such as hydrogels, and compatible with anesthetics. Sterilization techniques and sterilized products are also described. Particles for dermal filler products are described having desirable shapes and surface area/volume/packing properties to encourage cell invasion/growth and/or to provide good ratios of natural tissue to dermal filler in subjects.

In an embodiment, there is provided herein a non-resorbable dermal filler comprising decellularized plant or fungal tissue from which cellular materials and nucleic acids of the tissue are removed.

In another embodiment of the above dermal filler, the decellularized plant or fungal tissue may be chitin-based, chitosan-based, lignocellulosic-based, or cellulose-based.

In still another embodiment of any of the above dermal filler or dermal fillers, the decellularized plant or fungal tissue may be derived from leafy structure, root, flesh, hypanthium or pulp structures of a plant.

In yet another embodiment of any of the above dermal filler or dermal fillers, the decellularized plant or fungal tissue may be derived from lettuce, carrot, apple, or pear, or any combination thereof.

In another embodiment of any of the above dermal filler or dermal fillers, the decellularized plant or fungal tissue may be homogenized.

In still another embodiment of any of the above dermal filler or dermal fillers, the decellularized plant or fungal tissue may be dried, subjected to grinding, and optionally reconstituted or rehydrated.

In yet another embodiment of any of the above dermal filler or dermal fillers, the decellularized plant or fungal tissue may be disassembled into particles the size of single structural cells, or smaller.

In another embodiment of any of the above dermal filler or dermal fillers, the dermal filler may further comprise a hydrogel, matrix, or carrier fluid for the decellarized plant or fungal tissue.

In still another embodiment of any of the above dermal filler or dermal fillers, the hydrogel, matrix, or carrier fluid may comprise PBS, saline, hyaluronic acid (cross-linked or non-crosslinked), alginate, collagen, pluronic acid (e.g. pluronic F 127), agar, agarose, fibrin, calcium hydroxyapatite, Poly-L-lactic acid, autologous fat, silicone, dextran, methylcellulose, dissolved regenerated cellulose, or any combinations thereof.

In yet another embodiment of any of the above dermal filler or dermal fillers, the dermal filler may be dried, or hydrated.

In another embodiment of any of the above dermal filler or dermal fillers, the dermal filler may comprise lidocaine or other anesthetic.

In still another embodiment of any of the above dermal filler or dermal fillers, the decellularized plant or fungal tissue may be disassembled into particles having irregular 3D shapes and/or which are non-spherical, thin, flake-like structures.

In yet another embodiment of any of the above dermal filler or dermal fillers, the flake-like structures may have a thickness of about 0.01 to about 100 µm, for example about 0.1 µm.

In another embodiment of any of the above dermal filler or dermal fillers, the decellularized plant or fungal tissue may be disassembled into particles having a size sufficiently large so as not to be phagocytosed by a cell or cells; preferably, the decellularized plant or fungal tissue may be disassembled into particles having a size, diameter, or minimum ferret diameter of at least about 20 μm.

In another embodiment of any of the above dermal filler or dermal fillers, the decellularized plant or fungal tissue may be disassembled into particles having a size, diameter, or ferret diameter within a range of about 20 μm to about 1000 μm.

In still another embodiment of any of the above dermal filler or dermal fillers, the decellularized plant or fungal tissue may be disassembled into particles having a size, diameter, or maximum ferret diameter of less than about 200 μm.

In yet another embodiment of any of the above dermal filler or dermal fillers, the decellularized plant or fungal tissue may be disassembled into particles having a size, diameter, or ferret diameter distribution within a range of about 20 μm to about 200 μm.

In another embodiment of any of the above dermal filler or dermal fillers, the decellularized plant or fungal tissue may be disassembled into particles having a particle size, diameter, or ferret diameter distribution having a peak within about 30 μm to about 100 μm.

In still another embodiment of any of the above dermal filler or dermal fillers, the decellarized plant or fungal tissue may be disassembled into particles having a mean particle size, diameter, or ferret diameter within a range of about 30 μm to about 100 μm.

In still another embodiment of any of the above dermal filler or dermal fillers, the decellularized plant or fungal tissue may be disassembled into particles having a size, diameter, or maximum ferret diameter of less than about 300 μm.

In still another embodiment of any of the above dermal filler or dermal fillers, the decellularized plant or fungal tissue may be disassembled into particles having a size, diameter, or ferret diameter distribution within a range of about 100 μm to about 300 μm.

In still another embodiment of any of the above dermal filler or dermal fillers, the decellularized plant or fungal tissue may be disassembled into particles having a particle size, diameter, or ferret diameter distribution having a peak within about 100 μm to about 300 μm.

In still another embodiment of any of the above dermal filler or dermal fillers, the decellularized plant or fungal tissue may be disassembled into particles having a mean particle size, diameter, or ferret diameter within a range of about 100 μm to about 300 μm.

In yet another embodiment of any of the above dermal filler or dermal fillers, the decellularized plant or fungal tissue may be disassembled into particles having an average projected particle area within a range of about 200 to about 3000 μm², or within a range of about 200 to about 300 μm²; wherein the decellularized plant or fungal tissue is disassembled into particles having a surface area to volume ratio of about 0.1 to 100 μm⁻¹; wherein the decellularized plant or fungal tissue is disassembled into particles having a packing density of about $4 \times 10^5$ particles/mL to about $7 \times 10^9$ particles/mL; or any combinations thereof.

In yet another embodiment of any of the above dermal filler or dermal fillers, the dermal filler or dermal fillers may have a viscosity of less than about 500,000 cp.

In yet another embodiment of any of the above dermal filler or dermal fillers, the dermal filler or dermal fillers may have a viscosity within a range of about 100,000 cp to about 200,000 cp.

In another embodiment of any of the above dermal filler or dermal fillers, the decellularized plant or fungal tissue may be sterilized.

In still another embodiment of any of the above dermal filler or dermal fillers, the dermal filler may be sterilized.

In yet another embodiment of any of the above dermal filler or dermal fillers, the sterilization may be by gamma sterilization.

In yet another embodiment of any of the above dermal filler or derma fillers, the sterilization may be by autoclaving.

In another embodiment of any of the above dermal filler or dermal fillers, the decellularized plant or fungal tissue may be mercerized.

In yet another embodiment of any of the above dermal filler or dermal fillers, the mercerization may be by heating with sodium hydroxide and hydrogen peroxide.

In another embodiment of any of the above dermal filler or dermal fillers, the dermal filler may be formulated for subdermal injection, deep dermal injection, subcutaneous injection (e.g. subcutaneous fat injection), or any combinations thereof.

In still another embodiment of any of the above dermal filler or dermal fillers, the dermal filler may be provided in a syringe or injection device.

In yet another embodiment, there is provided herein a use of any of the dermal filler or dermal fillers as described herein as a soft tissue filler, for reconstructive surgery, or both.

In another embodiment, there is provided herein a use of any of the dermal filler or dermal fillers as described herein for improving cosmetic appearance of a subject in need thereof.

In still another embodiment, there is provided herein a use of any of the dermal filler or dermal fillers as described herein for increasing tissue volume, smoothing wrinkles, or both, in a subject in need thereof.

In yet another embodiment, there is provided herein a method for improving cosmetic appearance, increasing tissue volume, smoothing wrinkles, or any combinations thereof, in a subject in need thereof, said method comprising:

administering or injecting any of the dermal filler or dermal fillers as described herein to a region in need thereof, thereby improving cosmetic appearance, increasing tissue volume, smoothing wrinkles, or any combinations thereof, of the subject.

In another embodiment of any of the above use or uses or method or methods, native cells of the subject may infiltrate the dermal filler.

In still another embodiment of any of the above use or uses or method or methods, the dermal filler may be non-resorbable such that the decellularized plant or fungal tissue may remain substantially intact within the subject.

In yet another embodiment of any of the above use or uses or method or methods, the dermal filler may be degradable through the addition of one or more enzymes thereto.

In another embodiment of any of the above use or uses or method or methods, the plant or fungal tissue may be cellulose-based, and the one or more enzymes comprise cellulase.

In still another embodiment of any of the above use or uses or method or methods, the cellulase may be cellulase from *Trichoderma* sp.

In yet another embodiment, there is provided herein a method for preparing a non-resorbable dermal filler, comprising:

providing a plant or fungal tissue;

decellularizing and size-reducing the plant or fungal tissue to provide particles from which cellular materials and nucleic acids of the tissue are removed; and optionally, sterilizing the particles;

thereby providing the non-resorbable dermal filler.

In another embodiment of the above method, the decellularized plant or fungal tissue may be chitin-based, chitosan-based, lignocellulosic-based, or cellulose-based.

In still another embodiment of any of the above method or methods, the decellularized plant or fungal tissue may be derived from leafy structure, root, flesh, hypanthium or pulp structures of a plant.

In yet another embodiment of any of the above method or methods, the decellularized plant or fungal tissue may be derived from lettuce, carrot, apple, or pear, or any combination thereof.

In another embodiment of any of the above method or methods, the size-reducing may comprise a mechanical size reduction to provide the particles, optionally where the mechanical size reduction is performed on dried, lyophilized, or freeze-dried materials.

In still another embodiment of any of the above method or methods, the mechanical size reduction may comprise crushing, extrusion, grinding, milling, ultrasonication, electrospinning, chemical dissolution, enzymatic breakdown, or shearing the plant or fungal tissue, before or after decellularizing, to provide the particles.

In yet another embodiment of any of the above method or methods, size-reducing may comprise drying the plant or fungal tissue, before or after decellularizing; subjecting the dried plant or fungal tissue to mechanical size reduction to provide the particles; and, optionally, reconstituting, resuspending, or rehydrating the particles.

In another embodiment of any of the above method or methods, the size-reducing may provide particles the size of single structural cells, or smaller.

In still another embodiment of any of the above method or methods, the method may further comprise a step of formulating the particles with a hydrogel, matrix, or carrier fluid.

In yet another embodiment of any of the above method or methods, the hydrogel, matrix, or carrier fluid may comprise PBS, saline, hyaluronic acid (cross-linked or non-cross-linked), alginate, collagen, pluronic acid (e.g. Pluronic F 127), agar, agarose, fibrin, calcium hydroxyapatite, Poly-L-lactic acid, autologous fat, silicone, dextran, methylcellulose, dissolved regenerated cellulose, or any combinations thereof.

In another embodiment of any of the above method or methods, the dermal filler may be provided in dried, or hydrated, form.

In still another embodiment of any of the above method or methods, the method may further comprise a step of formulating with lidocaine or other anesthetic.

In yet another embodiment of any of the above method or methods, the size-reducing may provide particles having irregular 3D shapes and/or which are non-spherical, thin, flake-like structures.

In another embodiment of any of the above method or methods, the flake-like structures may have a thickness of about 0.01 to about 100 μm, for example about 0.1 μm.

In still another embodiment of any of the above method or methods, the size-reducing may further comprise performing extrusion, filtering, centrifuging, or other size separation to obtain particles having a target size, particles within a target size range, or particles having a target size distribution.

In still another embodiment of any of the above method or methods, the size-reducing may provide particles having particles having a size, diameter, or ferret diameter within a range of about 20 μm to about 1000 μm.

In yet another embodiment of any of the above method or methods, the size-reducing may provide particles having a size sufficiently large so as not to be phagocytosed by a cell or cells; preferably, the size-reducing may provide particles having a size, diameter, or minimum ferret diameter of at least about 20 μm.

In another embodiment of any of the above method or methods, the size-reducing may provide particles having a size, diameter, or maximum ferret diameter of less than about 200 μm.

In still another embodiment of any of the above method or methods, the size-reducing may provide particles having a size, diameter, or ferret diameter distribution within a range of about 20 μm to about 200 μm.

In yet another embodiment of any of the above method or methods, the size-reducing may provide particles having a particle size, diameter, or ferret diameter distribution having a peak within about 30 μm to about 100 μm.

In another embodiment of any of the above method or methods, the size-reducing may provide particles having a mean particle size, diameter, or ferret diameter within a range of about 30 μm to about 100 μm.

In another embodiment of any of the above method or methods, the size-reducing may provide particles having a size, diameter, or maximum ferret diameter of less than about 300 μm.

In another embodiment of any of the above method or methods, the size-reducing may provide particles having a size, diameter, or ferret diameter distribution within a range of about 100 μm to about 300 μm.

In another embodiment of any of the above method or methods, the size-reducing may provide particles having a particle size, diameter, or ferret diameter distribution having a peak within about 100 μm to about 300 μm.

In another embodiment of any of the above method or methods, the size-reducing may provide particles having a mean particle size, diameter, or ferret diameter within a range of about 100 μm to about 300 μm.

In still another embodiment of any of the above method or methods, the size-reducing may provide particles having an average projected particle area within a range of about 200 to about 3000 $\mu m^2$, or within a range of about 200 to about 300 $\mu m^2$; wherein the decellularized plant or fungal tissue is disassembled into particles having a surface area to volume ratio of about 0.1 to 100 $\mu m^{-1}$; wherein the decellularized plant or fungal tissue is disassembled into particles having a packing density of about $4 \times 10^5$ particles/mL to about $7 \times 10^9$ particles/mL; or any combinations thereof.

In yet another embodiment of any of the above method or methods, the size-reducing may comprise grinding while simultaneously passing resulting particles through a filter to obtain particles below an upper threshold size.

In another embodiment of any of the above method or methods, the method may further comprise filtering, differential or equilibrium centrifugation, or sieving to remove particles below a lower threshold size, obtaining particles above the lower threshold size.

In still another embodiment of any of the above method or methods, the filtering or sieving may be performed using an automated wet-sieve.

In yet another embodiment of any of the above method or methods, the size-reducing may comprise performing differential or equilibrium centrifugation to obtain particles having a target size, particles within a target size range, or particles having a target size distribution.

In another embodiment of any of the above method or methods, the method may further comprise formulating the particles with a hydrogel, matrix, or carrier fluid by loading a first syringe or vessel with the particles in a fluid such as water or buffer (e.g. saline) and loading a second syringe or vessel with the hydrogel, matrix, or carrier fluid; the first and second syringes or vessels being in fluid communication; and mixing by passing the contents of the syringes or vessels back and forth between the first and second syringes or vessels.

In another embodiment of any of the above method or methods, the method may further comprise formulating the particles with a hydrogel, matrix, or carrier fluid by mixing the particles with the hydrogel, matrix, or carrier fluid using a size exclusion mixer.

In another embodiment of any of the above method or methods, the size exclusion mixer may be a static mixer.

In still another embodiment of any of the above method or methods, the method may further comprise sterilizing the plant or fungal tissue, before or after decellularizing.

In yet another embodiment of any of the above method or methods, the method may further comprise sterilizing the dermal filler.

In another embodiment of any of the above method or methods, the sterilization may be by gamma sterilization.

In still another embodiment of any of the above method or methods, the sterilization may be by autoclaving.

In still another embodiment of any of the above method or methods, the sterilization may comprise a plurality of sterilization steps.

In still another embodiment of any of the above method or methods, wherein a first sterilization step comprises a heat treatment.

In yet another embodiment of any of the above method or methods, the method may further comprise mercerizing the plant or fungal tissue.

In another embodiment of any of the above method or methods, the mercerizing may be performed after the decellularizing.

In still another embodiment of any of the above method or methods, the mercerizing may comprise treatment of the decellularized plant or fungal tissue with a base and a peroxide.

In yet another embodiment of any of the above method or methods, the base may be a hydroxide base.

In still another embodiment of any of the above method or methods, the peroxide may be hydrogen peroxide.

In yet another embodiment of any of the above method or methods, the mercerizing may comprise treatment of the decellularized plat or fungal tissue with an aqueous sodium hydroxide solution and hydrogen peroxide while heating.

In still another embodiment of any of the above method or methods, the decellularized plant or fungal tissue may be treated with the aqueous sodium hydroxide solution for a first period of time before the hydrogen peroxide is added to the reaction.

In yet another embodiment of any of the above method or methods, the peroxide may be a 30% to 50% aqueous hydrogen peroxide stock solution.

In still another embodiment of any of the above method or methods, the aqueous hydrogen peroxide stock solution may be used in an amount of at least about 75 mL per 500 g of decellularized plant or fungal tissue.

In still another embodiment of any of the above method or methods, after addition of the aqueous hydrogen peroxide stock solution, the concentration of peroxide of a mixture of the decellularized plant or fungal tissue, the base, and the aqueous hydrogen peroxide stock solution may be about 1% to about 5%.

In yet another embodiment of any of the above method or methods, the base may be a 1M sodium hydroxide solution.

In still another embodiment of any of the above method or methods, the 1M sodium hydroxide solution may be used in an amount of about 2500 mL per 500 g of decellularized plant or fungal tissue.

In yet another embodiment of any of the above method or methods, the method may further comprise neutralizing the pH with one or more neutralization treatments.

In still another embodiment of any of the above method or methods, the one or more neutralization steps may comprise treatment with an aqueous HCl solution.

In yet another embodiment of any of the above method or methods, the mercerizing may be performed with heating to about 80° C.

In still another embodiment of any of the above method or methods, the mercerizing may be performed for about at least about 30 minutes.

In still another embodiment of any of the above method or methods, the method may further comprise formulating the dermal filler for subdermal injection, deep dermal injection, subcutaneous injection (e.g. subcutaneous fat injection), or any combinations thereof.

In yet another embodiment, there is provided herein a dermal filler prepared by any of the method or methods described herein.

In another embodiment of the above dermal filler, the dermal filler may be any of the dermal filler or dermal fillers as described herein.

In still another embodiment of any of the above dermal filler or dermal fillers, about 0.1% to about 5%, or less, of the particles of the dermal filler may have a ferret diameter, or a minimum ferret diameter, of less than about 20 μm.

In yet another embodiment of any of the above dermal filler or dermal fillers, less than about 0.5% of the particles of the dermal filler may have a ferret diameter, or a minimum ferret diameter, of less than 20 μm.

In yet another embodiment of any of the above dermal filler or dermal fillers, less than about 0.1% to about 5% (such as less than about 0.5%), or less, of the particles of the dermal filler may have a size sufficiently small so as to be phagocytosed by a cell or cells of a subject.

In another embodiment, there is provided herein a kit comprising any one or more of:

any of the dermal filler or dermal fillers as described herein;

a hydrogel, matrix, or carrier fluid;

PBS, saline, hyaluronic acid (cross-linked or non-cross-linked), alginate, collagen, pluronic acid (e.g. pluronic F 127), agar, agarose, fibrin, calcium hydroxyapatite, Poly-L-lactic acid, autologous fat, silicone, dextran, methylcellulose, dissolved regenerated cellulose, or any combinations thereof;

lidocaine or other aesthetic;

one or more syringes, or another injection device;

a luer-lock fitting or coupler for two or more syringes;

instructions for performing any of the use or uses or
    method or methods as described herein;
  one or more decellularization reagents;
  one or more containers, packages, or vessels;
  one or more buffers, water, or saline for injection;
  a reagent or enzyme (e.g. cellulase) for dissolving dermal
    filler at an undesirable region or location;
  or any combinations thereof.

BRIEF DESCRIPTION OF DRAWINGS

These and other features will become further understood
with regard to the following Figures in which:

FIG. 37 shows microscopy images of an in vitro cell culture test using a 20% v/v apple-derived particle solution and C1C12 cells, wherein FIG. 37A shows microscopy images of the control, FIG. 37B shows microscopy images of the cells of the 20% filtered particle sample, and FIG. 37C shows microscopy images of the cells of the 20% unfiltered particle sample, as described in Example 7;

FIG. 47 shows force-displacement curves for a gelatin (GE; without particles) sample as described in Example 10, wherein FIG. 47A shows the force-displacement curves for GE extrusion through a 27 G needle, and FIG. 47B shows the force-displacement curves for GE extrusion through a 30 G needle;

FIG. 49 shows force-displacement curves for a diluted GE sample as described in Example 10, wherein FIG. 49A shows the force-displacement curves for the diluted GE warmed prior to extrusion, and FIG. 47B shows the force-displacement curves for the diluted GE sample kept at room temperature prior to extrusion;

FIG. 52 shows microscopy images of the samples described in Example 14, wherein FIG. 52A is a 1:5 AA:NaOH sample, FIG. 52B is a 1:2 AA:NaOH sample, and FIG. 52C is a 1:1 AA:NaOH sample;

FIG. 54 shows microscopy images of a mercerized AA and pear powder mixture (before centrifugation) as described in Example 15, wherein FIG. 54A shows a microscopy image with a scale of 500 µm, and FIG. 54B shows a microscopy image with a scale of 100 µm;

FIG. 55 shows microscopy images of the supernatant collected after centrifuging the mercerized AA and pear power mixture as described in Example 15, wherein FIG. 55A shows a microscopy image with a scale of 500 µm, and FIG. 55B shows a microscopy image with a scale of 100 µm;

FIG. 56 shows microscopy images of a pellet formed after the mercerized AA and pear powder mixture as described in Example 15, wherein FIG. 56A shows a microscopy image with a scale of 500 µm, and FIG. 56B shows a microscopy image with a scale of 100 µm;

FIG. 57 shows microscopy images of a sample a mercerized AA and pear powder pellet after sieving as described in Example 15, wherein FIG. 57A shows a microscopy image with a scale of 500 µm, and FIG. 57B shows a microscopy image with a scale of 100 µm;

FIG. 58 shows microscopy images of a sample of a mercerized AA and pear powder pellet after the final centrifugation as described in Example 15, wherein FIG. 58A shows a microscopy image with a scale of 500 µm, and FIG. 58B shows a microscopy image with a scale of 100 µm;

FIG. 60 shows the particle distributions of each of the microscopy images taken at 2.5× shown in FIG. 54 to FIG. 58, wherein FIG. 60A shows the particle size distribution of the pellet after the final centrifugation, FIG. 60B shows the particle size distribution of the sieved pellet, FIG. 60C shows the particle size distribution of the pellet after the first centrifugation, FIG. 60D shows the particle size distribution of the supernatant, and FIG. 60E show the particle size distribution of the initial mercerized AA and pear powder mixture;

FIG. 62 shows the particle distributions of each of the microscopy images taken at 10× shown in FIG. 54 to FIG. 58, wherein FIG. 62A shows the particle size distribution of the pellet after the final centrifugation, FIG. 62B shows the particle size distribution of the sieved pellet, FIG. 62C shows the particle size distribution of the pellet after the first centrifugation, FIG. 62D shows the particle size distribution of the supernatant, and FIG. 62E show the particle size distribution of the initial mercerized AA and pear powder mixture;

FIG. 64 shows force-displacement curves for extrusions of a water sample a 20% (v/v) mercerized, decellularized AA diluted in 0.9% saline (Mer20Sal80) formulation, and a mercerized AA (Mer100) formulation as described in Example 17, wherein FIG. 64A shows the force-displacement curves the water sample, FIG. 64B shows the force-displacement curves for Mer20Sal80 formulation, and FIG. 64C shows the force-displacement curves for the Mer100 formulation;

FIG. 72 shows force-displacement curves for GE and mercerized AA formulations as described in Example 18, wherein FIG. 72A shows the force-displacement curves of the 5% GE formulation, FIG. 72B shows the force-displacement curves of the 2.5% GE formulation, FIG. 72C shows the force-displacement curves of the 1% GE formulation, FIG. 72D shows the force-displacement curves of the 0.5% GE formulation, and FIG. 72E shows the force-displacement curves of the 0.25% GE formulation;

FIG. 74 shows a chart of the stress and strain vs. time for mercerized AA samples described in Example 19, wherein FIG. 74A shows a chart of the stress and strain vs. time for the undiluted mercerized AA sample, and FIG. 74B shows a chart of the stress and strain vs. time for the diluted mercerized AA sample FIG. 75 shows the storage moduli, loss moduli, and loss factor curves for the mercerized AA samples described in Example 19, wherein FIG. 75A shows the storage moduli (E') and the loss moduli (E'') for the undiluted mercerized AA sample, FIG. 75B shows the loss factor curve for the undiluted mercerized AA sample, FIG. 75C shows the storage moduli (E') and the loss moduli (E'') for the diluted mercerized AA sample, FIG. 75D shows the loss factor curve for the diluted mercerized AA sample;

FIG. 76 shows microscopy images of the mercerized AA samples described in Example 20, wherein FIG. 76A shows a microscopy image of the mercerized AA sample stored at 4° C., and FIG. 76B shows a microscopy image of the mercerized AA sample maintained in the shaking incubator;

FIG. 78 shows the circularity and roundness distributions of the particles of the mercerized AA samples described in Example 20 and imaged in FIG. 76, wherein FIG. 78A shows the circularity distributions of the mercerized AA samples, and FIG. 78B shows the roundness distributions of the mercerized AA samples;

FIG. 89 shows photographs of resections taken from rats injected with dermal fillers according to some embodiments of the present disclosure as described in Example 27, wherein FIG. 89B shows a resection of a rat injected with a hyaluronic acid (HA) dermal filler formulation, and FIG. 89C shows a resection of a rat injected with a collagen dermal filler formulation;

FIG. 90 shows microscopy images of an injected saline dermal filler formulation after 12 weeks as described in Example 27, wherein FIG. 90A shows a microscopy image of the injected saline formulation stained with Masson's Trichrome (MT) at a magnification of 1×, FIG. 90B shows a microscopy image of the injected saline formulation stained with MT at a magnification of 10×, FIG. 90C shows a microscopy image of the injected saline formulation stained with MT at a magnification of 20×, FIG. 90D shows a microscopy image of the injected saline formulation stained with hematoxylin and eosin (HE) at a magnification of 1×, FIG. 90E shows a microscopy image of the injected saline formulation stained with HE at a magnification of 10×, and FIG. 90F shows a microscopy image of the injected saline formulation stained with HE at a magnification of 20×;

FIG. 91 shows microscopy images of an injected HA dermal filler formulation after 12 weeks as described in Example 27, wherein FIG. 91A shows a microscopy image of the injected HA formulation stained with MT at a magnification of 1×, FIG. 91B shows a microscopy image of the injected HA formulation stained with MT at a magnification of 10×, FIG. 91C shows a microscopy image of the injected HA formulation stained with MT at a magnification of 20×, FIG. 91D shows a microscopy image of the injected HA formulation stained with HE at a magnification of 1×, FIG. 91E shows a microscopy image of the injected HA formulation stained with HE at a magnification of 10×, and FIG. 91F shows a microscopy image of the injected HA formulation stained with HE at a magnification of 20×;

FIG. 92 shows microscopy images of an injected collagen dermal filler formulation after 12 weeks as described in Example 27, wherein FIG. 92A shows a microscopy image of the injected collagen formulation stained with MT at a magnification of 1×, FIG. 92B shows a microscopy image of the injected collagen formulation stained with MT at a magnification of 10×, FIG. 92C shows a microscopy image of the injected collagen formulation stained with MT at a magnification of 20×, FIG. 92D shows a microscopy image of the injected collagen formulation stained with HE at a magnification of 1×, FIG. 92E shows a microscopy image of the injected collagen formulation stained with HE at a magnification of 10×, and FIG. 92F shows a microscopy image of the injected collagen formulation stained with HE at a magnification of 20×;

FIG. 93 shows microscopy images of injected dermal filler formulations as described in Example 27 after 12 weeks and stained with Congo red at a magnification of 10×, wherein FIG. 93A shows an injected saline formulation, FIG. 93B shows an injected HA formulation, and FIG. 93C shows an injected collagen formulation;

DETAILED DESCRIPTION

Figure 1:
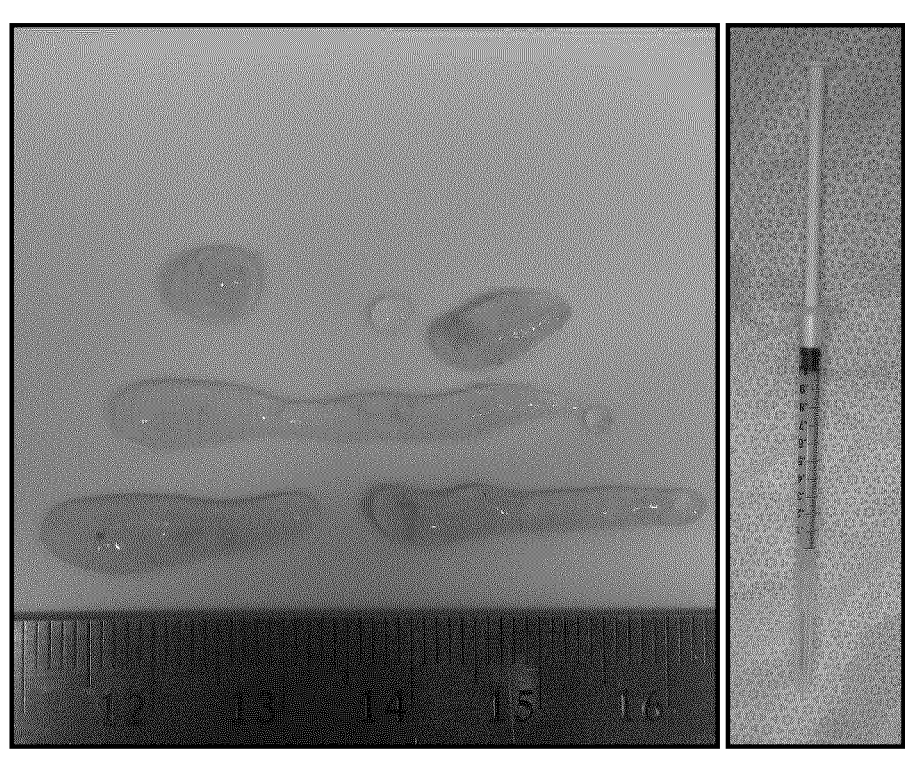
FIG. 1 shows extruded decellularized cellulose paste (left
panel) as described in Example 1, and a 1 mL syringe after
loading the paste with an 18 G needle is also shown (right
panel)

Described herein are dermal fillers, methods and uses thereof for cosmetic and/or reconstructive applications, as well as methods for preparing such dermal fillers and dermal filler kits relating thereto. It will be appreciated that embodiments and examples are provided for illustrative purposes intended for those skilled in the art, and are not meant to be limiting in any way.

Provided herein are dermal fillers comprising decellularized plant or fungal tissue from which cellular materials and nucleic acids of the tissue are removed; as well as methods and uses thereof for cosmetic and/or reconstructive applications. Also provided are methods for preparing such dermal fillers, and dermal filler kits.

As described herein, the present inventors have now developed dermal filler products comprising decellularized plant or fungal tissue. Data provided herein indicates dermal fillers had good biocompatibility, and were substantially non-resorbable—i.e. "permanent". Methods for preparing such dermal filler products are described, which may allow for control over size and various other beneficial properties, including the avoidance of small undesirable particles below 20 μm in size. Preparations are developed having good syringability/injectability through small gauge needles, as well as preparations compatible with carrier fluids such as hydrogels, and compatible with anesthetics. Sterilization techniques and sterilized products are also described. Particles for dermal filler products are described having desirable shapes and surface area/volume/packing properties to encourage cell invasion/growth and/or to provide good ratios of natural tissue to dermal filler in subjects.

Dermal fillers are commonly employed materials for cosmetic and/or aesthetic applications such as filling wrinkles, altering appearance, or addressing soft tissue damage due to disease or injury. In certain embodiments, dermal filler products as described herein may be considered "permanent" in that they provide long-term, natural, and biocompatible solutions for such applications. Many dermal fillers in the field have been temporary. After a certain period of time, conventional dermal fillers are resorbed by the body. Others may use synthetic particles, such as PMMA, to provide longer-term solutions. In certain embodiments, the presently described approach may provide for cellulose-based materials processed to a target size range for dermal fillers. These may be produced from natural plant polymers, and may be permanent due to the fact that humans do not have the enzymes to break down cellulose. As described in detail herein, such particles have been successfully produced, the particles being in the target desirable size range. Particles have been used in different dermal filler formulations, and have been injected into a rat model. The particles have a desirable SA:V ratio, may promote vascularization, may be biocompatible, and may provide for a tissue that is composed of more of the patient's own tissues rather than synthetic materials.

In an embodiment, there is provided herein a non-resorbable dermal filler comprising decellularized plant or fungal tissue from which cellular materials and nucleic acids of the tissue are removed.

As will be understood, a dermal filler may be considered non-resorbable when it comprises at least one filler or particle component which is substantially non-resorbable or long-lasting (e.g. resistant to degradation) following implantation in a subject. By way of example, in certain embodiments, dermal fillers as described herein may comprise decellularized plant tissue in the form of cellulose-based or cellulose-containing particles, which may be considered substantially non-resorbable since the human body lacks enzymes for degrading cellulose. In certain embodiments, non-resorbable dermal fillers may include one or more filler or particle components which are permanent, semi-permanent, or long-lasting in the body following injection or implantation, for example.

As will be understood, unless otherwise indicated, the meaning/definition of plant and fungi kingdoms used herein is based on the Cavalier-Smith classification (1998).

In certain embodiments, the plant or fungal tissue may comprise generally any suitable plant or fungal tissue or part containing a suitable scaffold structure appropriate for the particular application.

In certain embodiments the plant or fungal tissue may comprise an apple hypanthium (*Malus pumila*) tissue, a fern (Monilophytes) tissue, a turnip (*Brassica rapa*) root tissue, a gingko branch tissue, a horsetail (equisetum) tissue, a hermocallis hybrid leaf tissue, a kale (*Brassica oleracea*) stem tissue, a conifers Douglas Fir (*Pseudotsuga menziesii*) tissue, a cactus fruit (pitaya) flesh tissue, a *Maculata Vinca* tissue, an Aquatic Lotus (*Nelumbo nucifera*) tissue, a Tulip (*Tulipa gesneriana*) petal tissue, a Plantain (*Musa paradisiaca*) tissue, a broccoli (*Brassica oleracea*) stem tissue, a maple leaf (*Acer psuedoplatanus*) stem tissue, a beet (*Beta*

*vulgaris*) primary root tissue, a green onion (*Allium cepa*) tissue, a orchid (Orchidaceae) tissue, turnip (*Brassica rapa*) stem tissue, a leek (*Allium ampeloprasum*) tissue, a maple (*Acer*) tree branch tissue, a celery (*Apium graveolens*) tissue, a green onion (*Allium cepa*) stem tissue, a pine tissue, an aloe vera tissue, a watermelon (*Citrullus lanatus* var. *lanatus*) tissue, a Creeping Jenny (*Lysimachia nummularia*) tissue, a cactae tissue, a Lychnis *Alpina* tissue, rhubarb (*Rheum rhabarbarum*) tissue, a pumpkin flesh (*Cucurbita pepo*) tissue, a Dracena (Asparagaceae) stem tissue, a Spiderwort (*Tradescantia virginiana*) stem tissue, an *Asparagus* (*Asparagus officinalis*) stem tissue, a mushroom (Fungi) tissue, a fennel (*Foeniculum vulgare*) tissue, a rose (Rosa) tissue, a carrot (*Daucus carota*) tissue, or a pear (Pomaceous) tissue. Additional examples of plant and fungal tissues are described in Example 18 of WO2017/136950, entitled "Decellularised Cell Wall Structures from Plants and Fungus and Use Thereof as Scaffold Materials", herein incorporated by reference in its entirety.

In certain embodiments, the decellularized plant or fungal tissue may be cellulose-based, chitin-based, chitosan-based, lignin-based, lignan-based, hemicellulose-based, or pectin-based, or any combination thereof. In certain embodiments, the plant or fungal tissue may comprise a tissue from apple hypanthium (*Malus pumila*) tissue, a fern (Monilophytes) tissue, a turnip (*Brassica rapa*) root tissue, a gingko branch tissue, a horsetail (equisetum) tissue, a hermocallis hybrid leaf tissue, a kale (*Brassica oleracea*) stem tissue, a conifers Douglas Fir (*Pseudotsuga menziesii*) tissue, a cactus fruit (pitaya) flesh tissue, a *Maculata Vinca* tissue, an Aquatic Lotus (*Nelumbo nucifera*) tissue, a Tulip (*Tulipa gesneriana*) petal tissue, a Plantain (*Musa paradisiaca*) tissue, a broccoli (*Brassica oleracea*) stem tissue, a maple leaf (*Acer psuedoplatanus*) stem tissue, a beet (*Beta vulgaris*) primary root tissue, a green onion (*Allium cepa*) tissue, a orchid (Orchidaceae) tissue, turnip (*Brassica rapa*) stem tissue, a leek (*Allium ampeloprasum*) tissue, a maple (*Acer*) tree branch tissue, a celery (*Apium graveolens*) tissue, a green onion (*Allium cepa*) stem tissue, a pine tissue, an aloe vera tissue, a watermelon (*Citrullus lanatus* var. *lanatus*) tissue, a Creeping Jenny (*Lysimachia nummularia*) tissue, a cactae tissue, a Lychnis *Alpina* tissue, a rhubarb (*Rheum rhabarbarum*) tissue, a pumpkin flesh (*Cucurbita pepo*) tissue, a Dracena (Asparagaceae) stem tissue, a Spiderwort (*Tradescantia virginiana*) stem tissue, an *Asparagus* (*Asparagus officinalis*) stem tissue, a mushroom (Fungi) tissue, a fennel (*Foeniculum vulgare*) tissue, a rose (Rosa) tissue, a carrot (*Daucus carota*) tissue, or a pear (Pomaceous) tissue, or a genetically altered tissue produced via direct genome modification or through selective breeding, or any combinations thereof.

As will also be understood, cellular materials and nucleic acids of the plant or fungal tissue may include intracellular contents such as cellular organelles (e.g. chloroplasts, mitochondria), cellular nuclei, cellular nucleic acids, and/or cellular proteins. These may be substantially removed, partially removed, or fully removed from the plant or fungal tissue, and/or from the scaffold biomaterial. It will be recognized that trace amounts of such components may still be present in the decellularised plant or fungal tissues described herein. As will also be understood, references to decellularized plant or fungal tissue herein are intended to reflect that such cellular materials found in the plant or fungal source of the tissues have been substantially removed—this does not preclude the possibility that the decellularized plant or fungal tissue may in certain embodiments contain or comprise subsequently introduced, or reintroduced, cells, cellular materials, and/or nucleic acids of generally any kind, such as animal or human cells.

Various methods may be used for producing decellularized plant or fungal tissues as described herein. By way of example, in certain embodiments, the decellularised plant or fungal tissue may comprise plant or fungal tissue(s) which have been decellularised by thermal shock, treatment with detergent (e.g. SDS, Triton X, EDA, alkaline treatment, acid, ionic detergent, non-ionic detergents, and zwitterionic detergents), osmotic shock, lyophilisation, physical lysing (e.g. hydrostatic pressure), electrical disruption (e.g. non thermal irreversible electroporation), or enzymatic digestion, or any combination thereof. In certain embodiments, biomaterials as described herein may be obtained from plants and/or fungi by employing decellularization processes which may comprise any of several approaches (either individually or in combination) including, but not limited to, thermal shock (for example, rapid freeze thaw), chemical treatment (for example, detergents), osmotic shock (for example, distilled water), lyophilisation, physical lysing (for example, pressure treatment), electrical disruption and/or enzymatic digestion.

In certain embodiments, the decellularised plant or fungal tissue may comprise plant or fungal tissue which has been decellularised by treatment with a detergent or surfactant. Examples of detergents may include, but are not limited to sodium dodecyl sulphate (SDS), Triton X, EDA, alkyline treatment, acid, ionic detergent, non-ionic detergents, and zwitterionic detergents.

In still further embodiments, the decellularised plant or fungal tissue may comprise plant or fungal tissue which has been decellularised by treatment with SDS. In still another embodiment, residual SDS may be removed from the plant or fungal tissue by washing with an aqueous divalent salt solution. The aqueous divalent salt solution may be used to precipitate/crash a salt residue containing SDS micelles out of the solution/scaffold, and a $dH_2O$, acetic acid or dimethylsulfoxide (DMSO) treatment, or sonication, may have been used to remove the salt residue or SDS micelles. In certain embodiments, the divalent salt of the aqueous divalent salt solution may comprise, for example, $MgCl_2$ or $CaCl_2$.

In another embodiment, the plant or fungal tissue may be decellularised by treatment with an SDS solution of between 0.01 to 10%, for example about 0.1% to about 1%, or, for example, about 0.1% SDS or about 1% SDS, in a solvent such as water, ethanol, or another suitable organic solvent, and the residual SDS may have been removed using an aqueous $CaCl_2$ solution at a concentration of about 100 mM followed by incubation in $dH_2O$. In certain embodiments, the SDS solution may be at a higher concentration than 0.1%, which may facilitate decellularisation, and may be accompanied by increased washing to remove residual SDS. In particular embodiments, the plant or fungal tissue may be decellularised by treatment with an SDS solution of about 0.1% SDS in water, and the residual SDS may have been removed using an aqueous $CaCl_2$ solution at a concentration of about 100 mM followed by incubation in $dH_2O$.

Further examples of decellularization protocols which may be adapted for producing decellularized plant or fungal tissue as described herein may be found in WO2017/136950, entitled "Decellularised Cell Wall Structures from Plants and Fungus and Use Thereof as Scaffold Materials", herein incorporated by reference in its entirety.

In another embodiment the decellularized plant or fungal tissue may be chitin-based, chitosan-based, lignocellulosic-based, or cellulose-based. In still another embodiment, the decellularized plant or fungal tissue may be derived from leafy structure, root, flesh, hypanthium or pulp structures of a plant. In yet another embodiment, the decellularized plant or fungal tissue may be derived from lettuce, carrot, apple, or pear, or any combination thereof.

In another embodiment of any of the above dermal filler or dermal fillers, the decellularized plant or fungal tissue may be homogenized. In still another embodiment, the decellularized plant or fungal tissue may be dried, subjected to grinding, and optionally reconstituted or rehydrated.

Figure 7:
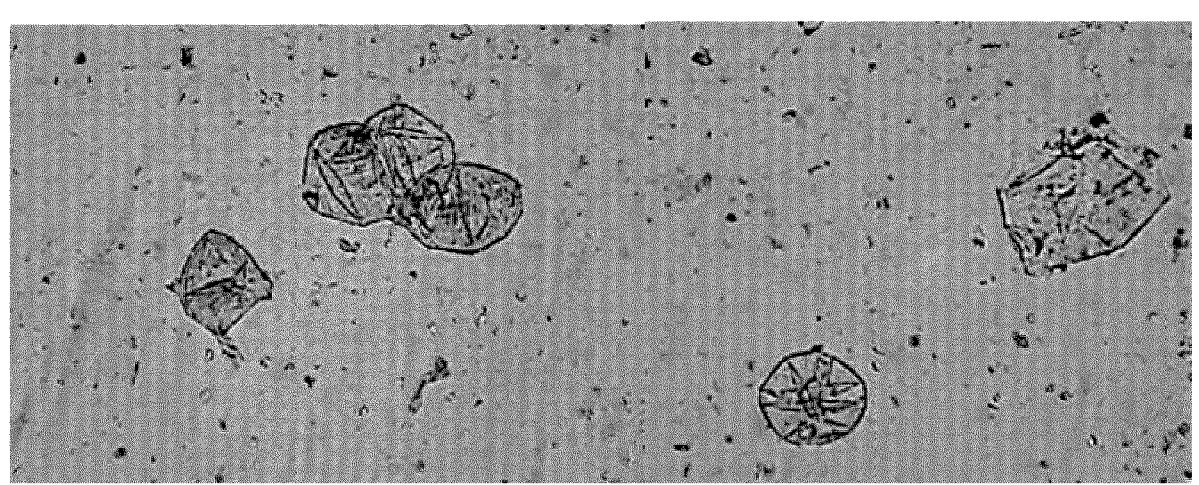
FIG. 7 shows that with the needle method described in
Example 2, biomaterial was sheared enough to get at least
some single intact structural cells (e.g. separated cell wall
pockets) that appeared to be fully formed and not collapsed.
Figure 18:
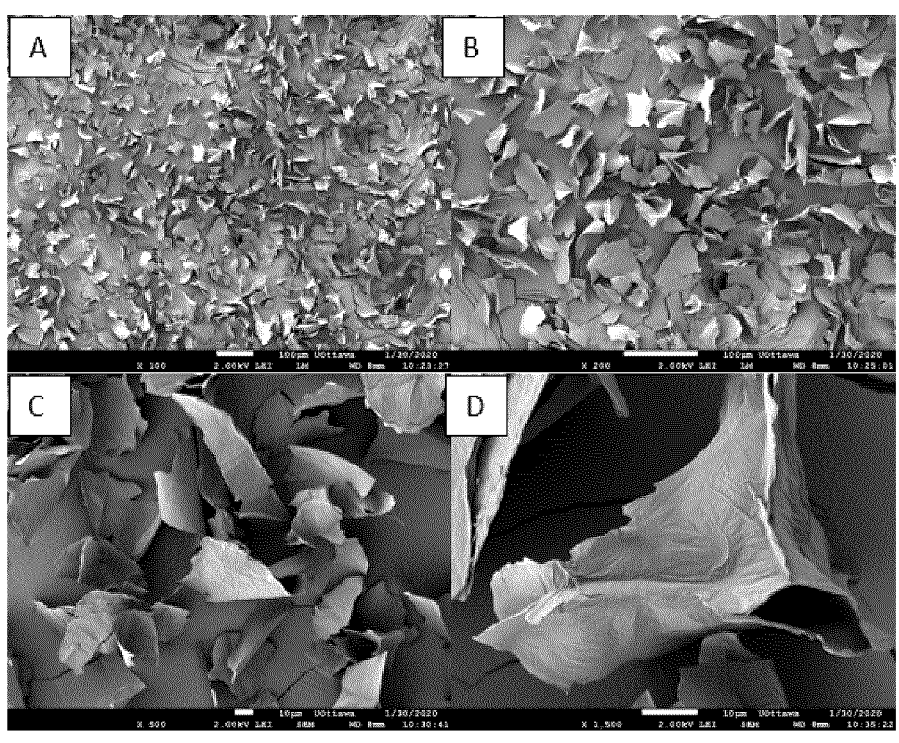
FIG. 18 shows SEM micrographs of the decellularized
apple powder at increasing magnification (A-D) as described
in Example 3.
Figure 19:
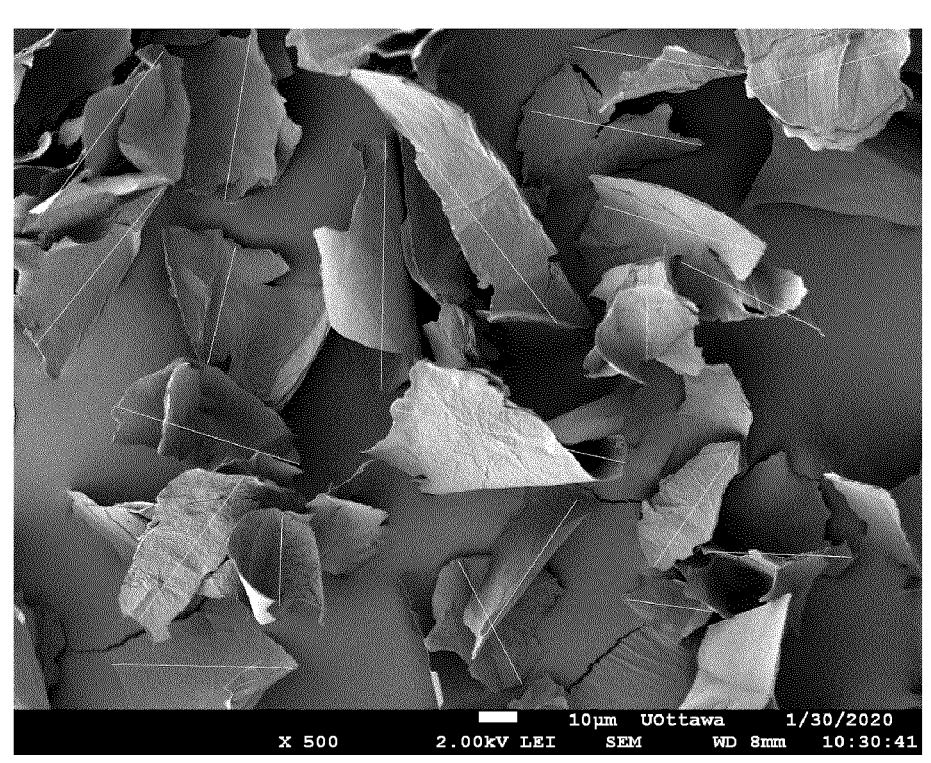
FIG. 19 shows manual image processing to determine
flake diameter as described in Example 3. The flakes are
irregularly shaped and single length descriptors fail to
capture this complexity (source: decellularized apple)

In yet another embodiment of any of the above dermal filler or dermal fillers, the decellularized plant or fungal tissue may be disassembled into particles the size of single structural cells, or smaller. In certain embodiments, the single structural cells may be derived from an extended 3D structure of the plant or fungal tissue, and may comprise isolated structural cells, the structural cells having a 3-dimensional structure typically resembling a hollow cell or pocket as shown in FIG. 7. As will be understood, such structures may typically comprise lignocellulosic materials, such as cellulose and/or lignin-based structures. It will be understood that in certain embodiments, such structures may comprise other building blocks such as chitin and/or pectin, for example. In certain embodiments, the single structural cells may be disassembled (for example, ground) into smaller particles such as flakes as depicted in FIGS. 18 and 19.

In another embodiment of any of the above dermal filler or dermal fillers, the dermal filler may further comprise a hydrogel, matrix, or carrier fluid for the decellarized plant or fungal tissue. In certain embodiments, the hydrogel, matrix, or carrier fluid may comprise PBS (saline), hyaluronic acid (cross-linked or non-crosslinked), alginate, collagen, pluronic acid (e.g. pluronic F 127), agar, agarose, fibrin, calcium hydroxyapatite, Poly-L-lactic acid, autologous fat, silicone, dextran, methylcellulose, dissolved regenerated cellulose, or any combinations thereof.

It is noted that, as used herein, the term "dissolved regenerated cellulose" refers to cellulose that has been dissolved and subsequently "regenerated" via solvent exchange and mixing with the plant or fungal tissue. Any suitable solvent may be used to dissolve the cellulose. For example, in one embodiment, the cellulose may be dissolved using a LiCl and dimethyl acetamide (DMAc) solution.

In certain embodiments, such a hydrogel(s), matrix(es), or carrier fluid(s) may be biological in origin (e.g. natural proteins), synthetic polymers, or synthetic analogues of naturally occurring polymers, for example.

Further discussions and examples of hydrogel(s), matrix(es), and/or carrier fluid(s) may be found in Nguyen et al. "Cosmetic Medicine: Facial Resurfacing and Injectables", Plast Reconstr Surg. 129, 142e (2012); and Luebberding et al. "Critical Appraisal of the Safety of Dermal Fillers: A Primer for Clinicians", Curr Derm Rep. 2, 150 (2013), each of which are herein incorporated by reference in their entireties.

In certain embodiments, hydrogel(s), matrix(es), or carrier fluid(s) may be used to resuspend the dermal filler particles so as to provide substantially uniform dispersion, as well as allowing for injection through small gauge needles, for example.

In certain embodiments, the viscosity of the dermal filler may be adjusted as desired. In certain embodiments, a low viscosity may allow for easier injection, whereas a high viscosity may maintain uniform particle arrangement and/or may maintain volume for longer periods of time, for example. In certain embodiments, viscosity values may range or be varied—for example, in certain examples, a saline carrier may provide about 1 cP, whereas more viscous carrier fluids may provide more viscosity such as about $3 \times 10^6$ cP (as in commercial products such as Bellafill), or beyond.

In a further embodiment, the dermal filler may have a viscosity of less than about 500,000 cp. In certain embodiments, the dermal filler may have a viscosity within a range of about 100,000 cp to about 500,000 cp.

In yet another embodiment of any of the above dermal filler or dermal fillers, the dermal filler may be dried, or hydrated. In certain embodiments, the dermal filler may be provided in dried or lyophilized form, which may be for reconstitution in water, a hydrogel, or other carrier fluid prior to use, for example.

In another embodiment of any of the above dermal filler or dermal fillers, the dermal filler may comprise lidocaine or other anesthetic.

In certain embodiments of the dermal fillers described herein, the decellularized plant or fungal tissue may be disassembled into particles which may have generally any suitable shape, such as a regular or irregular 3D or 2D shape, for example a flake-like structure which may have an irregular, squared, or circular shape, for example. A given shape may typically have a minimum and a maximum diameter or ferret diameter, although in some cases (such as for a circular structure) these may be equal or close to equal. Preferably, in certain embodiments, the particles, or at least most of the particles, may be sized/shaped sufficiently large so as to avoid or prevent cellular uptake or phagocytosis by cells. Accordingly, in certain embodiments, distributions of particles below 20 μm in diameter (whether that be in terms of regular diameter, minimum ferret diameter, and/or maximum ferret diameter) may be avoided where cellular uptake and/or phagocytosis is not desired.

In certain embodiments of the dermal fillers described herein, the decellularized plant or fungal tissue may be disassembled into particles having irregular 3D shapes and/or which are non-spherical, thin, flake-like structures. In certain embodiments, the flake-like structures may have a thickness of about 0.01 to about 100 μm, for example about 0.1 μm.

In some embodiments of the dermal fillers described herein, the decellularized plant or fungal tissue may be disassembled into particles having a size, diameter, or ferret diameter within a range of about 20 μm to about 500 μm.

In certain embodiments, the decellularized plant or fungal tissue may be disassembled into particles having a size sufficiently large so as not to be phagocytosed by a cell or cells (preferably, the decellularized plant or fungal tissue may be disassembled into particles having a size, diameter, or minimum ferret diameter of at least about 20 μm); may be disassembled into particles having a size, diameter, or maximum ferret diameter of less than about 200 μm; may be disassembled into particles having a size, diameter, or ferret diameter distribution within a range of about 20 μm to about 200 μm; may be disassembled into particles having a particle size, diameter, or ferret diameter distribution having a peak within about 30 μm to about 100 μm; may be disassembled into particles having a mean particle size, diameter, or ferret diameter within a range of about 30 μm to about 100 μm; or any combinations thereof.

In another embodiment, the decellularized plant or fungal tissue may be disassembled into particles having a size, diameter, or maximum ferret diameter of less than about 300 μm; may be disassembled into particles having a size, diameter, or ferret diameter distribution within a range of about 100 μm to about 300 μm; may be disassembled into particles having a particle size, diameter, or ferret diameter distribution having a peak within about 100 μm to about 300 μm; may be disassembled into particles having a mean particle size, diameter, or ferret diameter within a range of about 100 μm to about 300 μm; or any combinations thereof.

In yet another embodiment of the dermal fillers described herein, the decellularized plant or fungal tissue may be disassembled into particles having an average projected particle area within a range of about 200 to about 3000 μm², or within a range of about 200 to about 300 μm²; the decellularized plant or fungal tissue may be disassembled into particles having a surface area to volume ratio of about 0.1 to 100 μm⁻¹; the decellularized plant or fungal tissue may be disassembled into particles having a packing density of about $4 \times 10^5$ particles/mL to about $7 \times 10^9$ particles/mL; or any combinations thereof.

In another embodiment of any of the above dermal filler or dermal fillers, the decellularized plant or fungal tissue may be sterilized. In still another embodiment of any of the above dermal filler or dermal fillers, the dermal filler may be sterilized. In certain embodiments, the sterilization may be by radiation, such as by gamma sterilization.

In another embodiment, the plant or fungal tissue may be mercerized. As will be understood, mercerization of the plant or fungal tissue disassembles the plant or fungal tissue into tissue/cellular components (including single structural cells, groups of structural cells, or both). In certain embodiments, the mercerization may employ an alkaline/base solution and a peroxide. In certain embodiments, more than one treatment or solution may be used, either simultaneously or sequentially.

In certain embodiments, mercerization may comprise at least one treatment with a base solution. As will be understood, the base solution may comprise generally any suitable base, such as any suitable base capable of osmotic shock and/or disruption of hydrogen bonding and/or polymer crystal structure so as to extract intact tissue structures. As will be understood, particularly for dermal filler applications, the base may be selected to be, for example, physiologically occurring, easily washed away, non-harmful, or a combination thereof, as desired. In certain embodiments, the base may comprise NaOH, KOH, or a combination thereof. In an embodiment, the base may be dissolved/mixed in a suitable solvent, to form the base solution. Typically, the solvent may comprise water, although other solvents, or combinations of solvents (such as, for example, a mixture of water and ethanol), are also contemplated. The base solution may comprise a base concentration of about 0.1 to 10M, or any concentration therebetween (optionally rounded to the nearest 0.1), or any subrange spanning between any two of these concentrations. In certain embodiments, the base concentration may be about 0.5M to 3M, or any value (optionally rounded to the nearest 0.1) therebetween, or any subrange spanning between any two of these concentrations. By way of example, in certain embodiments, the base solution may comprise an aqueous solution of NaOH, having a concentration of about 0.5M-3M. As will be understood, the base solution, as well as the treatment conditions (i.e. heating, stirring) may be tailored to desired structures to be extracted, plant or fungal tissue being used, etc . . . , as desired.

In certain embodiments, bases may include a base selected from the group consisting of. Carbonates; Nitrates; Phosphates; Sulfates; Ammonia; Sodium hydroxide; Calcium hydroxide; Magnesium hydroxide; Potassium hydroxide; Lithium hydroxide; Zinc hydroxide; Sodium carbonate; Sodium bicarbonate; Butyl lithium; Sodium azide; Sodium amide; Sodium hydride; Sodium borohydride; or Lithium diisopropylamine. Depending on the base, neutralization and/or washing may be performed to remove residual base and other reagents so as to prevent undesirable contamination, for example.

In preferred embodiments, the mercerization may comprise treatment of the plant or fungal tissue (preferably decellularized plant or fungal tissue) using sodium hydroxide and hydrogen peroxide with heating.

However, it is noted that other extraction techniques may be used and are contemplated. For example, in another embodiment, the plant and/or fungal tissue may be macerated. As will be understood, like mercerization, maceration of the plant or fungal tissue disassembles the plant or fungal tissue into tissue/cellular components (including single structural cells, groups of structural cells, or both). However, unlike mercerization, maceration generally involves the use of an acidic solution rather than a basic solution. Thus, maceration may remove certain acid-soluble lignin components rather than base-soluble lignin components and therefore provide structural cells having different lignin content, for example.

In another embodiment of any of the above dermal filler or dermal fillers, the dermal filler may be formulated for subdermal injection, deep dermal injection, subcutaneous injection (e.g. subcutaneous fat injection), or any combinations thereof. In still another embodiment, the dermal filler may be provided in or with a syringe or injection device.

In yet another embodiment, there is provided herein a use of any of the dermal filler or dermal fillers as described herein as a soft tissue filler, for reconstructive surgery, or both; for improving cosmetic appearance of a subject in need thereof; for increasing tissue volume, smoothing wrinkles, or both, in a subject in need thereof, or any combinations thereof.

In yet another embodiment, there is provided herein a method for improving cosmetic appearance, increasing tissue volume, smoothing wrinkles, or any combinations thereof, in a subject in need thereof, said method comprising:

administering or injecting any of the dermal filler or dermal fillers as described herein to a region in need thereof;

thereby improving cosmetic appearance, increasing tissue volume, smoothing wrinkles, or any combinations thereof, of the subject.

In certain embodiments, native cells of the subject may infiltrate the dermal filler following administration/injection/implantation.

In still another embodiment, the dermal filler may be non-resorbable such that the decellularized plant or fungal tissue may remain substantially intact within the subject over at least about 3 months, at least about 4 months, at least about 5 months, or at least about 6 months, for example.

In yet another embodiment, the dermal filler may be degradable through the addition of one or more enzymes thereto. As described above, the dermal fillers of the present disclosure may be non-resorbable such that the decellularized plant or fungal tissue may remain substantially intact within the subject for a period of time and, in some cases, may be considered permanent. However, it will be appreciated that, in some circumstances, it may be desirable to remove the dermal fillers. Thus, in such embodiments, the dermal fillers may be removable by degrading the decellularized plant or fungal tissues thereof using one or more enzymes not produced by the subject to which the dermal fillers are administered or injected.

In certain embodiments, the one or more enzymes used to degrade the dermal filler may be selected based on the decellularized plant or fungal tissue thereof. For example, as previously described herein, the dermal fillers may comprise decellularized plant or fungal tissue that is chitin-based, chitosan-based, lignocellulosic-based, or cellulose-based. The one or more enzymes may therefore be selected to degrade, chitin, chitosan, lignocellulose, or cellulose. As a further example, if the plant or fungal tissue is cellulose-based, the one or more enzymes may comprise cellulase.

In certain embodiments, the one or more enzymes may be the same type of enzymes from different sources. For example, the one or more enzymes may comprise cellulase from *Aspergillus niger* and cellulase from *Trichoderma* sp. In certain embodiments, the one or more enzymes may comprise different enzymes. For example, the one or more enzymes may comprise cellulase and pectinase (e.g. from *Aspergillus niger*). Different types of enzymes may be selected based on the decellularized plant or fungal tissue used in the dermal filler. Further, the type of decellularized plant or fungal tissue used in the dermal filler may influence the ratios of the enzymes derived from different sources and/or the different types of enzymes used for the degradation thereof. For example, in certain embodiments where two enzymes derived from different sources and/or different types of enzymes are selected, the enzymes may be used at ratios of about 25:75 to about 50:50.

In certain embodiments, the one or enzymes may be provided in a solution such as a buffer solution. The buffer solution may be a PBS buffer solution, a sodium acetate buffer solution, a sodium citrate buffer solution, or any other suitable buffer solution. The one or more enzymes may be provided in the buffer solution at an enzyme(s):buffer ratio of about 25:75 to about 75:25.

The one or more enzymes may be administered to degrade the dermal fillers using any suitable technique. For example, a solution of the one or more enzymes may be injected into the dermal filler that had been previously administered to a subject.

In yet another embodiment, there is provided herein a method for preparing a non-resorbable dermal filler, comprising:

providing a plant or fungal tissue;

decellularizing and size-reducing the plant or fungal tissue to provide particles from which cellular materials and nucleic acids of the tissue are removed; and optionally, sterilizing the particles;

thereby providing the non-resorbable dermal filler.

In certain embodiments, the decellularized plant or fungal tissue may be chitin-based, chitosan-based, lignocellulosic-based, or cellulose-based. In another embodiment, the decellularized plant or fungal tissue may be derived from leafy structure, root, flesh, hypanthium or pulp structures of a plant. In yet another embodiment, the decellularized plant or fungal tissue may be derived from lettuce, carrot, apple, or pear, or any combination thereof.

In another embodiment of any of the above method or methods, the size-reducing may comprise a mechanical size reduction to provide the particles, optionally where the mechanical size reduction may be performed on dried, lyophilized, or freeze-dried materials.

In still another embodiment of any of the above method or methods, the mechanical size reduction may comprise crushing, extrusion, grinding, milling, ultrasonication, electrospinning, chemical dissolution, enzymatic breakdown, or shearing the plant or fungal tissue, before or after decellularizing, to provide the particles.

In certain embodiments, the mechanical size reduction may comprise molding and shaping particles from dissolved material which may be reconstituted/regenerated (for example, spherification and/or emulsions).

In yet another embodiment of any of the above method or methods, size-reducing may comprise drying the plant or fungal tissue, before or after decellularizing; subjecting the dried plant or fungal tissue to mechanical size reduction to provide the particles; and, optionally, reconstituting, resuspending, or rehydrating the particles. In certain embodiments, reconstituting, resuspending, or rehydrating may comprise introducing or mixing with water, saline, hydrogel, or another carrier fluid.

In another embodiment of any of the above method or methods, the size-reducing may provide particles the size of single structural cells, or smaller.

In certain embodiments, the size-reducing may comprise a maceration, such as a chemical maceration, to provide the particles, or to provide single structural cells which may optionally be subject to further processing to provide the particles. Examples of maceration approaches are described in PCT patent application number PCT/CA2020/050655 filed May 14, 2020 and entitled "Composite Biomaterials", which is herein incorporated by reference in its entirety.

In still another embodiment of any of the above method or methods, the method may further comprise a step of formulating the particles with a hydrogel, matrix, or carrier fluid. In certain embodiments, the hydrogel, matrix, or carrier fluid may comprise PBS, saline, hyaluronic acid (cross-linked or non-crosslinked), alginate, collagen, pluronic acid (e.g. Pluronic F 127), agar, agarose, fibrin, calcium hydroxyapatite, Poly-L-lactic acid, autologous fat, silicone, dextran, methylcellulose, dissolved regenerated cellulose, or any combinations thereof.

In another embodiment of any of the above method or methods, the dermal filler may be provided in dried, or hydrated, form. In still another embodiment of any of the above method or methods, the method may further comprise a step of formulating with lidocaine or other anesthetic.

In yet another embodiment of any of the above method or methods, the size-reducing may provide particles having irregular 3D shapes and/or which are non-spherical, thin, flake-like structures. In still another embodiment, the flake-like structures may have a thickness of about 0.01 to about 100 μm, for example about 0.1 μm.

In still another embodiment of any of the above method or methods, the size-reducing may further comprise performing extrusion, filtering, centrifuging, or other size separation to obtain particles having a target size, particles within a target size range, or particles having a target size distribution. For example, in some embodiments, the size-reducing may provide particles having particles having a size, diameter, or ferret diameter within a range of about 20 μm to about 1000 μm.

In yet another embodiment of any of the above method or methods, the size-reducing may provide particles having a size sufficiently large so as not to be phagocytosed by a cell or cells (preferably, the size-reducing may provide particles having a size, diameter, or minimum ferret diameter of at least about 20 μm); may provide particles having a size, diameter, or maximum ferret diameter of less than about 200 μm; may provide particles having a size, diameter, or ferret diameter distribution within a range of about 20 μm to about 200 μm; may provide particles having a particle size, diameter, or ferret diameter distribution having a peak within about 30 μm to about 100 μm; may provide particles having a mean particle size, diameter, or ferret diameter within a range of about 30 μm to about 100 μm; or any combinations thereof.

In yet another embodiment of any of the above method or methods, the size-reducing may provide particles having a size, diameter, or maximum ferret diameter of less than about 300 μm; may provide particles having a size, diameter, or ferret diameter distribution within a range of about 100 μm to about 300 μm; may provide particles having a particle size, diameter, or ferret diameter distribution having a peak within about 100 μm to about 300 μm; may provide particles having a mean particle size, diameter, or ferret diameter within a range of about 100 μm to about 300 μm; or any combinations thereof.

In still another embodiment of any of the above method or methods, the size-reducing may provide particles having an average projected particle area within a range of about 200 to about 3000 $\mu m^2$, or within a range of about 200 to about 300 $\mu m^2$; wherein the decellularized plant or fungal tissue is disassembled into particles having a surface area to volume ratio of about 0.1 to 100 $\mu m^{-1}$; wherein the decellularized plant or fungal tissue is disassembled into particles having a packing density of about $4 \times 10^5$ particles/mL to about $7 \times 10^9$ particles/mL; or any combinations thereof.

In yet another embodiment of any of the above method or methods, the size-reducing may comprise grinding while simultaneously passing resulting particles through a filter to obtain particles below an upper threshold size.

In another embodiment of any of the above method or methods, the method may further comprise filtering, differential or equilibrium centrifugation, or sieving to remove particles below a lower threshold size, obtaining particles above the lower threshold size.

In still another embodiment of any of the above method or methods, the filtering or sieving may be performed using an automated wet-sieve.

In yet another embodiment of any of the above method or methods, the size-reducing may comprise performing differential or equilibrium centrifugation to obtain particles having a target size, particles within a target size range, or particles having a target size distribution.

In another embodiment of any of the above method or methods, the method may further comprise formulating the particles with a hydrogel, matrix, or carrier fluid by loading a first syringe or vessel with the particles in a fluid such as water or buffer (e.g. saline) and loading a second syringe or vessel with the hydrogel, matrix, or carrier fluid; the first and second syringes or vessels being in fluid communication; and mixing by passing the contents of the syringes or vessels back and forth between the first and second syringes or vessels.

In another embodiment, the formulating of the particles with a hydrogel, matrix, or carrier fluid may comprising mixing the particles with a hydrogel, matrix, or carrier fluid using a planetary mixer, a disperser, a high-shear mixer, a kneader, a multi-shaft mixer, a ribbon-paddle blender, a static mixer, a roll mill, a homogenizer, an agglomeration, the like, or any combination thereof.

In some embodiments, it may be useful to remove agglomerated material prior to, during, or after mixing with a hydrogel, matrix, or carrier fluid. For example, in an embodiment, the particles may be mixed with the hydrogel, matrix, or carrier fluid with a size-exclusion mixer such as a static cross-hatch mixer or mesh. Such embodiments may allow for the mixing of the particles with the hydrogel, matrix, or carrier fluid while removing, excluding, or breaking-up agglomerated material (e.g. agglomerated particles).

In still another embodiment of any of the above method or methods, the method may further comprise sterilizing the plant or fungal tissue, before or after decellularizing. In yet another embodiment, the method may comprise sterilizing the dermal filler. In certain embodiments, the sterilization may be by gamma sterilization. In other embodiments, the sterilization may be by autoclaving.

In some embodiments, a plurality of sterilizations may be performed. For example, the sterilization may comprise a first sterilization and a second sterilization. The first sterilization may be a heat treatment (e.g. autoclaving) and the second sterilization may be sterilization by way of gamma radiation, autoclaving, and the like. A plurality of sterilizations may be useful for reducing the bioburden levels of the materials. As well, employing a first sterilization that is a heat treatment may modulate hydration plateau levels of the materials. As will be appreciated, modulation of the hydration plateau levels may allow the amount of solvent held by the particles of the dermal fillers of the present disclosure to be modulated and/or stabilized.

In still another embodiment of any of the above method or methods, the method may further comprise mercerizing the plant or fungal tissue. As described herein, mercerization of the plant or fungal tissue (preferably decellularized plant or fungal tissue), disassembles the plant or fungal tissue into tissue/cellular components (including single structural cells, groups of structural cells, or both). In certain embodiments, the mercerization may employ an alkaline/base solution and a peroxide. In certain embodiments, more than one treatment or solution may be used, either simultaneously or sequentially. In certain embodiments it is contemplated that mercerization may be performed on plant or fungal tissue and decellularization may be performed afterwards, or mercerization may be performed on plant or fungal tissue and mercerization conditions may be selected so as to simultaneously provide decellularization. However, as described herein, it is preferred that mercerization be performed on plant or fungal tissue that has already previously been decelluarized.

In certain embodiments, mercerization may comprise at least one treatment with a base solution. As will be understood, the base solution may comprise generally any suitable base, such as any suitable base capable of osmotic shock and/or disruption of hydrogen bonding and/or polymer crystal structure so as to extract intact tissue structures. As will be understood, particularly for derma filler applications, the base may be selected to, for example, be physiologically occurring, easily washed away, non-harmful, or any combination thereof, as desired. In certain embodiments, the base may comprise NaOH, KOH, or a combination thereof. In an embodiment, the base may be dissolved/mixed in a suitable solvent, to form the base solution. Typically, the solvent may comprise water, although other solvents, or combinations of solvents (such as, for example, a mixture of water and ethanol), are also contemplated. Typically, the base solution may comprise a base concentration of about 0.1 to 10M, or any concentration therebetween (optionally rounded to the nearest 0.1), or any subrange spanning between any two of these concentrations. In certain embodiments, the base concentration may be about 0.5M to 3M, or any value (optionally rounded to the nearest 0.1) therebetween, or any subrange spanning between any two of these concentrations. By way of example, in certain embodiments, the base solution may comprise an aqueous solution of NaOH, having a concentration of about 0.5M-3M. As will be understood, the base solution, as well as the treatment conditions (i.e. heating, stirring) may be tailored to suit the particular application, desired structures to be extracted, plant or fungal tissue being used, etc . . . , as desired.

In certain embodiments, bases may include a base selected from the group consisting of: Carbonates; Nitrates; Phosphates; Sulfates; Ammonia; Sodium hydroxide; Calcium hydroxide; Magnesium hydroxide; Potassium hydroxide; Lithium hydroxide; Zinc hydroxide; Sodiumcarbonate; Sodium bicarbonate; Butyl lithium; Sodium azide; Sodium aminde; Sodium hydride; Sodium borohydride; or Lithium diisopropylamine. Depending on the base, the products, neutralization and/or washing may be performed to remove residual base and other reagents so as to prevent undesirable contamination, for example.

In preferred embodiments, the mercerization may comprise treatment of the plant or fungal tissue (preferably decellularized plant or fungal tissue) using sodium hydroxide and hydrogen peroxide with heating.

In certain embodiments of the above method, the mercerization may comprise treatment of the decellularized plant or fungal tissue with a base and a peroxide, preferably sodium hydroxide or another hydroxide base as base, and hydrogen peroxide as peroxide. Mercerization may chemically disassemble the decellularized plant or fungal tissue into single structural cells, groups of structural cells, or both, without destroying lignocellulose structures thereof.

In still another embodiment of any of the above method or methods, the mercerization may comprise treatment of the decellularized plant or fungal tissue with aqueous sodium hydroxide solution and hydrogen peroxide while heating.

In still another embodiment of any of the above method or methods, the mercerization may be performed with heating to about 80° C. In certain embodiments, such heating may allow for reduced reaction time, particularly when using sodium hydroxide, for example.

In yet another embodiment of any of the above method or methods, the decellularized plant or fungal tissue may be treated with the aqueous sodium hydroxide solution for a first period of time before the hydrogen peroxide is added to the reaction. In certain embodiments, the first period of time may be about 1 minute to about 24 hours, or any time point therebetween, or any subrange spanning between any two such time points.

In another embodiment of any of the above method or methods, the hydrogen peroxide may be added as a 30% to 50% aqueous hydrogen peroxide stock solution.

In still another embodiment of any of the above method or methods, the hydrogen peroxide for mercerization may be used in a ratio of:

about 20 mL to about 5 mL of 30% hydrogen peroxide solution:about 100 g decellularized plant or fungal tissue:about 500 mL of 1M NaOH solution;

such as:

about 20 mL of 30% hydrogen peroxide solution:about 100 g decellularized plant or fungal tissue:about 500 mL of 1M NaOH solution;

about 10 mL of 30% hydrogen peroxide solution:about 100 g decellularized plant or fungal tissue:about 500 mL of 1M NaOH solution; or about 5 mL of 30% hydrogen peroxide solution:about 100 g decellularized plant or fungal tissue:about 500 mL of 1M NaOH solution.

As will be understood, these ratios may be scaled up or down to suit the particular components as desired—the recited quantities are provided for showing relative ratios, not absolute quantities.

For example, in certain embodiments, the 30% aqueous hydrogen peroxide solution is used in an amount of at least about 75 mL per 500 g of decellularized plant or fungal tissue. In certain embodiments, the 1M sodium hydroxide solution is used in an amount of about 2500 mL per 500 g of decellularized plant or fungal tissue. In general, the aqueous hydrogen peroxide solution may be added to a final hydrogen peroxide concentration of about 1% to about 5% of the total volume of the decellularized plant or fungal tissue, the sodium hydroxide solution, and the aqueous hydrogen peroxide solution mixture.

In yet another embodiment of any of the above method or methods, the method may further comprise a step of neutralizing the pH with one or more neutralization treatments. In another embodiment of any of the above method or methods, the neutralization treatment may comprise treatment with an acid solution, preferably an aqueous HCl solution.

In yet another embodiment of any of the above method or methods, the mercerization may be performed using a ratio of decellularized plant or fungal tissue:aqueous sodium hydroxide solution (m:v, in g:L) of about 1:5 for a 1M aqueous sodium hydroxide solution, or an equivalent ratio for another aqueous sodium hydroxide solution concentration. As will be understood, these ratios may be scaled up or down to suit the particular components as desired—the recited quantities are provided for showing relative ratios, not absolute quantities.

In another embodiment of any of the above method or methods, the mercerization may be performed for at least about 30 minutes, preferably for about 1 hour.

In still another embodiment of any of the above method or methods, the method may further comprise formulating the dermal filler for subdermal injection, deep dermal injection, subcutaneous injection (e.g. subcutaneous fat injection), or any combinations thereof.

In another embodiment, there is provided herein a dermal filler prepared by any of the method or methods described herein.

In another embodiment of any of the dermal filler or dermal fillers described herein, about 0.1% to about 5%, or less, of the particles of the dermal filler may have a ferret diameter, or a minimum ferret diameter, of less than about 20 μm. In yet another embodiment of any of the dermal filler or dermal fillers described herein, less than about 0.5% of the particles of the dermal filler may have a ferret diameter, or a minimum ferret diameter, of less than 20 μm.

In yet another embodiment of any of the above dermal filler or dermal fillers, less than about 0.1% to about 5% (such as less than about 0.5%), or less, of the particles of the dermal filler may have a size sufficiently small so as to be phagocytosed by a cell or cells of a subject.

In another embodiment, there is provided herein a kit comprising any one or more of:

any of the dermal filler or dermal fillers as described herein;

a hydrogel, matrix, or carrier fluid;

PBS, saline, hyaluronic acid (cross-linked or non-cross-linked), alginate, collagen, pluronic acid (e.g. pluronic F 127), agar, agarose, fibrin, calcium hydroxyapatite, Poly-L-lactic acid, autologous fat, silicone, dextran, methylcellulose, dissolved regenerated cellulose, or any combinations thereof;

lidocaine or other aesthetic;

one or more syringes, or another injection device;

a leur-lock fitting or coupler for two or more syringes;

instructions for performing any of the use or uses or method or methods as described herein;

one or more decellularization reagents;

one or more containers, packages, or vessels;

one or more buffers, water, or saline for injection;

a reagent or enzyme (e.g. cellulase) for dissolving dermal filler at an undesirable region or location;

or any combinations thereof.

In certain embodiments, it is contemplated that dermal fillers as described herein may be for use in cosmetic applications to improve wrinkles, acne scars, or for reconstructive surgery.

In certain embodiments, dermal fillers as described herein may be shaped (mechanically or chemically, optionally into spheres), functionalized, and/or combined with a delivery vehicle (optionally, a temporary delivery vehicle) such as a cellulose-derived gel formulation or cellulose-based hydrogel, for example, as desired.

In certain embodiments, it is contemplated that dermal filler particles may be prepared from dissolved material that is reconstituted into spheres or particular sizes/shapes. By way of example, in certain embodiments, it is contemplated that cellulose-based biomaterials such as decellularized plant or fungal tissue may be dissolved with DMAc and LiCl or cellulase (and/or similar such enzymes, such as Endoglucanase (EG, endo-1,4-D-glucanohydrolase, or EC 3.2.1.4.), Exoglucanase or cellobiohydrolase (CBH, 1,4-β-D-glucan cellobiohydrolase, or EC 3.2.1.91.), Beta-glucosidase (EC 3.2.1.21)), and then subjected to spherification during regeneration of the cellulose, for example.

In certain embodiments, it is contemplated that dermal fillers as described herein may be adapted for use as bone filler paste for bone reconstruction, or as a filler material in food applications (e.g. for food engineering, to provide scaffolding for texture and/or mouthfeel) or foam (e.g. for bone, cartilage, soft tissue reconstruction, food, insulation, packaging, etc. . . . ), for example.

In certain embodiments, it is contemplated that a cellulose may be provided or used for dissolution of particles following implantation, for example to degrade unwanted material such as material inadvertently injected into an undesirable location or a blood vessel.

In the following Examples, naturally derived plant-based polymers, which are non-resorbable, are developed and tested as attractive replacements for synthetic particles such as PMMA microspheres.

Example 1—Apple-Based Dermal Filler Paste

In this Example, to develop a cellulose-based dermal filler, apple hypanthium tissue was first decellularized using decellularization protocols as described in WO2017/136950, entitled "Decellularised Cell Wall Structures from Plants and Fungus and Use Thereof as Scaffold Materials", which is herein incorporated by reference in its entirety. Briefly, apple tissue was sectioned on a mandolin slicer to 1.2 mm thick. Cylindrical discs of apple tissue were created by using a 10 mm biopsy punch. The discs were decellularized in 0.1% SDS (as described in WO2017/136950).

After obtaining decellularized 10 mm apple discs, an injectable paste was created. Several discs were spun down in a 50 mL falcon tube and all remaining fluid removed. Under aseptic conditions, the plunger of a 1 mL syringe was then used to crush and homogenize the discs into a thick paste. The paste was then suctioned into a new 1 mL syringe (without needle). After placing a sterile 18 G needle on the syringe it was found the paste could be extruded. Difficulty was encountered when attempting to extrude the paste through higher gauge needles, 18 G was the smallest inner diameter needle that was used. While 18 G may indeed be acceptable for certain dermal filler applications, sizes of 26-27 G are often desirable for certain applications in the cosmetic field, for example.

FIG. 1 shows extruded decellularized cellulose paste (left panel) as described in this Example, and a 1 mL syringe after loading the paste with an 18 G needle is also shown (right panel).

Figure 2:
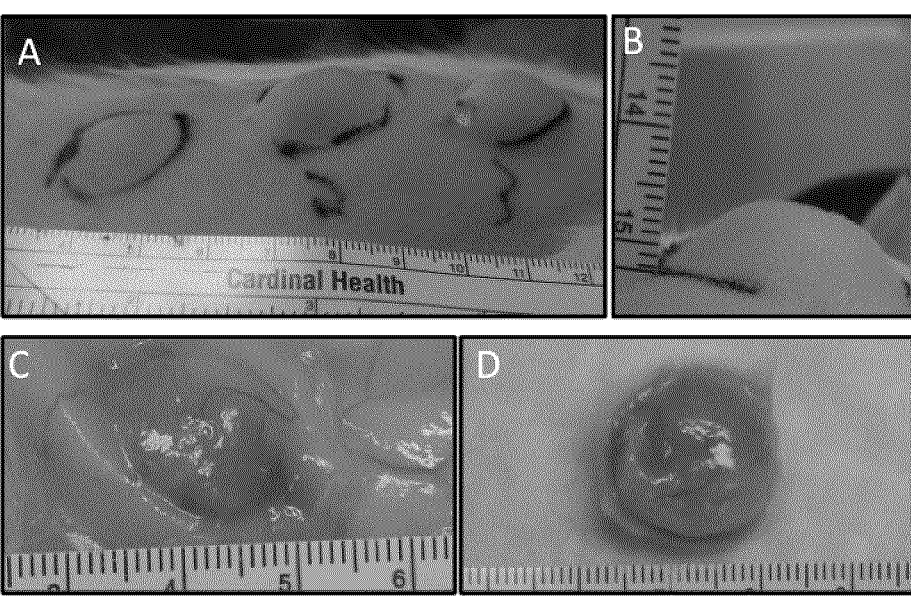
FIG. 2 shows cellulose-based dermal filler paste that was
injected subcutaneously into 3 different sites, as described in
Example 1, wherein (A) shows side view and (B) shows
close-up. Vascularisation was present around the implant at
4 weeks (C), and after resection the implant held its shape
(D)

To test for biocompatibility, a pilot animal study was performed. Briefly, 1 mL of dermal filler paste was injected subcutaneously at three sites (3×1 mL) through an 18 G syringe in the back of female sprague-Dawley rats (400-700 g). The cellulose was injected subcutaneously into 3 different sites (see FIG. 2 for side view (A) and close-up (B)). Vascularisation was present around the implant at 4 weeks (see FIG. 2 (C)), and after resection the implant held its shape (see FIG. 2(D)).

Figure 3:
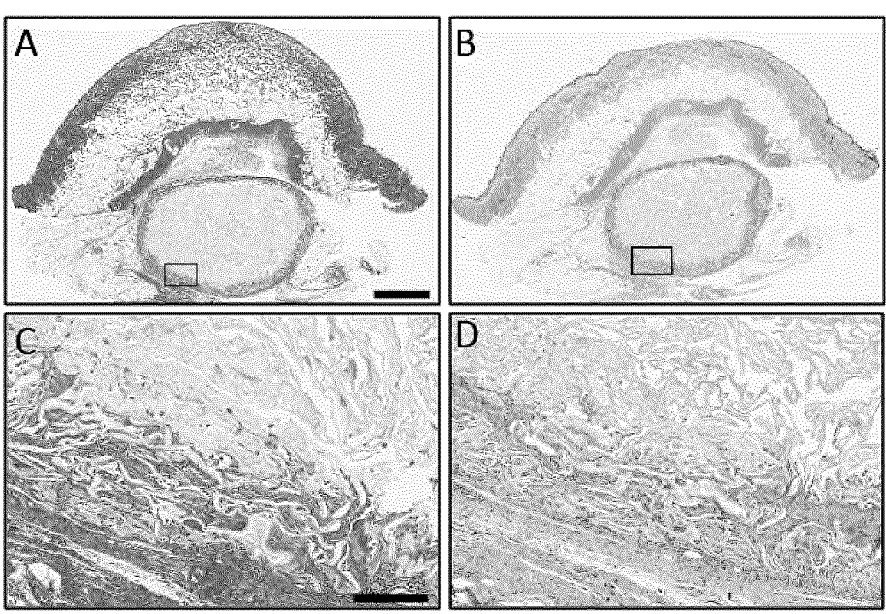
FIG. 3 shows that cell infiltration and matrix deposition
was observed after 8 weeks inside the animal, as described
in Example 1. The cellulose filler appeared to be biocom-
patible and generally maintained a bulbous shape over time.
8 week subcutaneous injection, and Masson trichrome
(shown in (A), (C)) and Hematoxylin & Eosin (shown in
(B), (D)) is shown (Scale bar=2 mm for (A, B); Scale
bar=200 μm for (C, D))
Figure 4:
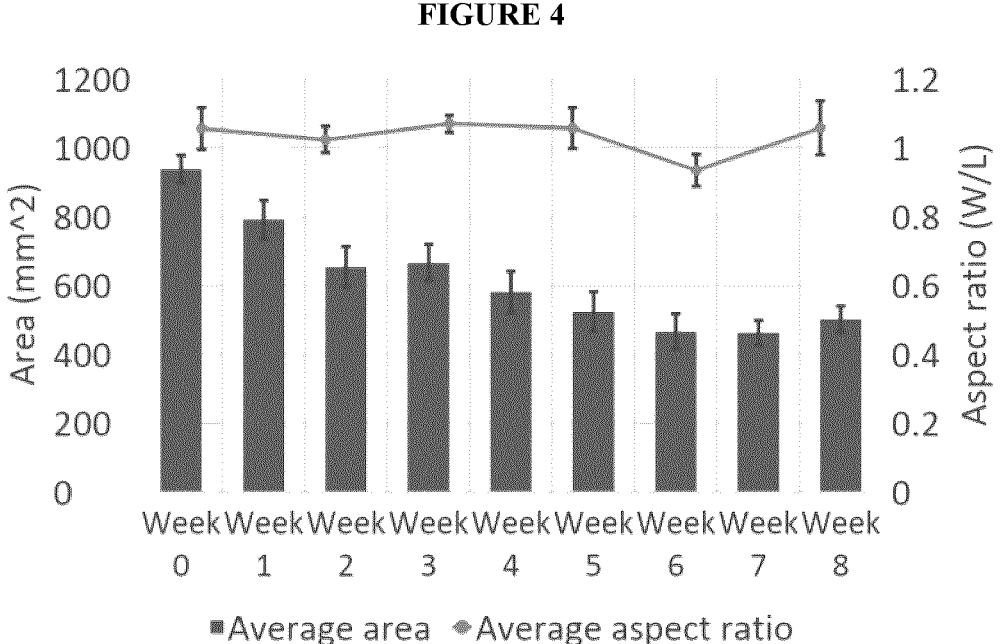
FIG. 4 shows results of manual measurements of the
implant sites from the exterior of the animal utilizing
calipers, as described in Example 1. Over the 8-week study
period, implant area was observed to decrease. However, the
aspect ratio (the ratio of its width in the x and y direction)
did not change significantly.
Figure 5:
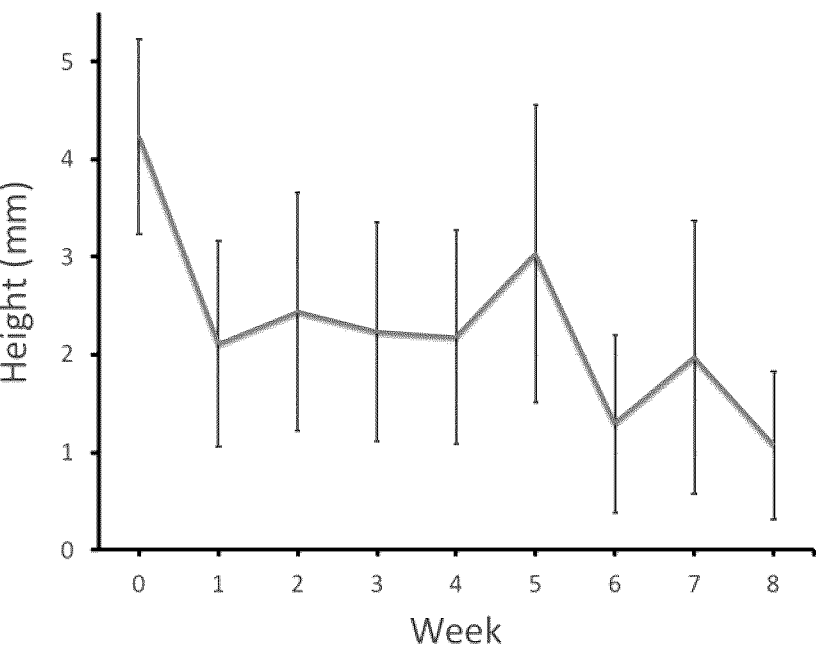
FIG. 5 shows the height of the implant decreased signifi-
cantly by ~75% over the 8-week study period as measured
on the exterior of the animal with calipers, as described in
Example 1. This correlates with a decrease in the area of the
injection site observed above.

The injected material appeared to integrate with surrounding tissue, demonstrating cell infiltration and matrix deposition around the injected material. The injection sites were easily visible and were measured weekly (height, x and y width) with calipers to obtain a measure of how well the implant retained its shape over time. Animals were monitored and sacrificed at 4 and 8 weeks post injection. FIG. 3 shows that cell infiltration and matrix deposition was observed after 8 weeks inside the animal. The cellulose filler appeared to be biocompatible and generally maintained a bulbous shape over time. 8 week subcutaneous injection, and Masson trichrome (shown in FIG. 3 (A), (C)) and Hematoxylin & Eosin (shown in FIG. 3 (B), (D)) is shown (Scale bar=2 mm for (A, B); Scale bar=200 μm for (C, D)). FIG. 4 shows results of manual measurements of the implant sites from the exterior of the animal utilizing calipers. Over the 8-week study period, implant area was observed to decrease. However, the aspect ratio (the ratio of its width in the x and y direction) did not change significantly. FIG. 5 shows that the height of the implant decreased significantly by ~75% over the 8-week study period as measured on the exterior of the animal with calipers. This correlates with a decrease in the area of the injection site observed above.

This study revealed promising data (creation of an injectable, biocompatible cellulose). However, in this example, due to the nature of its creation, the cellulose filler was amorphous and likely composed of a variable and ill-defined collection of particles and crushed cellulose structures. This may lead to difficulty with attempting to extrude through a 26-27 G needle, which is desirable particularly for certain cosmetic applications. Most commercial dermal filler products are composed of materials in a carrier hydrogel (HA or collagen are most common), which was not used in this example. Creation of further refined particles of ground cellulose with controllable size characteristics, and the ability to be controllably mixed with carrier hydrogels, is described in further detail below.

Example 2—Controlled Size Dermal Filler

Building on the results in Example 1 above, a more controlled method of producing cellulose particles for use as a dermal filler was developed in this Example. Using decellularization approaches, several methods of crushing or grinding up the biomaterial were tested to develop dermal fillers compatible with being injected through smaller gauge needles, and to develop methods for production of the dermal filler in a highly controllable and reproducible manner.

In this example, a protocol is developed and described for creating a dry powder according to the following methods.

Figure 6:
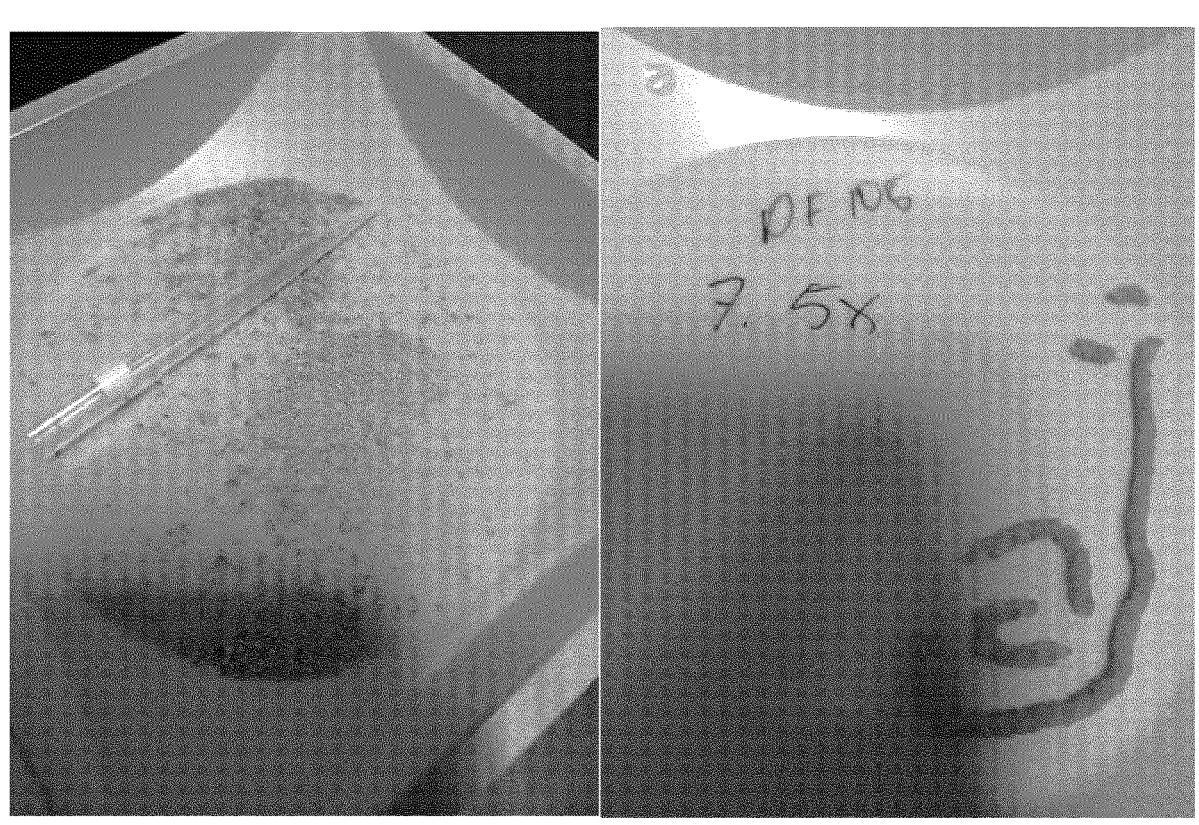
FIG. 6 shows ground up dried biomaterial (left) and a
rehydrated extruded dermal filler (right) as described in
Example 2.

Apple cellulose biomaterials were first decellularized as previously described (see WO2017/136950, entitled "Decellularised Cell Wall Structures from Plants and Fungus and Use Thereof as Scaffold Materials", which is herein incorporated by reference in its entirety). After obtaining the decellularized apple biomaterial, it was allowed to dry, on drying racks, for 24 hours in the air. Once dry, an adjustable burr grinder was utilized to break down the material into fine particles, these particles were repeatedly ground several times to create a collection of particles, which could then be sifted for desired size and shape (see FIG. 6, showing ground up dried biomaterial (left panel) and a rehydrated extruded dermal filler (right panel)). Once a dry powder was obtained, the particles were then resuspended in a volume of DPBS between 10-15 times the weight of the dried biomaterial to create a paste or filler material (see FIG. 6).

It was found that a good way to refine (and reduce) the size of the ground particles was to excessively dilute them and pass them through progressively smaller needle sizes multiple times. With this methodology, the smallest gauge needle that could be used to extrude the filler was a 22.5 G needle in this study. This was still larger than desired for certain applications, as for certain applications dermal fillers are desirably injectable with gauge 26-31 size needles, for example.

Under microscopic observation, it was found that the method for creating this powder resulted in large clumps of material, as well as single intact structural cells. As these cells are typically >200 μm in diameter, this becomes the limiting factor in passing the filler material through fine gauge needles. Of note, is that the grinding method used also produced very fine particles that appear to be in the 1-20 μm region. Particles of this size may, in certain applications, have adverse effects after implantation, potentially leading to inflammation, granulomas, and/or chronic/persistent foreign body reactions.

FIG. 7 shows that with the needle method described above, biomaterial was sheared enough to get at least some single intact structural cells (e.g. separated cell wall pockets) that appeared to be fully formed and not collapsed.

Due to the smaller powder size prepared in this Example, three formulations of dermal fillers were created. In all cases, the dermal fillers contained 4% cellulose particles (w/v) and 0.3% lidocaine (w/v) in a carrier fluid of saline, hyaluronic acid or bovine collagen. The formulations were created as follows:

Cellulose Suspended in PBS Dermal Filler:
    0.2943 mg of cellulose powder was dissolved in the following:
        6.54 mL $dH_2O$
        0.73 mL 10×PBS
        0.145 mL 15% Lidocaine (w/v, dissolved in dH2O)
Cellulose Suspended in Hyaluronic Acid Dermal Filler:
    0.2031 mg of cellulose powder was dissolved in the following:
        5.078 mL of 0.2% non-crosslinked Hyaluronic Acid (m/v, dissolved in PBS)
        0.102 mL 15% Lidocaine (w/v, dissolved in $dH_2O$)
Cellulose Suspended in Collagen Dermal Filler:
    0.1835 mg of cellulose powder was dissolved in the following:
        3.6 mL of 0.3% (m/v) Corning® Collagen I, Bovine
        0.45 mL 10×PBS
        0.36 mL 0.1N NaOH
        0.09 mL 15% Lidocaine (w/v, dissolved in $dH_2O$)
As above, to test for biocompatibility, a small animal study was performed. Briefly, 0.4 mL of each dermal filler was injected subcutaneously at three sites (3×0.4 mL) through a 22.5 G syringe in the back of female sprague-Dawley rats (300-700 g). In all cases, animals were sacrificed and tissue sections were collected four weeks post implantation.

During the course of the 4-week study, the injection sites were easily visible and were measured weekly (height, x and y width) with calipers (see FIG. 8) to obtain a measure of how well the implant retained its shape over time.

Figure 8:
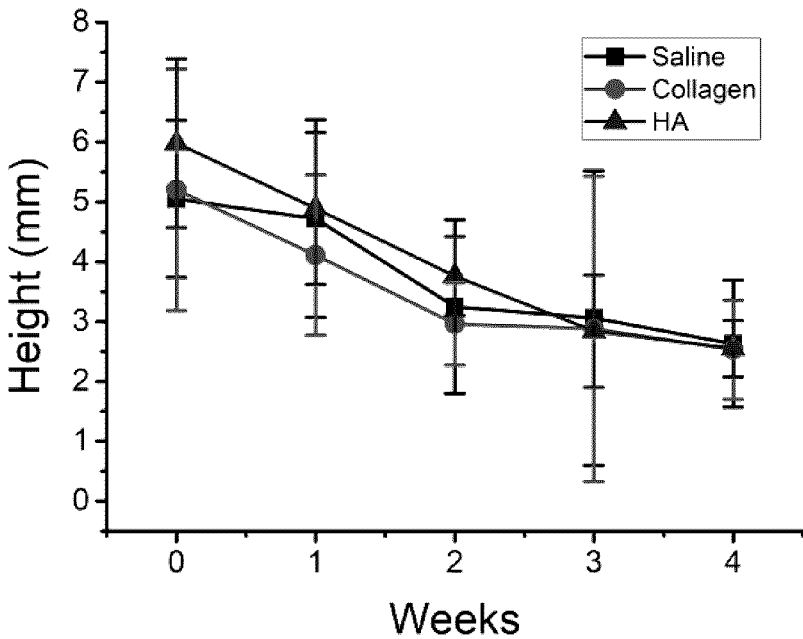
FIG. 8 shows the height of the implants as a function of
time, as described in Example 2. No statistically significant
differences were observed between the various formulations.
However, it was noted that they differed significantly from
commercial products in terms of the concentration of HA
and collagen by about a factor of 10. Consistent with the low
w/v concentration of Collagen/HA hydrogel, the results
appear to behave in a similar to saline-based filler resulting
in ~50% decrease in height.

FIG. 8 shows the height of the implants as a function of time. No statistically significant differences were observed between the various formulations. However, it was noted that they differed significantly from commercial products in terms of the concentration of HA and collagen by about a factor of 10. Consistent with the low w/v concentration of Collagen/HA hydrogel, the results appear to behave in a similar to saline-based filler resulting in ~50% decrease in height.

Figure 9:
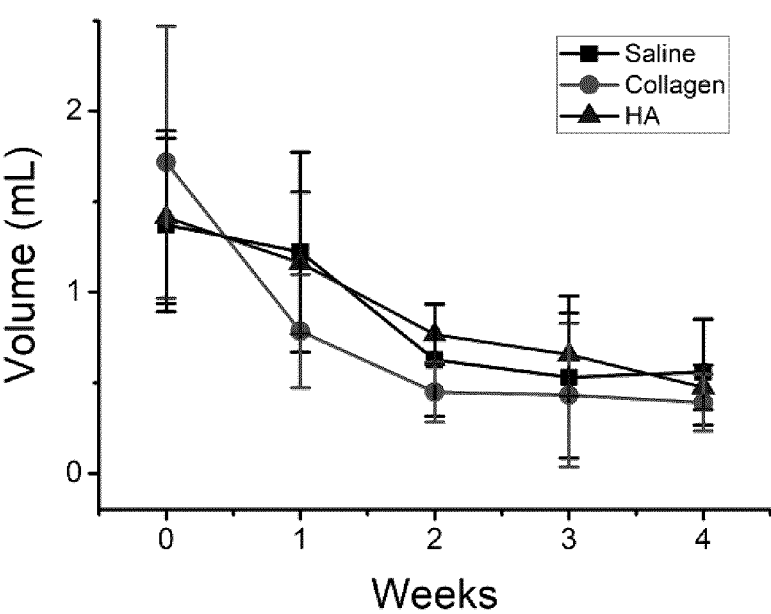
FIG. 9 shows the calculated volume of the implant mass
measured from the exterior of the animal with calipers as a
function of time, as described in Example 2. Using the
height, x and y widths and assuming a half ellipsoid, the
implant volume was calculated. No statistically significant
differences were observed between the various formulations
and followed a trend consistent with a decrease in height.

FIG. 9 shows the calculated volume of the implant mass measured from the exterior of the animal with calipers as a function of time. Using the height, x and y widths and assuming a half ellipsoid, the implant volume was calculated. No statistically significant differences were observed between the various formulations and followed a trend consistent with a decrease in height.

Similar to Example 1, this approach provided cellulose powders which may be injected subcutaneously in a rat animal model. However, without fine control over particle geometry, a wide distribution in sizes may result, which may include undesirable small particles (<20 um) which may produce undesirable effects, and/or may include large clumps of particles (>200 um) which may lead to needle clogging. Accordingly, further studies and development for enhanced particle size control were performed as described below.

Example 3—Dermal Fillers Having Highly Controlled Particle Size

The development and studies described in this Example sought to provide the following:
1. Fabricate a cellulose powder from decellularized plants with a controllable average diameter such as, for example, an average diameter of <100 um;
2. Determine whether the resulting particles may be sterilized with gamma radiation at a level of 15 kGy;
3. Create three dermal filler formulations composed of 20% particles (v/v), 0.3% lidocaine (v/v) and 79.3% carrier fluid (saline, 3.5% bovine collagen (w/v) or 1% cross-linked hyaluronic acid (w/v)) to compare with formulations of other dermal filler products;
4. Perform an animal biocompatibility study in a number of animals; and
5. Perform an in vitro cell culture assay.

Particle Geometry

Figure 10:
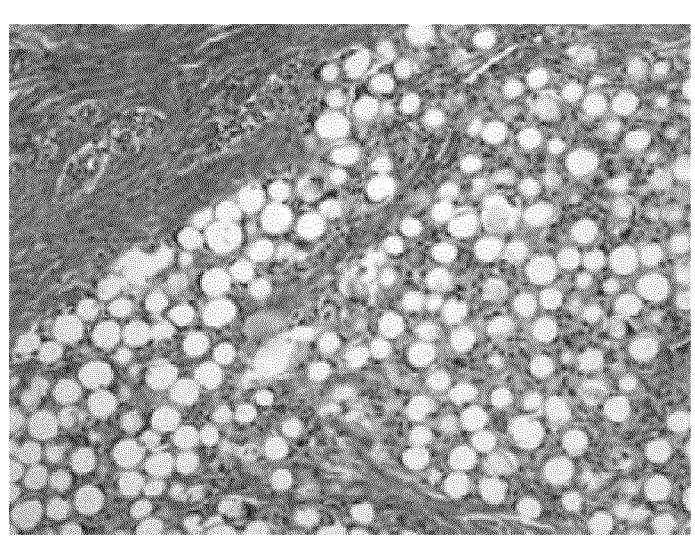
FIG. 10 shows 30-50 um PMMA microspheres (white
circles) three months after implantation. While natural tissue is growing around the implant, the volume fraction of
PMMA in the tissue is very high. This indicates that the
tissue is primarily composed of synthetic materials rather
than natural cells and proteins.

PMMA particles have become a gold standard in permanent dermal fillers. They are easily produced and their size accurately controlled. However, given that the spheres are hard and impermeable, the resulting tissue after integration in the body remains primarily composed of synthetic microspheres, as opposed to human tissue. FIG. 10 shows 30-50 um PMMA microspheres (white circles) three months after implantation. While natural tissue is growing around the implant, the volume fraction of PMMA in the tissue is very high. This indicates that the tissue is primarily composed of synthetic materials rather than natural cells and proteins.

Considering a 30 µm diameter sphere, in this case, the sphere has a surface area of 2827 µm² and a volume of 14137 µm³. The volume represents the total excluded volume of natural tissue which can grow in the region which received the injection. The surface area to volume (SA:V) ratio is 0.2. Meaning that while cells and matrix proteins can be deposited on the surface of the sphere, it is a very small amount compared to the total volume excluded by the hard particle itself.

On the other hand, consider a particle, or flake, which is thin (~0.1 µm) which is roughly circular with a diameter of 60 µm, or a radius of 30 µm. In this case, the surface area of 2846 µm² (almost identical to the 30 µm sphere) and an excluded volume of 283 µm³. Therefore the SA:V is ~10. This represents a 50× increase in available surface area to excluded volume. In other words, a 60 µm diameter flake provides a similar amount of surface area to support cell growth and matrix deposition, but excludes much less relative volume to growing natural tissues.

As we have observed in numerous studies, the thin walls (~0.1 µm) of plant tissue provides an excellent support structure onto which cells and tissues can grow and infiltrate while also leaving plenty of space for blood vessels, matrix deposition and tissue integration.

Therefore, this Example sought to produce a permanent dermal filler with a superior SA:V ratio of natural tissue to permanent filler particles compared to other dermal filler products. Therefore the efforts described below aimed to develop natural, plant-derived flakes, rather than spherical particles. Moreover, flakes with a diameter of <100 µm may be injectable through 26-27 G syringes as opposed to previous formulations described above. This may provide benefit—a natural product, a non-resorbable permanent structure, high biocompatibility, and significantly increased natural tissue as a result. It is desirable in dermal filler procedures to enable the patient's own body to replace a defect with as much natural tissue as possible. The present strategy has been designed with these goals in mind.

Cellulose Flake Fabrication

Figure 11:
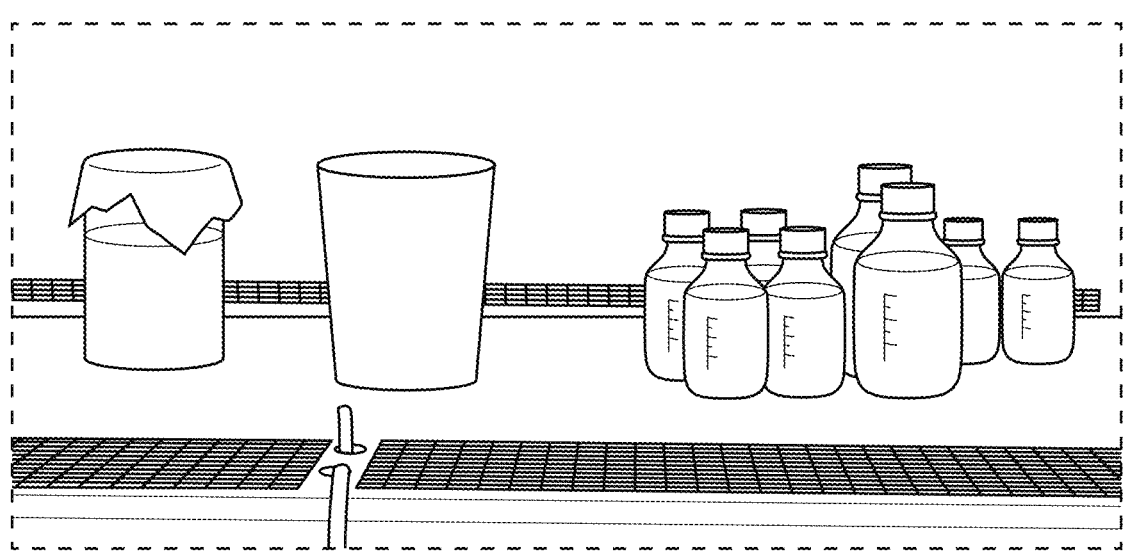
FIG. 11 shows sterile sample processing. As described in
Example 3, the GLP version of the decellularization process
was performed with sterile materials and aseptic technique.

The first step in creating natural particle replacements in this example was to decellularize the plant material. This process was accomplished using the established protocol outlined in Hickey, R. et al., Customizing the Shape and Microenvironment Biochemistry of Biocompatible Macroscopic Plant-Derived Cellulose Scaffolds. *ACS Biomater. Sci. Eng.,* 4, 3726 (2018), which is herein incorporated by reference in its entirety. As the end product was intended to be usable in patients, it was important that standardized GLP and GMP methods were established. Here, the materials were produced in a GLP compliant manner. FIG. 11 shows sterile sample processing, the GLP version of the decellularization process was performed with sterile materials and aseptic technique.

In order to process the soft materials and create cellulose flakes, the scaffolds were freeze-dried in a lyophilizer (48 h, −46 C, 0.05 mbar). Once the materials were dry, they were immediately placed in a Retsch grinder. The bulk grinding was performed at 18000 rpm, 12000 rpm, and 6000 rpm. The high-speed reduced processing time. An 80 µm filter was used to restrict the size of the powder to below 80 µm. With the filter in place, we did not observe any dependence of grinding speed on the final particle size, geometry or yield. Therefore, high speed grinding was utilized to decrease processing time.

Figure 12:
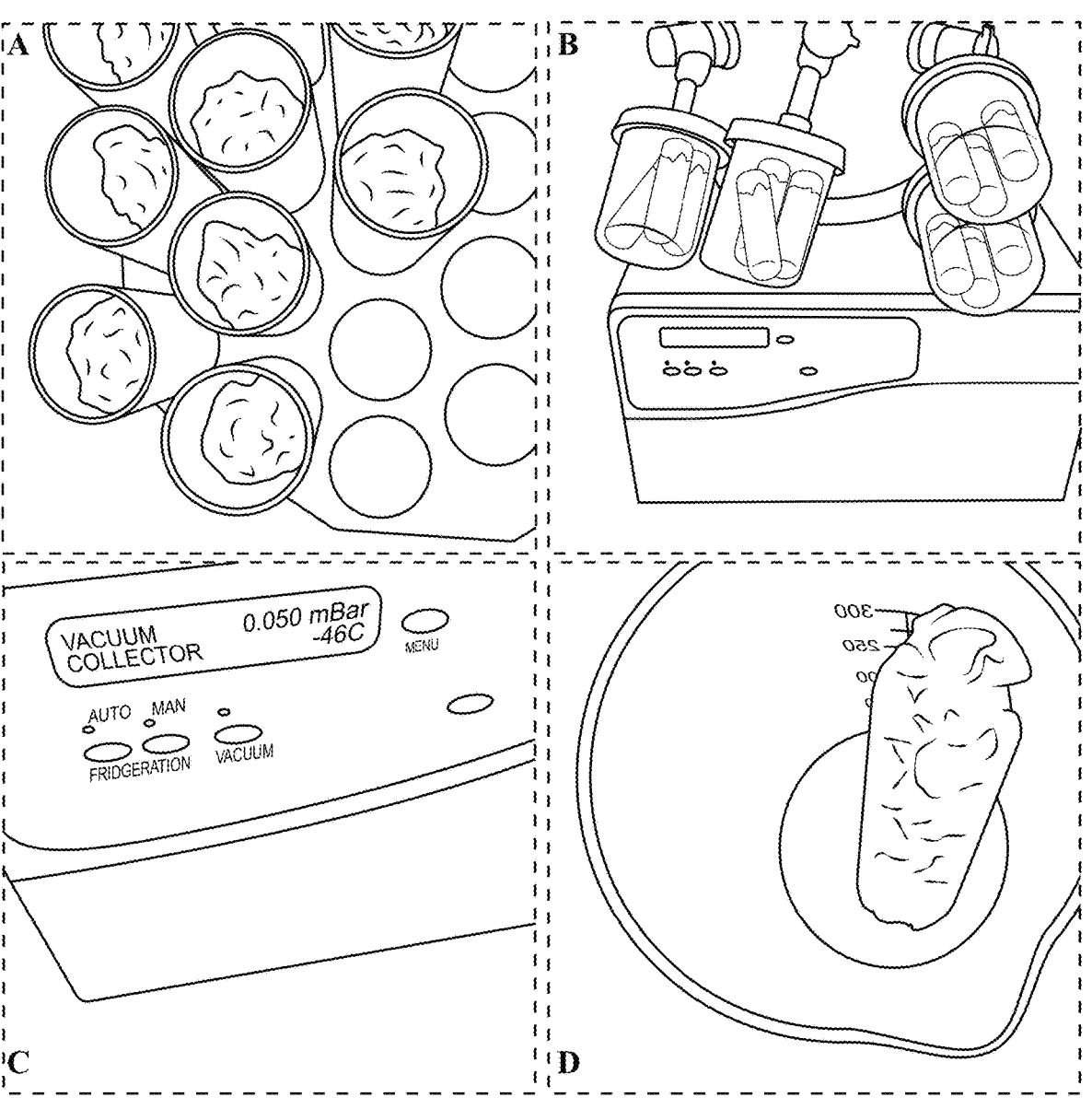
FIG. 12 shows the process of lyophilizing apple derived
decellularized cellulose scaffolds as described in Example 3.
(A) The decellularized material was collected and placed in
Falcon tubes and a channel was pressed into the material in
order for evaporating/sublimating the water vapour to
escape. (B) The material was attached to a lyophilizer. (C)
Freeze-drying was performed for 48 h at −46 C, 0.05 mbar.
(D) shows the freeze dried material end product.
Figure 13:
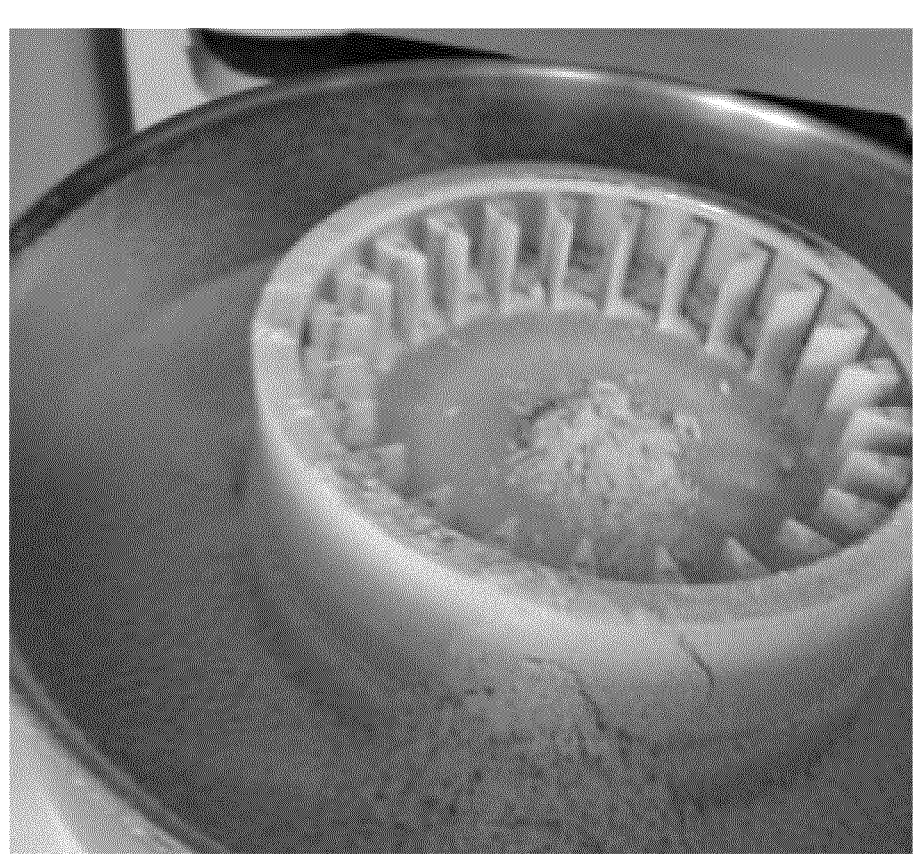
FIG. 13 shows the dried cellulose biomaterial was ground
into a powder at 18000, 12000, and 6000 rpm while simul-
taneously passed through an 80 um filter, as described in
Example 3. The collection tray is shown after the process.
The highest RPM setting was used in order to decrease
processing time. No observable impact of grinding speed
was observed on the distribution of particles sizes (data
shown in Example 3)

FIG. 12 shows the process of lyophilizing apple derived decellularized cellulose scaffolds as described. FIG. 12(A) shows that the decellularized material was collected and placed in Falcon tubes, and a channel was pressed into the material in order for evaporating/sublimating the water vapour to escape. FIG. 12(B) shows that the material was attached to a lyophilizer, and FIG. 12(C) shows that freeze-drying was performed for 48 h at −46 C, 0.05 mbar. FIG. 12(D) shows the freeze dried material end product. FIG. 13 shows that the dried cellulose biomaterial was ground into a powder at 18000, 12000, and 6000 rpm while simultaneously passed through an 80 um filter, as described. The collection tray is shown after the process. The highest RPM setting was used in order to decrease processing time. No observable impact of grinding speed was observed on the distribution of particles sizes (data shown below).

Figure 14:
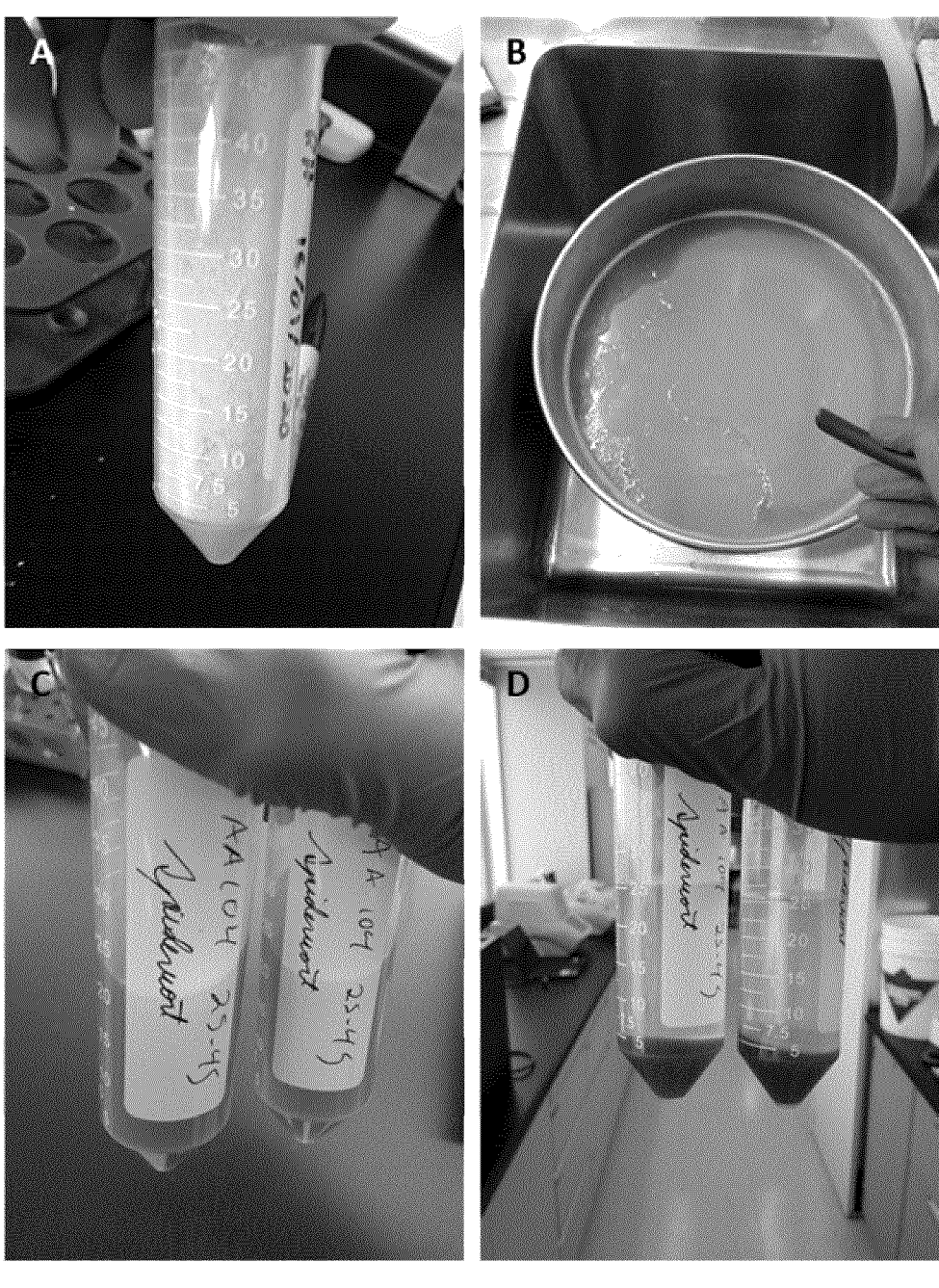
FIG. 14 shows the filtration process as described in
Example 3. (A) The powder obtained from grinding the
material through the 80 μm filter was (B) wet sieved through
45 μm and 25 μm sieves (B) to restrict the size range of the
powder (C). The narrow size range of particles was concen-
trated via centrifugation (D). An automated wet-sieve dra-
matically improved processing time and efficiency and is
now in use.

FIG. 14 shows the filtration process in further detail. FIG. 14(A) shows that the powder obtained from grinding the material through the 80 μm filter was (B) wet sieved through 45 μm and 25 μm sieves (B) to restrict the size range of the powder (C). The narrow size range of particles was concentrated via centrifugation (see FIG. 14(D)). An automated wet-sieve dramatically improved processing time and efficiency and was subsequently used routinely.

The process was first performed as follows: 5 mL of loosely packed powder was resuspended in dH$_2$O to a final volume of 45 mL and was poured on the sieve. The particles were washed continuously for 3 min. After 3 min, the top sieve (45 μm) was removed and the second sieve (25 μm) was agitated and washed for an additional 3 minutes. The material was collected in Falcon tubes and was centrifuged: The yield was approximately 20% (a 5 mL volume of wet powder was isolated from a 25 mL volume of dry powder).

The automated wet-sieving was performed with a Gilson SS 23 Wet/Dry Sieve Vibrator with ISO 565 BS 410 ISO 3310-1 25 and 50 μm stainless steel 8 inch sieves and a notched collection bucket. 5 mL of dry powder was diluted in 45 mL of dH$_2$O. The sieves were placed on the vibrator with the larger mesh on top. The vibrator was turned on and the particles were poured onto the 50 μm mesh. The particles were rinsed with 150 mL of dH$_2$O three times over the course of 3 minutes. The vibrator was then turned off and the top sieve was removed. The vibrator was restarted, and the bottom sieve was washed three times with dH$_2$O for 3 minutes in 50 mL aliquots. Next, the filtered material was collected by washing the surface of the mesh with dH$_2$O on an angle. The sieved material was concentrated via centrifugation. The yield was approximately 20% (a 5 mL volume of wet powder was isolated from a 25 mL volume of dry powder).

In order to assess the yield of the powder, the mass was recorded at key stages in the process.

The initial mass was recorded before any manipulation was done to the apples. As the mass varies from apple to apple, the number of apples was not a sufficient measure of the starting material content. Together, the number of apples and the total mass of the set of apples provides a reference point for the yield determination. After the decellularization, the material was lyophilized to obtain a dry decellularized mass as outlined above. The dry material was then ground into particulate form. There was some sample loss during processing; therefore, the ground mass was calculated to assess the loss during the grinding process. The next step involved filtering the particles to restrict the size distribution with automatic sieving using 50 μm and 25 μm sieves. In order to quantify the final yield, the sieved particles were lyophilized to remove water content.

TABLE 1

| | | | Yield of dermal filler particles | | |
|---|---|---|---|---|---|
| Trial | Number of apples | Starting mass (g) | Dry decellularized mass (g) | Ground powder mass (g) | Dry filtered mass (g) |
| 1 (AA124) | 16 | 1927.58 | 22.01 | 19.67 | 2.68 |
| 2 (AA125) | 15 | 1902.36 | 15.08 | 14.15 | 2.56 |
| 3 (AA126) | 15 | 1885.11 | 12.79 | 11.45 | 1.59 |

Transferring the powder from the Retsch tray to the tubes was done easily in the fume hood with a scoopula to avoid static charging with the gloves, tubes, and air. Certain existing products on the market have shown that a particle size less than 20 μm may lead to phagocytosis and/or an increased immune response. Therefore, it was sought to restrict the size of the particles. The particles were passed through two sieves (45 and 25 μm) in a wet sieving process.

Particle Size Characterization

Figure 15:
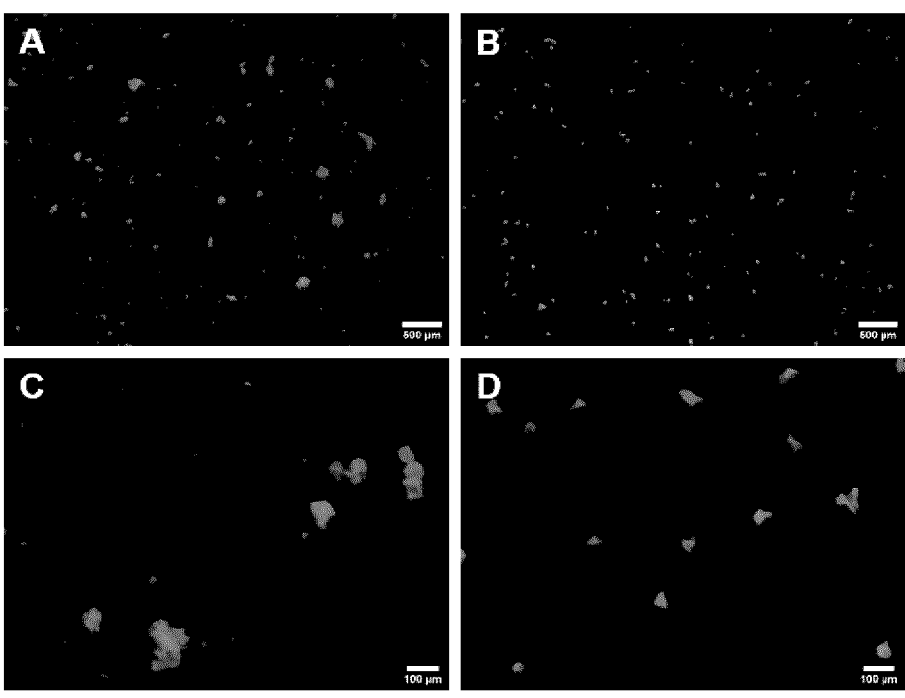
FIG. 15 shows particles stained with Congo Red as
described in Example 3. The particles were stained with
0.1% Congo Red and imaged at 2.5× (A,B) and 10× (C,D).
(A,C) unfiltered particles. (B,D) filtered particles. Images
such as these are collected to quantify the particle size
distribution. Typically, 10 images at 2.5× yields ~1000
particles, which is a statistically significant sample size.

Particle size characterization was accomplished using fluorescent microscopy and scanning electron microscopy (SEM). For the fluorescent microscopy, the particles were stained with 0.22 m filtered 0.1% Congo Red stain. They were imaged at 2.5× and 10×. The SEM samples were imaged as dried specimens using lyophilization. To allow conduction to occur, gold sputtering was performed to coat the particles with a 5-10 nm layer of gold. FIG. 15 shows particles stained with Congo Red. The particles were stained with 0.1% Congo Red and imaged at 2.5× (A,B) and 10× (C,D). (A,C) unfiltered particles. (B,D) filtered particles. Images such as these are collected to quantify the particle size distribution. Typically, 10 images at 2.5× yields ~1000 particles, which is a statistically significant sample size.

The microscopy images were used to analyze the particle size distributions. Fiji (ImageJ) was used for the image processing and Origin 2020 was used to analyze the results. In order to batch process the images, the raw images were assembled into a stack in Fiji (ImageJ). The images were first converted to grayscale, and then they were thresholded using the automatic thresholding function. The thresholding was visually inspected to ensure the proper limits were applied. Next, the analyze particles function was applied to calculate the area, shape descriptors, centroid, fit ellipse, and Feret's diameter. No size restrictions or shape limitations were imposed on the particle analysis. All particles were analyzed except for those on the edges of the field of view in order to avoid skewing the distribution. The output image file of the analyzed particle outlines was compared to the original image to ensure proper segmentation.

Figure 16:
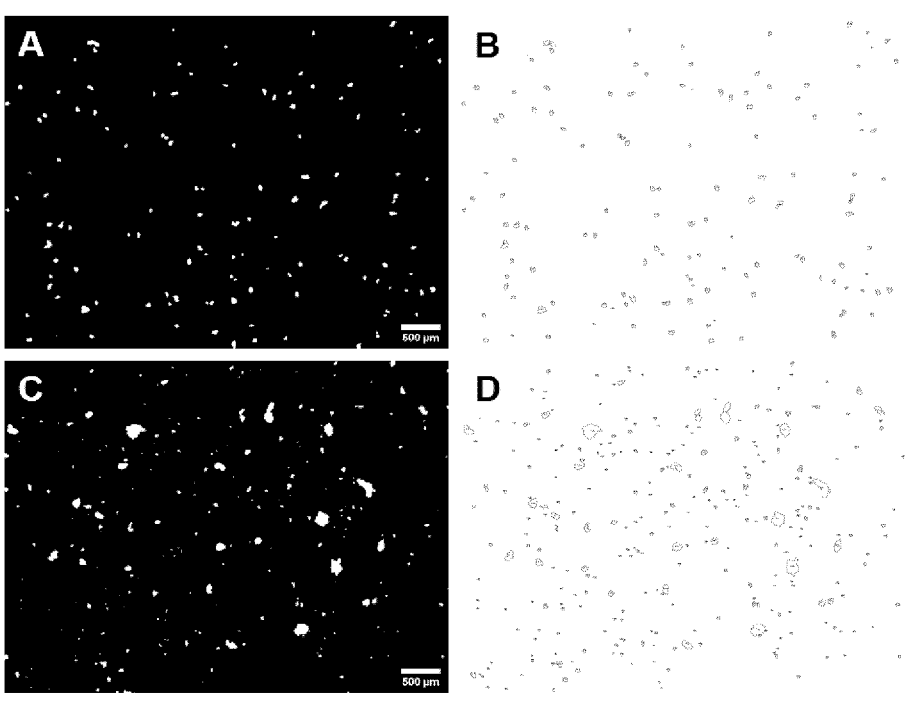
FIG. 16 shows particle size analysis as described in
Example 3. The particles were thresholded and segmented
using Fiji (ImageJ). (A,B) Filtered particles. (C,D) Unfil-
tered particles. (A,C) Thresholded image. (B,D) Outlines of
particles from the size analysis.

FIG. 16 shows particle size analysis as described. The particles were thresholded and segmented using Fiji (ImageJ). FIGS. 16(A,B) shows filtered particles, and FIGS. 16(C,D) shows unfiltered particles. FIGS. 16(A,C) shows thresholded image, and FIGS. 16(B,D) shows outlines of particles from the size analysis.

Optical and fluorescence microscopy reveals that the ground cellulose powder appears to be forming flakes rather than spherical particles. There are many different quantitative descriptors which can be calculated to investigate irregularly shaped objects such as roundness, circularity, aspect ratio, minimum and maximum ferret diameter, etc. As the material was a collection of irregular flakes, it was determined that the most useful shape descriptors are the maximum and minimum ferret diameters, thickness, and projected 2D area to describe the particle morphologies.

Applying these analytical approaches to the powders revealed that prior to sieving the samples displayed a very large distribution of sizes, whereas after sieving, the samples had a more narrow size distribution. Notably, the small particles are filtered out. The broad size distribution of the unfiltered particles is apparent in the projected particle area as well. The average projected particle area for the unfiltered sample was 2036.42±242.53 $\mu m^2$, whereas the filtered particles had a mean area of 236.92±38.18 $\mu m^2$. The mean maximum Feret diameters were significantly different ($P=7.4\times10^{-55}$) (unfiltered=47.34±1.04 $\mu m$ and filtered=68.84±0.63 $\mu m$). Using the maximum Feret diameter, the percentage of particles <20 $\mu m$ was 1.6% for the filtered case and 29.5% for the unfiltered case. Likewise, the mean minimum Feret diameter was also significantly different ($P=6.67\times10^{-56}$). The unfiltered particles had a mean minimum Feret diameter of 31.73±0.72 $\mu m$, and the filtered particles had a size of 46.51±0.37 $\mu m$. All values are mean and s.e.m. N unfiltered=2292, N filtered=1595.

Figure 17:
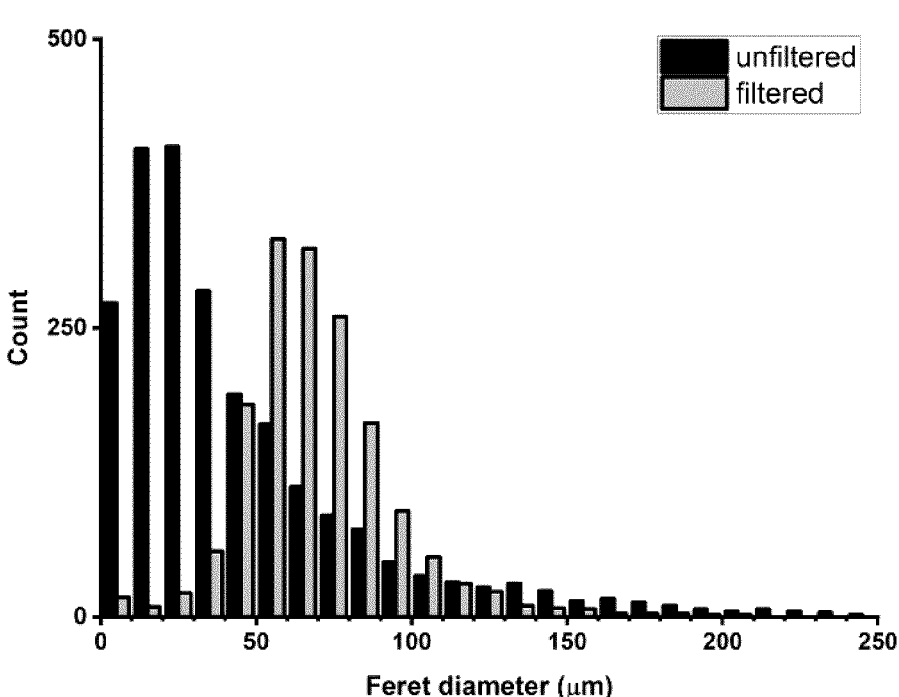
FIG. 17 shows particle size analysis for filtered and
unfiltered decellularized apple particles. The Feret diameter
was used to quantify particle size. N=15 images for each
condition were analyzed from fluorescent microscope
images of the particles stained with Congo Red. N unfil-
tered=2292, N filtered=1595. The means were statistically
significantly different (P=$7.4 \times 10^{-55}$)

FIG. 17 shows particle size analysis for filtered and unfiltered decellularized apple particles. The Feret diameter was used to quantify particle size. N=15 images for each condition were analyzed from fluorescent microscope images of the particles stained with Congo Red. N unfiltered=2292, N filtered=1595. The means were statistically significantly different ($P=7.4\times10^{-55}$).

In order to confirm the optical microscopy results, and to gain a better understanding of the morphology of the particles in the cellulose powder, scanning electron microscopy (SEM) was employed. Although a powerful imaging technique, the preparation of the powder for SEM required further drying, grinding and gold coating. This may lead to flakes being oriented in a variety of angles relative to the imaging direction, potential changes in size and the potential introduction of artifacts.

Figure 20:
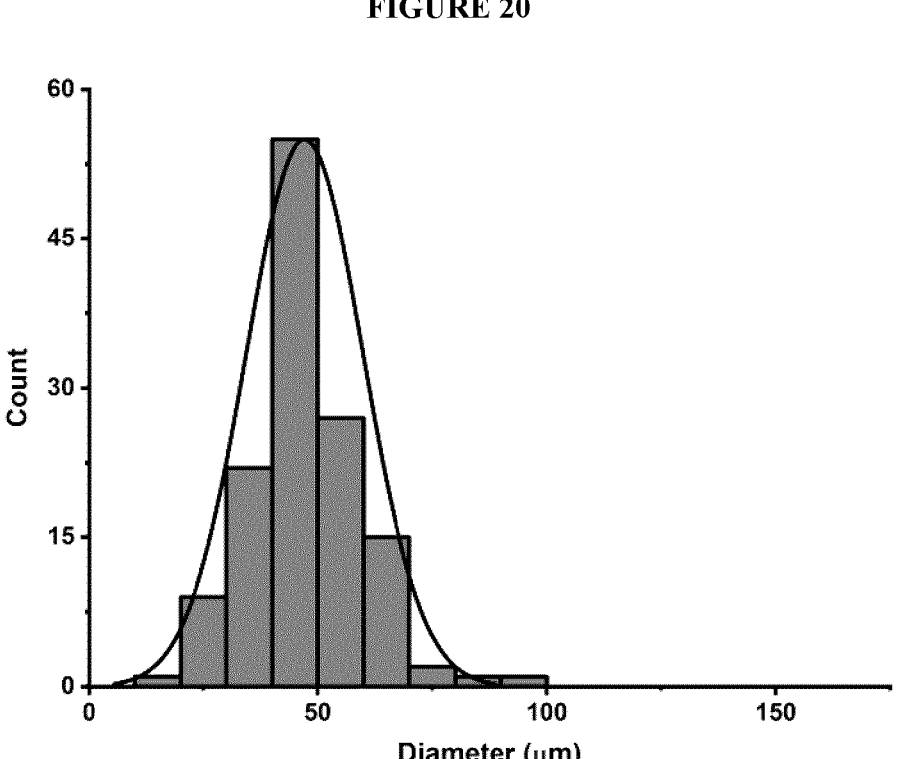
FIG. 20 shows particle size distribution from SEM on
decellularized apple as described in Example 3. The distri-
bution revealed a peak at 47.11±1.11 um (N=133 flakes).
The distribution obtained from SEM image analysis was
much narrower than optical methods. However, there are
drawbacks to this method, such as the manual approach to
measure particles one at a time leading to small N values, the
influence of particle angle orientation, and the ability to
confidently detect edges. These issues made this methodol-
ogy undesirable for characterizing particle size.

FIG. 18 shows SEM micrographs of the decellularized apple powder at increasing magnification (A-D). FIG. 19 shows manual image processing to determine flake diameter. The flakes are irregularly shaped and single length descriptors fail to capture this complexity (source: decellularized apple). FIG. 20 shows particle size distribution from SEM on decellularized apple. The distribution revealed a peak at 47.11±1.11 um (N=133 flakes). The distribution obtained from SEM image analysis was much narrower than optical methods. However, there are drawbacks to this method, such as the manual approach to measure particles one at a time leading to small N values, the influence of particle angle orientation, and the ability to confidently detect edges. These issues made this methodology undesirable for characterizing particle size.

Effects of Grinding Speeds on Different Particle Formulations

Grinding speed was an important variable during the fabrication of the cellulose flakes. Data is presented below demonstrating that the speed did not impact the particle size characteristics (determined from automated optical analysis), nor did it vary by the plant species type (apple and pear are compared) in this study.

Figure 21:
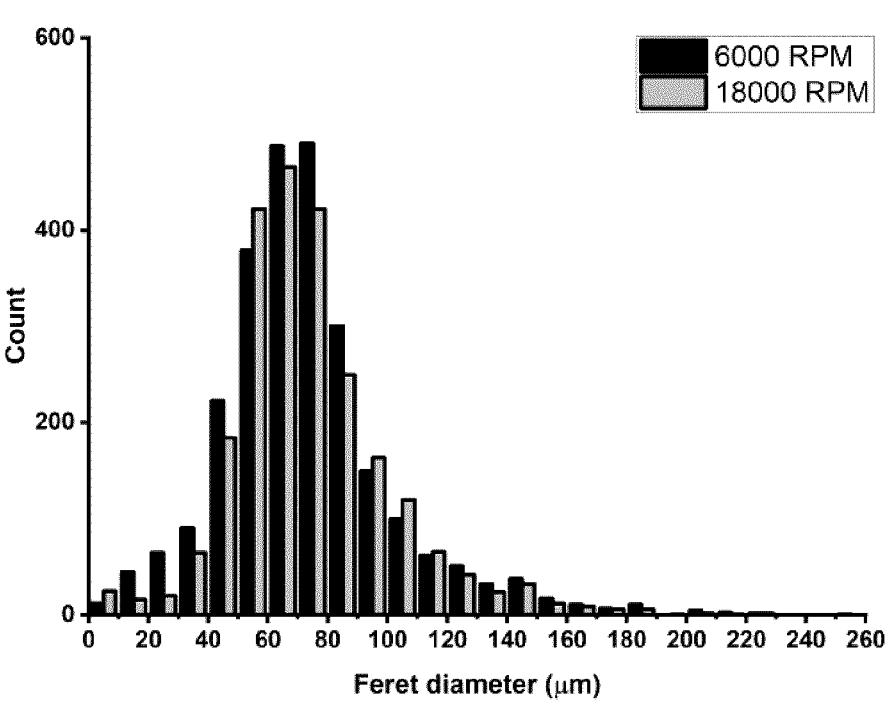
FIG. 21 shows particle size distribution after grinding decellularized apple at different speeds measured prior to automated wet sieve filtration as described in Example 3. The particles were generated by grinding at 6000 RPM (black) and 18000 (grey) prior to sieving. The two distributions were similar. The mean particle sizes were 73.07±0.58 μm and 73.50±0.56 μm for 6000 and 18000 RPM respectively. Values are mean and s.e.m. N=2579 for 6000 RPM and N=2354 for 18000 RPM. It was found that there was no significant difference in the mean particle size (P=0.58)

FIG. 21 shows particle size distribution after grinding decellularized apple at different speeds measured prior to automated wet sieve filtration. The particles were generated by grinding at 6000 RPM (black) and 18000 RPM (grey) prior to sieving. The two distributions were similar. The mean particle sizes were 73.07±0.58 $\mu m$ and 73.50±0.56 $\mu m$ for 6000 and 18000 RPM respectively. Values are mean and s.e.m.

N=2579 for 6000 RPM and N=2354 for 18000 RPM. It was found that there was no significant difference in the mean particle size (P=0.58).

TABLE 2

| Comparison of particle sizes from different grinding speeds for pear derived powder | | | |
|---|---|---|---|
| Parameter | 6000 RPM (N = 810) | 18000 RPM (N = 790) | Significant difference (P = 0.05) |
| Max Feret Diameter ($\mu m$) | 65.94 ± 1.01 | 67.07 ± 1.16 | No (P = 0.4619) |
| Min Feret Diameter ($\mu m$) | 46.47 ± 0.68 | 45.86 ± 0.71 | No (P = 0.5349) |
| Area ($\mu m^2$) | 2370.29 ± 57.97 | 2455.54 ± 81.55 | No (P = 0.3924) |

TABLE 3

| Comparison of apple and pear derived powder sizes ground at 18000 RPM. | | | |
|---|---|---|---|
| Parameter | Apple (N = 1595) | Pear (N = 790) | Significant difference (P = 0.05) |
| Max Feret Diameter ($\mu m$) | 68.83 ± 0.63 | 67.07 ± 1.16 | No (P = 0.1464) |
| Min Feret Diameter ($\mu m$) | 46.51 ± 0.37 | 45.86 ± 0.71 | No (P = 0.3702) |
| Area ($\mu m^2$) | 2366.92 ± 38.18 | 2455.54 ± 81.55 | No (P = 0.2619) |

Gamma Sterilization

Gamma irradiation is an important step to sterilizing biomaterials for use in clinical settings. It has been determined that gamma-irradiation at a level of 15 kGy is sufficient to produce sterile plant-based biomaterials. The findings presented below reveal that gamma-irradiated and non-irradiated samples display no significant change in particle size.

As above, McIntosh apples from Canada Fancy were purchased from local supermarkets and were used the following day. To prepare decellularized raw material, SOPs were followed. Briefly, the apples were peeled and then sliced on a Mandolin slicer to a thickness of 1 mm. The slices were then transferred to a 0.1% SDS solution and placed on a shaker at 120 RPM for 3 days. The solution was changed once each day. Next, the slices were washed 3 times with sterile $dH_2O$, transferred to a 100 mM $CaCl_2$ solution, and were returned to the shaker for 24 h. The biomaterials were then washed 3 times with sterile $dH_2O$ and then sterilized with 70% ethanol for 30 min. The samples were then washed with sterile $dH_2O$ 3 times and stored in sterile $dH_2O$ until the next day. The water was then removed and the samples were lyophilized for 2 days at −46° C. and 0.050 mbar. Once dry, the decellularized materials were ground in a Retsch grinder set at a speed of 18000 RPM with a 80 $\mu m$ filter.

The size of the cellulose powder was further restricted with 45 and 25 $\mu m$ sieves using wet sieving. The powder was concentrated with centrifugation at a speed of 1000 RPM for a duration of 3 minutes. The particles were then stored in Nalgene bottles at a concentration of 1 mL of particles in 10 mL of sterile $dH_2O$. Three samples were prepared from each condition from separate batches of starting materials.

Figure 22:
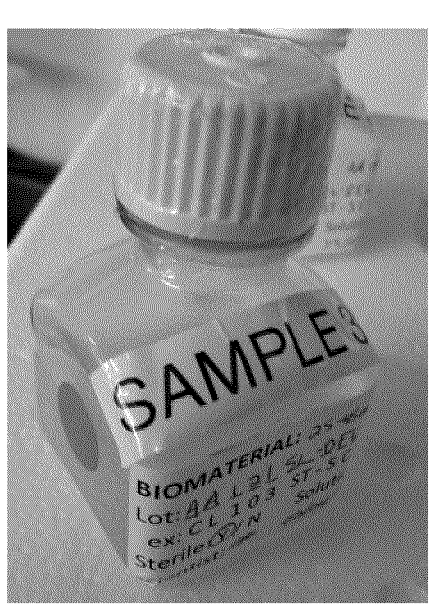
FIG. 22 shows a sample of the particle suspension in the sealed Nalgene bottle for gamma irradiation with the indicator sticker as described in Example 3.

FIG. 22 shows a sample of the particle suspension in the sealed Nalgene bottle for gamma irradiation with the indicator sticker.

The Nalgene bottles were sealed with shrink-wrap to provide a tamper-free environment. The bottles were labeled with a colour indicator for gamma irradiation; the colour changes from orange to red after exposure to gamma radiation. The samples were irradiated at a minimum of 15 kGy. The samples were then stored at 4° C. until testing.

Figure 23:
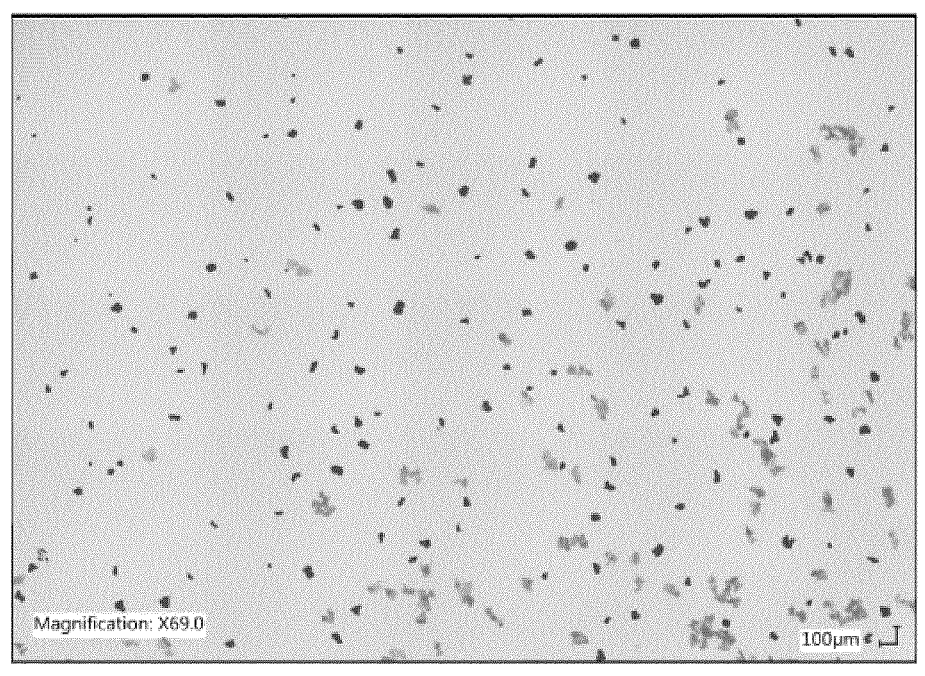
FIG. 23 shows sample image obtained from Keyence Digital Microscopy as described in Example 3. The bright red overlays indicate the particles that were used for analysis.

Irradiated and non-irradiated samples were analyzed. Keyence Digital Microscopy was used to assess the particle size. The parameters recorded were the particle area, maximum area, minimum area, and perimeter. The particles were stained with Congo Red to enable visualization of the particles. An automated micropipette was used to add 500 μL of samples and 150 μL of 0.2% triple filtered (0.22 μm) Congo Red to 1 mL vials. The vials were mixed and stored overnight in the fridge. Small aliquots of the stained suspension were deposited between glass slides and coverslips. Each specimen was prepared just before imaging to avoid interference from evaporation. The specimens prepared as described above were tested using a Keyence VHX-5000 digital microscopy system fitted with the Z20T lens, in accordance with SGS PSI Method ID 27940 Revision 3. Imaging was conducted with polarized transmitted light at a native magnification of 200×. The two-dimensional stitching feature was used to image specimens prepared from each sample suspension. Areas of the specimens were selected with more even random dispersion of particles, avoiding concentrated sections or air bubbles. The auto-area function of the Keyence software was used to measure the "grain sizes" in each image. After selecting for the color of the stain's preferential binding to the particles, the list of measured objects was examined for the approximate maximum diameter at the transition from clumps of touching or overlapping particles to individuals. Exclusions were then applied for larger grains and those interrupted at the edges of the image. The analysis was repeated until a minimum of 1,000 particles per sample had been measured. FIG. 23 shows sample image obtained from Keyence Digital Microscopy. The bright red overlays indicate the particles that were used for analysis.

Figure 24:
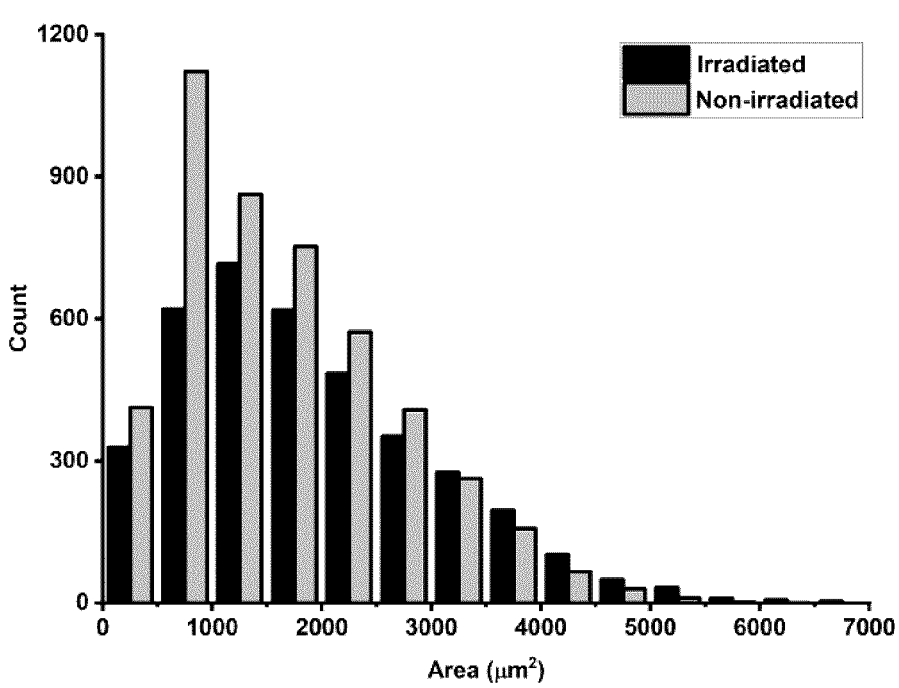
FIG. 24 shows particle areas for the gamma-irradiated (N=3800) and non-irradiated (N=4692) particles as described in Example 3.

The average area of the particles was not significantly different for the gamma irradiated and non-irradiated particles (P=0.91, N=3 samples). The mean particle areas were 1885.3±1144.6 m² and 1705.4±984.9 μm² respectively. The histogram of the areas is displayed in FIG. 24. The total number of particles analyzed was 3800 for the irradiated samples and 4692 particles for the non-irradiated samples. FIG. 24 shows particle areas for the gamma-irradiated (N=3800) and non-irradiated (N=4692) particles.

Figure 25:
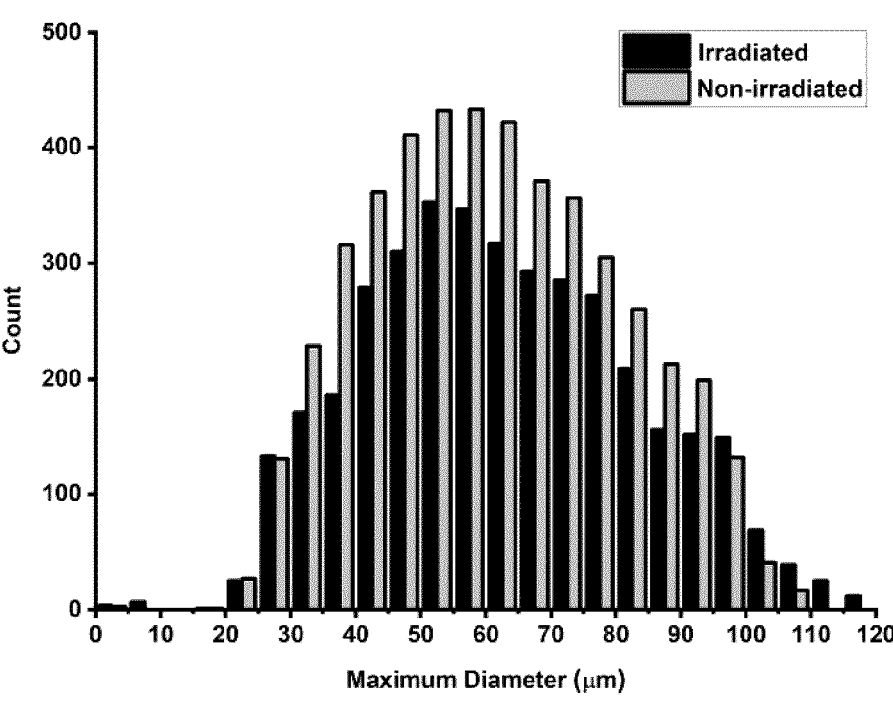
FIG. 25 shows particle maximum diameter histogram for the gamma-irradiated (N=3800) and non-irradiated (N=4692) particles as described in Example 3.

As the particles were not purely spherical, the maximum Feret diameter (or maximum diameter) was a useful quantity to assess the size of irregularly shaped particles. This measurement is common practice in powder and particle analysis. The maximum diameter of the particles was not significantly different for the gamma irradiated and non-irradiated particles (P=0.97, N=3 samples). The mean particle diameters were 62.0±20.1 μm and 61.0±18.4 μm respectively. The histogram of the diameters is displayed in FIG. 25. FIG. 25 shows particle maximum diameter histogram for the gamma-irradiated (N=3800) and non-irradiated (N=4692) particles.

Figure 26:
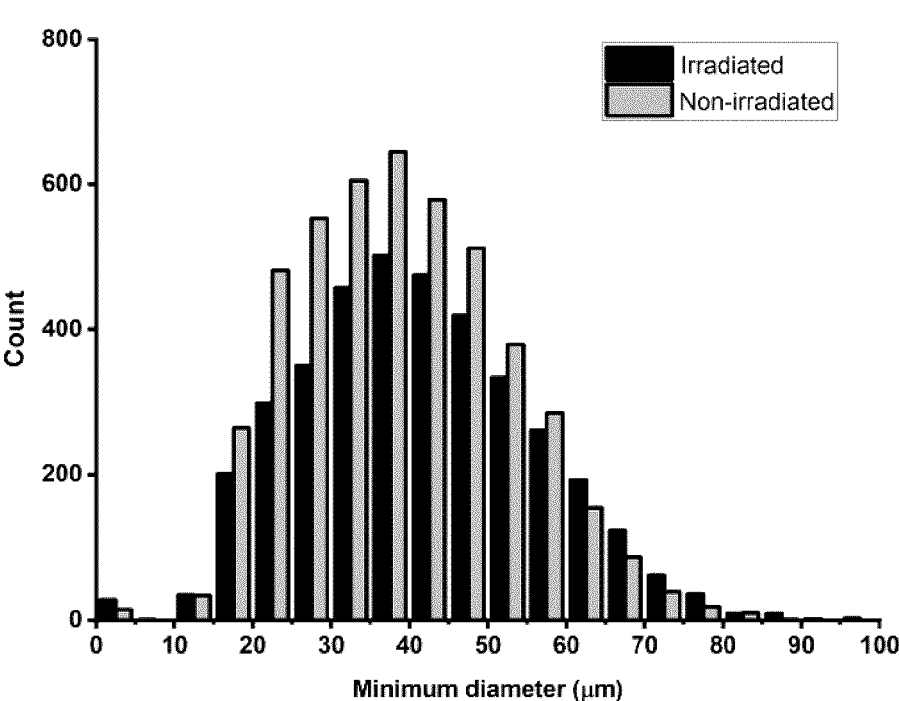
FIG. 26 shows particle minimum diameter histogram for the gamma-irradiated (N=3800) and non-irradiated (N=4692) particles as described in Example 3.

In contrast to the maximum diameter, it is also valuable to assess the minimum particle diameter. The minimum diameter was also not significantly different for the gamma irradiated and non-irradiated particles (P=0.90, N=3 samples). The mean minimum particle diameters were 46.5±15.0 μm and 44.4±13.2 μm respectively. The histogram of the diameters is displayed in FIG. 26. The total number of particles analyzed was 3800 for the irradiated samples and 4692 particles for the non-irradiated samples. FIG. 26 shows particle minimum diameter histogram for the gamma-irradiated (N=3800) and non-irradiated (N=4692) particles.

Taken together, the results show that the particle size was not significantly altered by gamma irradiation. Further inspection of the data showed that with the current manufacturing method utilizing wet sieving <0.32% of the particles had a maximum diameter less than 20 μm. This result is particularly interesting for in vivo use, as particles below 20 μm may be phagocytosed and/or may trigger immune responses. In contrast, BellaFill dermal filler particles on the market report that <1% of their material has a diameter of <20 km.

The particles are not spherical in nature; thus, several shape descriptors, as presented above, may be employed to describe their geometry. Importantly, none of these characteristics changed after exposure to gamma irradiation at 15 kGy.

Alternate Approach for Size Restriction

In addition to wet sieving, differential centrifugation may be used to separate the particles. Differential centrifugation may also be a closed production process that may reduce processing time and water usage. Differential centrifugation is a technique that may be used to separate particles based on their size. Centrifugation is used to accelerate the sedimentation process. The rate of separation is dependent on the effective gravitational force, the viscosity of the fluid, the path length, and the time. The following equations summarize the relationships between the aforementioned variables. These equations assume the particles are uniform and spherical, which is not the case for the present particles— nevertheless, these considerations provide a starting point for variable configuration.

$$z^* = \frac{k_B T}{(m - v\rho_m)g}$$

$$g_c = \frac{v^2}{r}$$

$$g_c = \omega^2 r$$

$$v_{drift} = \frac{F}{\gamma}$$

$$= \frac{m_{eff} g_c}{6\pi\eta R}$$

$$= \frac{(\rho_p - \rho_m)v g_c}{6\pi\eta R}$$

$$= \frac{(\rho_p - \rho_m)\left(\frac{4}{3}\right)\pi R^3 g_c}{6\pi\eta R}$$

$$= \frac{2(\rho_p - \rho_m)R^2 g_c}{9\eta}$$

$$g_c > \frac{1}{L}\left(\frac{m_1}{\gamma_1}\right)\left(\frac{\sqrt{2D_1} + \sqrt{2D_2}}{\left|\frac{m_1}{\gamma_1} - \frac{m_2}{\gamma_2}\right|}\right)^2$$

Figure 27:
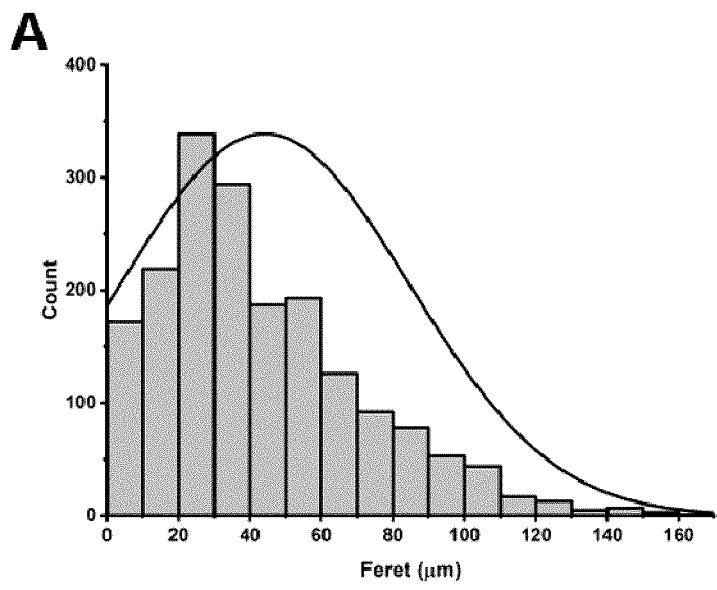
FIG. 27 shows particle size distribution of apple-derived particles obtained via differential centrifugation as described in Example 3. (A) shows the size distribution of unfiltered particles after an initial large particle size exclusion with manual sieving (45 μm) and (B) shows the distribution after 5 iterations of centrifuging for 1 minute at 1000 rpm. To collect all the material, centrifugation for 7 minutes at 5000 rpm was used.
Figure 27:
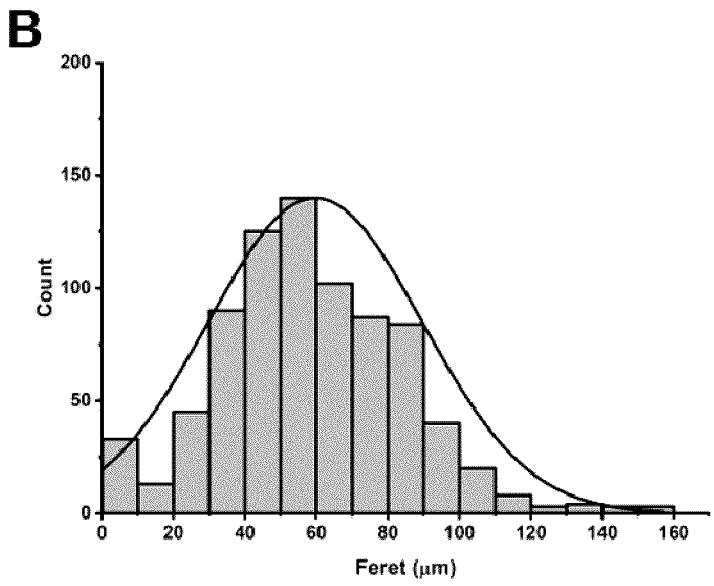

FIG. 27 shows particle size distribution of apple-derived particles obtained via differential centrifugation. (A) shows the size distribution of unfiltered particles after an initial large particle size exclusion with manual sieving (45 μm) and (B) shows the distribution after 5 iterations of centrifuging for 1 minute at 1000 rpm. To collect all the material, centrifugation for 7 minutes at 5000 rpm was used.

In Vitro Biocompatibility

To assess the impact of the powder on cell viability, an in vitro biocompatibility assay was performed. This test was carried out to compare the impact of the filtered and unfiltered particles on NIH3T3 mouse cells, which is often used as a model line. Sterile powder was used for the assay. Six plates containing 3T3 cells in DMEM media were used, with the following conditions:

Control—no particles or dye, only cells

Filtered particles pre-stained with CR;

Filtered particles—no dye;

Unfiltered particles pre-stained with CR;

Unfiltered particles—no dye;

Dye control—cells with dye only.

To prepare the samples with the filtered particles, the filtered biomaterial (apple particles created as above via grinding, followed by wet sieving) was used. The 20 mL volume (containing 2 mL of particles) was split into two tubes and centrifuged for 7 minutes at 5000 RPM. The pellets were resuspended in distilled water for a final volume of 3.5 mL. 175 µL of 0.2% CR was added to one of the samples (0.01% CR concentration in the tube). The particles were stained for 10 minutes. The contents of the tubes were pipetted in the corresponding plates (each plate received the equivalent of 1 mL of wet particles).

To prepare the samples with unfiltered particles, the unfiltered biomaterial (apple particles created as above via grinding, followed by wet sieving) was used. 2 mL of powder was resuspended in distilled water for a final volume of 7 mL. This solution was split into two tubes and 175 µL of 0.2% CR was added to one of the samples (0.01% CR concentration in the tube). The contents of the tubes were pipetted in the corresponding plates (each plate received the equivalent of 1 mL of wet particles).

To prepare the dye control, 175 µL of 0.2% CR was added to the plate containing 3T3 cells without particles.

All the plates were incubated at 37° C., 5% $CO_2$ for 48 hours prior to observation.

Figure 28:
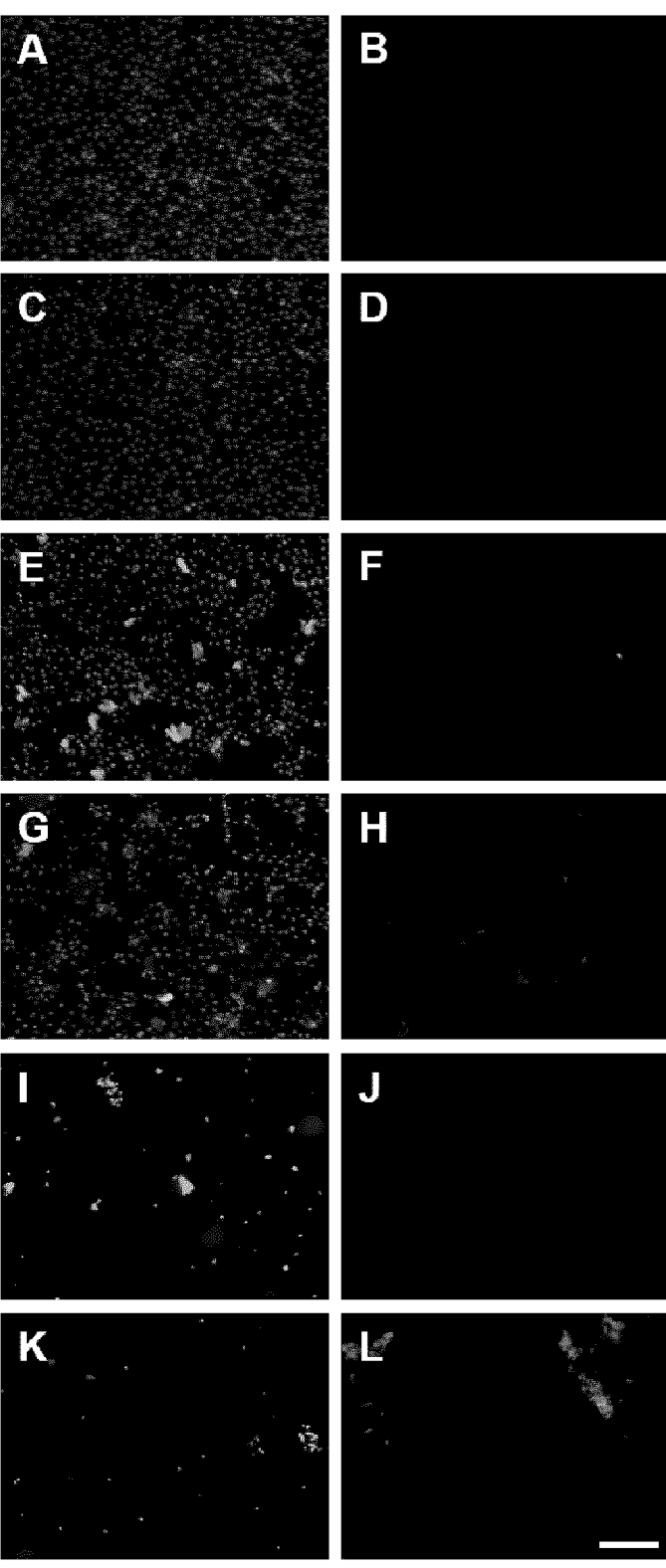
FIG. 28 shows in vitro cell culture test with AA (apple) particles as described in Example 3. Blue=3T3 cell nuclei. In some cases, large particle flakes also are visible as a result of Hoechst 33342 staining. Red=particles stained with 0.01% Congo Red dye that remained after washing loose particles away. (A,B) shows control. (C,D)=Control and dye. (E,F)=Filtered: 25-45 μm. (G,H)=Filtered: 25-45 μm and dye. (I,J)=Unfiltered. (K,L)=Unfiltered and dye. Scale=250 μm.

FIG. 28 shows in vitro cell culture test with AA (apple) particles. Blue=3T3 cell nuclei. In some cases, large particle flakes also are visible as a result of Hoechst 33342 staining. Red=particles stained with 0.01% Congo Red dye that remained after washing loose particles away. FIG. 28(A,B) shows control. FIG. 28(C,D)=Control and dye. FIG. 28(E, F)=Filtered: 25-45 µm. FIG. 28 (G,H)=Filtered: 25-45 µm and dye. FIG. 28(I,J)=Unfiltered. FIG. 28(K,L)=Unfiltered and dye. Scale=250 µm.

The results demonstrate that the unfiltered powder has a detrimental impact on cell viability. A significant number of cells died and were clearly necrotic and/or floating in the culture plate after 48 hours. In contrast, in the plate with filtered particles, cell density is high and comparable with controls. Cells appear normal and viable. Although the precise mechanism of powder induced cell death has not been studied in great detail, the results are consistent with particles <20 um in diameter having cytotoxicity. In this case, the unfiltered solutions contain a number of particles below the 20 µm threshold, and may be the cause of increased cell death. The reason for cell death was not investigated in great detail, however both osmotic effects and apoptosis resulting from phagocytosis of small particles were hypothesized. Results with a lower concentration of particle suspension to alter the severity of the osmotic shock suggest that is a major contributor to the observed cell death. Cells cultured with both unfiltered and filtered particles at a 50× dilution were viable in preliminary studies.

Excellent results were obtained with filtered particles, indicating that with filtered particles, cell density was high and comparable with controls. Cells appeared normal and viable.

Formulations of Dermal Filler and Fabrication

As the particles may be for use in dermal fillers and dermal filler applications, their applicability for syringe and needle delivery was tested. Alginate was used for viscous mixing of the particles.

The formulations contained 0.5% alginate and 20% particles by volume. In the first attempt to generate the formulation the liquid component was created by mixing 5 mL of 1% alginate into 5 mL of water. The solution was slightly viscous; however, it easily mixed with conventional pipetting techniques. Next, 2 mL of unfiltered powder was added to the liquid component (prepared as stated above). Conventional pipetting and stirring did not yield a uniform solution of particles. Likewise, vortexing did not produce a uniform suspension.

In another approach, the 2 mL of unfiltered powder was combined with the 5 mL of water initially. This mixture was gradually introduced into the 5 mL of 1% alginate in 500 µL aliquots. This approach made the solution much easier to mix and obtained a more uniform final composition.

These two formulations were then used for a needle occlusion test. A 27 G needle was used. Both formulations occluded the needle and became clogged; the first method clogged immediately.

The third formulation prepared was identical to the second prototype, except 25-45 µm particles were used instead of unfiltered particles. The same needle occlusion test was applied and the particle mixture did not occlude the needle.

Figure 29:
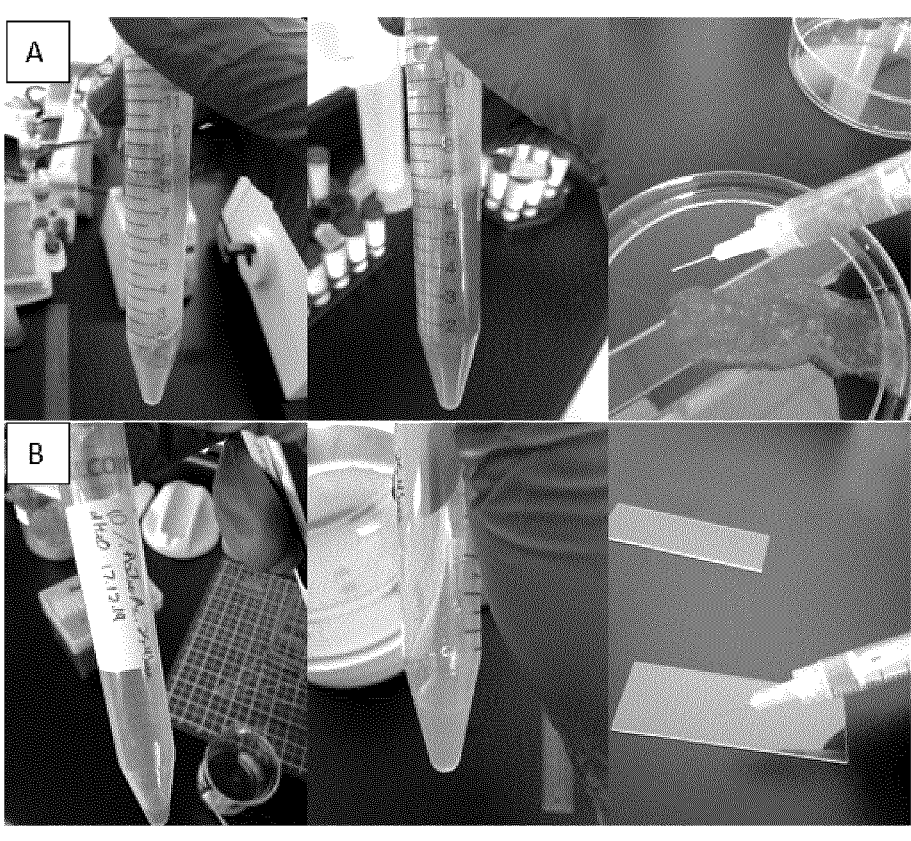
FIG. 29 shows injectable dermal filler formulation with alginate as described in Example 3. The particles made up 20% of the volume. Two mixing methods were tested. (A) shows mixing the powder into the water and alginate solution. (B) shows mixing the powder into the water component first and then slowly adding the alginate. The first method did not mix well and clogged the needle. The second method mixed well, but the unfiltered particles clogged the needle. When the unfiltered particles were replaced with filtered ones, the mixture was easy to extrude.

FIG. 29 shows injectable dermal filler formulation with alginate. The particles made up 20% of the volume. Two mixing methods were tested. (A) shows mixing the powder into the water and alginate solution. (B) shows mixing the powder into the water component first and then slowly adding the alginate. The first method did not mix well and clogged the needle. The second method mixed well, but the unfiltered particles clogged the needle. When the unfiltered particles were replaced with filtered ones, the mixture was easy to extrude.

These results show that the mixing process used for the prototypes may be further optimized. Slowly adding one component to another is time consuming, and the more involved material transfer increases the risk for contamination as well as error propagation.

Therefore, Luer-Lock (F/F) syringe connectors were used to mix the components of the filler. One syringe was loaded with the particles mixed in 0.9% saline and 0.1% Congo Red dye to visualize the mixing process. The second syringe was loaded with 1% alginate. The two syringes were connected with Luer-Lock (F/F). The solutions were mixed by passing the material from one syringe to the other 60×. After the mixing was completed, the material was transferred to one of the syringes. The empty syringe was disconnected, and a 1 cc syringe was attached in its place. The desired volume (in this case 400 µL) was loaded into the syringe. The 1 cc syringe was disconnected and an appropriately sized needle was mounted.

Figure 30:
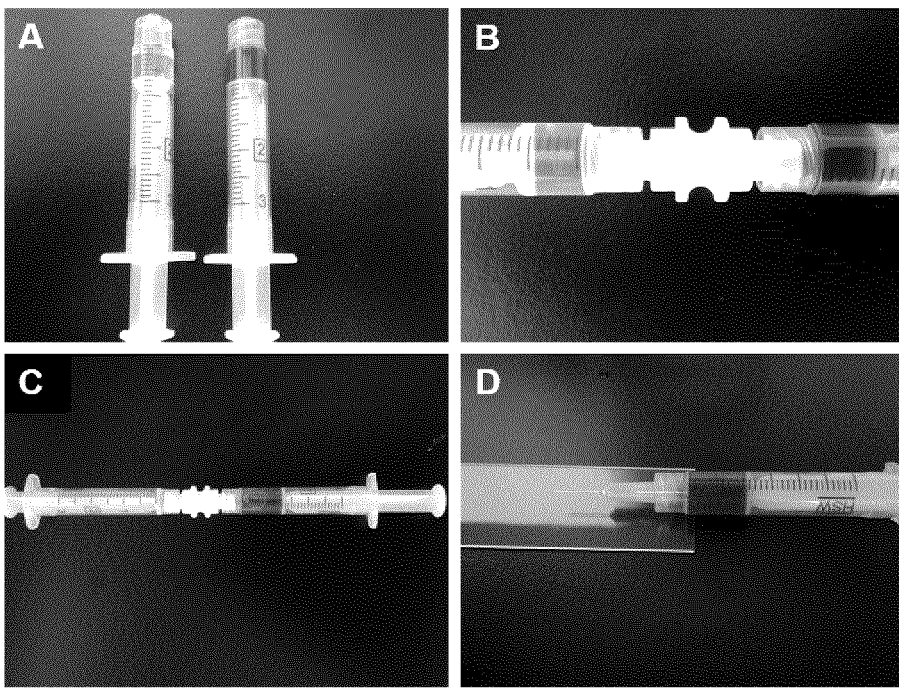
FIG. 30 shows mixing of dermal filler components with the syringe Luer Lock connector as described in Example 3. (A) shows the two components loaded in individual syringes. The clear liquid is the 1% alginate, and the red liquid is the particles suspended in 0.9% saline and lidocaine (final concentration=0.3%). Congo Red (final concentration of 0.1%) was added for visualization. (B) shows the Luer Lock connector. (C) shows mixing the components (a total of 60 passes were performed). (D) shows disconnecting the Luer-Lock and replacing it with a needle for extrusion. Note the solution did not occlude a 27 G needle.

FIG. 30 shows mixing of dermal filler components with the syringe Luer Lock connector. (A) shows the two components loaded in individual syringes. The clear liquid is the 1% alginate, and the red liquid is the particles suspended in 0.9% saline and lidocaine (final concentration=0.3%). Congo Red (final concentration of 0.1%) was added for visualization. (B) shows the Luer Lock connector. (C) shows mixing the components (a total of 60 passes were performed). (D) shows disconnecting the Luer-Lock and replacing it with a needle for extrusion. Note the solution did not occlude a 27 G needle.

Additional examples of dermal filler formulations and approaches/procedures for the preparation thereof used in this Example are as follows:

Dermal Filler Formulation with a Saline Carrier Fluid

Key Equipment

1. Biosafety cabinet
2. Centrifuge (both 50 mL Falcon tubes and microcentrifuge capability)
3. Pipette gun
4. Micropipette Solutions 1. 70% ethanol.
2. Sterile water
3. Sterile saline (0.9%)
4. Lidocaine 2%

Procedure

Set-Up

1. Turn on the biosafety cabinet (BSC).
2. Wipe down the BSC with Accel wipes.
3. Use 70% ethanol to spray down the 50 mL Falcon tubes and racks and place them in the BSC. One Falcon tube was used to collect the particles; the other was used as a waste container.
4. Using an Accel wipe, wipe down the pipette gun, and transfer it to the BSC.
5. Take photographs of the gamma irradiated particles in their unopened, shrink-wrapped bottles with the radiation indicator sticker visible.
6. Wipe down the particle bottles with Accel wipes, and bring them into the BSC.
7. Shake the containers to resuspend the particles.
8. Wipe down a new bottle of sterile 0.9% saline and transfer it to the BSC.

Particle Preparation

1. All material transfer steps were completed in the BSC using aseptic technique. Sterile gloves were used.
2. Pour the entire contents (20 mL) of the gamma irradiation bottle into a 50 mL Falcon tube.
3. Centrifuge the particles at 1000 rpm for 3 minutes at room temperature.
4. Wipe down the Falcon tube with Accel wipes and return it to the BSC.
5. Discard the supernatant with the pipette gun. Do not decant or jostle the vial, as some particles may resuspend in the solution.
6. Resuspend the pellet in 6.8 mL of sterile 0.9% saline. Mix well.
7. Add 1.2 mL of 2% lidocaine. Mix well.
8. Transfer the solution to sterile autoclaved microcentrifuge tubes in 500 $\mu$L aliquots. Note: the sterile autoclaved microcentrifuge tube packages were opened in the hood. The outer wrappings did not touch any surface of the hood and did not pass over open containers.

Syringe Loading

1. Inside the BSC, create a sterile field by placing a sterile huck towel down on one side of the BSC.
2. One researcher put on sterile gloves using the open gloving technique. This researcher is identified as the sterile researcher.
3. The non-sterile researcher brought sterile 1 cc syringes into the BSC. The packages did not touch any surface.

The packages are opened and either dropped onto the sterile field, or placed there by the sterile researcher.

4. Step 3 was repeated for the needles. The needle gauge was 26 G.
5. The non-sterile researcher held the microcentrifuge tube containing the dermal filler at a 45 degree angle while the sterile researcher draws 400 $\mu$L into the syringe.
6. The loaded syringes were loosely recapped. Note: the cap was lying on the sterile field and the needle was inserted into the cap with one hand. Using two hands was avoided in case the needle is touched or is pushed through the plastic cap.
7. Transfer the loaded syringes to a sterile field adjacent to the rat on the surgical area.

Dermal Filler Formulation with a Hyaluronic Acid Carrier Hydrogel

Key Equipment

1. Biosafety cabinet
2. Centrifuge (both 50 mL Falcon tubes and microcentrifuge capability)
3. Pipette gun
4. Micropipette Hyaluronic Acid Kit 1. HyStem Kit—Advanced BioMatrix—Cat GS311

Solutions 1. 70% ethanol.
2. Sterile water
3. Sterile saline (0.9%)
4. Lidocaine 2%

Procedure

Set-Up

1. Turn on the biosafety cabinet (BSC).
2. Wipe down the BSC with Accel wipes.
3. Remove the HyStem packages from the freezer/ice packs. Open the HyStem packages and allow the vials to warm up to room temperature.
4. Use 70% ethanol to spray down the 50 mL Falcon tubes and racks and place them in the BSC. One Falcon tube was used to collect the particles; the other was used as a waste container.
5. Using an Accel wipe, wipe down the pipette gun, and transfer it to the BSC.
6. Take photographs of the gamma irradiated particles in their unopened, shrink-wrapped bottles with the radiation indicator sticker visible.
7. Wipe down the particle bottles with Accel wipes, and bring them into the BSC.
8. Shake the containers to resuspend the particles.
9. Wipe down a new bottle of sterile 0.9% saline and transfer it to the BSC.

Particle Preparation

1. All material transfer steps must be completed in the BSC using aseptic technique. Sterile gloves were used.
2. Pour the entire contents (20 mL) of the particle solution from the gamma irradiation bottles to a 50 mL Falcon tube.
3. Centrifuge the particles at 1000 rpm for 3 minutes at room temperature.
4. Wipe down the Falcon tube with Accel wipes and return it to the BSC.
5. Discard the supernatant with the pipette gun. Do not decant or jostle the vial, as some particles may resuspend in the solution.
6. Resuspend the pellet in 10 mL of sterile 0.9% saline. Mix well.

7. Transfer the solution to sterile autoclaved microcentrifuge tubes in 500 µL aliquots. Note: the sterile autoclaved microcentrifuge tube packages were opened in the hood. The outer wrappings did not touch any surface of the hood and did not pass over open containers.

8. Centrifuge the microcentrifuge tubes at 1000 rpm for 3 minutes at room temperature.

9. Wipe down the vials with Accel wipes and bring them back into the BSC.

10. Discard the supernatant using a micropipette.

Hyaluronic Acid Preparation

1. Wipe all the vials down with Accel wipes. Aseptic technique was used throughout the preparation process.

2. Using a syringe and needle, add 1 mL of degassed (DG) water to the Glycosil vial. Note: the Glycosil crosslinks in the presence of oxygen; do not remove the cap.

3. Shake the vial in the horizontal position until the solid fully dissolves.

4. Using a syringe and needle, add 0.5 mL of DG water to the Extralink-Lite vial. Invert several times to dissolve.

5. Once the Glycosil has dissolved, resuspend the pellet of particles in 260 µL of the Glycosil solution using a syringe and needle.

6. Add 65 µL of the Extralink-Lite solution to the particle-Glycosil mixture.

7. Add 75 µL of the 2% lidocaine solution to the mixture, and mix well with a sterile 1 mL pipette.

Syringe Loading

1. Inside the BSC, create a sterile field by placing a sterile huck towel down on one side of the BSC.

2. One researcher put on sterile gloves using the open gloving technique. This researcher was identified as the sterile researcher.

3. The non-sterile researcher brought sterile 1 cc syringes into the BSC. The packages did not touch any surface. The packages are opened and either dropped onto the sterile field, or placed there by the sterile researcher.

4. Step 3 was repeated for the needles. The needle gauge was 26 G.

5. The non-sterile researcher held the microcentrifuge tube containing the dermal filler at a 45 degree angle while the sterile researcher draws 400 µL into the syringe.

6. The loaded syringes were loosely recapped. Note: the cap was lying on the sterile field and the needle was inserted into the cap with one hand. Using two hands was avoided in case the needle was touched or was pushed through the plastic cap.

7. Transfer the loaded syringes to a sterile field adjacent to the rat on the surgical area.

8. The injection was performed within 30 minutes of the addition of the Extralink-Lite solution. The Glycosil could be prepared and left in the microcentrifuge tubes for up to 4 h before the addition of the Extralink-Lite.

Dermal Filler Formulation with a Collagen Carrier Hydrogel

Key Equipment

1. Biosafety cabinet

2. Centrifuge (both 50 mL Falcon tubes and microcentrifuge capability)

3. Pipette gun

4. Micropipette

5. Luer-lock syringe connectors

Collagen 1. 65 mg/mL fibrillar atelocollagen

Solutions 1. 70% ethanol.

2. Sterile water

3. Sterile saline (0.9%)

4. Lidocaine 2%—CDMV Cat:123683

Procedure

Set-Up

1. Turn on the biosafety cabinet (BSC).

2. Wipe down the BSC with Accel wipes.

3. Remove the HyStem packages from the freezer/ice packs. Open the HyStem packages and allow the vials to warm up to room temperature.

4. Use 70% ethanol to spray down the 50 mL Falcon tubes and racks and place them in the BSC. One Falcon tube was used to collect the particles; the other was used as a waste container.

5. Using an Accel wipe, wipe down the pipette gun, and transfer it to the BSC.

6. Take photographs of the gamma irradiated particles in their unopened, shrink-wrapped bottles with the radiation indicator sticker visible.

7. Wipe down the particle bottles with Accel wipes, and bring them into the BSC.

8. Shake the containers to resuspend the particles.

9. Wipe down a new bottle of sterile 0.9% saline and transfer it to the BSC.

Particle Preparation

1. All material transfer steps was completed in the BSC using aseptic technique. Sterile gloves were used.

2. Pour the entire contents (20 mL) of two of the gamma irradiation bottles into two 50 mL Falcon tubes.

3. Centrifuge the particles at 1000 rpm for 3 minutes at room temperature.

4. Wipe down the Falcon tube with Accel wipes and return it to the BSC.

5. Discard the supernatant with the pipette gun. Do not decant or jostle the vial, as some particles may resuspend in the solution.

6. Resuspend and combine the pellets in 8.5 mL of sterile 0.9% saline. Mix well.

7. Transfer the solution to sterile autoclaved microcentrifuge tubes in 1000 µL aliquots. Note: the sterile autoclaved microcentrifuge tube packages were opened in the hood. The outer wrappings did not touch any surface of the hood and did not pass over open containers.

8. Centrifuge the microcentrifuge tubes at 1000 rpm for 3 minutes at room temperature.

9. Wipe down the vials with Accel wipes and bring them back into the BSC.

10. Discard the supernatant using a micropipette.

Particle and Collagen Mixing

1. Inside the BSC, create a sterile field by placing a sterile huck towel down on one side of the BSC.

2. One researcher put on sterile gloves using the open gloving technique. This researcher is identified as the sterile researcher.

3. The non-sterile researcher brought sterile 3 cc syringes into the BSC. The packages did not touch any surface. The packages were opened and either dropped onto the sterile field, or placed there by the sterile researcher.

4. The non-sterile researcher brought sterile Luer-lock F/F syringe connectors into the BSC. The packages did not touch any surface. The packages were opened and either dropped onto the sterile field, or placed there by the sterile researcher.

5. The non-sterile researcher removed the collagen syringes from the fridge and wiped them with Accel wipes. The collagen syringes were transferred to the sterile field.

6. Using a sterile syringe and needle, add 0.58 mL of saline to the microcentrifuge tube containing the particles.

7. Using a sterile syringe and needle, add 0.28 mL of 2% lidocaine.

8. The sterile researcher draws up the particle solution with a 3 cc syringe and needle.

9. Connect the particle solution syringe to a 3 cc collagen syringe containing 1 mL of 65 mg/mL collagen. Avoid bubble formation. Expel as much air as possible before making the connection with the Luer-lock. This was done by the sterile researcher.

10. Mix the contents 40 times by injecting the contents of one syringe into the other. Start by adding the particles to the collagen syringe.

Syringe Loading

1. The non-sterile researcher brought sterile 1 cc syringes into the BSC. The packages did not touch any surface. The packages were opened and either dropped onto the sterile field, or placed there by the sterile researcher. These syringes were for the final injections.

2. Step 1 was repeated for the needles. The needle gauge was 21 G.

3. All materials were handled by only the sterile researcher at this point.

4. Transfer all 2.33 mL of the dermal filler to one syringe in the mixing system. Disconnect the empty syringe from the Luer-lock.

5. Attach the 1 cc syringe to the Luer-lock.

6. Load 400 µL of the dermal filler into the 1 cc syringe. Caution: the 1 cc syringe does not lock on the Luer-lock; maintain pressure against the Luer-lock when loading, so the loading pressure does not eject the 1 cc syringe.

7. The loaded syringes were loosely recapped. Note: the cap was lying on the sterile field and the needle was inserted into the cap with one hand. Using two hands was avoided in case the needle was touched or was pushed through the plastic cap.

8. Transfer the loaded syringes to a sterile field adjacent to the rat on the surgical area.

As a comparison, commercially available BellaFill was purchased and used to assess its particle size distribution compared to the presently developed cellulose particles suspended in Collagen as described above. The measured particle size distribution of the PMMA beads confirms the stated average particle size in BellaFill. The PMMA spheres were easily identified in the microscope images and appear spherical. To visualize the presently developed cellulose particles they were stained with congo red (0.1%) prior to mixing with collagen as described above (no non-specific staining of the collagen by congo red was confirmed). In the presently developed formulation, the cellulose particles are found well distributed throughout the collagen gel.

Figure 31:
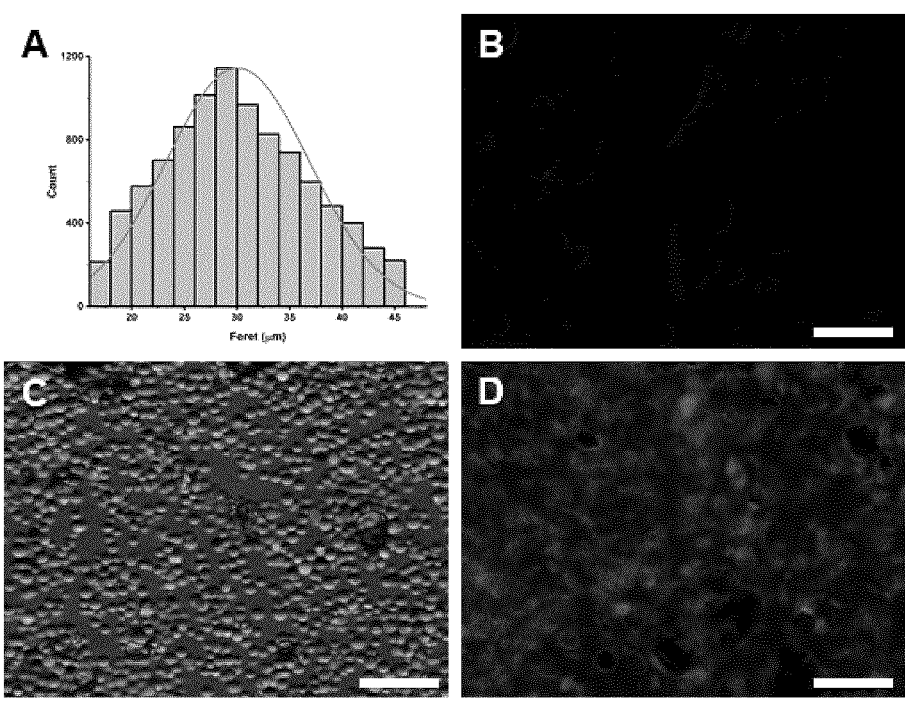
FIG. 31 shows collagen fillers as described in Example 3. (A) shows particle size distribution of PMMA beads in BellaFill. (B) shows Congo Red stained collagen used in the presently developed dermal fillers reveals very little secondary non-specific staining. (C) shows PMMA beads of BellaFill. (D) shows presently developed cellulose particles used in collagen dermal fillers stained with Congo Red. Note: the background staining of the collagen is low compared to the signal from the cellulose particles. Scale=250 um.

FIG. 31 shows collagen fillers as described. FIG. 31(A) shows particle size distribution of PMMA beads in BellaFill. FIG. 31(B) shows Congo Red stained collagen used in the presently developed dermal fillers reveals very little secondary non-specific staining. FIG. 31(C) shows PMMA beads of BellaFill. FIG. 31(D) shows presently developed cellulose particles used in collagen dermal fillers stained with Congo Red. Note: the background staining of the collagen is low compared to the signal from the cellulose particles. Scale=250 um.

In Vivo Biocompatibility

A key performance characteristic of the presently developed dermal filler formulations may be assessed with a subcutaneous animal model. For each formulation (AAS, AAHA, AAC, produced as above), may be injected into 4 sites in the back of N=9 animals. Every week, the implant sites may be measured (height, x and y widths) and 4 weeks, N=3 animals may be sacrificed and the implants resected. During week 12, only 2 of the 3 animals in a formulation chort may be sacrificed and the remaining animal may be maintained for a longitudinal study (6-12 months, for example). This means that for each formulation (AAS, AAHA, AAC) data may be obtained at a longer term time point to provide data from four implants each, with one animal per formulation. Commercially available BellaFill may be used in a companion study. Data may be gathered in a study of 3 animals (2×400 uL injections each). These studies may to produce GLP data that may be used to inform a study with similar formulations and a larger number of animals, for example. Contemplated surgical procedures are described below:

TABLE 4

Dermal fillers

| Dermal filler (with 20% v/v particles and 0.3% lidocaine) | Observations | Comments |
|---|---|---|
| Saline (AAS) | This was the easiest and fastest to produce. The particles settled out of suspension. It did not hold its shape as well inside the animal. | This served mainly as a control test on the particle biocompatibility and host response in the absence of the other components. |
| Hyaluronic Acid (AAHA) | The HA used was the HyStem kit. This was the most time-consuming production method because of all the transferring of solutions with syringes | The HA held its shape more than the saline solution. The particles were easy to mix and remained in suspension. |
| Collagen (AAC) | The collagen was difficult to mix with pipetting. The female-female luer-lock approach drastically improved the mixing ability. The collagen solution was the most viscous. | The mixing and loading of the syringes was expedited by the luer-locks. |

Implantation Surgery

Pre-Surgery Check

1. Check to make sure all materials and supplies are available prior to beginning the procedure. Check the following items:
   a. oxygen tank level
   b. isoflurane level
   c. sterile pack
   d. suture material
   e. sterile saline
   f. sterile water
   g. tear gel
   h. buprenorphine
   i. heater for the anaesthesia station
2. Ensure the animal has been weighed and given the corresponding amount of buprenorphine: 0.05 mg/kg.
3. Calculate the amount of saline to administer: 5 mL/kg.
4. Turn on the oxygen supply. Set to level 2.
5. Turn on the isoflurane. Connect the supply to the anaesthesia box. Set to level 3.

Animal Preparation

1. Transfer the rat to the anaesthesia box.
2. Once the rat is unconscious, transfer it to the preparation station. Connect the isoflurane to the preparation station.
3. Turn the isoflurane level down to 2.
4. Apply tear gel to the eyes of the rat.
5. Shave one side of the back of the rat.
6. Vacuum the fur.
7. Wipe the skin with a water soaked cotton swab to remove any loose hair.
8. Using a dry cotton swab, remove the water from the skin and brush off any remaining hair.
9. Inject the saline to maintain hydration into the non-shaved side of the rat.
10. Transfer the rat to the surgical area.
11. Sterilize the skin by soaking cotton swabs in chlorhexidine (4%). Wipe on unidirectionally. Make sure all the skin gets wiped.

Injections

1. One researcher gowns and puts on sterile gloves. The appropriate gloving technique (closed/open) is used depending on whether or not the researcher puts on a new gown or not.
2. The four 400 μL injections are brought to the sterile field adjacent to the animal.
3. The non-sterile researcher photographs the injection sites pre-injection.
4. The sterile researcher injects the contents of the syringes into four separate locations on the sterile, shaved, back of the rat.
5. The non-sterile researcher photographs the injection sites.
6. The rat is transferred to the measurement station.
7. The rat is then transferred to the recovery station and the animal ID card is placed on the recovery cage.

Weekly Size Measurements

To assess the implant sizes, the following procedure may be applied starting on the day of the injection and weekly thereafter for all animals.

Anaesthetizing the Animal

1. Open the oxygen gas tank.
2. Connect the isoflurane line to the anaesthetization box.
3. Turn up the isoflurane to 3.
4. Transfer the animal to the anaesthetization box.

5. Once the animal is unconscious and is breathing deeply (1 breath every 3 seconds), transfer the rat to the measurement station. The isoflurane is set to 2 for the measurement station.

Measurements

1. To make the measurements as reliable as possible, the fur may be shaved from the implant sites.
2. Using the Vernier calipers, measure the size of the bumps under the skin caused by the dermal filler injection. The calipers should be zeroed before starting each set of measurements.
3. Collect and record the size measurements (e.g. diameter X, diameter Y, height).
4. Draw a circle around the implant sites when finished.
5. The order of the sites is from the cranial to the caudal direction; for examples, site 1 is closest to the head of the rat.
6. The X direction is in the medial-lateral direction, whereas the Y direction is in the caudal-cranial direction.
7. The Diameter X and Diameter Y measurements may be taken with the front end of the caliper.
8. The height is measured with the prong of the bottom of the caliper.
9. Once the measurements have been taken and recorded, the animal may be returned to the cage and animal room.
10. Ensure all water bottles are placed back in the proper orientation.

Sacrifice and Tissue Collection

1. Transfer the animal to the euthanasia box.
2. When doing two rats at once (two boxes connected) set the initial flow rate of the $CO_2$ to 6 and then increase to 12 when the rats become unconscious.
3. Monitor the breathing pattern of the animal. Wait at least 5 minutes.
4. Ensure the breathing has stopped for 1 minute.
5. Turn off the $CO_2$.
6. Remove the rat from the euthanasia box and place the rat on its backside.
7. Locate the xiphoid and make an incision in the skin.
8. Pierce the diaphragm. The heart should be visible.
9. Cut the heart and ensure blood starts to pool.
10. Turn the animal onto its stomach to expose the back.
11. Cut the skin from the hip, along the centre of the spine, to the shoulder. Peel down the skin and cut away the connective tissue. The flap of skin should contain the implant/injected material.
12. Take a photograph of the material in the skin flap with a ruler for scale.
13. Cut out the implants individually. Make sure the skin stays underneath the material. This will help orient the samples during histology and provide a direct comparison with the native tissue.
14. Quickly transfer the samples to formalin (4%).
15. Depending on the size of the implant and the staining to be done, transfer the sample to 70% ethanol after 48 or 72 h of formalin fixation.

Histology

Samples may be sent to histology for embedding in paraffin blocks followed by sectioning. The blocks may be sectioned perpendicular to the plane of the skin in order to observe the implant in cross section. The implant may be sectioned at one level ~500 um from its edge and at a second level ~1.5 mm further into the tissue. This may allow to examine both the outer edge and the approximate middle of the implants. H&E and Masson's Trichrome stains are ordered as well as several unstained slides.

The following in vivo biocompatibility results have been obtained.

In Vivo Biocompatibility Results Collected

The dermal fillers investigated were saline (AAS), hyaluronic acid (AAHA), and collagen (AAC) based fillers comprising the filtered, gamma sterilized cellulose-based particles described hereinabove. All three dermal fillers were injected into a rat model.

Figure 32:
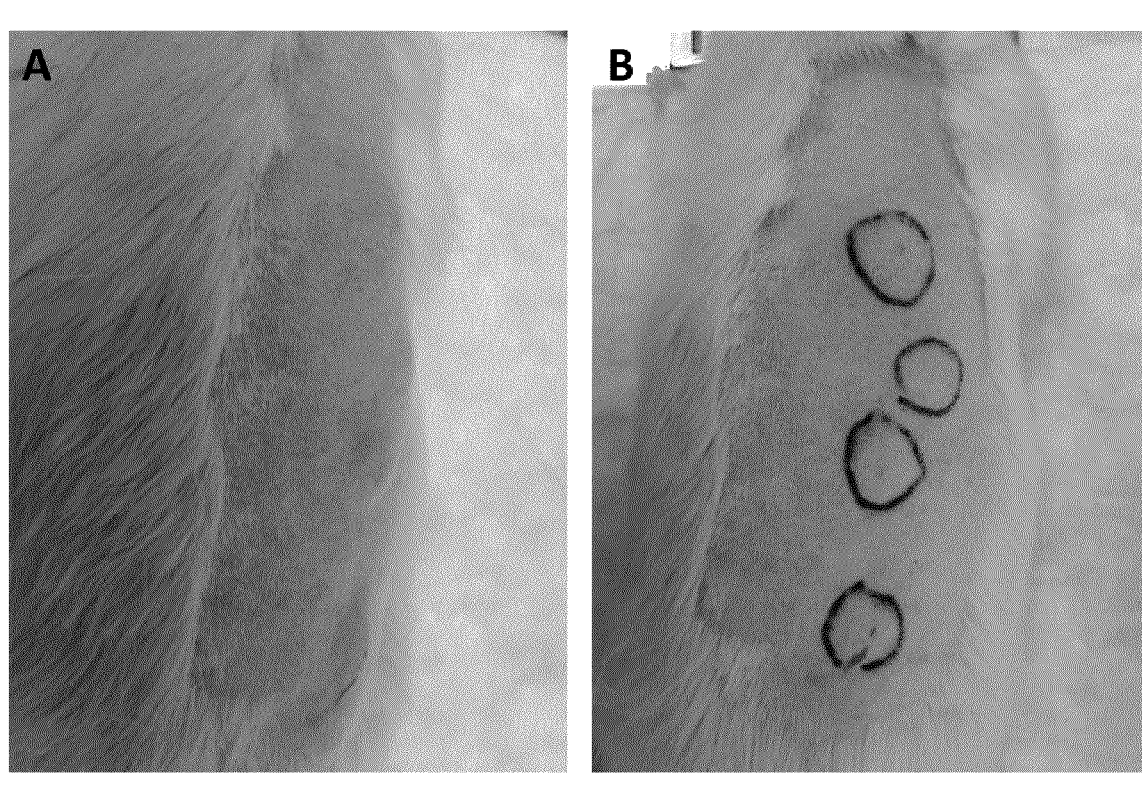
FIG. 32 shows dermal filler injection results as described in Example 3. (A) shows pre-injection and (B) shows post-injections with the bump border outlined.
Figure 33:
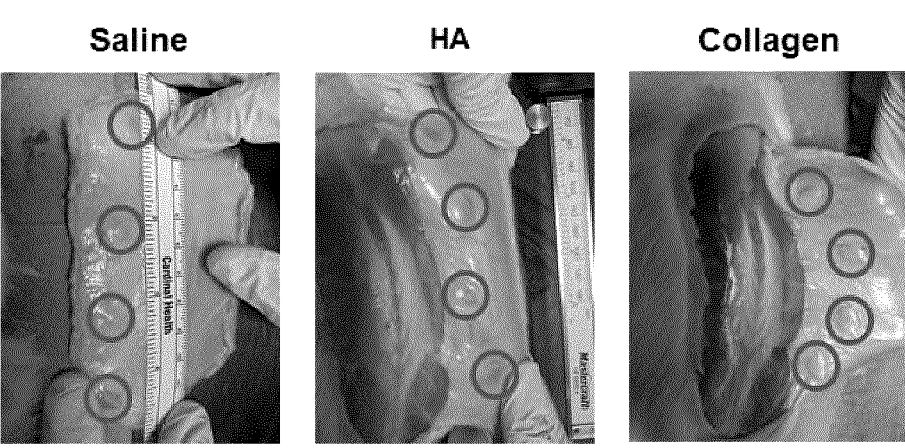
FIG. 33 shows resection of Saline, Hyaluronic acid (HA) and Collagen based fillers combined with 20% decellularized apple-derived filtered particles and 0.3% lidocaine as described in Example 3.

FIG. 32 shows dermal filler injection results. FIG. 32(A) shows pre-injection and (B) shows post-injections with the bump border outlined. FIG. 33 shows resection of Saline, Hyaluronic acid (HA) and Collagen based fillers combined with 20% decellularized apple-derived filtered particles and 0.3% lidocaine.

Figure 34:
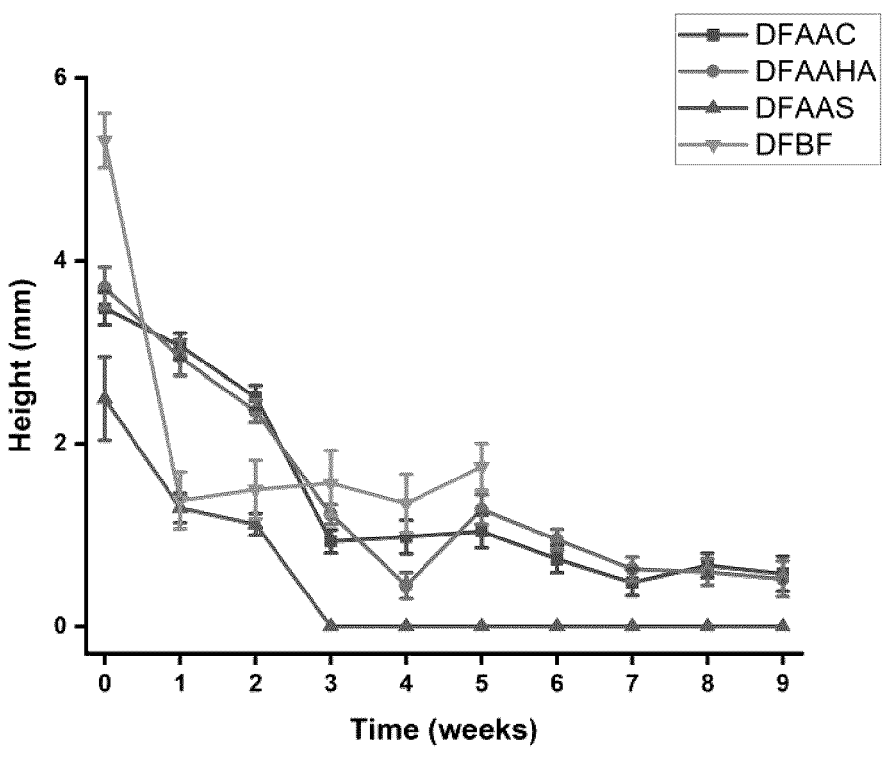
FIG. 34 shows implant sizes as described in Example 3. The height of the AAS (blue), AAHA (red), AAC (black) and BellaFill (purple) implants. All implants were shrinking with time due to resorption of the carrier fluid/hydrogels. The AAS formulation quickly resorbed.
Figure 35:
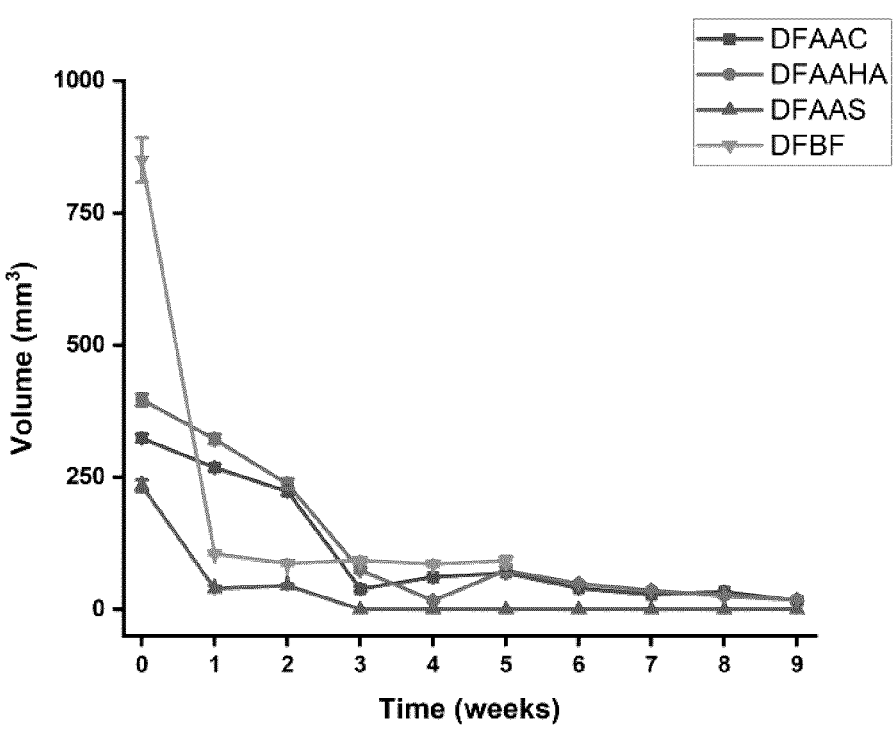
FIG. 35 shows implant volume as described in Example 3. The volume of the AAS (blue), AAHA (red), AAC (black) and BellaFill (purple) implants. All implants were shrinking with time due to resorption of the carrier fluid/hydrogels. The AAS formulation quickly resorbed.

As described above, the implant sites for all animals and all formulations were measured weekly. The implant size characteristics were as show in FIGS. 34 and 35. FIG. 34 shows implant sizes. The height of the AAS (blue), AAHA (red), AAC (black) and BellaFill (purple) implants. All implants were shrinking with time due to resorption of the carrier fluid/hydrogels. The AAS formulation quickly resorbed. FIG. 35 shows implant volume. The volume of the AAS (blue), AAHA (red), AAC (black) and BellaFill (purple) implants. All implants were shrinking with time due to resorption of the carrier fluid/hydrogels. The AAS formulation quickly resorbed.

The data supports that the AAS filler quickly shrinks due to the resorption of saline into the animal's body. In the case of collagen, HA and bellafill, the implants slowly shrink in size but remain visible several months after the initial injection. Although the number of animals is small, qualitatively the implant size characteristics of BellaFill and the presently developed dermal fillers are roughly similar. Potentially, the presently developed fillers may shrink less rapidly than the BellaFill product, however they appear to have reached a similar baseline size.

After 4, 8 and 12 weeks the appropriate animals were sacrificed and the implant tissues were collected. In the case of AAS, only the filler particles are visible beneath the skin as the saline quickly resorbs into the animal's body (consistent with the measured size data). Thus, while the dermal filler was indeed non-resorbable, the carrier fluid used in the dermal filler formulation did resorb.

Example 4—Modified Dermal Fillers

Modified dermal fillers are contemplated in this example. In order to endow greater control of the shape and size distribution of the material, it is contemplated that the cellulose-based materials may be dissolved in order to cross-link it into particular geometries and/or sizes. Several cross-linking methods are contemplated in certain embodiments, such as chemical crosslinking with succinic acid, sodium hydroxide and urea treatment, and composites with alginate and calcium chloride. A sample dissolution protocol being contemplated is outlined below:

Ratio: 50 g of decellularized apple=1.568 g of cellulose material

Solvent Preparation:

DMAc: 115° C. for 15 minutes

LiCl: 180° C. for 48 hours

Protocol:

Weigh 50 g of decellularized material

Soak in acetone (15 minutes in ultrasonic bath)

Centrifuge to remove the acetone

Repeat the previous two steps twice more

Soak in DMAc (15 minutes in ultrasonic bath)

Centrifuge to remove the acetone

Repeat the previous two steps twice more

Add LiCl at a ratio of 6 g per 50 mL of DMAc

Maintain at 100° C. for 1 hour

Reduce the temperature to 50° C. for 72 hours (while stirring)

Regenerate the cellulose with water exchange.

Example 5—Efficiency of Cellulose Particle Production

The studies described in this example sought to provide insight into the potential yields for cellulose-based particle production using apples as a starting material.

Decellularization of Apple Samples

McIntosh apples provided by Canada Fancy were separated into three separate batches and each of the three batches was weighed. The weights of each batch are shown below in Table 5.

TABLE 5

| Batch Weights | | |
|---|---|---|
| Batch | Number of Apples in Batch | Batch Starting Mass (g) |
| 1 (AA124) | 16 | 1927.58 |
| 2 (AA125) | 15 | 1902.37 |
| 3 (AA126) | 15 | 1885.11 |

The apples of each batch were washed with 70% ethanol and Accel TB disinfectant prior to peeling. After peeling, the samples of each batch were sliced to a thickness of 1 mm. The cores of the apples were removed and the slices were quartered.

To decellularize the samples, they were then placed in 0.1% SDS for 72 hours, with solution changes once per day. The samples of each batch were then washed three times with distilled water and subsequently immersed in a 100M $CaCl_2$ solution for 24 hours. During the decellularization process, the samples were shaken at 120 RPM.

The samples of each of the batches were then washed a further three times with distilled water and sterilized for 30 minutes in 70% ethanol. The samples were then stored in distilled water at 4° C. until further use.

Freeze-Drying Decellularized Samples

The decellularized samples were drained to remove as much distilled water as possible and then placed in 50 mL Falcon test tubes. The samples were then frozen at −20° C. and subsequently mounted on a Labconco freeze-dryer in a glass container, with 3-4 test tubes per glass container. The samples were freeze-dried for 48 hours at 55 mbar and −47° C. The samples were weighed after drying, the results of which are shown in Table 6 below.

Grinding of the Dried Samples

The decellularized, freeze-dried samples of each batch were ground with a Retsch Mill ZM-200 at 18,000 RPM, with an 80 μm sieve. The particles were collected in 50 mL tubes and weighed, as shown in Table 6 below. The samples were then stored at 4° C. until further use.

Sieving the Ground Samples

The ground samples of each batch were sieved with a Gilson vibratory sieve shaker (SS-23) system that allows for continuous sieving. The top sieve had a 50 μm mesh and the bottom sieve had a 25 μm mesh. The 50 μm sieve retained particles >50 μm. Particles <25 μm passed through the 25

μm sieve. The filtered particles (25 μm to 50 μm in size) were collected from the 25 μm sieve and weighed.

After grinding, 5 mL of ground sample from each of the batches was resuspended in distilled water for a final volume of 45 mL. The resuspension was poured onto the 50 μm sieve and after two minutes, 150 mL of distilled water was added. After one minute, another 150 mL of water was added to the top sieve (this step was repeated twice). The 50 μm sieve was then removed and 50 mL of distilled water was added to the 25 μm sieve. After one minute, another 50 mL of water was added to the sieve (this step was repeated twice). The wet particles of the ground samples on the 25 μm sieve were collected and placed in a centrifuge tube. This process was repeated until all of the ground samples had been filtered. The filtered samples were then centrifuged for 7 minutes at 5000 RPM to pelletize the particles, which were then stored at 4° C.

The filtered, pelletized samples were then freeze-dried under the same conditions described above and subsequently weighed, as shown in Table 6 below.

TABLE 6

| | Processed Batch Weights | | |
| --- | --- | --- | --- |
| Batch | Freeze-dried Batch Mass (g) | Ground Batch Mass (g) | Mass of dried 25-50 μm particles (g) |
| 1 (AA124) | 22.0118 | 19.6693 | 2.6786 |
| 2 (AA125) | 15.0805 | 14.1494 | 2.5615 |
| 3 (AA126) | 12.7896 | 11.4461 | 1.5875 |

It is noted that the second freeze-drying was carried out only to measure the dry mass of the samples and is not necessary for dermal filler sample production.

Determination of Particle Yield

Using the data collected during the above procedures, three different particle yields were calculated, namely from the starting batch masses (the whole apples), from the freeze-dried batch masses, and the ground batch masses. The results are shown in Table 7.

TABLE 7

| | Particle Production Yields | | |
| --- | --- | --- | --- |
| Batch | Percent Yield from Batch Starting Mass (%) | Percent Yield from Freeze-dried Batch Mass (%) | Percent Yield from Ground Batch Mass (%) |
| 1 (AA124) | 0.139 | 12.2 | 13.6 |
| 2 (AA125) | 0.135 | 17.0 | 18.1 |
| 3 (AA126) | 0.0882 | 12.4 | 13.9 |

The averages of the yields were taken and are shown in Table 8.

TABLE 7

| | Mean, Standard Deviation, and Standard Error of Particle Production Yields | | |
| --- | --- | --- | --- |
| | Percent Yield from Batch Starting Mass (%) | Percent Yield from Freeze-dried Batch Mass (%) | Percent Yield from Ground Batch Mass (%) |
| Mean | 0.119 | 13.9 | 15.2 |
| Standard deviation | 0.030 | 2.7 | 2.5 |
| Standard error | 0.018 | 1.6 | 1.5 |

Results

The yield from the batch starting mass was calculated using the mass of the dried 25-50 μm particles and the batch starting mass. The percent yield from the batch starting mass was 0.119%±0.018%, meaning that 0.119 g of dried particles are obtained from 100 g of starting material, or that 83,843.38 g of apple is required to produce 100 g of the dried particles.

The yield from the freeze-dried batch mass was calculated using the mass of the dried 25-50 μm particles and the freeze-dried batch mass. The percent yield from the freeze-dried batch mass was 13.9%±1.6%, meaning that 13.9 g of dried particles are obtained from 100 g of the freeze-dried samples, or that 721.7 g of freeze-dried batch samples are required to produce 100 g of dried particles.

The yield from the ground batch mass was calculated using the mass of the dried 25-50 μm particles and the ground batch mass. The percent yield from the ground batch mass was 15.2%±1.5%, meaning that 15.2 g of dried particles are obtained from 100 g of the ground samples, or that 658.0 g of ground samples are required to produce 100 g of dried particles.

The variation of the yields from the batches may be in part due to the sample preparation. Without being bound to any particular theory, it is postulated that, the size of the apple, the amount of flesh remaining on the apple core, powder loss during grinding, and variations in the degree of separation during sieving may individually or together impact the yields.

Regardless, the studies provide insight into the materials that may be required when up-scaling the methods of the present disclosure.

Example 6—Densities of Cellulose Particles

The studies described in this example sought to determine the number density (number of particles per volume) of the cellulose particles of the present disclosure. Generally, standard industry practice is to describe the particle concentration of dermal fillers in terms of mass/volume concentration. However, it may be useful in some cases to describe the particle concentration of fillers in terms of number density.

Density Determination

Decellularized, sterile (unfiltered) apple particles produced as described above in Example 5 were filtered using the Gilson vibratory sieve shaker as also described in Example 5. The filtered particles were collected in a 15 mL Falcon tube and pelletized by centrifuging for 7 minutes at 5000 RPM. The process was repeated until 2.5 mL of wet 25-50 μm particles were obtained.

The particles were resuspended in 15 mL of water and then split equally between 3 tubes (0.833 mL of particles in each tube). The equivalent of 33 μL of particles suspended in 198 μL of water (16.7% v/v resuspension) were removed from each tube for the particle count analysis using a Multisizer 4.

The 0.800 mL of filtered particles remaining in each tube were pelleted, frozen, freeze-dried for 4 days with a Labconco freeze-dryer at 55 mbar, −46° C., and then weighed to calculate the particle mass density, as shown in Table 8.

TABLE 8

| | | Mass of Dried Particles Per Wet Volume | |
| --- | --- | --- | --- |
| Sample | Wet particle volume (mL) | Mass of freeze-dried particles (g) | Particle mass density (g/mL) |
| 1 | 0.800 | 0.0929 | 0.116 |
| 2 | 0.800 | 0.0935 | 0.117 |
| 3 | 0.800 | 0.0972 | 0.122 |

The mean density of dried particles per wet volume were then calculated and are shown in Table 9.

TABLE 9

| | Mean, Standard Deviation and Standard Error of Particle Mass Density |
| --- | --- |
| | Density of dried particles per wet volume (g/mL) |
| Mean | 0.118 |
| Standard deviation | 0.00291 |
| Standard error | 0.00168 |

The density of dried particles was 0.118 g/mL 0.00168 g/mL, meaning that there is 0.118 g of dried particles per 1 mL of wet particles, or that 8.47 mL of wet particles weigh 1 g once dried.

A standard 400 μL dermal filler injection volume with 20% volume being occupied by particles results in 80 μL of particles per injection. Therefore, based on the concentration and density results presented above, the dry mass of particles per 400 μL injection was 9.4 mg.

Particle Count Analysis

Two samples were prepared from each of the three samples: (4) 10 μL of the 16.7% v/v particle resuspension were mixed with 10 mL of ISOTON and (5) 20 μL of the 16.7% v/v particle resuspension were mixed with 10 mL of ISOTON. Particle count analysis was performed on each sample using a Multisizer 4 Coulter Counter using an aperture of 100 μm and an analyzed volume of 200 μL, meaning that 0.0336 μL of particles were analyzed in samples (4) and 0.0673 μL of particles were analyzed in samples (5). A first run analyzed the particles 2-60 μm and a second run analyzed particles between 10-60 μm.

Between each run, an ISOTON (blank) sample was also analyzed with the same settings with the instrument to quantify the number of bubbles counted by the Coulter Counter. These values were used to adjust those obtained for the samples (4) and (5). The blank values are shown in Table 10.

TABLE 10

| ISOTON (Blank) Particle Counts | |
| --- | --- |
| Interval of particle size (μm) | Number of particles counted (mean) |
| 2-60 | 541 |
| 10-60 | 26 |

The results from the particle count analysis of each of the samples (4) and the samples (5) are shown below in Table 11.

TABLE 11

| | Sample Particle Counts | | | |
| --- | --- | --- | --- | --- |
| Interval (μm) | Volume of the particle resuspension added to 10 mL of ISOTON (μL) | Number of particles counted (mean) | Adjusted number of particles counted (mean) | Particle count per mL of wet, pelleted filtered particles |
| 2-60 | 10 | 4607 | 4066 | 120,915,052 |
| | 20 | 9066 | 8525 | 126,753,151 |
| 10-60 | 10 | 2549 | 2523 | 75,023,037 |
| | 20 | 5244 | 5218 | 77,582,781 |

Figure 36:
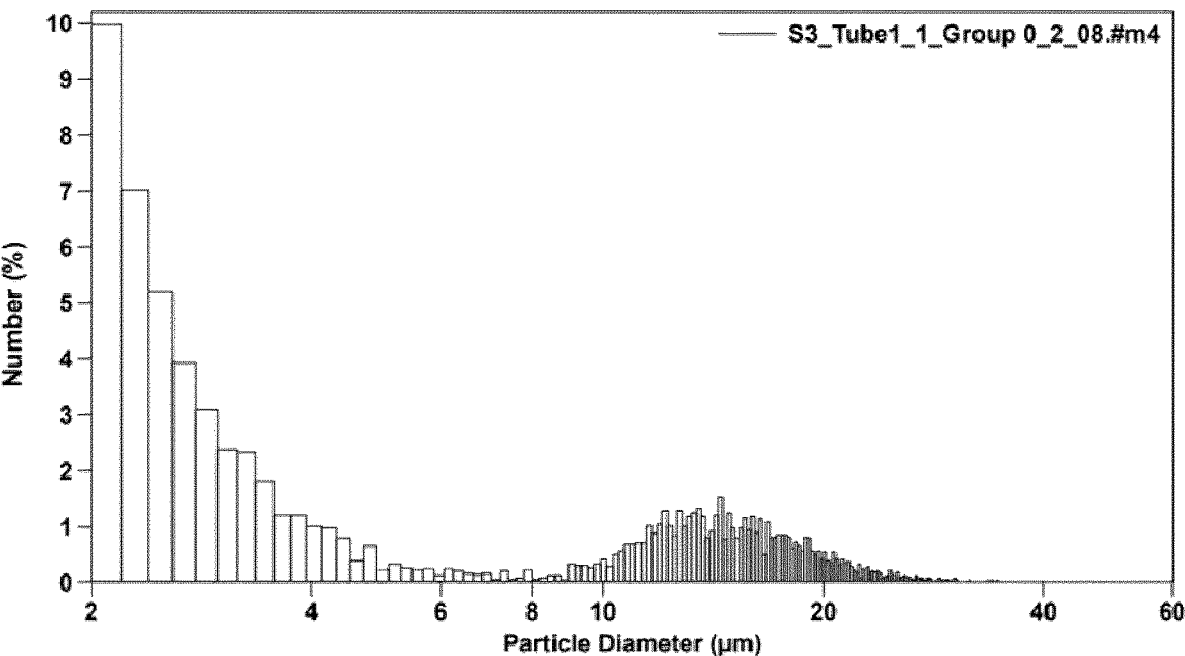
FIG. 36 shows a particle size distribution of apple-derived particles obtained as described in Example 6.

For illustrative purposes, a particle size distribution of the samples (4) is shown in FIG. 36. The particle counts of the samples (4) and samples (5) from each of the samples 1-3 were averaged, the results of which are shown in Table 12.

TABLE 12

| Particle Count Analysis Averaged from 10 μL and 20 μL Samples | | |
| --- | --- | --- |
| Particle count per mL of wet, pelleted filtered AA particles | 2-60 μm Analysis | 10-60 μm Analysis |
| Mean | 123,834,101 | 76,302,909 |
| Standard deviation | 4,128,159 | 1,810,012 |
| Standard error | 2,919,049 | 1,279,872 |

As discussed above, the aperture used was 100 μm. This aperture can count particles between 2 μm and 60 μm in diameter. According to the 2-60 μm analysis, there were 123,834,101±2,919,049 particles per mL of wet particles and the 10-60 um analysis shows 76,302,909±1,279,872 particles per mL of wet particles.

This means that there were 9,906,728 particles (2-60 μm analysis) or 6,104,233 particles (10-60 μm analysis) per 400 μL dermal filler injection.

A simplified theoretical estimate for the number concentration of the particles based on a cylindrical particle geometry assumption with a radius of 15 μm and a thickness of 1 μm is shown below. If the thickness is assumed to be 0.1 μm, then the number of particles would increase by a factor of 10.

$$V_{flake} = \pi (15 \ \mu m)^2 (1 \ \mu m)$$

$$V_{flake} = 706.5 \ um^3$$

$$\text{Number of particles} = V_{particles}/V_{flake}$$

$$\text{Number of particles} = (80 \ \mu L (1 \times 10^9 \ \mu m^3/\mu L))/(706.5 \ um^3)$$

$$\text{Number of particles} = 1.13 \times 10^8$$

The discrepancy between the theoretical value and the observed value may be due to a number of factors including inaccuracies in the Coulter Counter analysis (e.g. bubbles, particles settling out of suspension), particle size variations, and packing parameters (void volume not accounted for in the calculation).

Despite these discrepancies, the number density of about $1 \times 10^7$ particles/400 μL injection taken together with the dry particle mass density of 9.4 mg/400 μL injection and the single particle (or flake) volume estimate of 706.5 μm³ gives a single particle density of 1.33 g/cm³, which is about the same as that of literature value for cellulose density (1.5 g/cm³).

Example 7—Cellular Response to Cellulose
Particles In Vitro

This study sought to assess the in vitro cellular response to filtered and unfiltered cellulose particles of the present disclosure.

Particle Preparation

To prepare filtered particles, sterile unfiltered decellularized ground apple particles were sieved with the Gilson vibratory sieve shaker (SS-23) system using sterile water using the following procedure.

5 mL of particles were resuspended in sterile distilled water to a final volume of 45 mL. The resuspension was poured onto the 50 µm sieve and after two minutes 150 mL of distilled water was added. After one minute, another 150 mL of water was added to the top sieve (this step was repeated twice). The 50 µm sieve was removed and 50 mL of distilled water were added to the 25 µm sieve. After one minute, another 50 mL of water was added to the sieve (this step was repeated twice). The wet particles on the 25 µm sieve were collected and placed in a 50 mL Falcon tube. The sieving process was repeated until a sufficient amount of filtered particles were collected.

Both the filtered and unfiltered particles were centrifuged for 7 minutes at 5000 RPM to pelletize the particles. The volumes of the pelleted filtered and unfiltered particles were used to calculate the volume added to plates during the different trials.

Assays

Before being added to plates, the particles were resuspended in preheated DMEM to a final volume of 2.5 mL. 50,000 C2C12 cells were plated into each well of a 6 well plate (9.6 cm$^2$) 24 hours prior to the experiment. The cells were incubated at 37° C., 5% CO$_2$ for 48 hours with the particle solution. Then, 2.5 mL of the particle solution were added to each well.

The conditions used for the studies were volume:volume percentages of the particles with respect to the cell culture media. The percentages used were 1%, 2%, 3%, and 20%. In other words, the 1% concentration had 25 µL of particles in a total volume of 2.5 mL of media.

The 20% concentration was selected to replicate the in vivo concentration previously used herein. However, as will be appreciated, in vitro and in vivo conditions are very different and concentrations had to be selected to not disrupt cell morphology. For example, in vitro systems lack the ability to modulate gas exchange and maintain isotonic conditions and, as a result, may require reduced concentrations such as about 1% to not affect cell morphology. Thus, the in vitro results may not directly translate to in vivo toxicity results.

Cell Culture, Fixation, Staining, and Imaging

The media and particles contained therein were removed from the plates for imaging. The relatively high particle concentrations made it difficult to see the underlying layer of cells, so the particles were removed before fixing.

The cells were washed three times using 5 mL of PBS. 3 mL of 3.5% PFA was added to each plate. After a 10 minute incubation, cells were washed again with 5 mL of PBS. Then, 5 mL of PBS was added to the cells and the plates were sealed with parafilm and stored at 4° C. 5 µL of Hoechst 33342 were added to each plate containing 5 mL of PBS. The plates were incubated at room temperature in the dark for 30 minutes and then were sealed with parafilm and stored at 4° C.

The plates were then imaged with an Olympus SZX16 microscope.

Results

The addition of 20% v/v of particles to C2C12 cells had a clear effect on the cell density in the plates after 48 hours of incubation at 37° C., 5% CO$_2$. Though there were some cells adhered to plates for both the filtered and unfiltered particles, the cell morphology was altered such that they appeared shrivelled. The plates containing particles had significantly fewer cells than the control, and the control cells displayed normal myoblast morphologies. The confluency is higher in the plates that received filtered particles than in the plates with unfiltered particles. Without being bound to any particular theory, it is postulated that, in an in vitro environment, small particles may cause cell death due to an osmotic effect, necrosis due to chemical leaching, and/or phagocytosis and apoptosis.

In the 20% samples, the high concentration of particles in the dish made it difficult to observe the cells attached to the plate and, as a result, only floating cells were visible. Imaging the cells without the particles allowed for more accurate cell density quantification as there were no particles to block the signal while imaging.

Figure 37:
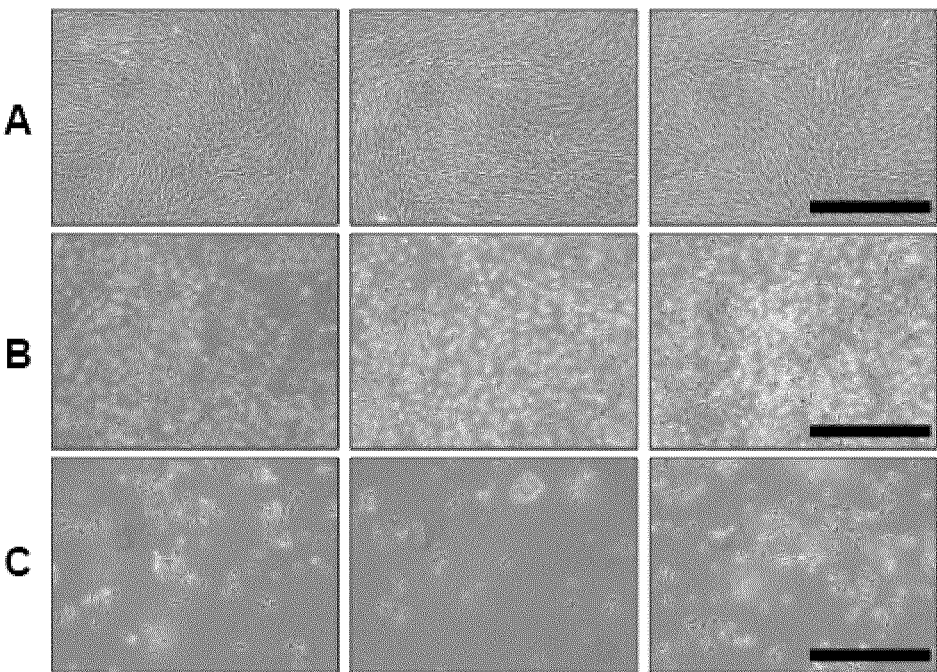

FIG. 37 shows the microscopy images of the 20% samples, wherein FIG. 37A shows microscopy images of the control, FIG. 37B shows microscopy images of the cells of the 20% filtered particle sample, and FIG. 37C shows microscopy images of the cells of the 20% unfiltered particle sample. The magnification was 10× and the scale bar is 500 µm.

Figure 38:
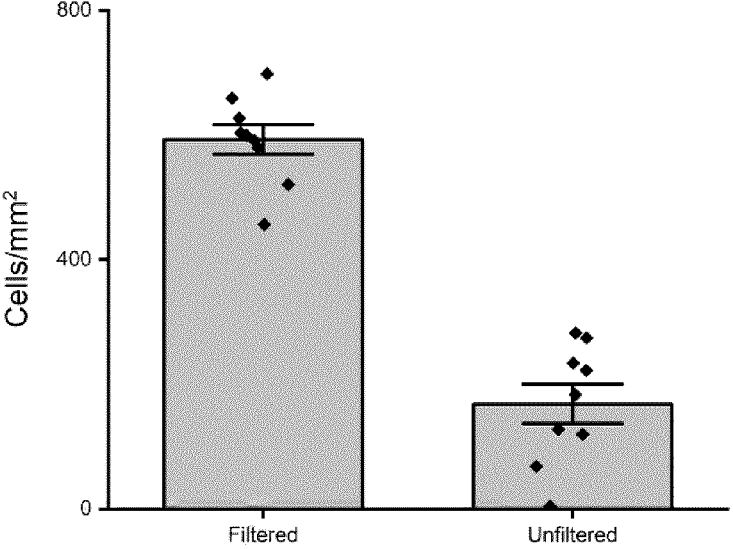
FIG. 38 shows the cell concentrations (cells/mm²) for the 20% v/v filtered and unfiltered apple-derived particle samples as described in Example 7.

FIG. 38 shows the cell concentrations (cells/mm$^2$) for the 20% filtered and unfiltered particle samples.

As described above, it was expected that the 20% samples may affect the cell morphology under in vitro conditions. As also discussed above, in vitro and in vivo conditions are drastically different. As a result, it is expected a 20% particle concentration will not lead to altered cell morphologies in vivo.

The high concentration of particles in the media may have altered the osmolarity of the solution and, as a result, water may be pulled out of the cells due to entropic factors. In addition, the layer of particles on top of the cells may have prevented efficient gas exchange and, in turn, lead to cell death. Under in vivo conditions, there are natural systems that regulate gas exchange and compensate for changes in solute concentrations and osmotic gradients or pressures.

Thus, the lower concentrations discussed below were selected to assess the effects of particle concentration when normal cell morphology is observed. For the lower particle concentrations of 1%, 2%, and 3%, particle suspensions were used for both filtered and unfiltered samples.

Figure 39:
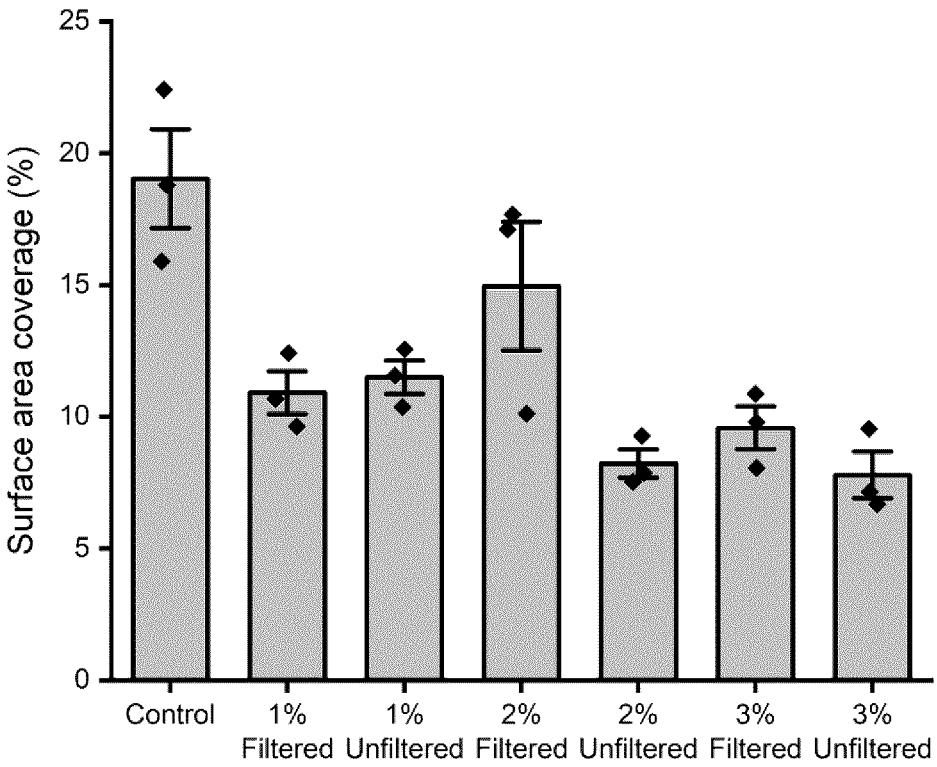
FIG. 39 shows the surface area coverage of the cells of the of the control and the filtered and unfiltered lower-concentration samples as described in Example 7.

FIG. 39 shows the surface area coverage of the cells of the control and the filtered and unfiltered lower-concentration samples. As shown, for the 2% concentration, there was a significant difference between the filtered and unfiltered particles.

The results suggest that particle concentration may have an effect on the ability of cells to survive—increased amounts of particles in the media may lead to higher rates of cell death. Moreover, the filtration also appeared to impact the amount of adhered cells. Unfiltered particles generally resulted in less cell growth/cell area coverage and greater cell death.

Again, as discussed above, the exact particle concentrations do not directly translate from in vitro systems to in vivo systems because of the osmotic pressure regulation, gas exchange processes, immune cells, etc.

For example, there are significant variations in oxygen diffusion between in vitro and in vivo systems. In more detail, in vitro systems rely on the diffusion of oxygen through the cell culture medium. The distance the oxygen must diffuse through is generally much larger than the distance typically required in mammalian tissues. In addition, the oxygen consumption rates in standard cell culture conditions often exceed the diffusion rate of oxygen through the cell culture medium and the presence of cellulose particles may further reduce the diffusion rate.

Another variable that is different between in vitro and in vivo systems is the maintenance of osmotic pressure, specifically turgor pressure for the cells. The physiological values for hydrostatic pressure (HP) vary substantially across tissues (e.g. from about 0.5 kPa to about 6 MPa). The number of solutes in the solution may affect the osmotic pressure and, in turn, the cell volume. Thus, in in vitro systems, the addition of the cellulose particles may affect the osmotic pressure and lead to cell death.

Further, the types of cells in cell culture systems are distinct from in vivo cells. In immunocompetent animals, the immune cells are triggered to respond to the foreign body. However, in vitro, there are limited processes (e.g. phagocytosis) that can occur.

Regardless, the above studies may generally illustrate the effects of increased concentration of particles on cells.

Example 8—Use of UV-VIS Spectroscopy to Assess Cellulose Particle Concentrations This study sought to determine if UV-VIS spectroscopy was a viable alternative to graduated cylinders, graduated falcon tubes, and microcentrifuge tubes for measuring the concentration of cellulose particles.

In more detail, the study aimed to determine whether the absorbance or transmittance of light through a sample may be suitable to more accurately determine the concentration of cellulose particles therein.

Without being bound to any particular theory, the principle behind this experiment is that the cellulose particles may scatter incident light and that the amount of scattering may be indicative of the concentration of the particles in a sample. Absorbance is the negative logarithm of the transmittance or, put differently, is the logarithm of the ratio of the incident and transmitted radiant fluxes, as shown below.

$$A = -\log 10 T$$

$$A = \log(\Phi i/\Phi t)$$

Wherein A=absorbance, T=transmittance, $\Phi i$=incident radiant flux, and $\Phi t$=transmitted radiant flux.

Sample Preparation

Ground, decellularized pear-derived particles were suspended in a 2M sucrose solution. A sucrose solution was used because the particles would not remain suspended in water alone. The prepared solutions are outlined below in Table 12.

Spectroscopy

Cary 1E model and Synergy model UV-Vis spectrophotometers were used. For the Carey model, the wavelength was set to 500 nm, the average time was set to 0.1 s, and the SBW was set to 1.5 nm. Standard 1 cm cuvettes were used. Because the Carey model is a dual beam model; therefore, two 2M sucrose solutions were used as blanks. The machine was zeroed, and then the cuvette closest to the user was changed for the sample readings.

Figure 40:
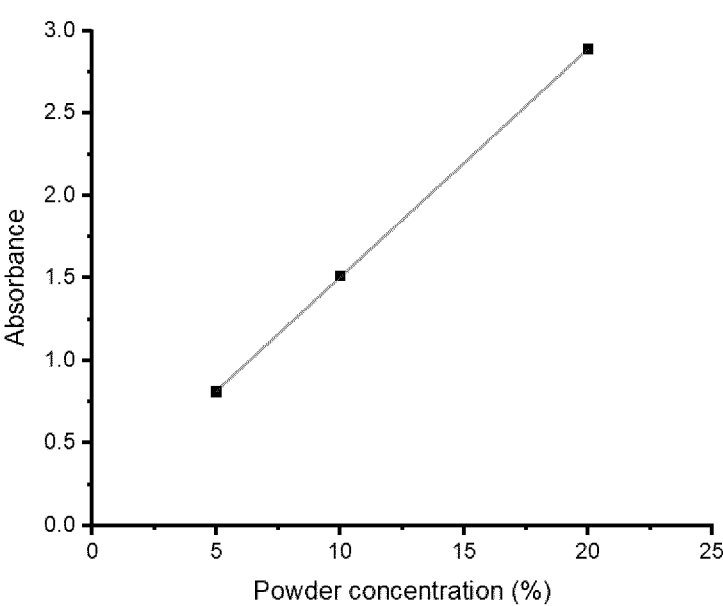
FIG. 40 shows the standard absorbance-concentration curve developed using the samples described in Example 8.

The samples were used to generate a standard absorbance-concentration curve, as shown in FIG. 40. However, as shown, the intercept of the high concentration regime (5-20%) was not close to zero, which suggest that a measurement was incorrect, or that the portion of the curve being analyzed was after a nonlinearity occurring at lower concentrations.

Figure 41:
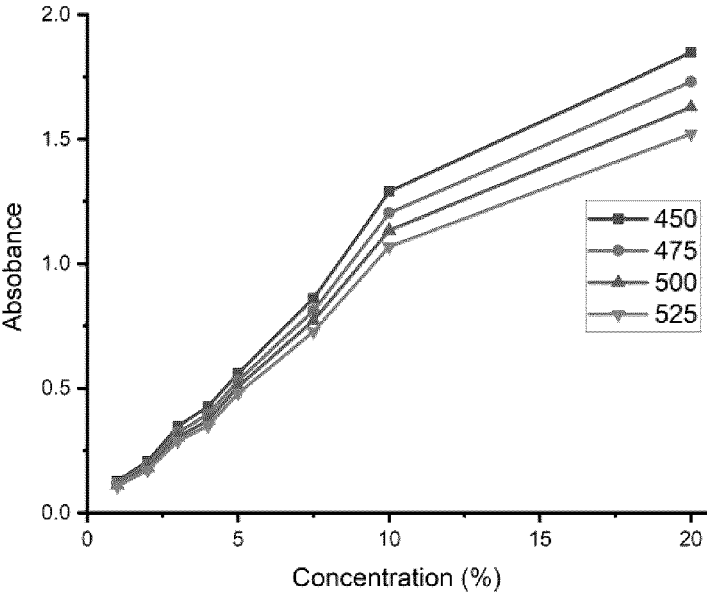
FIG. 41 shows absorbance-concentration curves at absorbances of 450 nm, 475 nm, 500 nm, and 525 nm of the samples described in Example 8.

The Synergy model UV-VIS spectrometer was used to test lower concentration ranges. The 20% stock solution was serially diluted and absorbance was measured at 450 nm, 475 nm, 500 nm, and 525 nm. The results are shown in FIG. 41.

Figure 42:
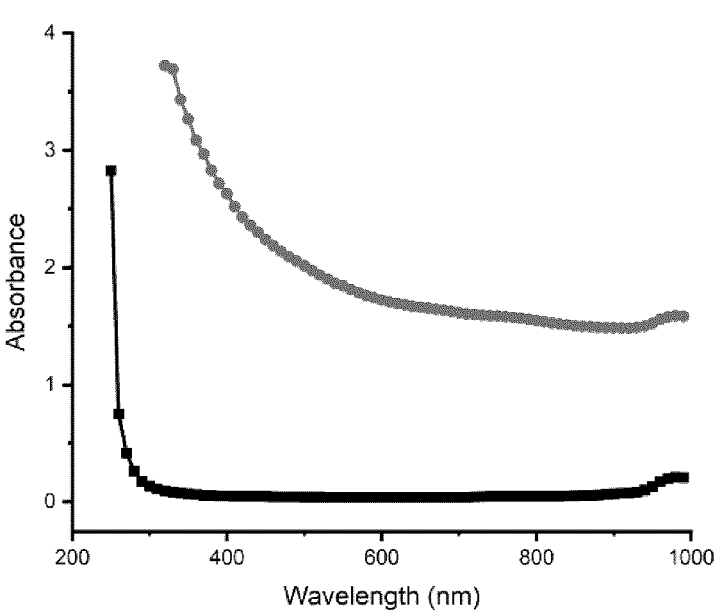
FIG. 42 shows a wavelength sweep for a 20% pear-derived particle stock solution and a 2 M sucrose control solution as described in Example 8.

Synergy model UV-VIS spectrometer was also used to conduct wavelength sweeps on the 20% stock solution and a 2 M sucrose control solution. The results are shown in FIG. 42, wherein the black line represents the sucrose and the red line represents the pear-derived particles. As shown, no peak absorbance was found in the tested range, and both the particles and the sucrose had higher absorbances at smaller wavelengths.

Figure 43:
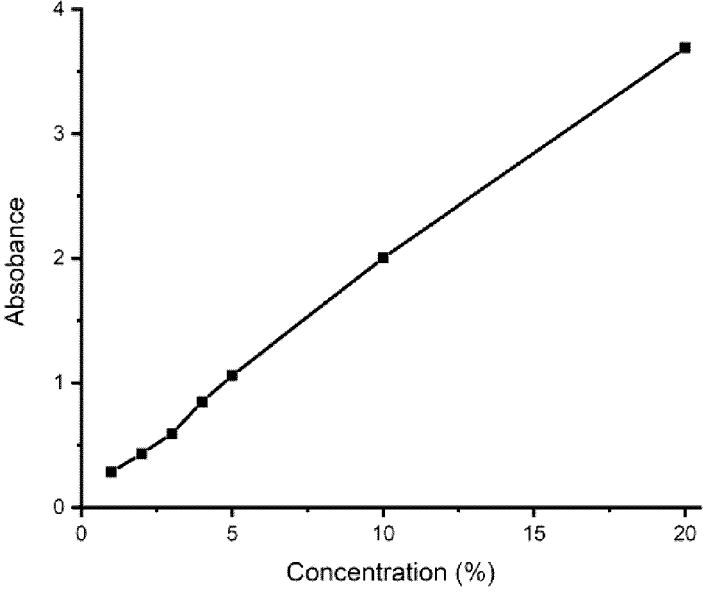
FIG. 43 shows an absorbance-concentration curve at 320 nm of the samples described in Example 8.

As the absorbance was high at 320 nm, the absorbance of the serial dilutions described above were analyzed with 320 nm light. The results are shown in FIG. 43. As shown, a more gradual non-linear deviation occurred. A linear fit up to the 5% powder concentration yielded an R2 of 0.99, a slope of 0.2 and a y-intercept of 0.05.

Conclusions

These preliminary results show that the particle concentrations up to 5% may be used for building a standard curve to determining the concentration of cellulose particles in a sample.

Example 9—Extrusion Force of Various Carriers Containing Cellulose Particles This study sought to examine the effect of carriers as well as other variables on the extrusion forces of dermal fillers of the present disclosure.

Four formulations were prepared for testing and are detailed below in Table 13. The freeze-dried decellularized apples particles used in the formulations were ground into flakes with a Retsch Grinder and an 80 μm filter. The flakes were then wet-sieved using 45 μm and 25 μm custom soldered Gilson sieves and a Gilson Test Vibrator. The filtered particles were concentrated by centrifugation for 7 min at 5000 rpm.

TABLE 12

Sample Concentrations

| Volume of particles (mL) | Volume of 2M sucrose (mL) | Concentration of particles (v/v %) |
|---|---|---|
| 0.5 | 9.5 | 5 |
| 1 | 9 | 10 |
| 2 | 8 | 20 |

TABLE 13

Formulations Summary

| Formulation | Percent of Particles (v/v) | Concentration of Stock Carrier Gel (% m/v) | Final gel concentration (% m/v) |
|---|---|---|---|
| Gelatin without particles (GE) | 0 | 25 | 25 |
| Gelatin with apple particles (GEAA) | 20 | 25 | 20 |

TABLE 13-continued

| | Formulations Summary | | |
|---|---|---|---|
| Formulation | Percent of Particles (v/v) | Concentration of Stock Carrier Gel (% m/v) | Final gel concentration (% m/v) |
| HyStem HA with apple particles (HAAA) | 20 | 8 | 6.4 |
| Alginate without particles (AL) | 0 | 5 | 5 |

It is noted that the gelatin and alginate formulations were melted by heating to 37° C. in a water bath prior to use.

For the testing, an extrusion distance was of 5 mm was selected. For the syringe used, an initial loading volume was set to 0.3 mL, which corresponded to a distance of 5 mm for the plunger cross-head displacement. As the formulations are viscoelastic fluids, the compression or extrusion rate influences the measured extrusion force. Extrusion rates (also referred to as cross-head speeds) of 1 mm/s, 2.5 mm/s, and 5 mm/s were investigated along with the effects of different sized needles, namely 27 G needles and 30 G needles.

Results

Figure 44:
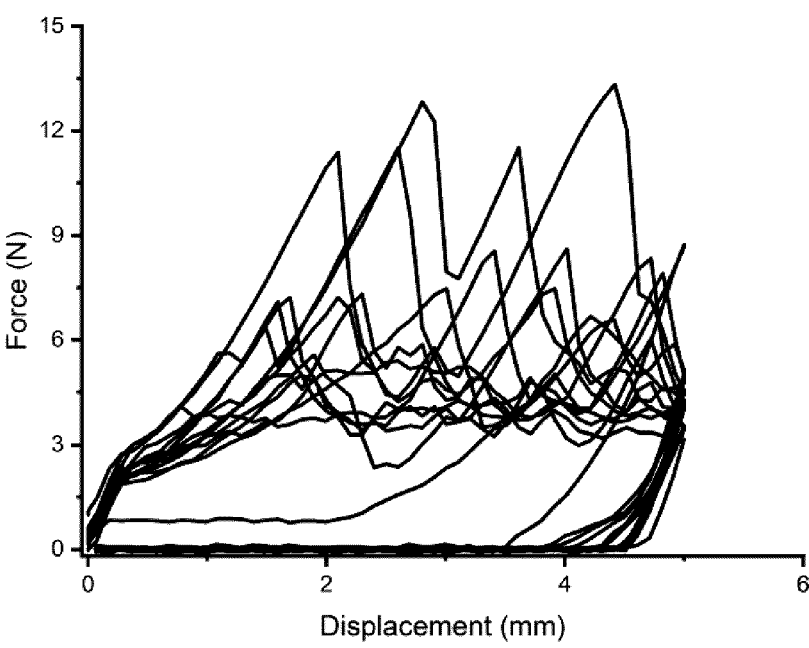
FIG. 44 shows force-displacement curves for a HyStem HA with apple-derived particles (HAAA) sample as described in Example 10.

The extrusion force for HAAA formulation was measured at a cross-head speed of 1 mm/s. The force-displacement curves for N=14 extrusions are shown in FIG. 44. The needle size was 27 G.

As the extrusion rate has an effect on the apparent force, it may be useful to define the extrusion rate so as to facilitate comparison between the dermal fillers described herein to the conventional dermal fillers. BellaFill extrusion properties are included below in Table 14.

TABLE 14

| | BellaFill Extrusion Properties for 1 mm/s rate and 26 G Needle | | | |
|---|---|---|---|---|
| Product | N | Max force (N) | SD | SEM |
| BellaFill | 3 | 26.3798 | 3.8020 | 2.1953 |

Figure 45:
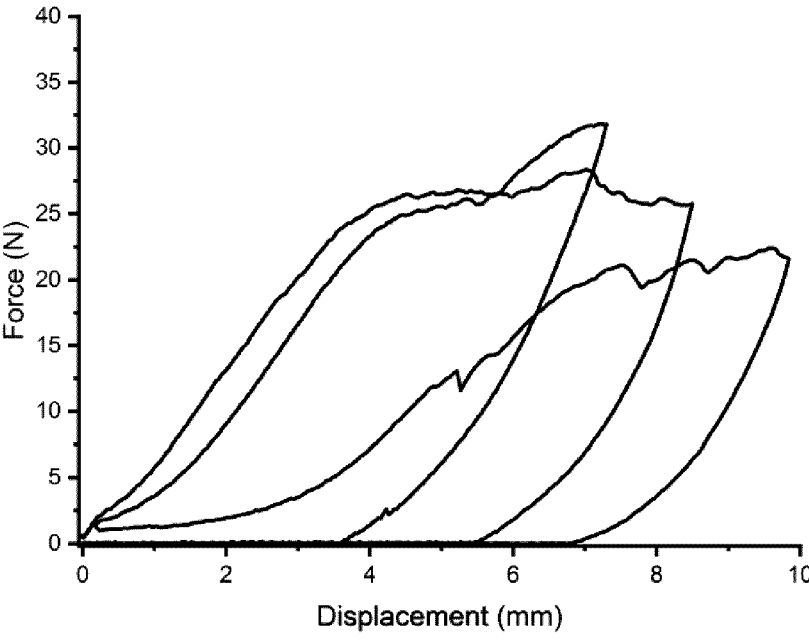
FIG. 45 shows force-displacement curves for a BellaFIll dermal filler as described in Example 10.

A complementary force-displacement plot for BellaFill extrusion force through a 26 G at 0.48 mm/s is shown in FIG. 45.

Figure 46:
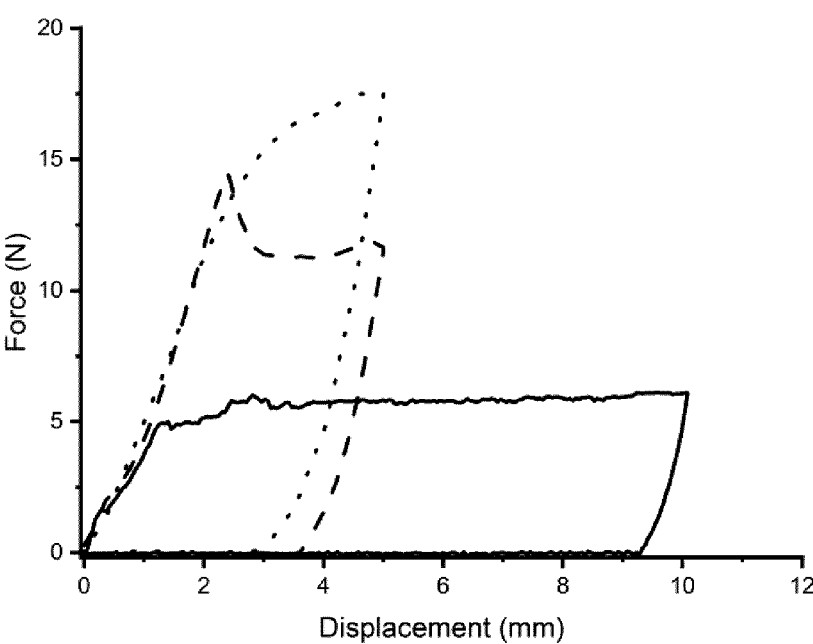
FIG. 46 shows force-displacement curves for a diluted HAAA sample as described in Example 10.

Similar results were observed for the HAAA formulation. Another run using a HAAA is shown in FIG. 46. In that run, the HAAA was different than that indicated above, as additional cross-linker and particles were added, which resulted in an HA concentration of 4.8% and a particle concentration of 28%. The cross-head speed was set to 1 mm/s (solid line), 2.5 mm/s (dashed line), and 5 mm/s (dotted line). As shown, higher speeds resulted in a larger force and, for the highest speed, no plateau was observed. Further, the initial peak force observed in the intermediate speed was not present in the slow extrusion. Without being bound to any particular theory, the lack of peak may be due to the rate response fluid during the shearing in the syringe and needle.

Figure 47:
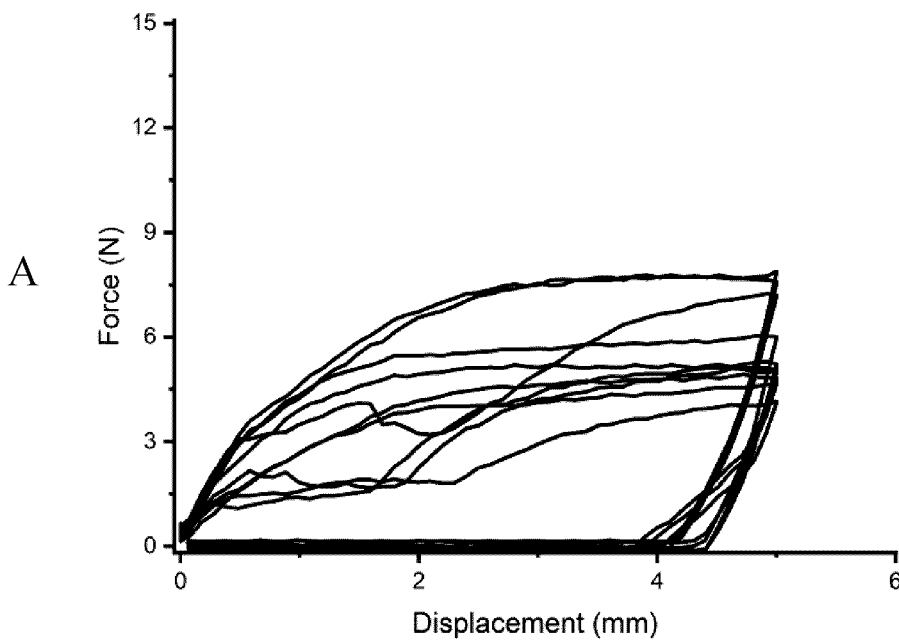
Figure 47:
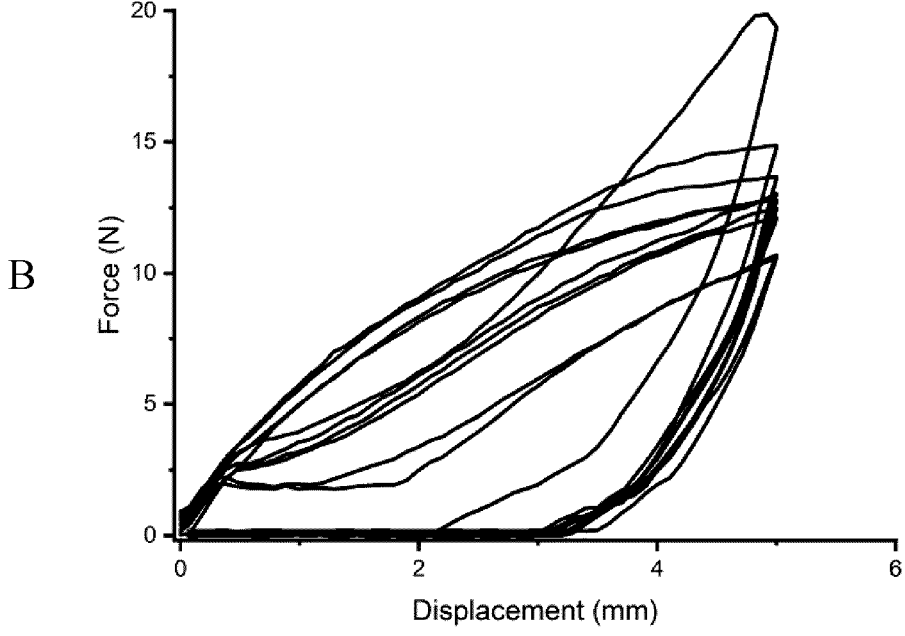

The extrusion force for the GE sample was measured at a 1 mm/s cross-head speed and compared between 27 G needles and 30 G needles. The results are shown in FIG. 47, wherein FIG. 47A shows the GE extrusion force through the 27 G needle, and FIG. 47B shows the GE extrusion force through the 30 G needle. The measured maximum extrusion forces are shown below in Table 15.

TABLE 15

| | GE Formulation Maximum Extrusion Force | | | |
|---|---|---|---|---|
| Needle size (G) | N | Mean | SD | SEM |
| 27 | 10 | 5.8201 | 1.3500 | 0.1133 |
| 30 | 10 | 12.5858 | 2.4788 | 0.7838 |

The smaller needle resulted in a significantly higher maximum extrusion force.

Figure 48:
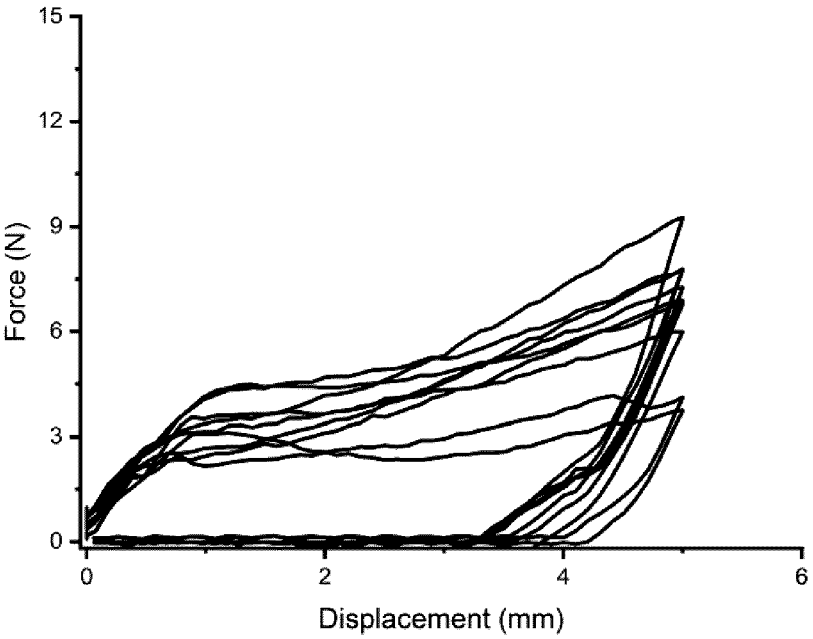
FIG. 48 shows force-displacement curves for a gelatin and apple-derived particle (GEAA) sample as described in Example 10.

The extrusion force for the GEAA sample was measured at an extrusion rate of 1 mm/s through a 27 G needle. The results are shown in FIG. 48. The measured maximum extrusion force is shown below in Table 16. As shown, the inclusion of particles significantly increased the extrusion force of the GE formulation. It is also noted that the GEAA formulation results are not significantly different than the HAAA results.

Figure 49:
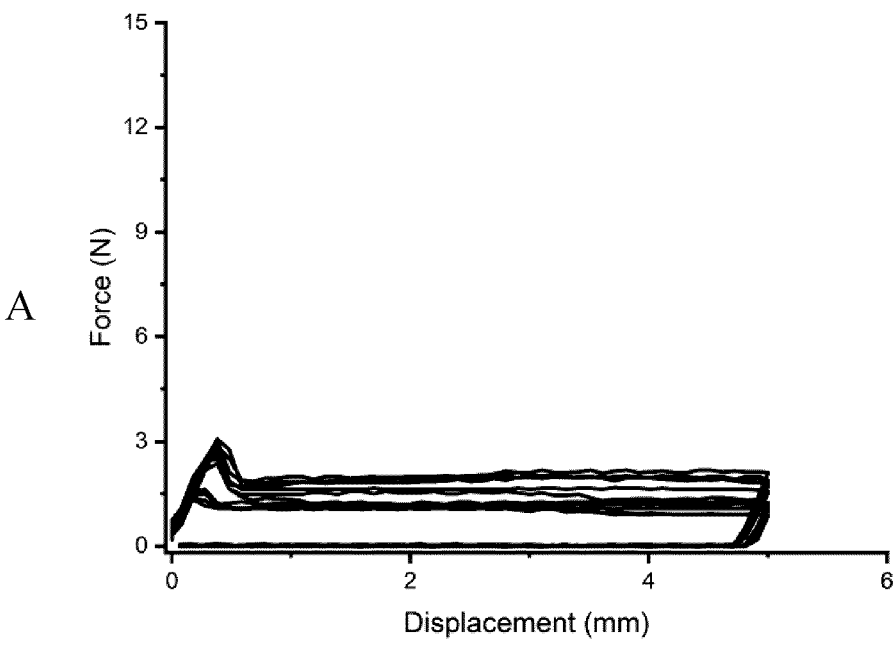
Figure 49:
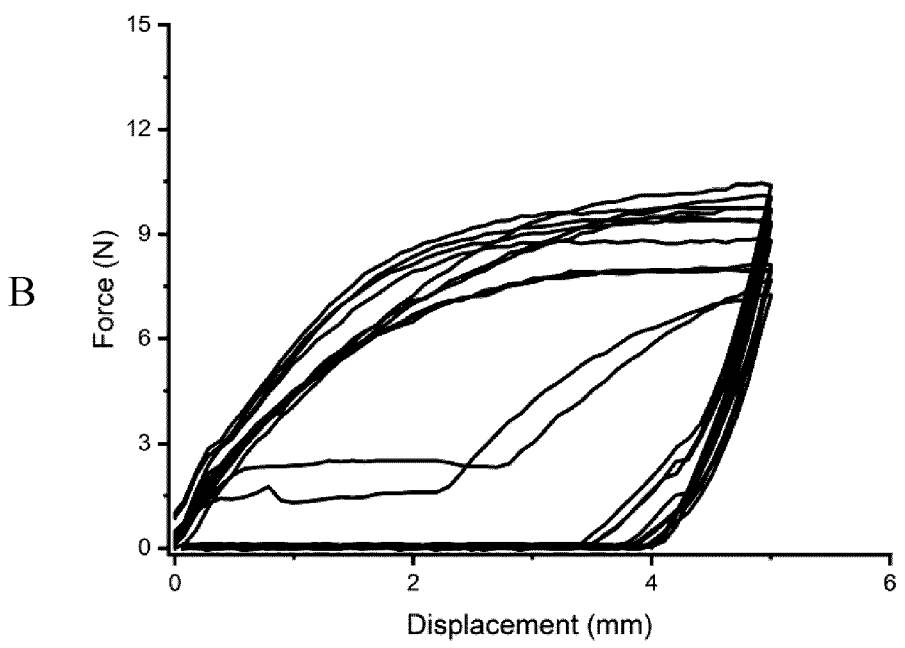

In order to directly compare the results of the GE and GEAA formulations, the GE formulation was diluted to 20% (m/v). The diluted GE formulation was kept warm prior to extrusion by maintaining the formulation a 37° C. water bath. The temperature during extrusion was about 24.5° C. The results of the diluted GE extrusion are shown in FIG. 49A. As shown, the diluted GE exhibited a "classic" extrusion-force curve having an initial peak followed by a plateau.

As the gelation of gelatin is temperature dependent, the extrusion force of the diluted GE formulation was also measured at room temperature (about 21° C.) using the same operating parameters. The results are shown in FIG. 49B. As shown, the room temperature diluted GE formulation, which did not contain particles, had higher extrusion forces than both the warmed diluted GE formulation and the GEAA formulation. A comparison of the maximum extrusion forces is shown in Table 16.

TABLE 16

| | Diluted GE and GEAA Formulations Maximum Extrusion Force | | | |
|---|---|---|---|---|
| Formulation | N | Mean | SD | SEM |
| GE 20% (warm) | 12 | 2.228 | 0.671 | 0.192 |
| GE 20% (RT) | 12 | 8.958 | 1.074 | 0.313 |
| GE AA (warm) | 9 | 6.669 | 1.772 | 0.592 |

Figure 50:
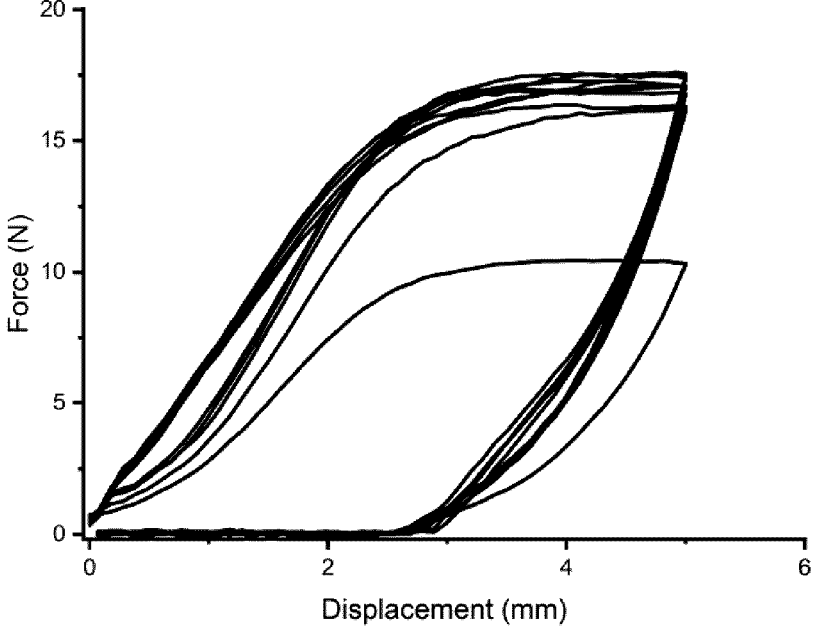
FIG. 50 shows force-displacement curves for an alginate (AL; without particles) sample as described in Example 10.

The extrusion force of the AL formulation was measured using a 27 G needle and an extrusion rate of 1 mm/s. The results are shown in FIG. 50.

Thus, the extrusion force of the dermal fillers described here may be affected by the carrier used, the concertation of the carrier, and the extrusion rate.

Example 10—Comparison Between Wet and Dry Mass of Mercerized Decellularized Tissues Mercerized apple (AA) was produced by adding decellularized apple to 1 M NaOH at a 1:5 (m/v) ratio. The mercerization was performed at 80° C. for 1 hour while stirring, and hydrogen peroxide (stock 30%) was added to lighten the colour. After the reaction was complete, the beaker was removed from the heat source, and the solution was neutralized with HCl. The material was concentrated by centrifugation in a Sorvall ST 16 R centrifuge or an Avanti J-26XPI High-Performance centrifuge. After, the supernatant was removed and the pellet of mercerized AA material was resuspended in water. Neutralization and centrifugation processes were repeated until the pH remained between 6.8 and 7.2 for back-to-back cycles. Once neutralized, a final centrifugation was performed, and the material was collected in 50 mL Falcon tubes and subsequently stored in a fridge.

Comparison Between Wet and Dry Masses

About 1 g of three different batches of mercerized AA material were weighed. Weighed samples were frozen at −20° C. and then freeze-dried using a LabConco freeze-dryer for 24 hours at 55 mbar and −46° C. The samples were weighed again once dried. The results are summarized in Table 17 below.

TABLE 17

| | | | Yield (dry mass/wet |
|---|---|---|---|
| Sample | Wet mass (g) | Dry mass (g) | mass) (%) |
| 1 | 0.99 | 0.04 | 4.04 |
| 2 | 1.00 | 0.07 | 7.00 |
| 3 | 1.00 | 0.04 | 4.00 |
| 4 | 1.0059 | 0.0597 | 5.93 |
| 5 | 1.007 | 0.0398 | 3.95 |
| 6 | 1.0034 | 0.0570 | 5.68 |
| 7 | 1.0084 | 0.0558 | 5.53 |

Wet and Dry Masses of Mercerized AA Material

Despite the wet mass being the same for the mercerized AA materials, the final dry mass varied. The mean dry mass was 0.052±0.005 g (mean±standard error of the mean). The variations in dry mass yields may be the result of variations in the wetness of the starting materials, the use of different centrifuges, and/or where on the pellet the sample material was taken from.

Example 11—Effect of Centrifugation on Mercerized Apple Density

Two batches of mercerized AA were prepared using the same process outlined above in Example 10, except that both batches were spun down in 1 L Avanti centrifuge bottles with a volume of 0.75 L using an Avanti Centrifuge (8000 rpm, 15 min). The volume was held constant during centrifuging to standardize the packing force as much as possible. After, one batch was centrifuged in 50 mL tubes with 50 mL total volume using a Sorvall Benchtop Centrifuge (5000 rpm, 15 min).

After preparation, the batch that was further centrifuged (batch 1) produced about 3.5 50 mL tubes of material, while the batch that was not further centrifuged (batch 2) produced about 2.5 50 mL tubes of material. Thus, the densities were different.

In order to quantify the changes in the density, 0.5 mL sample volumes measured with 1 cc syringes were extruded into pre-weighed 15 mL Falcon tubes. The masses were subsequently recorded (the wet mass). The tubes were then placed in a −20° C. freezer. Once frozen, the samples were mounted on a Buchi freeze dryer at 0.1 mbar and −55° C. and were left overnight. The following day, the mass of the tubes with the dry material was recorded. The recorded and calculated masses are shown below in Table 18.

TABLE 18

| | | | | | | Dry/wet | |
|---|---|---|---|---|---|---|---|
| | Tube | Wet | Calculated | Dry mass | Calculated | mass | |
| | mass | mass in | wet mass | in tube | dry mass | density | Mass/volume |
| Batch | (g) | tube (g) | (g) | (g) | (g) | (%) | density (%) |
| Batch 1 | 6.1838 | 6.6987 | 0.5149 | 6.1960 | 0.0122 | 2.37 | 2.44 |
| Batch 2 | 6.2498 | 6.9704 | 0.7206 | 6.2689 | 0.0191 | 2.65 | 3.82 |

Measured and Calculated Masses of Mercerized AA Batches

Thus, varying centrifuge parameters may affect the densities of the produced mercerized AA materials. Such changes may affect mixing capabilities, rheological properties, and extrusion forces of the mercerized AA materials.

Example 12—Mass Density and Dry Mass Percentages of Mercerized Apple Under Set Centrifuge Conditions Mercerized AA samples were prepared according to the procedure outlined in Example 10. It is noted that the mercerized AA material was concentrated (pelletized) using only an Avanti centrifuge at 8000 RPM for 15 min.

The wet mass of the mercerized AA material was recorded for each sample. The material was then transferred to a 15 mL Falcon tube. The weight of the tube, lid, and mercerized AA material was recorded.

The samples were then frozen at −20° C. and mounted on a Buchi freeze-dryer at 0.1 mbar and −55° C. After 24 hours, the samples were removed. The mass of the tubes, lids, and samples were recorded to have a subtractable mass from which the dry mercerized AA material could be calculated in the event that material loss occurred during removal of the dry AA material from the tubes.

Lastly, the dry mercerized AA material was removed and weighed. The mass measurements are shown below in Table 19.

TABLE 19

| | Wet Mass in | Dry Mass in | Mass of | Wet Mass | Dry Mass |
|---|---|---|---|---|---|
| Sample | Tube (g) | Tube (g) | Tube (g) | (g) | (g) |
| 1 | 7.3040 | 6.4368 | 6.3960 | 0.9080 | 0.0408 |
| 2 | 7.3397 | 6.4494 | 6.4053 | 0.9344 | 0.0441 |
| 3 | 7.4154 | 6.4575 | 6.4099 | 1.0055 | 0.0476 |
| 4 | 7.4244 | 6.3962 | 6.3719 | 1.0525 | 0.0243 |
| 5 | 7.4085 | 6.4081 | 6.3810 | 1.0275 | 0.0271 |

Mass Measurements of Mercerized AA Samples before and after Freeze-drying

Using the dry masses, the dry mass percentages of the wet masses were calculated. The results are shown in Table 20.

TABLE 20

| Dry Mass Percentages of Wet Mass | |
| --- | --- |
| Sample | Dry Mass (%) |
| 1 | 4.49 |
| 2 | 4.72 |
| 3 | 4.73 |
| 4 | 2.31 |
| 5 | 2.64 |

The average dry mass percentage was therefore 3.78, with a standard deviation of 1.20 and a standard error of 0.54.

In addition to dry mass percentage, the mass densities of the samples were also calculated. To calculate the mass densities, 1 mL of wet mercerized AA material from each sample was loaded into a syringe and extruded. The results are shown in Table 21.

TABLE 21

| Mass Densities of Wet Mercerized AA Material | |
| --- | --- |
| Sample | Wet Mass Density (g/mL) |
| 1 | 0.93 |
| 2 | 0.87 |
| 3 | 0.94 |
| 4 | 0.94 |

Thus, the average density was 0.92, with a standard deviation of 0.03 and a standard error of 0.02.

The calculated density matches the semi-quantitative observation made during preparation of the mercerized AA materials—that that 50 mL Falcon tubes contained about 50 g of material. This means that the mass densities of the wet mercerized AA materials is similar to that of water. As such, a wet density measurement alone may be insufficient to gauge the concentration of the mercerized AA material. A lyophilized dry mass may be used instead of or in combination with the wet mass.

Conclusion

The results of this Example may be used for quality assurance purposes when up-scaling the methods of the present disclosure. For example, the data may be used to standardize the amount the mercerized material that is present in a particular product.

As well, the results may influence potential standard operating procedures (SOP) when up-scaling the methods described herein. For example, SOPs may be implemented to reduce variabilities in mass throughout the procedures caused by "dead" head-space in syringes or by the transferring of mass into, out of, or between tubes.

Example 13—Mass Densities and Dilutions of Mercerized Apple

This study sought to determine whether the dry mass content of mercerized AA could be adjusted by calculating the mass density of the stock material and diluting accordingly.

Wet and dry mercerized AA samples were prepared according to the procedure outlined in Example 10 and Example 12. After the samples were prepared, they were diluted. The masses of the samples during preparation and before and after dilution are shown below in Table 22.

TABLE 22

| | Masses of Diluted Mercerized Apple (merAA) Samples | | | | | |
| --- | --- | --- | --- | --- | --- | --- |
| Sample | Empty tube + lid (g) | Tube + wet merAA (g) | Wet mass (g) | Tube + dried merAA (g) | Dry mass (g) | Dry/ wet mass (%) |
| | | | Undiluted | | | |
| 1 | 6.3891 | 7.9768 | 1.5877 | 6.4952 | 0.1061 | 6.6826 |
| 2 | 6.3499 | 7.9368 | 1.5869 | 6.4628 | 0.1129 | 7.1145 |
| 3 | 6.2721 | 7.8584 | 1.5863 | 6.3783 | 0.1062 | 6.6948 |
| 4 | 6.3523 | 7.8705 | 1.5182 | 6.5218 | 0.1695 | 11.1645 |
| 5 | 6.3691 | 7.9250 | 1.5559 | 6.4236 | 0.0545 | 3.5028 |
| 6 | 6.3520 | 7.9066 | 1.5546 | 6.4430 | 0.0910 | 5.8536 |
| Average | 6.3474 | 7.9124 | 1.5649 | 6.4541 | 0.1067 | 6.8355 |
| | | | Intermediate Dilution | | | |
| 1 | 6.3763 | 7.9099 | 1.5336 | 6.4370 | 0.0607 | 3.9580 |
| 2 | 6.347 | 7.9078 | 1.5608 | 6.4098 | 0.0628 | 4.0236 |
| 3 | 6.3274 | 7.8943 | 1.5669 | 6.3942 | 0.0668 | 4.2632 |
| Average | 6.3502 | 7.9040 | 1.5538 | 6.4137 | 0.0634 | 4.0816 |
| | | | Diluted | | | |
| 1 | 6.3412 | 7.8371 | 1.4959 | 6.3751 | 0.0339 | 2.2662 |
| 2 | 6.4169 | 7.9348 | 1.5179 | 6.4611 | 0.0442 | 2.9119 |
| 3 | 6.0841 | 7.5938 | 1.5097 | 6.1310 | 0.0469 | 3.1066 |
| Average | 6.2807 | 7.7886 | 1.5078 | 6.3224 | 0.0417 | 2.7616 |

Then densities of the samples were calculated as the dry mass % of the original wet mass, as shown above in Table 22. Thus, it is clear that the densities of mercerized cellulose materials described herein may be adjusted via dilution.

Figure 51:
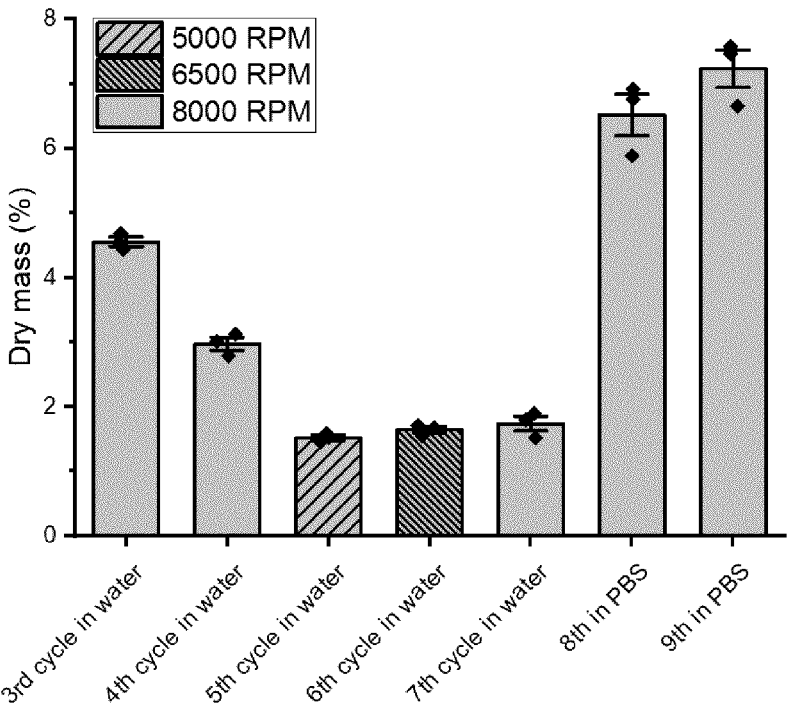
FIG. 51 shows the dry mass % of a mercerized apple (AA) sample after centrifugations in water or PBS as described in Example 13.

Further, as shown above, dilution by way of increased water washing and centrifugation in distilled water produced a less dense mercerized AA material after centrifugation. However, it was also found that incubation of the samples with PBS before the final centrifugation may restore the originally observed density of the sample. The effect of PBS on the density of a mercerized AA sample is shown in FIG. 51.

Qualitatively, it appeared that a density of about 4% to about 5% or more were suitable for use in dermal fillers.

Example 14—Relationship Between NaOH and Apple During Mercerization

This study sought to investigate suitable mass to volume ratios of AA material to NaOH solution for AA mercerization. In more detail, generally, a 1:5 ratio of decellularized AA to 1M NaOH is used for mercerization procedures. This study aimed to determine a minimum ratio of AA material to NaOH solution that will yield mercerized AA in particle sizes small enough to be suitable for use in dermal fillers.

Figure 53:
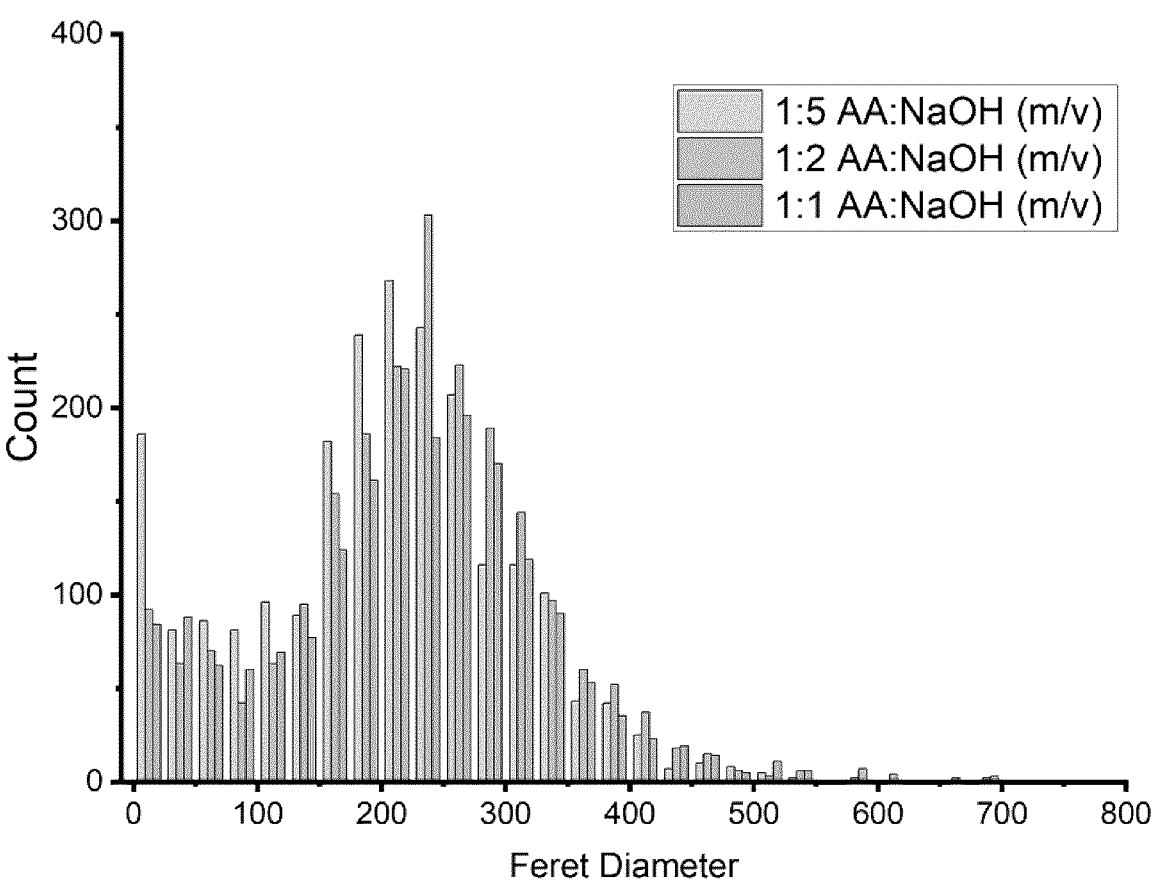
FIG. 53 shows the particle size distributions of the samples described in Example 14 and imagined in FIG. 52.

The experimental protocol is described below:
1. Three portions of decellularized AA were weighed: 20 g, 50 g, and 100 g. All AA material was pressed to remove excess water.
2. Three 1 L beakers were filled with 100 mL of 1M NaOH and placed on magnetic stir plates.

calculated with the Analyze Particles plugin. The results are shown in FIG. 53. As shown, the histograms of particle sizes were similar across the three different ratios of AA:NaOH.

An ANOVA analysis was also performed with a Tukey post-hoc analysis at a significance level of 0.05. The results are shown in Tables 23 and 24.

TABLE 23

| Statistics of the Particle Size Distributions | | | | |
|---|---|---|---|---|
| Ratio (AA:NaOH) | N | Mean | Standard Deviation | SE of Mean |
| 1:5 | 2237 | 199.81148 | 106.08425 | 2.24294 |
| 1:2 | 2158 | 228.0239 | 106.3168 | 2.28863 |
| 1:1 | 1878 | 219.72194 | 109.23839 | 2.52074 |

TABLE 24

| ANOVA of the Particle Size Distributions | | | | | | | | |
|---|---|---|---|---|---|---|---|---|
| Ratios | MeanDiff | SEM | q Value | Prob | Alpha | Sig | LCL | UCL |
| 1:2 and 1:5 | 28.21242 | 3.23208 | 12.34451 | 3.33E−16 | 0.05 | 1 | 20.63741 | 35.78744 |
| 1:1 and 1:5 | 19.91046 | 3.35247 | 8.39907 | 8.60E−09 | 0.05 | 1 | 12.05327 | 27.76764 |
| 1:1 and 1:2 | −8.30197 | 3.38036 | 3.47323 | 0.03739 | 0.05 | 1 | −16.2245 | −0.37942 |

3. All solutions were heated to 80° C.; then, a stir bar and one of the portions of decellularized AA was added to each and labelled appropriately, corresponding to the weight of AA added.
4. 5 mL of 30% hydrogen peroxide ($H_2O_2$) was added to each beaker.
5. All three solutions were stirred for 1 hour at 80° C.
6. After the mercerization, all beakers were removed from their respective hot plates and left to cool completely to room temperature.
7. Once cooled, all three solutions were neutralized and centrifuged separately until a neutral and stable pH was obtained (pH range: 6.8-7.2).
8. The three conditions tested (i.e. 20 g of AA in 100 mL NaOH, 50 g of AA in 100 mL NaOH, and 100 g of AA in 100 mL NaOH) were stored separately in 50 mL Falcon tubes in a fridge for subsequent microscopy.
9. For particle analysis, each of the three AA to NaOH conditions were resuspended in distilled water, stained with Congo red for 10 minutes, and mounted on a microscope slide.
10. Using a SZX16 Olympus microscope, slides were imaged at 2.5× magnification using fluorescence microscopy (BV light filter).

Figure 52:
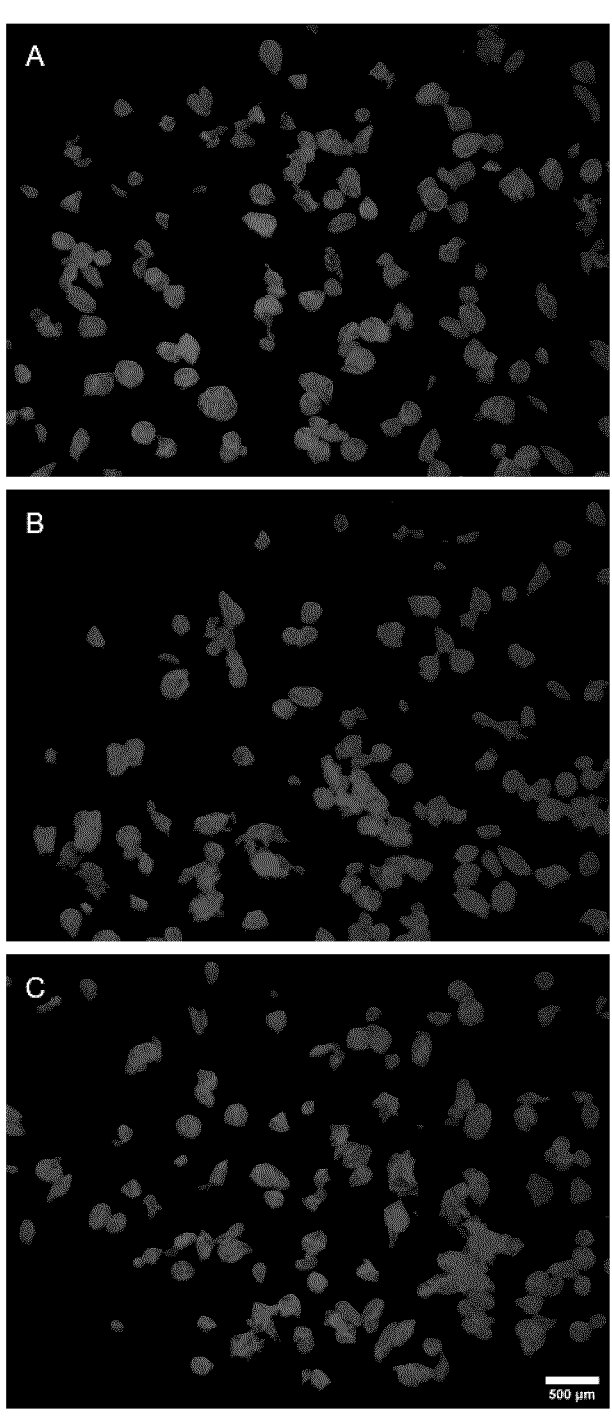

The microscopy images are shown in FIG. 52, wherein FIG. 52A is the 1:5 AA:NaOH, FIG. 52B is the 1:2 AA:NaOH, and FIG. 52C is the 1:1 AA:NaOH. As shown, sufficient mercerization may be achievable with a 1:1 ratio of AA to NaOH solution. As well, while the 1:1 and 1:2 ratios of AA:NaOH had some larger particles, the larger particles were generally infrequent throughout the images.

The microscopy images were thresholded and segmented using Fiji ImageJ. A watershed was applied to the image after it was converted to binary. The ferret diameter was Thus, while the particle size distributions were qualitatively similar, the means of the three distributions were statistically different from each other. Tests for variances showed no significant differences and, as a result, the differences in the means may be a result of real differences, limited sample size, clumping in the higher concentration of AA samples, or variations in the stating apple material.

In view of the above, while the 1:1 and 1:2 ratios of AA:NaOH may be used for mercerization, a 1:5 ratio may be optimal due at least in part to the solution being the least viscous. It is noted that higher concentrations of AA may yield similar results but may be more difficult to mix.

Example 15—Removing Small Particles from Mercerized Apple

This study sought to investigate removing smaller particles (e.g. less than 20 μm) during particle filtration of mercerized material.

In this study, unfiltered, ground decellularized pear particles were mixed with mercerized decellurized AA material because such pear particles generally comprise more particles having a size of less than 20 μm than apple particles.

10 mL of mercerized AA was combined with 10 mL of unfiltered decellularized pear powder. The sample was diluted with distilled water to a final volume of 750 mL.

The study was conducted according to the below procedure:
1. Create the mixture.
2. Collect an aliquot for staining and imaging.
3. Centrifuge the material on the Avanti centrifuge (8000 RPM for 15 min) to form a pellet.
4. Collect an aliquot from the supernatant for staining and imaging.

5. Remove the supernatant.

6. Collect an aliquot from the pellet for staining and imaging.

7. Sieve the pellet on a 45 μm autoclavable Gilson sieve with a sieve vibrator to filter the material and three washings with 150 mL of dH₂O.

8. Collect an aliquot of the sieved material for staining and imaging.

9. Concentrate the material by centrifugation again.

10. Discard the supernatant.

11. Collect a sample from the final material for staining and imaging.

Staining was completed by adding an equal volume of 0.2% Congo Red (0.5 mL) to the sample. Due to variations in concentration, the samples were diluted as necessary. The stained particles were imaged with a SZX16 Stereo Microscope at 2.5× and 10× magnification with the BV filter. The images were analyzed using Fiji ImageJ.

N=20 images per condition were assembled into a stack. The stack was converted into binary and the brightness and contrast settings were adjusted appropriately. In order to segment the image without spurious noise, a Gaussian filter was applied (2 px for 2.5× and 5 px for 10×). The Analyze Particles plugin was used. No particle size restrictions were applied to the 2.5× images due to the small size of the single pixels. For the 10× images, the lower bound was set to single pixel noise (0.8 μm²). The ferret diameter was used as a measure of the particle size.

Results

Figure 54:
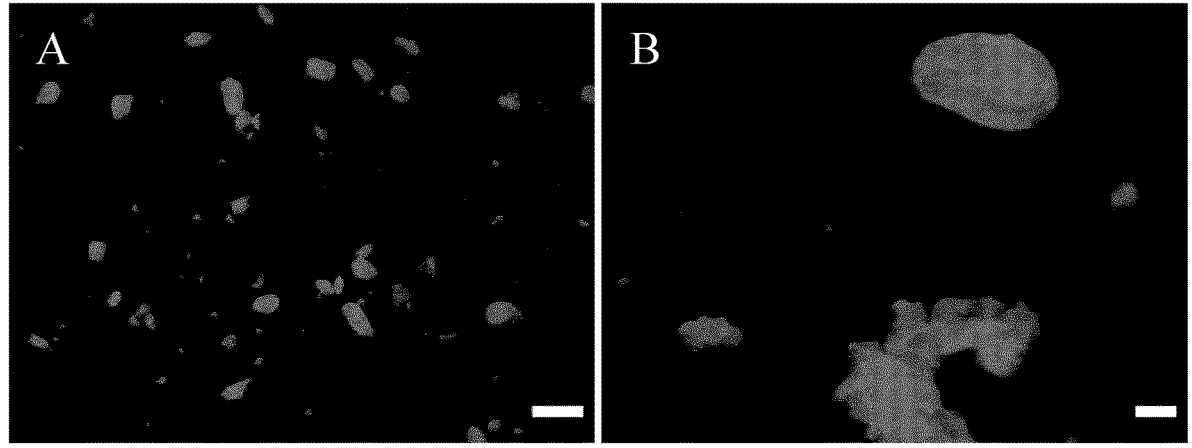

FIG. 54 shows microscopy images of the initial mercerized AA and pear powder mixture (before centrifugation) stained with Congo Red, wherein FIG. 54A shows a microscopy image with a scale of 500 μm, and FIG. 54B shows a microscopy image with a scale of 100 μm. As shown, particles having a size of less than 20 μm were observed. As discussed above, this was expected because of the addition of the pear powder.

Figure 55:
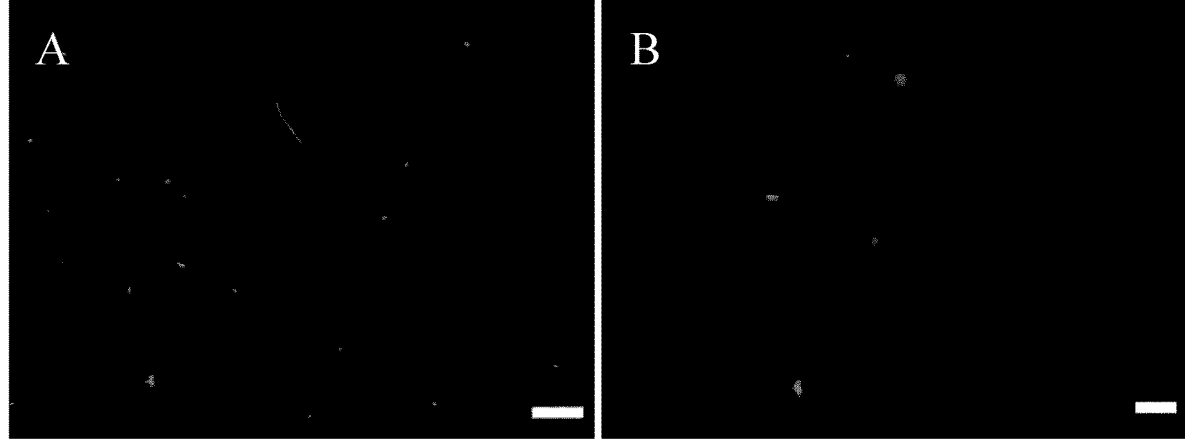

FIG. 55 shows microscopy images of the supernatant stained with Congo Red collected after the first centrifugation of the mixture, wherein FIG. 55A shows a microscopy image with a scale of 500 μm, and FIG. 55B shows a microscopy image with a scale of 100 μm. As shown, the supernatant had small particles that were not concentrated in the pellet.

Figure 56:
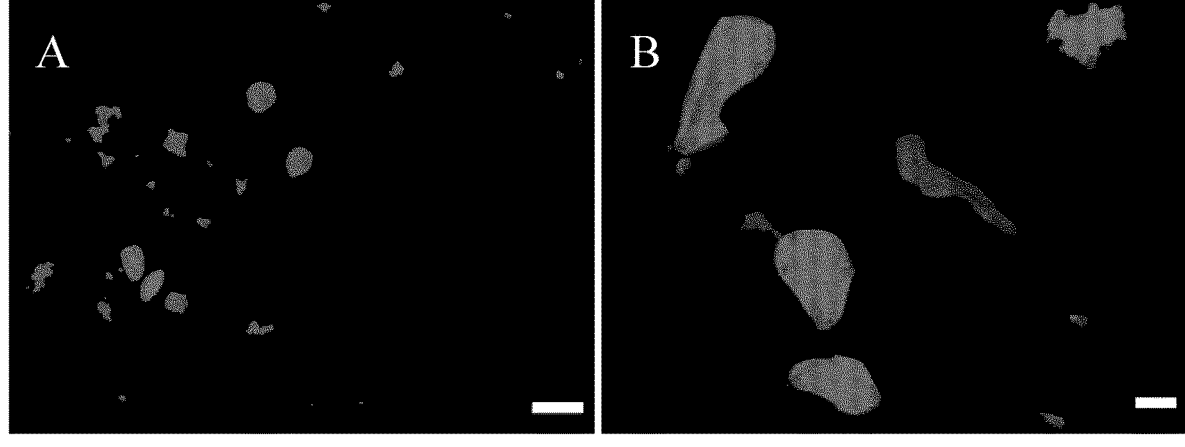

FIG. 56 shows microscopy images of the pellet formed after the first centrifugation of the mixture stained with Congo Red, wherein FIG. 56A shows a microscopy image with a scale of 500 μm, and FIG. 56B shows a microscopy image with a scale of 100 μm. As shown, particles having a size of less than 20 μm were observed, similar to the initial mixture.

Figure 57:
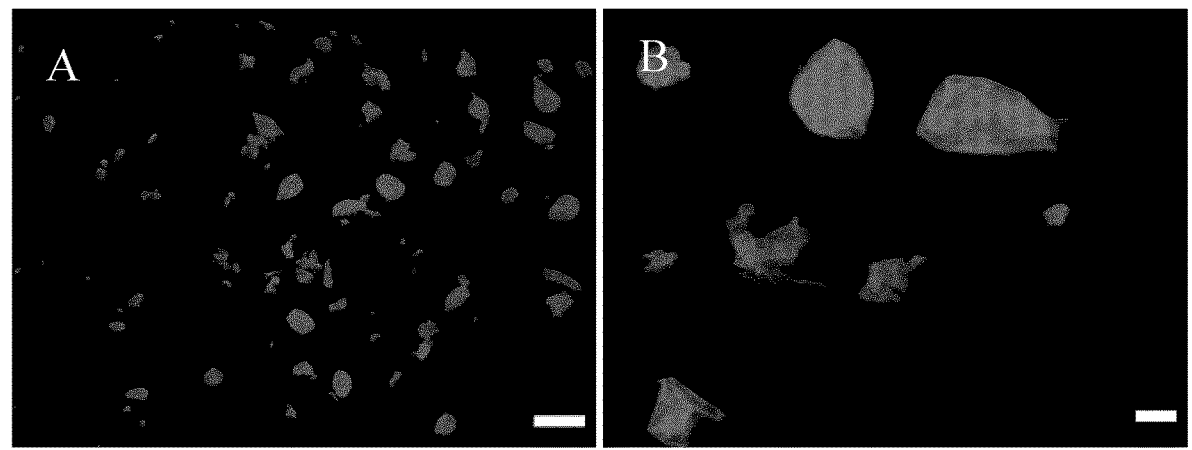

FIG. 57 shows microscopy images of a sample the pellet after sieving stained with Congo Red, wherein FIG. 57A shows a microscopy image with a scale of 500 μm, and FIG. 57B shows a microscopy image with a scale of 100 μm. As shown, there were few particles having a size of less than 20 μm observed.

Figure 58:
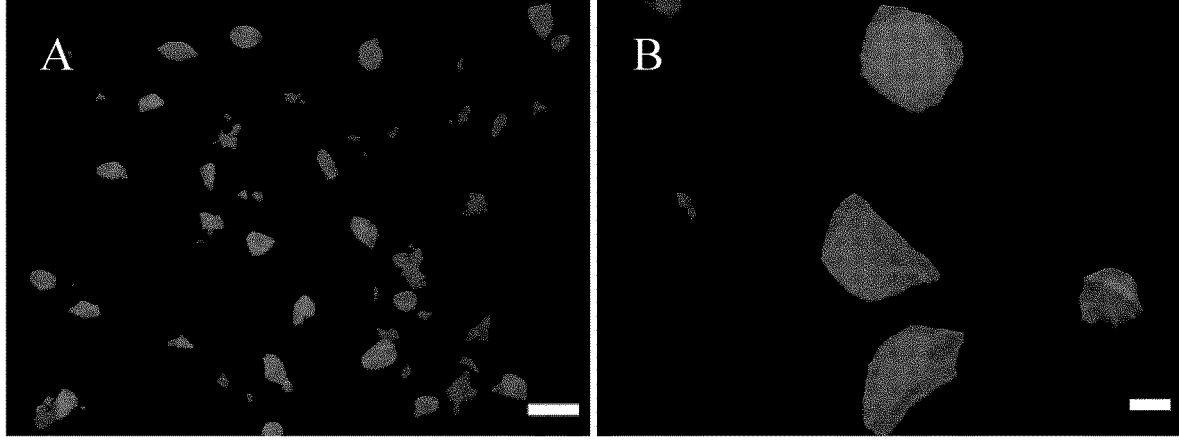

FIG. 58 shows microscopy images of a sample of the pellet after the final centrifugation stained with Congo Red, wherein FIG. 58A shows a microscopy image with a scale of 500 am, and FIG. 58B shows a microscopy image with a scale of 100 am. As shown, there were few particles having a size of less than 20 μm observed. It is noted that the size distribution of particles is large due to the two types of material present in the mixture.

Figure 59:
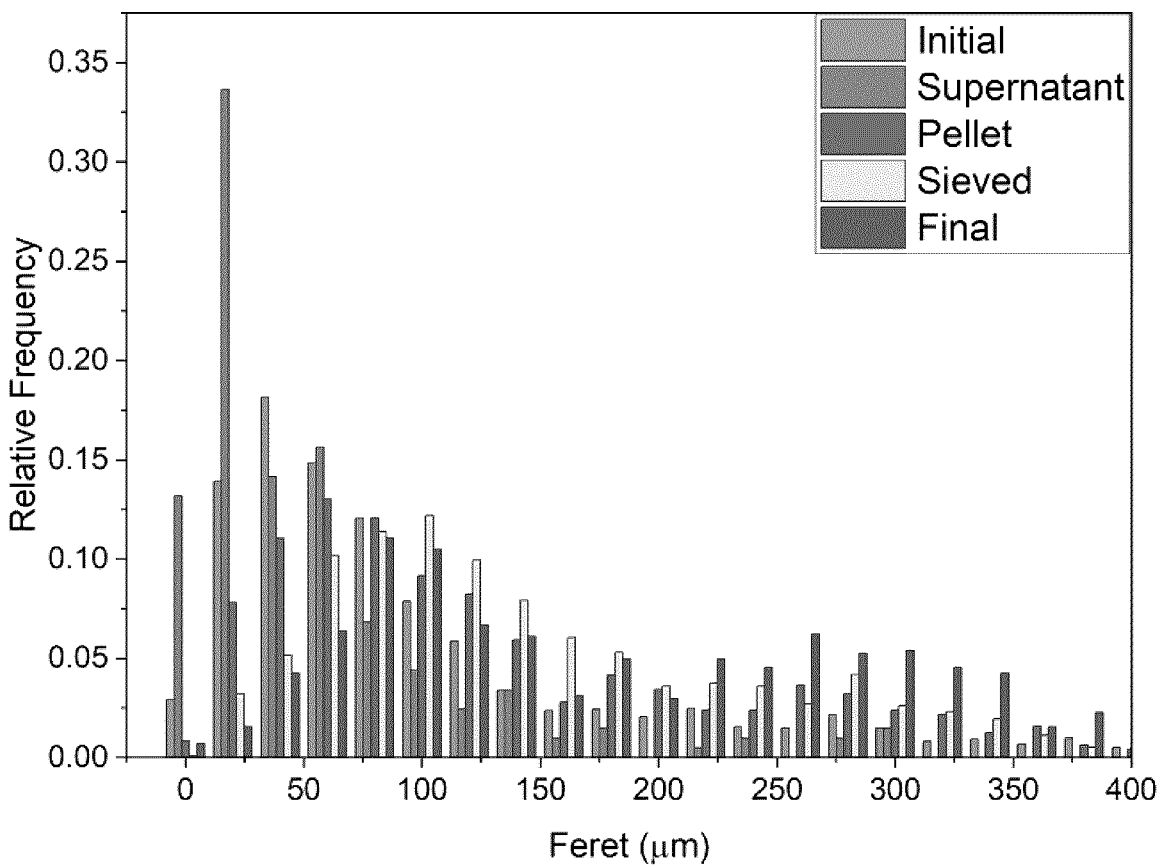
FIG. 59 shows the relative frequencies of certain particle diameters of each of the microscopy images taken at 2.5× shown in FIG. 54 to FIG. 58.
Figure 60:
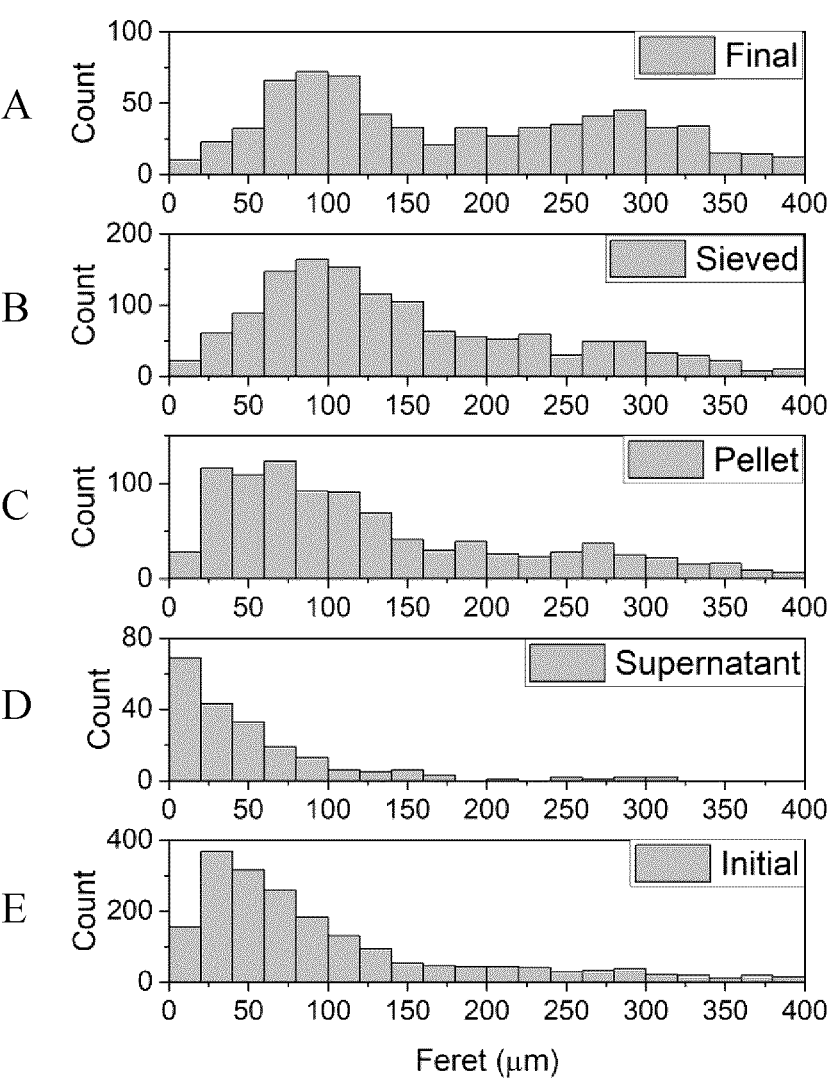

FIG. 59 shows the particle distributions of each of the microscopy images taken at 2.5× presented as relative frequencies of the ferret diameters of the particles. FIG. 60 shows the particle distributions of each of the microscopy images taken at 2.5×, wherein FIG. 60A shows the particle size distribution of the pellet after the final centrifugation, FIG. 60B shows the particle size distribution of the sieved pellet, FIG. 60C shows the particle size distribution of the pellet after the first centrifugation, FIG. 60D shows the particle size distribution of the supernatant, and FIG. 60E show the particle size distribution of the initial mixture.

Figure 61:
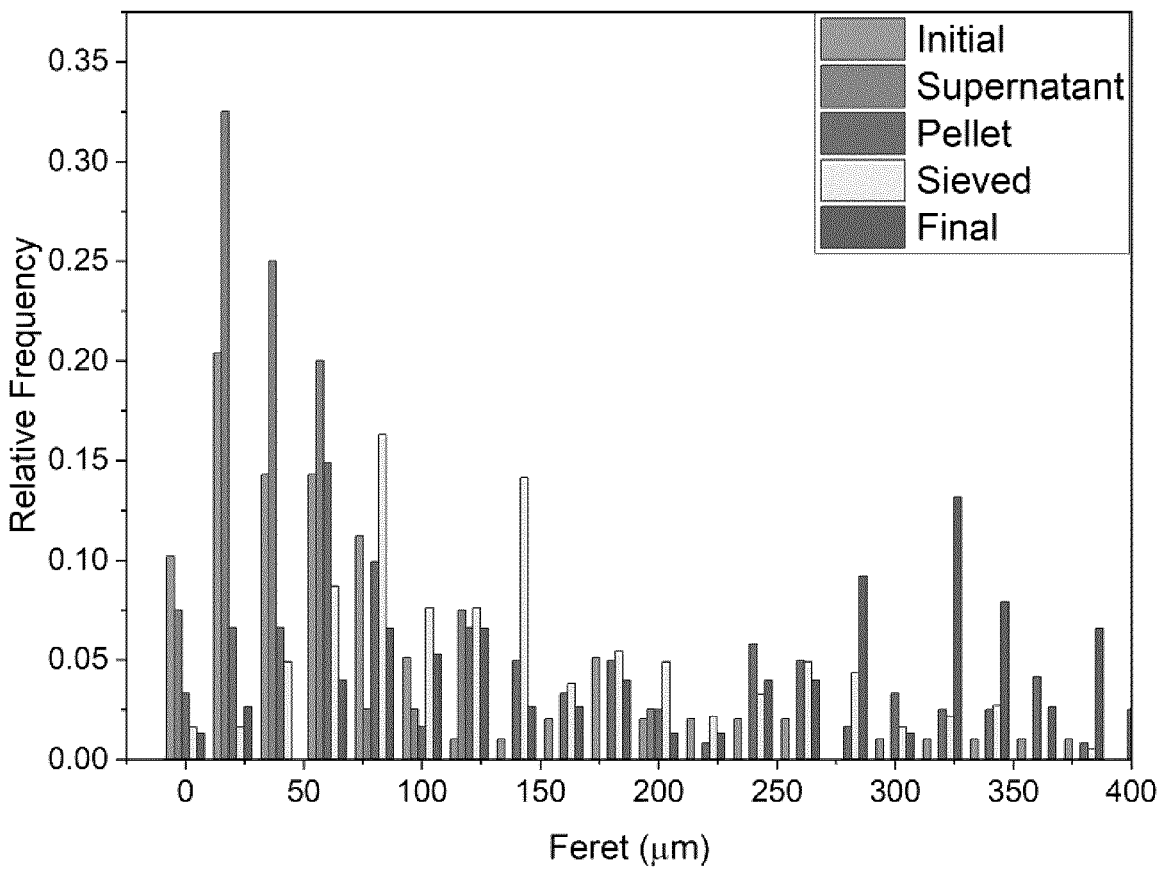
FIG. 61 shows the relative frequencies of certain particle diameters of each of the microscopy images taken at 10× shown in FIG. 54 to FIG. 58.
Figure 62:
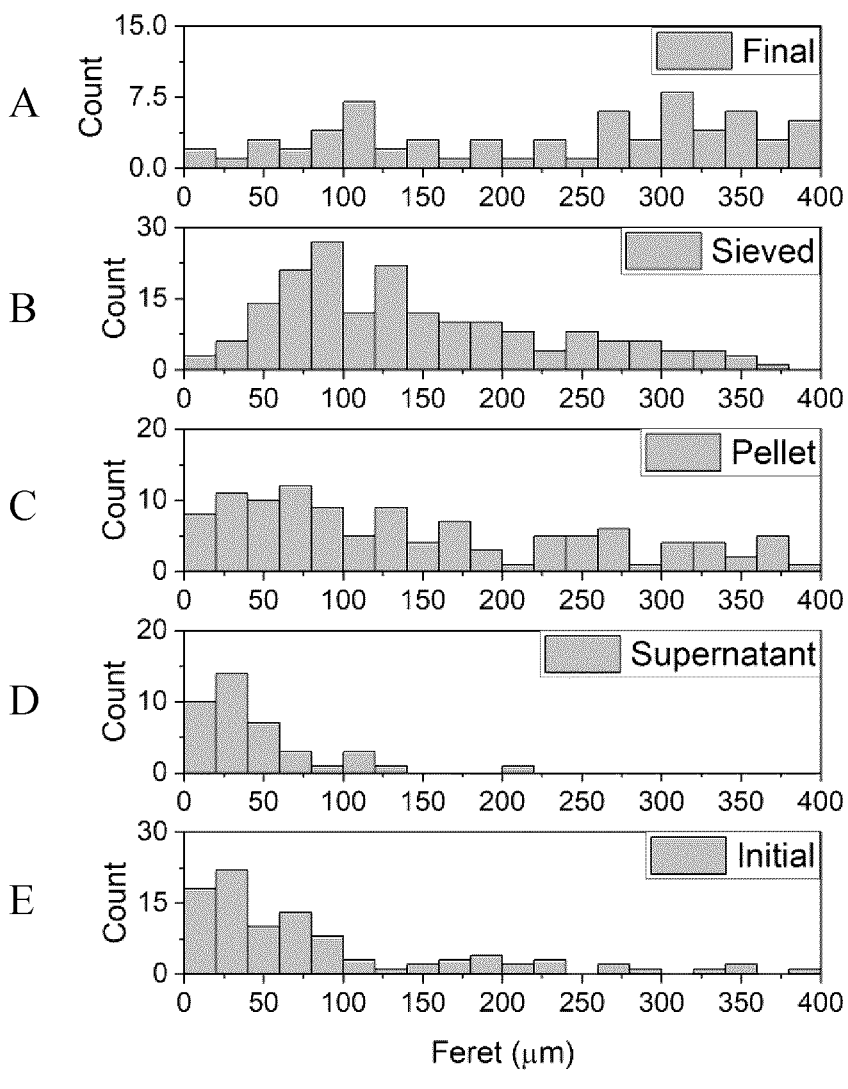

FIG. 61 shows the particle distributions of each of the microscopy images taken at 10× presented as relative frequencies of the ferret diameters of the particles. FIG. 62 shows the particle distributions of each of the microscopy images taken at 10×, wherein FIG. 62A shows the particle size distribution of the pellet after the final centrifugation, FIG. 62B shows the particle size distribution of the sieved pellet, FIG. 62C shows the particle size distribution of the pellet after the first centrifugation, FIG. 62D shows the particle size distribution of the supernatant, and FIG. 62E show the particle size distribution of the initial mixture.

As shown, the presence of particles having a size of less than 20 μm was significantly reduced after sieving. It appears that centrifugation after sieving does not result in the creation of many small particles. Moreover, the supernatant sample contained small particles. Therefore, the centrifugation may help remove small particles by means of differential centrifugation. This conclusion is supported at least in part by the 10× images. The 2.5× images have greater N values; however, the complement of the 10× images is useful as the single pixel size for the 2.5× image is 12.25 μm².

Further, it is be noted that the distributions do not match those of the pure materials. The bimodal distributions were expected as this test involved a mixture of two components.

The percentages of particles having a size of less than 20 μm were also calculated and are shown in Table 24.

TABLE 25

| Percentages of Particles having a Size of less than 20 μm | | | | |
| --- | --- | --- | --- | --- |
| Initial Mixture | Supernatant | Pellet After first Centrifugation | Sieved material | Material After Final Centrifugation |
| 8.04% | 36.67% | 2.91% | 1.65% | 1.42% |

Thus, it is clear that the methods of the present disclosure may be effective for removing smaller-sized particles that may not be suitable for use in dermal fillers.

Example 16—Particle Size of Mercerized Material after Extrusion

This study sought to examine the particle sizes of mercerized decellularized plant tissue before and after extrusion through a syringe.

Undiluted mercerized AA material prepared using the procedure outlined in Example 10 was loaded into a syringe by back-filling the material after the plunger shaft was removed. Once the material was transferred, the plunger was inserted and a 27 G needle was affixed to the syringe. Next, the plunger from a second syringe was removed, and the first syringe was used to extrude material through the 27 G needle. This step was performed to remove any large material that could clog the needle.

The AA material was stained with a final concentration of 0.1% Congo Red. To perform the staining, 1 mL of the AA material was combined with 1 mL of 0.2% 0.22 µm filtered Congo Red with an F/F luer lock connector. The solutions were mixed back and forth 30 times. The stained solution was left to incubate for 10 min at room temperature. The resultant solution was too concentrated for particle analysis imaging, so a 1/64 dilution with sterile water for irrigation was used. For the control sample, the AA material was not extruded through the 27 G needle at any point.

A SZX16 Stereo Microscope was used to image the samples at 2.5× with a 2-pixel Gaussian blur filter. Ten separate images of representative areas were collected for both the control (before) and the after-extrusion samples.

For the particle analysis, the images were imported into Fiji ImageJ and combined into a stack. Preliminary brightness and contrast settings were adjusted. The images were converted to 8-bit files, and then they were thresholded to ensure the particles were captured. The images were converted to binary and a watershed plugin was applied. The resultant stack was analyzed with the Analyze plugin. The ferret diameter was used as the particle size parameter.

Figure 63:
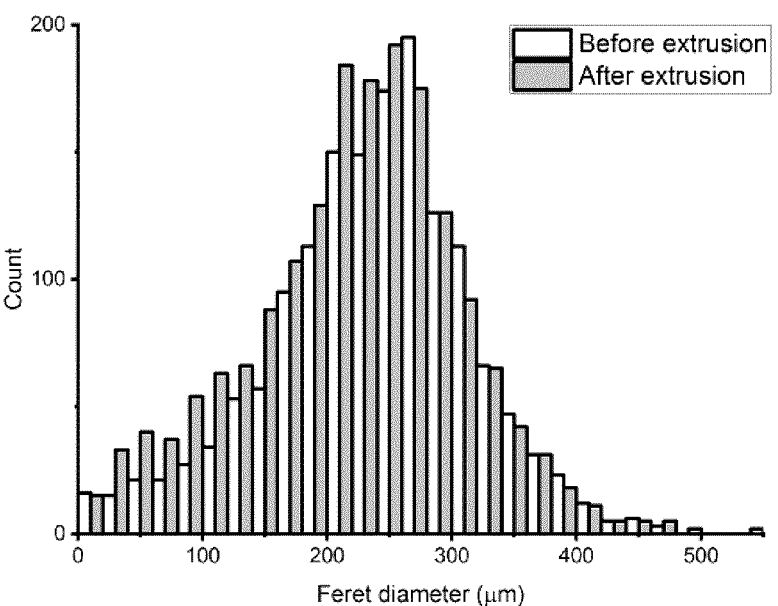
FIG. 63 shows the particle size distributions of a mercerized AA sample before and after extrusion as described in Example 16.

FIG. 63 shows the particle size distributions for the AA material before and after extrusion. Descriptive statistics of the particle size distributions are shown in Table 26.

TABLE 26

| Descriptive Statistics of the Particle Size Analyses | | | | |
| --- | --- | --- | --- | --- |
| Solution | N | Mean (µm) | Standard deviation (µm) | Standard error (µm) |
| Before extrusion | 1958 | 236.136 | 81.43 | 2.06 |
| After extrusion | 1763 | 220.66 | 85.37 | 2.03 |

Thus, it is clear that extrusion through a 27 G needle does not cause an increase in particles having a size of less than 20 µm.

It was also found that the percentages of particles under 20 µm were 1% and 0.85% for the before and after extrusion populations respectively, which is in line with conventional dermal filler formulations.

Example 17—Effect of Concentration of Mercerized Particles on Extrusion Force

This study sought to investigate the effect of the concentration of mercerized particles on the extrusion force of dermal fillers.

Three formulations were tested. The formulations were made in 5 ml syringes and transferred to 1 cc syringes for a

TABLE 27

| Formulations Prepared for Extrusion Force Study | |
| --- | --- |
| Formulation | Components |
| Water | Water |
| Mer20Sal80 | 20% (v/v) mercerized, decellularized AA diluted in 0.9% saline |
| Mer100 | Undiluted mercerized, decellularized AA |

A CellScale Univert device was used to test the extrusion forces of the formulations. One of the 1 cc syringes containing one of the formulations was positioned within the device using two clamps secured to two adjacent retort stands.

The effects of needle size, syringe type, and extrusion rate were also investigated. With respect to needle sizes, the 1 cc syringes were equipped with 27 G needles and 30 G needles and the results were compared therebetween. For the comparison between syringe types, tests were completed using standard 1 cc syringes and BellaFill syringes. For the extrusion rates, the formulations were extruded from the 1 cc syringes equipped with 27 G needles at extrusion rates of 1 mm/s, 2.5 mm/s, and 5 mm/s. These tests were completed using only the Mer100 formulation.

Results

Figure 64:
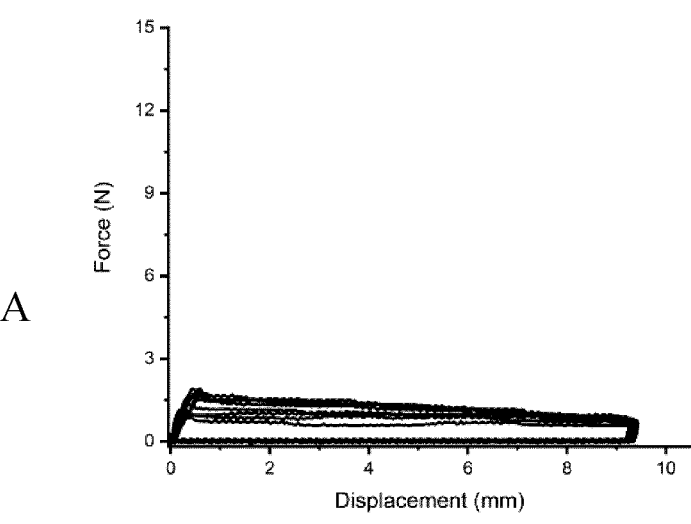
Figure 64:
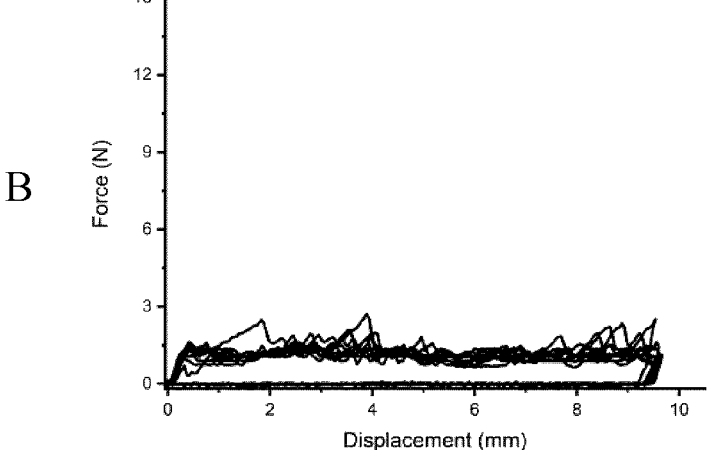
Figure 64:
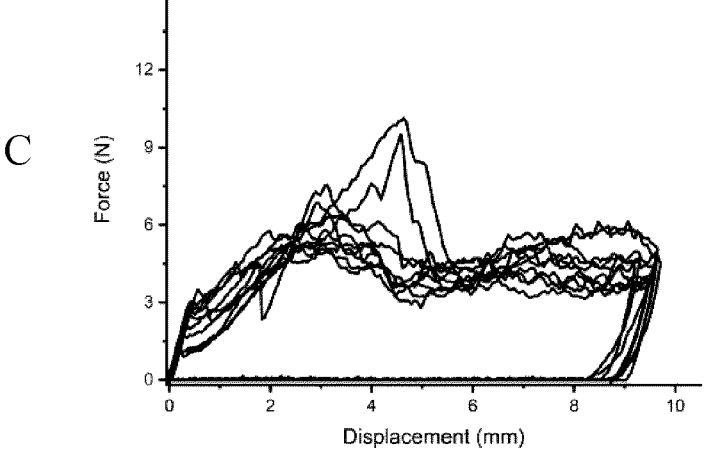

FIG. 64 shows the results of the extrusion force tests, wherein FIG. 64A shows the force-displacement curves for N=10 extrusions of water from the 1 cc syringe, FIG. 64B shows the force-displacement curves for N=10 extrusions of the Mer20Sal80 formulation from the 1 cc syringe, and FIG. 64C shows the force-displacement curves for N=10 extrusions of the Mer100 formulation from the 1 cc syringe.

Figure 65:
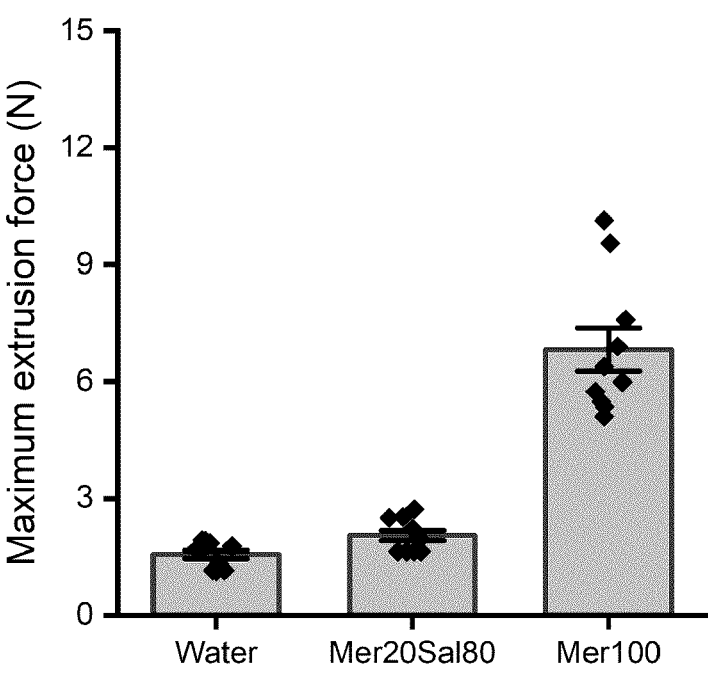
FIG. 65 shows the maximum extrusion forces of the force-displacement curves shown in FIG. 64.

FIG. 65 shows the maximum extrusion forces recorded for each of the formulations. The statistics of the maximum extrusion forces are shown in Table 28.

TABLE 28

| Statistics of Maximum Extrusion Forces | | | | |
| --- | --- | --- | --- | --- |
| Formulation | Number of Runs | Mean (N) | Standard deviation (N) | Standard error (N) |
| Water | 10 | 1.55 | 0.35 | 0.11 |
| Mer100 | 10 | 6.82 | 1.77 | 0.57 |
| Mer20Sal80 | 10 | 2.04 | 0.41 | 0.15 |

An ANOVA analysis was performed on the recorded maximum extrusion forces, the results of which are shown below in Table 29.

TABLE 29

| ANOVA Analysis of the Maximum Extrusion Forces | | | | | | | | |
| --- | --- | --- | --- | --- | --- | --- | --- | --- |
| Comparison | MeanDiff | SEM | q Value | Prob | Alpha | Sig | LCL | UCL |
| Mer20Sal80 + Water | 0.48633 | 0.47671 | 1.44276 | 0.5708 | 0.05 | 0 | −0.69561 | 1.66827 |
| Mer100 + Water | 5.26518 | 0.47671 | 15.61984 | 0 | 0.05 | 1 | 4.08324 | 6.44713 |
| Mer100 + Mer20Sal80 | 4.77885 | 0.47671 | 14.17708 | 0 | 0.05 | 1 | 3.59691 | 5.9608 | volume of 0.3 ml. Interlock connectors were used to thoroughly mix the formulations between the syringes. The formulations were mixed back and forth between the syringes 30 times. The formulations tested are outlined below in Table 27.

The plateau extrusion forces of the formulations were also analysed. The plateau extrusion forces represent the average extrusion of the formulations and therefore exclude the ramping up of the extrusion forces as well as the release of the extrusions forces after the extrusions are completed.

With respect to the recorded force-displacement curves, the plateau extrusion forces correspond to the displacement range of about 1 mm to about 8 mm.

Figure 66:
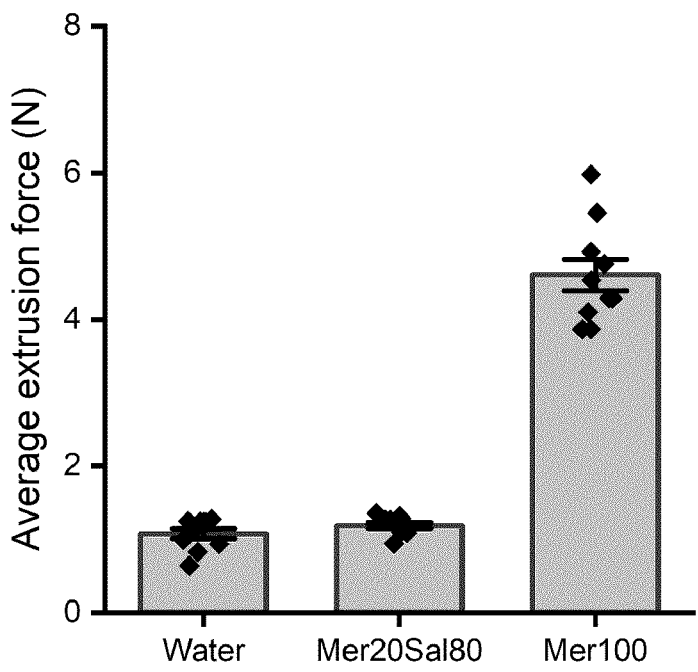
FIG. 66 shows the average (plateau) extrusion forces of the force-displacement curves shown in FIG. 64.

A comparison of the plateau extrusion forces is shown in FIG. 66. The descriptive statistics of the plateau extrusion forces are shown in Table 29, and the ANOVA analysis there of is shown in Table 30.

refers to the BellaFill syringe. The descriptive statistics of the maximum extrusion forces are shown in Table 31 and the ANOVA analysis thereof is shown in Table 32.

TABLE 29

Descriptive Statistics of Plateau Extrusion Forces

| Formulation | Number of Runs | Mean (N) | Standard deviation (N) | Standard error (N) |
|---|---|---|---|---|
| Water | 10 | 1.08 | 0.22 | 0.07 |
| Mer100 | 10 | 4.60 | 0.69 | 0.22 |
| Mer20Sal80 | 10 | 1.19 | 0.13 | 0.04 |

TABLE 31

Descriptive Statistics of Maximum Extrusion Forces for Different Needle Sizes and Syringe Types

| Syringe/Needle Combination | Number of Runs | Mean (N) | Standard deviation (N) | Standard error (N) |
|---|---|---|---|---|
| BF 27 G | 3 | 6.27 | 0.36 | 0.21 |
| BD 27 G | 3 | 5.58 | 0.40 | 0.23 |
| BD 30 G | 3 | 7.58 | 0.66 | 0.38 |

TABLE 30

ANOVA Analysis of the Plateau Extrusion Forces

| Comparison | MeanDiff | SEM | q Value | Prob | Alpha | Sig | LCL | UCL |
|---|---|---|---|---|---|---|---|---|
| Mer20Sal80 + Water | 0.11286 | 0.19029 | 0.83873 | 0.82498 | 0.05 | 0 | −0.35895 | 0.58466 |
| Mer100 + Water | 3.52897 | 0.19029 | 26.22704 | 0 | 0.05 | 1 | 3.05717 | 4.00077 |
| Mer100 + Mer20Sal80 | 3.41612 | 0.19029 | 25.38831 | 0 | 0.05 | 1 | 2.94432 | 3.88792 |

Thus, in light of the above, undiluted mercerized material (i.e. Mer100) has a significantly greater extrusion force than the Mer20Sal80 and water formulations. As well, there is no significant difference between the extrusion forces of the Mer20Sal80 and the water formulations. This means that,

TABLE 32

ANOVA Analysis of Maximum Extrusion forces for Different Needle Sizes and Syringe Types

| Combination | MeanDiff | SEM | q Value | Prob | Alpha | Sig | LCL | UCL |
|---|---|---|---|---|---|---|---|---|
| 27G BD + 27G BF | −0.68991 | 0.3992 | 2.44411 | 0.27061 | 0.05 | 0 | −1.91479 | 0.53497 |
| 30G BD + 27G BF | 1.30819 | 0.3992 | 4.63445 | 0.03876 | 0.05 | 1 | 0.08331 | 2.53307 |
| 30G BD + 27G BD | 1.9981 | 0.3992 | 7.07856 | 0.00585 | 0.05 | 1 | 0.77322 | 3.22298 | while the viscosities of Mer20Sal80 and the water formulations were slightly different, the difference was not discernable by the experiments outlined in this Example.

Figure 67:
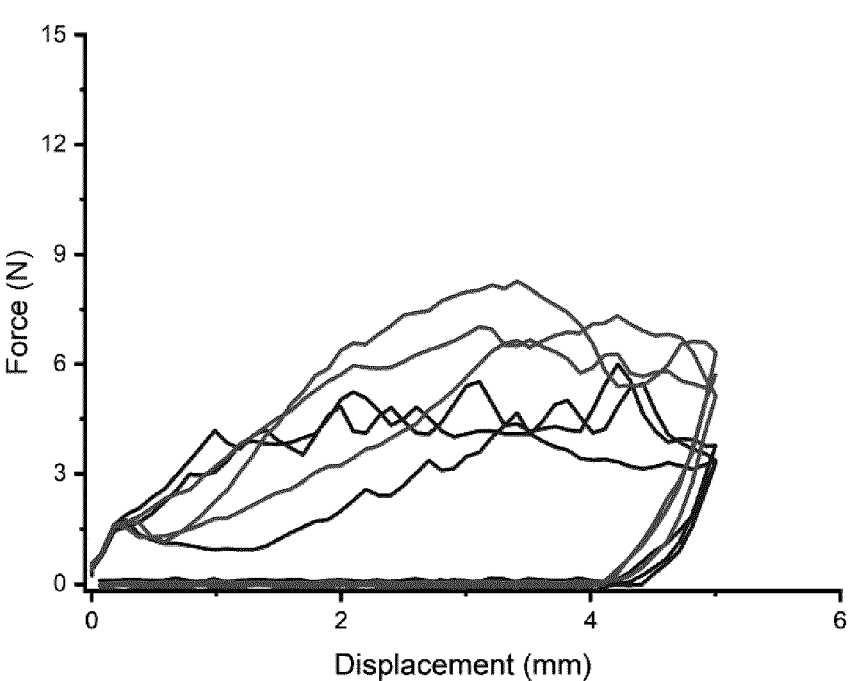
FIG. 67 shows the force-displacement curves of the Mer100 formulation extruded through a 27 G needle and a 30 G needle as described in Example 17.

FIG. 67 shows the force-displacement curves of the Mer100 formulation extruded through a 27 G needle (blue lines) and through a 30 G needle (red lines) at a cross-head rate of 1 mm/s.

Figure 68:
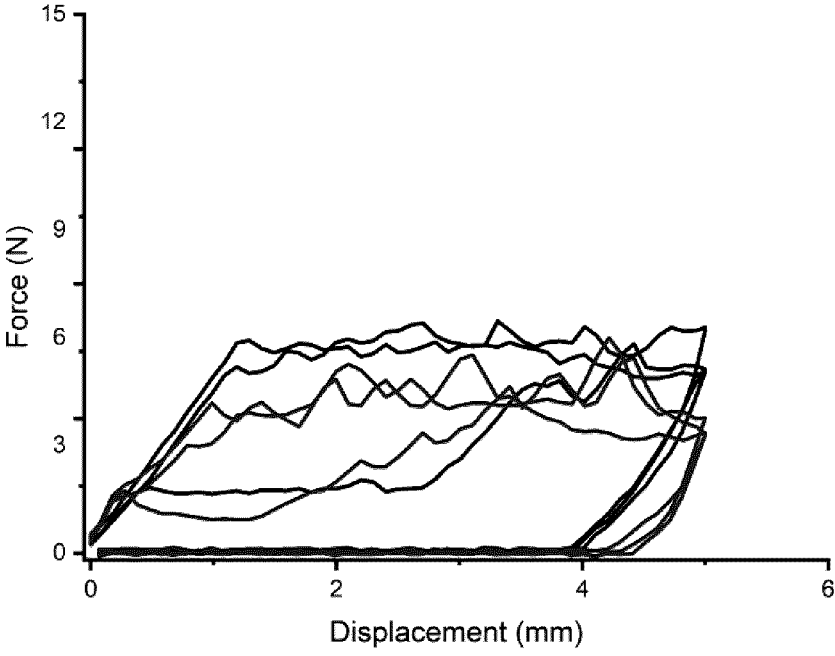
FIG. 68 shows the force-displacement curves of the Mer100 formulation extruded through a 27 G needle from a standard 1 cc syringe and a BellaFill syringe.

FIG. 68 shows the force-displacement curves of the Mer100 formulation extruded through 27 G needles at a cross-head rate of 1 mm/s from a standard 1 cc syringe (blue lines) and a BellaFill syringe (black lines).

Figure 69:
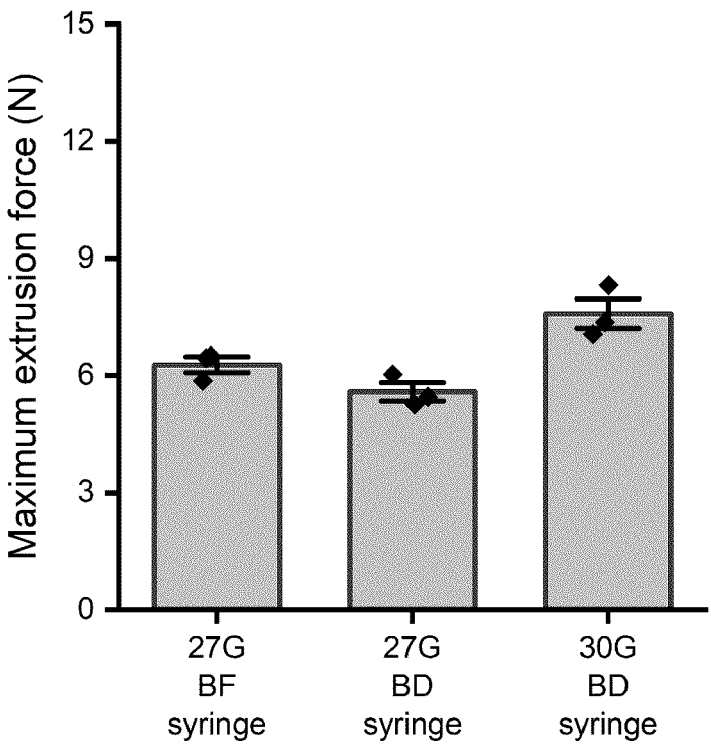
FIG. 69 shows the maximum extrusion forces of the force-displacement curves shown in FIG. 67 and FIG. 68.

The maximum extrusion forces for the runs performed in FIG. 67 and FIG. 68 are shown in FIG. 69, wherein "BD syringe" refers to the standard 1 cc syringe and "BF syringe"

One-way ANOVA shows that no significant difference in the maximum extrusion force was observed between the two syringe types. However, the 30 G needle had significantly higher extrusion forces than the 27 G needle.

Figure 70:
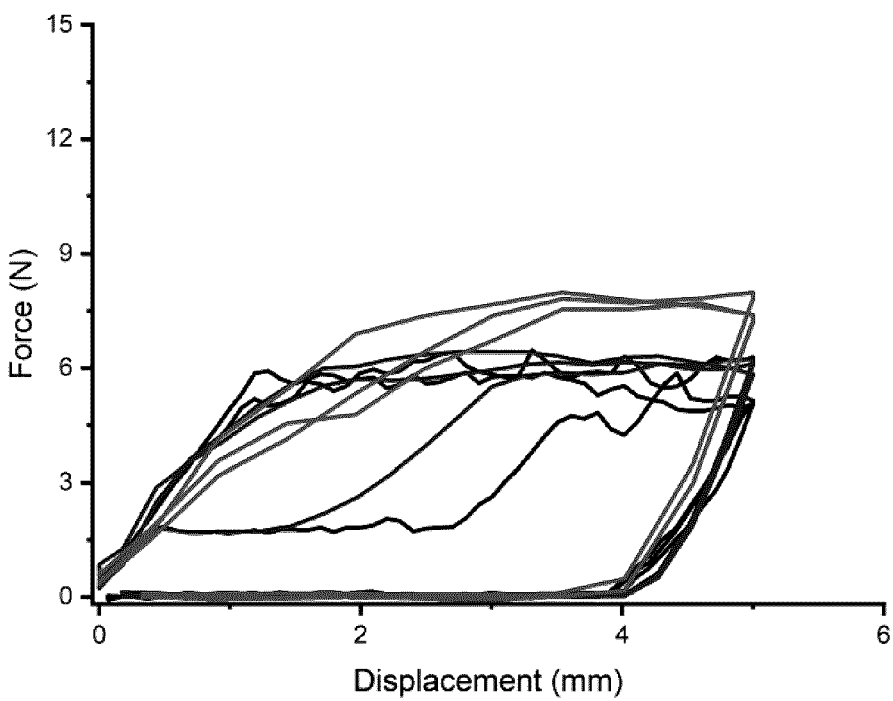
FIG. 70 shows the force-extrusion curves of the Mer100 formulation extruded through a 27 G needle at an cross-head speed of 1 mm/s, 2.5 mm/s, and 5.0 mm/s as described in Example 17.
Figure 71:
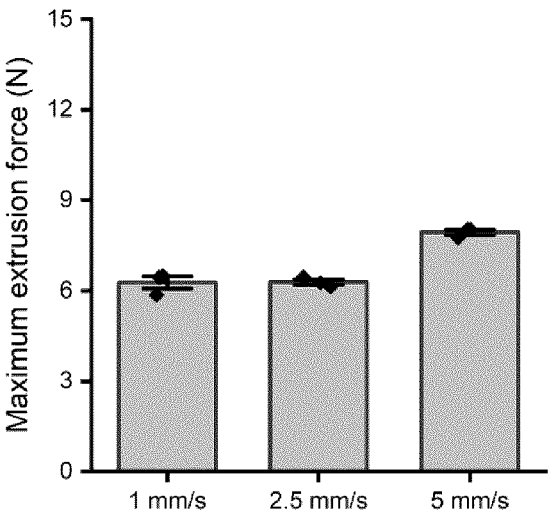
FIG. 71 shows the maximum extrusion forces of the force-displacement curves shown in FIG. 70.

FIG. 70 shows the force-extrusion curves of the Mer100 formulation extruded through 27 G needles at an cross-head speed of 1 mm/s (black lines), 2.5 mm/s (blue lines), and 5.0 mm/s (red lines). The maximum extrusion forces for each of the cross-head speeds are shown in FIG. 71. The descriptive statistics for the maximum extrusion forces for each of the cross-head speeds are shown in Table 33 and the ANOVA analysis thereof is shown in Table 34.

TABLE 33

| Maximum Extrusion Forces for Different Cross-head Speeds | | | | |
|---|---|---|---|---|
| Cross-head speed (mm/s) | Number of Runs | Mean (N) | Standard deviation (N) | Standard error (N) |
| 1 | 3 | 6.27 | 0.36 | 0.21 |
| 2.5 | 3 | 6.29 | 0.16 | 0.10 |
| 5 | 3 | 7.93 | 0.17 | 0.10 |

TABLE 33

| ANOVA Analysis of the Maximum Extrusion Forces for Different Cross-head Speeds | | | | | | | | |
|---|---|---|---|---|---|---|---|---|
| Comparison | MeanDiff | SEM | q Value | Prob | Alpha | Sig | LCL | UCL |
| 2.5 mm/s + 1 mm/s | 0.01508 | 0.20163 | 0.10577 | 0.99692 | 0.05 | 0 | −0.60359 | 0.63375 |
| 5 mm/s + 1 mm/s | 1.66131 | 0.20163 | 11.65236 | 4.23E-04 | 0.05 | 1 | 1.04265 | 2.27998 |
| 5 mm/s + 2.5 mm/s | 1.64623 | 0.20163 | 11.54659 | 4.45E-04 | 0.05 | 1 | 1.02757 | 2.2649 |

As shown, at a cross-head speed of 5 mm/s, the extrusion forces were significantly higher than the 1 mm/s and 2.5 mm/s forces.

Example 18—Effect of Carrier on Extrusion Force of Dermal Filler Formulations

This study sought to investigate the effect of gelatins on the extrusion forces of dermal filler formulations.

Mercerized AA was prepared using the procedure outlined in Example 10. The mercerized AA material was then loaded into a 3 mL HSW syringe and transferred to a 1 cc syringe using a F/F luer-lock connector. The mercerized AA material was then extruded through a 30 G needle into a clean 3 mL syringe through a 27 G needle.

1 g of crystalline gelatin (GE) powder was added to 1.25 mL of non-sterile water to prepare a 40% (m/v) stock solution. An additional 1.25 mL of water was added to the stock solution. The solution was left to swell at room temperature for 1 hour. After the solution was allowed to swell, the temperature was increased to 60° C. and the gelatin dissolved in several minutes. The resulting gelatin remained fluid at 4° C., whereas standard Knox gelatin produced a viscous solution that gelled at temperatures below about 30° C.

Various formulations were prepared using the mercerized AA and the gelatin. The formulations are outlined below in Table 34. The formulations were prepared using gelatin solutions (prepared via pipettes) that were loaded into 3 mL syringes. The mercerized AA material was transferred to the 3 mL syringes via a luer-lock connector. Once the mercerized AA material was transferred, the syringe was discarded and a new 3 mL syringe was connected to the luer-lock connector. The solution was then passed between the 3 mL syringes 30 times to produce a formulation.

TABLE 34

| Summary of Gelatin (GE) and Mercerized AA (MerAA) Formulations | | | | | |
|---|---|---|---|---|---|
| Final [GE] (% m/v) | Volume of MerAA (mL) | Volume of GE solution (mL) | Stock [GE] (% m/v) | Volume of GE stock (mL) | Volume of water (mL) |
| 5 | 1.7 | 0.3 | 40 | 0.250 | 0.0500 |
| 2.5 | 1.7 | 0.3 | 20 | 0.250 | 0.0500 |
| 1 | 1.7 | 0.3 | 10 | 0.200 | 0.0500 |
| 0.5 | 1.7 | 0.3 | 5 | 0.200 | 0.0500 |
| 0.25 | 1.7 | 0.3 | 2.5 | 0.200 | 0.0500 |

A CellScale UniVert device was used to test the extrusion forces of the formulations at a cross-head rate of 1 mm/s. The set-up was the same as that described in Example 17 except that a support bar was secured between the two stands. Five runs were completed using a 12 mm compression. A sixth run was completed using a 15 mm compression.

The BellaFill dermal filler was also tested as a control. The control was compared visually and texturally to the tested gelatin formulations. Generally, both BellaFill and the formulations of the present disclosure could be manipulated to form a little ball that held their shapes. As well, the formulations of the present disclosure felt more hydrated to the touch and were more translucent.

Results

Figure 72:
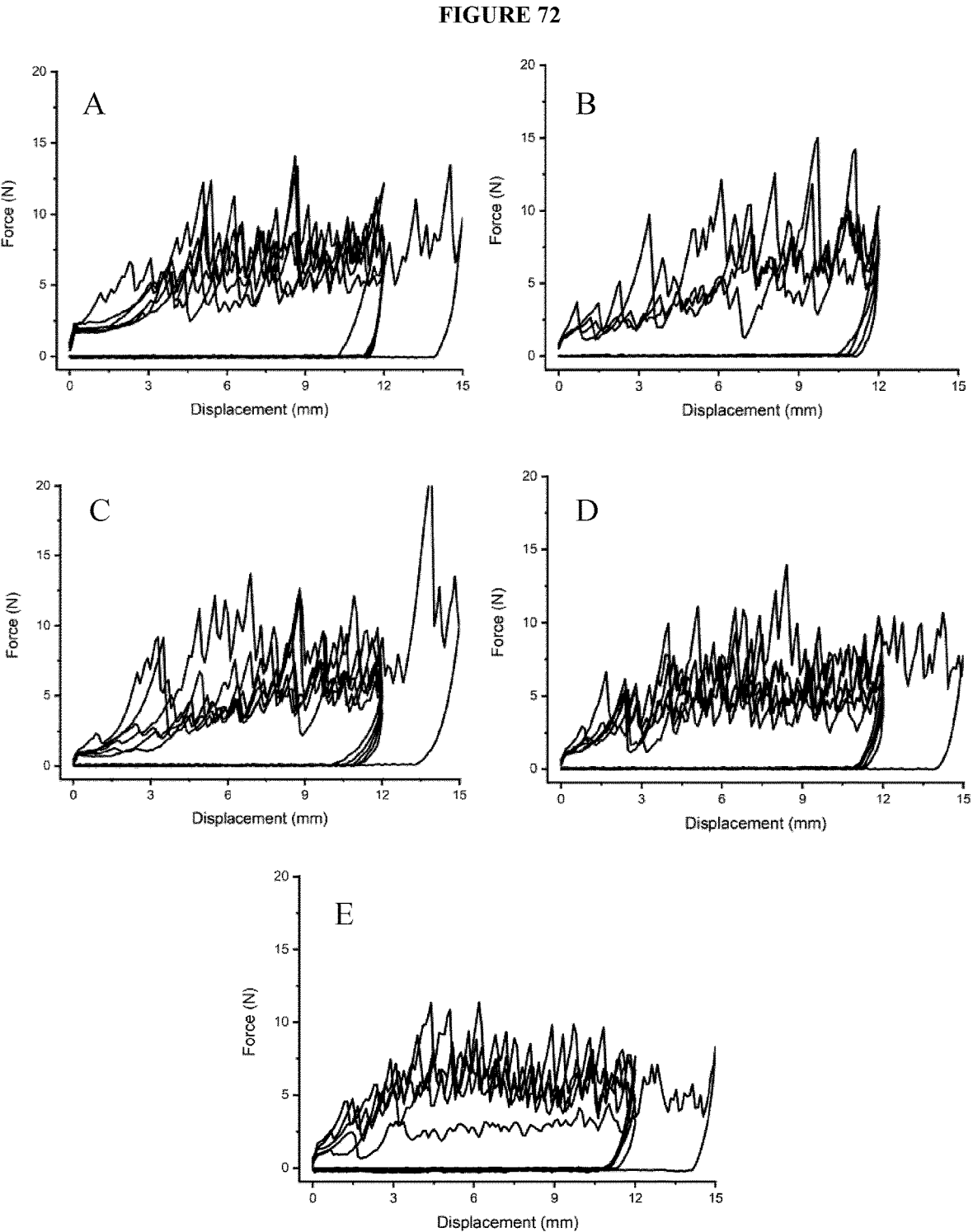
Figure 73:
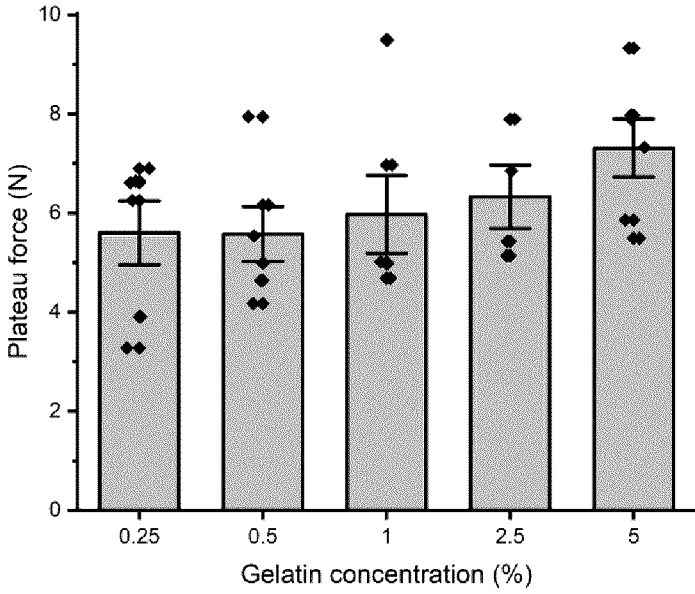
FIG. 73 shows the maximum extrusion forces of the force-displacement curves shown in FIG. 72.

FIG. 72 shows the force-displacement curves of the formulations extruded through 27 G needles at a cross-head rate of 1 mm/s, wherein FIG. 72A shows the force-displacement curves of the 5% GE formulation, FIG. 72B shows the force-displacement curves of the 2.5% GE formulation, FIG. 72C shows the force-displacement curves of the 1% GE formulation, FIG. 72D shows the force-displacement curves of the 0.5% GE formulation, and FIG. 72E shows the force-displacement curves of the 0.25% GE formulation. The maximum extrusion forces of each of the formulations is shown in FIG. 73. It is noted that only four runs were performed using the 2.5% GE formulation.

The tested BellaFill dermal filler exceeded the ION load cell of the UniVert device.

Conclusion

As shown, very the concentration of the gelatin did not have a significant effect on the extrusion forces of the formulations. As well, formulations exhibited lower maximum extrusion forces than the BellaFill dermal filler used as the control.

The observed force-displacement curves generally had more noise than previous studies. Without being bound to a particular theory, it is postulated that the more-secure set-up (resulting from the use of the support bar) may have contributed to the noise, as any bending or flexing of the set-up that may have smoothed or damped the curves was prevented by the support bar.

Example 19—Rheology of Dermal Fillers of the Present Disclosure

This study sought to investigate rheological properties of the dermal fillers of the present disclosure.

Mercerized AA material was prepared according to the procedure outlined in Example 10. Once prepared, a portion of the mercerized AA material was diluted 50% with water.

Oscillatory mechanical testing was performed using a CellScale UniVert device equipped with a 1 N load cell. The samples were placed in a beaker that was positioned in the UniVert device using a clamp.

Cyclical compressions were used to apply a sinusoidal strain (5%) to the mercerized AA samples. The oscillatory motion allowed the phase angle between the stress and the strain to be calculated. As the strain was an oscillating function, the dynamic modulus was measured. Young's modulus was used with the phase difference to calculate the storage and loss moduli of the material.

Results

Figure 74:
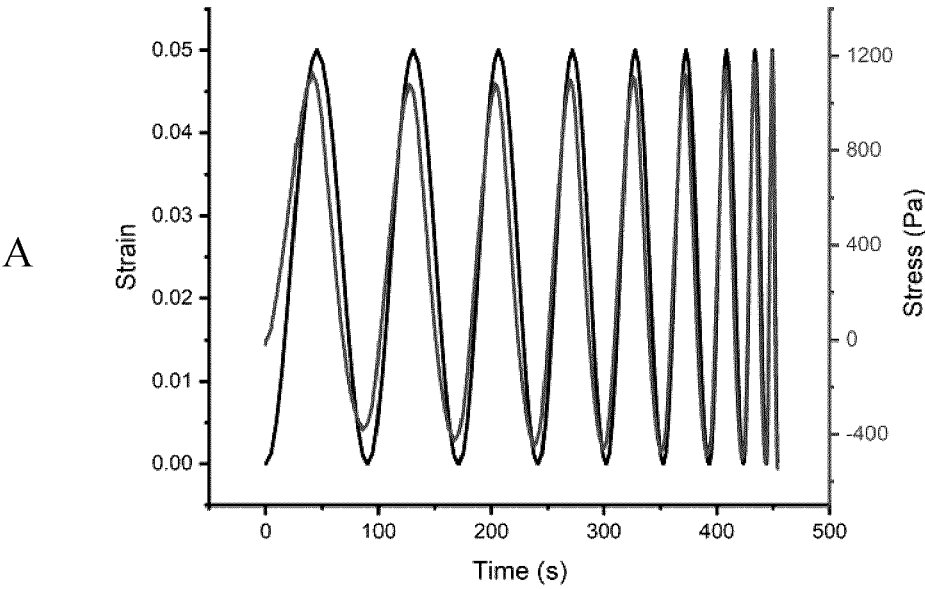
Figure 74:
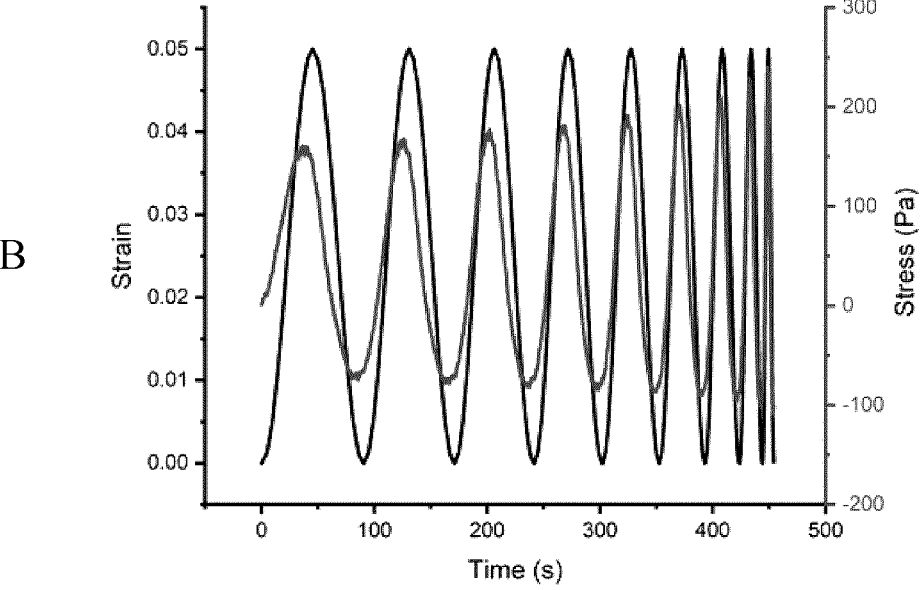

FIG. 74 shows a chart of the stress and strain vs. time for the mercerized AA samples, wherein FIG. 74A shows a chart of the stress and strain vs. time for the undiluted mercerized AA sample, and FIG. 74B shows a chart of the stress and strain vs. time for the diluted mercerized AA sample. The black curves represent the strain measurements and the red curves represent the stress measurements.

As shown, the stress and strain peak offset was greater for the diluted sample. As well, the stress amplitudes were greater for the undiluted mercerized AA sample.

The phase angle was calculated by dividing the time difference between the peaks by the period of each cycle, which corresponds to $2\pi$ radians. The value of the complex dynamic modulus (stress amplitude for each frequency) was multiplied by $\cos(\delta)$ or $\sin(\delta)$ to obtain the real (storage or elastic modulus) and imaginary (loss modulus) components, respectively. The loss factor was also calculated from the phase shift as $\tan(\delta)$.

Figure 75:
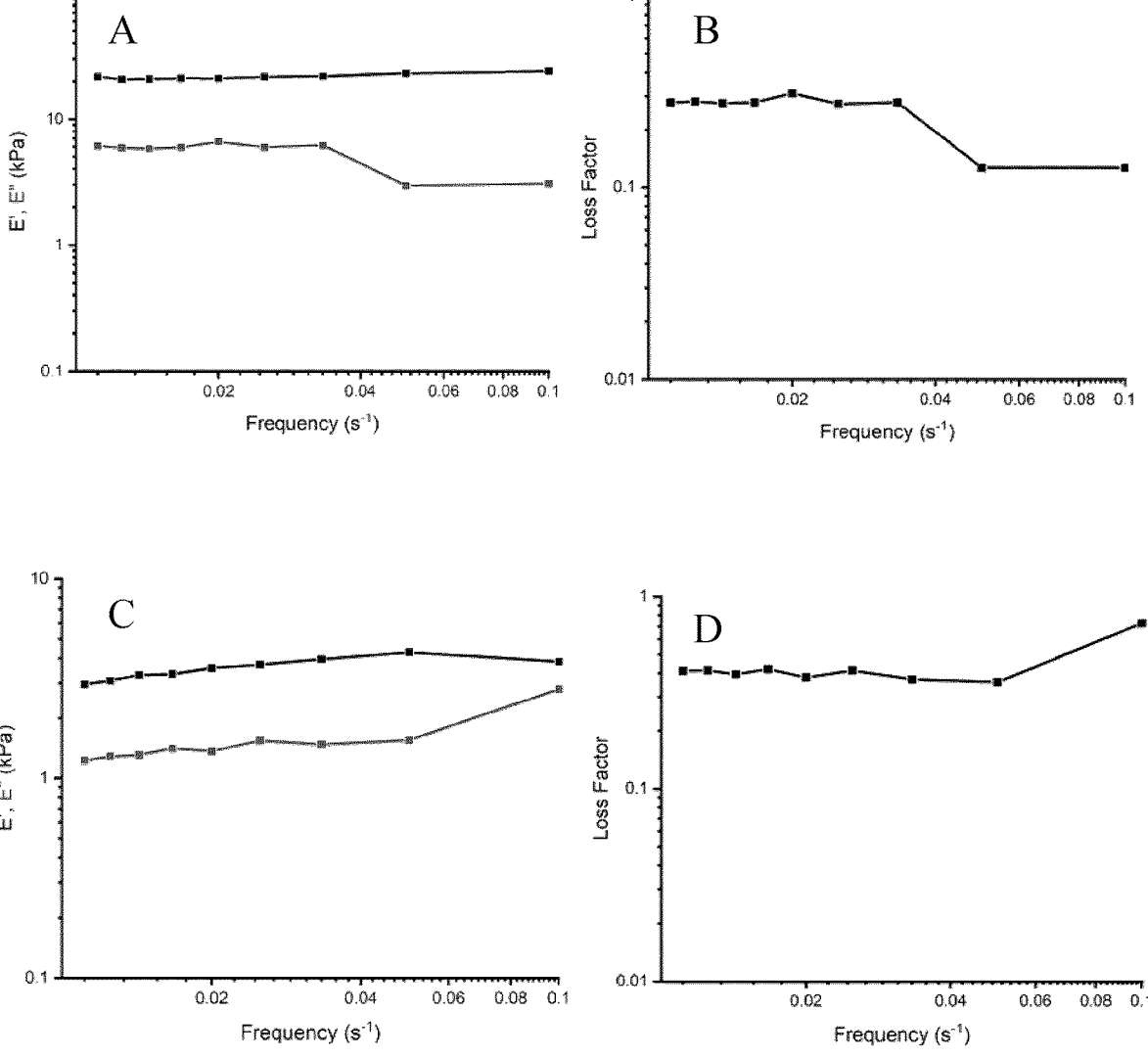

FIG. 75 shows the storage moduli, loss moduli, and loss factor curves for each of the samples, wherein FIG. 75A shows the storage moduli (E'; black line) and the loss moduli (E"; grey line) for the undiluted mercerized AA sample, FIG. 75B shows the loss factor curve for the undiluted mercerized AA sample, FIG. 75C shows the storage moduli (E'; black line) and the loss moduli (E"; grey line) for the diluted mercerized AA sample, FIG. 75D shows the loss factor curve for the diluted mercerized AA sample.

As shown, the storage and loss moduli were linear at the low frequency regions in the undiluted sample, which may indicate that the measurements were taken in the linear viscoelastic regime (LVR) and that the material may be characterized as primarily an elastic solid. With respect to the diluted sample, there was shown slight increases in storage and loss moduli with frequency at lower frequencies.

Further, while both the undiluted and diluted mercerized AA samples were mainly elastic at the frequencies and strains tested, the diluted sample had a greater fluid contribution.

Additionally, the viscosities of the samples was tested using a helical path t-bar spindle viscometer. It was found that each of the samples had a viscosity within a range of about 100,000 cp to about 200,000 cp.

Example 20—Stability of Mercerized Tissue Materials

This study sought to investigate the stability of mercerized tissue materials over time.

Mercerized decellularized AA was prepared according to the procedure outlined above in Example 10 except that the material was extruded through a 27 G needle prior to sieving on an autoclavable soldered 45 μm sieve using the Gilson SS 23 Test Sieve Vibrator with three 150 mL washes of distilled water. 0.5 mL of the mercerized AA material was mixed with 0.5 mL of 0.2% Congo Red between two 3 mL syringes connected via an F/F luer-lock connector 30 times. The resultant mixture was diluted with 7 mL of water and mixed a further 30 times between interconnected 20 mL syringes.

The contents of the mixture were then split into two equal volumes in two 15 mL Falcon tubes. One tube was stored in the fridge at 4° C. (the control), and the other tube was placed on a Thermo Scientific shaking incubator at 40° C. and 120 RPM in order to accelerate the aging of the sample. The two tubes were left undisturbed for 5 days.

An aliquot of the sample contained in each tube was removed and used for imaging on a SZX16 Stereo Microscope at 2.5× and 10× magnifications. The images were then analyzed on Fiji ImageJ. The 2.5× images were grouped in a stack and then converted to 8 bit. Initial brightness and contrast settings of the images were adjusted and a 2 px Gaussian blur was applied to the images. The images were then thresholded and had a watershed applied thereto. The particles in the images were analyzed using the Analyze Particles plugin without size restrictions.

Results

Figure 76:
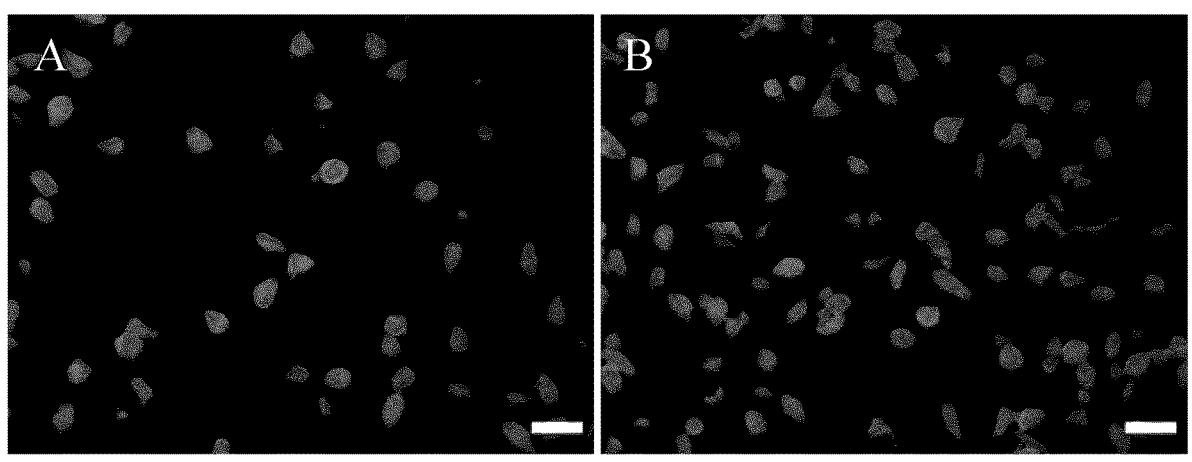
Figure 77:
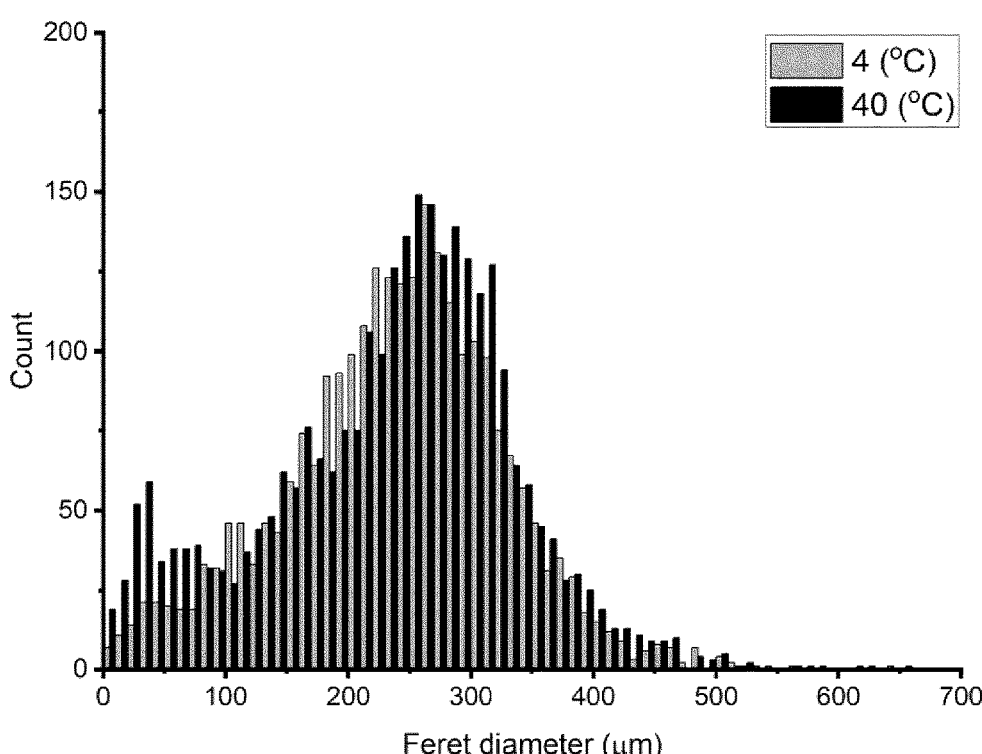
FIG. 77 shows the particle size distributions of the mercerized AA samples described in Example 20 and imaged in FIG. 76.

FIG. 76 shows microscopy images of the analyzed samples, wherein FIG. 76A shows a microscopy image of the sample stored at 4° C., and FIG. 76B shows a microscopy image of the sample maintained in the shaking incubator. The particle size distributions of the samples were determined and are shown in FIG. 77, wherein the grey bars represent the particle size distribution of the sample stored at 4° C. and the black bars represent the particle size distribution of the sample maintained in the shaking incubator.

As shown, that the distributions were similar. While a small shoulder peak of 30-50 μm particles was observed for the sample maintained in the shaking incubator, the percentage of particles less than 20 μm remained small (1.62%).

Figure 78:
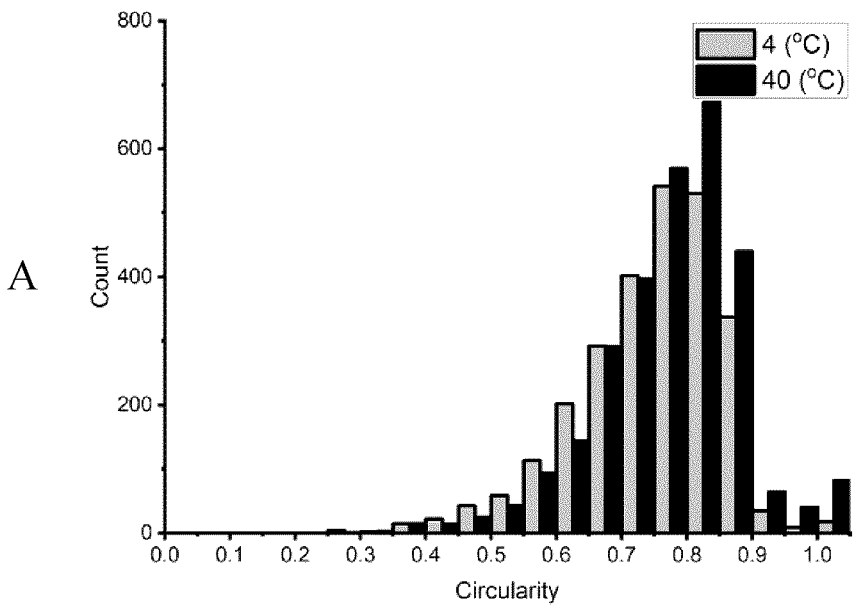
Figure 78:
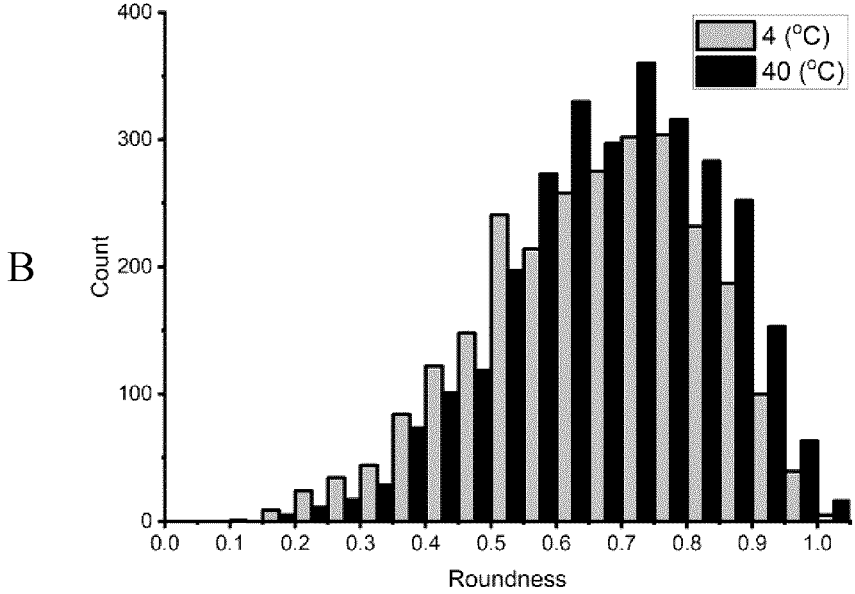

The circularity of the particles was also analyzed. The circularity parameter C is defined as: $C = 4\pi A/P^2$, wherein A is the area and P is the perimeter. A C value of 1 represents a perfect circle, while a value approaching 0 represents increased elongation of the shape. As well, the roundness of the particles was evaluated $R=4A/(\pi R_m^2)$, wherein $R_m$ is the major axis of the fitted ellipse. Like circularity, the values range from 0 to 1, with a value of 1 being perfectly round. The results are shown in FIG. 78, wherein FIG. 78A shows the circularity distributions of the particles of the sample stored at 4° C. (grey bars) and the sample maintained in the shaking incubator (black bars), and FIG. 78B shows the roundness distributions of the particles of the sample stored at 4° C. (grey bars) and the sample maintained in the shaking incubator (black bars).

As shown, the particles of both samples were both fairly circular and fairly round.

Thus the particles of both samples had similar particle size and shape distributions, which means that the particles may not swell or change shape over time.

Example 21—Microbial Testing of Dermal Fillers of the Present Disclosure

This study sought to investigate the sterilization cycles of the methods of producing dermal fillers of the present disclosure.

Mercerized decellularized AA material was prepared according to the procedure outlined in Example 10. A portion of the mercerized AA material was mixed with lidocaine and gelatin as previously described herein to form a dermal filler and front loaded into commercially available 1 cc syringes using a luer lock connector after degassing for 15 min. The syringes were autoclaved for 3 min in a wet cycle at either 130° C. or 135° C.

Two agar media were used, namely Sabouraud Dextrose Agar (SDA) and Tryptic Soy Agar (TSA). Five plates of each medium were prepared by calculating and adjusting the media content ratios for the necessary volume (final volume of 200 ml) for a 100 mm×16 mm dish. The compositions of each medium are shown below in Table 35.

TABLE 35

| TSA and SDA Medium Compositions | | |
| --- | --- | --- |
| Ingredient | Quantity for 1 L | Quantity for 200 mL |
| TSA Medium | | |
| dH2O | 1000 mL | 200 mL |
| Pancreatic digest of casein | 17 g | 3.4 g |
| Papaic digest of soybean | 3 g | 0.6 g |
| Dextrose | 2.5 g | 0.5 g |
| Sodium chloride | 5 g | 1 g |
| Dipotassium phosphate | 2.5 g | 0.5 g |
| Agar | 15 g | 3 g |
| Final mass | 45 g | 9 g |
| SDA Medium | | |
| dH2O | 1000 mL | 200 mL |
| Pancreatic digest of casein | 5 g | 1 g |
| Peptic digest of animal tissue | 5 g | 1 g |
| Dextrose | 40 g | 8 g |
| Agar | 15 g | 3 g |
| Final mass | 65 g | 13 g |

The media were autoclaved at 121° C. for 1 hour and then cooled in a water bath at 60° C. The plates were poured with about 15 mL to about 30 mL of medium in a biosafety cabinet. The plates filled with media were left in the cabinet with the lid half open until solidified. Once the media was solidified, the plates were sealed with paraffin and placed in a sterile fridge at 4° C.

The agar plates were then prepared under five different conditions: unopened control plate, streaked with dermal filler autoclaved at 130° C., streaked with dermal filler autoclaved at 135° C., streaked with mercerized AA material (not autoclaved), and streaked control. The streaking pattern used was a standard quadrant technique.

Once prepared, TSA plates were incubated at 32.5° C. for 5 days, and SDA plates were incubated at 22.5° C. for 7 days.

Results

Only colonies and growth were observed for the plates streaked with the non-autoclaved mercerized AA material.

Thus, the 3 minute autoclave cycles at 130° C. and 135° C. were sufficient to sterilize the syringe. The unopened controls also verified that the pouring techniques were aseptic. The streaked controls verified that any, if any contamination occurred, it may be due to the mercerized AA material or dermal fillers rather than the environment or pouring technique.

It was also observed that the autoclave sterilization of the mercerized AA material caused a slight yellowing of the material. Without being bound to any particular theory, it is postulated that the yellowing may be a result of the caramelization of reducing sugars present in the mercerized AA material.

Example 22—SDS Quantification in Dermal Fillers of the Present Disclosure

This study sought to determine the amount of residual SDS in the dermal fillers of the present disclosure.

A Bio Basic Residual SDS Detection Kit was used to determine residual SDS content. The Kit has a working range of 0.002%-0.014% SDS. The assay was a spectrophotometry-based assay.

The experimental protocols are outlined below.

Standard Curve

The experimental value of SDS is referenced to a standard curve created from known concentrations of SDS:

1. Weigh 0.1 g of SDS powdering into 10 mL of dH$_2$O to make a 0.1% solution for creation of standards.

2. For SDS estimation, prepare a calibration plot with known concentrations of SDS ranging from 0.002% to 0.014%, as shown in Table 36.

TABLE 36

| | | | SDS Dilutions | | | | | |
|---|---|---|---|---|---|---|---|---|
| Dilution # | 0 | 1 | 2 | 3 | 4 | 5 | 6 | 7 |
| dH$_2$O (µL) | 1000 | 980 | 960 | 940 | 920 | 900 | 880 | 860 |
| SDS 0.1% stock solution (µL) | 0 | 20 | 40 | 60 | 80 | 100 | 120 | 140 |
| Final SDS concentration (%) | 0 | 0.002 | 0.004 | 0.006 | 0.008 | 0.010 | 0.012 | 0.014 |

3. Transfer 50 µL from each of the SDS solutions into eight new 2 mL microcentrifuge tubes.

4. Add 50 µL of Solution A (from the Kit) into the tubes from step 3. Mix well.

5. Add 1.5 mL of Solution B (from the Kit) to each tube from step 3, and mix vigorously by vortexing for 30 s$^{-1}$ min.

6. Allow the tube to stand at room temperature for 5 minutes. Spin at 5000 rpm (2000×g) for 5 min.

7. Transfer 150 µL of the supernatant to a 96-well plate.

8. Blank a microplate reader, and then measure the optical density at OD 499 nm.

9. Plot the standard curve where the x-axis is % SDS concentration and the y-axis is OD 499 nm reading.

Detection of SDS in Samples

1. Dilute the samples accordingly so that the estimated SDS falls within the range of the standard curve.

2. Prepare three 2 mL microcentrifuge tubes. Add 50 µL of diluted samples to tube 1 and tube 2. Add 50 µL of dH$_2$O as a blank control to tube 3.

3. Add 50 µL of Solution A into the tubes from step 2. Mix well.

4. Add 1.5 mL of Solution B (from the Kit) to each tube, and mix vigorously by vortexing for 30 s$^{-1}$ min.

5. Allow the tube to stand at room temperature for 5 minutes. Spin at 5000 rpm (2000×g) for 5 min.

6. Transfer 150 µL of the supernatant to a 96-well plate.

7. Blank the microplate reader, and then measure the optical density at OD 499 nm.

8. Use the standard curve to obtain the % of SDS in the diluted sample. Use the following formula to calculate SDS concentration in the sample:

% of SDS in the sample=(% of diluted sample)(dilution factor)

Decellularized Material Preparation

Without being bound to any particular theory, it is postulated that SDS quantification may be best suited for decellularized material, rather than mercerized, decellularized material.

Decellularized AA material was prepared according to the procedure outlined in Example 5. SDS content was analyzed at various points throughout the procedure.

Results

The standard curve was developed using the below data obtained from the known SDS solutions.

TABLE 37

| | | | | SDS Standard Curve | | | | |
|---|---|---|---|---|---|---|---|---|
| Dilution # | 0 | 1 | 2 | 3 | 4 | 5 | 6 | 7 |
| Reading 1 | 0.073 | 0.111 | 0.150 | 0.196 | 0.246 | 0.288 | 0.343 | 0.393 |
| Reading 2 | 0.059 | 0.1 | 0.147 | 0.194 | 0.240 | 0.280 | 0.339 | 0.402 |
| Reading 3 | 0.052 | 0.097 | 0.145 | 0.198 | 0.246 | 0.280 | 0.344 | 0.404 |
| Average | 0.061 | 0.103 | 0.147 | 0.196 | 0.244 | 0.283 | 0.342 | 0.400 |
| Blank corrected | 0.000 | 0.042 | 0.086 | 0.135 | 0.183 | 0.222 | 0.281 | 0.339 |

The linear fit of the standard curve had an R2=0.997. The equation of the linear fit was y=23.952x−0.0067.

The curve was used to detect the SDS content in the decellularized AA samples:

1:10 dilution of SDS solution used for decellularization=0.10±0.01, N=3 replicates and 3 samples.

1:10 dilution from the liquid phase of the decellularized AA material after the CaCl$_2$) incubation and subsequent washing and a 72 hour incubation=undetectable.

Undiluted liquid phase of the decellularized material after the CaCl$_2$ incubation and subsequent washing and a 72 hour incubation=0.008% or 80 ppm.

Thus, the SDS content of the decellularized samples was sufficiently low. As well, the SDS content will further decrease during mercerization procedures due to the plurality of centrifugation and washing steps.

Example 23—Peroxide Quantification in Dermal Fillers of the Present Disclosure

This study sought to determine the amount of residual peroxide remaining in the dermal fillers of the present disclosure.

To test the peroxide content, Bartovation test strips (0-100 ppm) were dipped into mercerized apple material produced according to the procedure outlined in Example 10. In general, a test strip is dipped into the material for 1 second and excess material is shaken off. After 10 seconds, the colour of the strip is compared to the test pad, which as calibrated colour markings of 0 ppm, 1 ppm, 3 ppm, 10 ppm, 50 ppm, and 100 ppm.

Four batches of mercerized AA were produced and tested. A first batch had a peroxide content of between 1 ppm and 3 ppm, a second batch had a peroxide content of about 3 ppm, a third batch had peroxide content of about 0 ppm, and a fourth batch had a peroxide content of about 0 ppm. In general, it was found that the peroxide content decreased with washing and centrifuging cycles.

Spike tests were also performed to validate the above results. The spike tests involved spiking one of the batches of mercerized AA with about 10 ppm of hydrogen peroxide. The spiked sample was found to have a peroxide content of about 10 ppm, indicting that the tests were successful and the results were valid.

Example 24—Concentrations of Peroxide Suitable for Bleaching

This study sought to determine a range of peroxide concentrations suitable for bleaching decellularized material.

Decellularized AA material was mercerized using the procedure outlined above in Example 10. The volumes of hydrogen peroxide were varied by 25 mL for this study.

In a first trial, when producing the mercerized AA, 50 mL of hydrogen peroxide was used for bleaching. While the AA material was lightened, the material was not completely bleached.

In a second trial, when producing the mercerized AA, 75 mL of hydrogen peroxide was used for bleaching, which sufficiently bleached the AA material.

In a third trial, when producing the mercerized AA, 150 mL of hydrogen peroxide was used for bleaching. While the AA material was sufficiently bleached, an additional centrifugation cycle was required to lower the peroxide content of the AA material to below 10 ppm.

Example 25—pH of Components of the Dermal Fillers

This study sought to determine the pH of the individual components of a dermal filler of the present disclosure in order to evaluate their effect on the overall pH of the dermal filler.

Table 38 shows the pH levels of the components of a dermal filler of the present disclosure:

TABLE 38

| pH Levels of Various Components of the dermal Filler | |
| --- | --- |
| Material | pH |
| 2.5% Gelatin Carrier | 5.19 |
| 5% Gelatin Carrier | 4.72 |
| Lidocaine and 6.67X PBS | 6.89 |
| GMP PBS | 7.16 |
| Concentrated MerAA in PBS | 7.16 |
| Concentrated MerAA in PBS after 1 week | 7.10 |
| Concentrated MerAA in PBS after 1 month | 7.10 |

In some embodiments, the target range for the dermal filler is about 6.5 to about 7.5. Without being bound to any particular theory, it is postulated that the PBS may be maintaining the pH of the mercerized AA within such a range.

Example 26—Enzymatic Degradation of Dermal Fillers of the Present Disclosure

This study sought to investigate enzymes capable of degrading the dermal fillers of the present disclosure. As described above, the dermal fillers of the present disclosure are considered permanent in that the human body does not naturally produce enzymes capable of degrading the fillers. However, it will be appreciated that, in some cases, it may be desirable to remove a permanent dermal filler. One way to remove a permanent dermal filler may be through enzymatic degradation using enzymes not produced by the human body.

Chemicals and Instruments 3,5-dinitrosalicylic Acid (DNSA) and D-(+)-glucose was obtained from Alfa Aesar (Canada). Sodium sulfite was obtained from ANKOM technologies (USA). Acetic acid, Congo red, sodium acetate trihydrate, sodium hydroxide, and phosphate-buffered saline (PBS) were obtained from Fisher Scientific (Canada). Potassium sodium tartrate tetrahydrate was obtained from Acros Organics (Canada). The enzymes used were cellulase and pectinase from *Aspergillus niger* from TCI America (USA), cellulase from *Trichoderma* sp. from Sigma (Canada), and Macerozyme R-10 from *Rhizopus* sp. from Plantmedia (USA). A benchtop pH Meter (Sartorius), Synergy Mx spectrometer (BioTek), MaxQ agitation incubator (Thermo Scientific), and a SZX16 Stereo microscope with fluorescent filters (Olympus) were used to execute the investigation.

Reagents and Solutions Preparation

Dinitrosalicylic acid reagent 1% (DNSA reagent) was prepared by dissolving 10 g DNSA, 500 mg sodium sulfite, and 10 g sodium hydroxide (NaOH) in 1 L of distilled water and was stored at room temperature. A 40% potassium sodium tartrate solution (Rochelle salt) was prepared by dissolving 40 g of potassium sodium tartrate tetrahydrate in 100 mL of distilled water and was stored at room temperature. Sodium citrate buffer (50 mM) was prepared by diluting 50 mL of 100 mM of Sodium citrate in distilled water to a final volume of 100 mL and adjusting the pH to 6 and was stored at room temperature. Sodium acetate buffer (100 mM) was prepared by dissolving 1.3 g sodium acetate and 5 mg of acetic acid in 100 mL of distilled water and adjusting the pH to 6 and was stored at room temperature. PBS buffer 1× was prepared by diluting 10 mL of 10×PBS in distilled water to a final volume of 100 mL and was stored at room temperature. The enzyme stock solutions were prepared in various buffers at the same enzymatic concentration of 1 mg/mL, and stored at 4° C. Congo Red staining solution 0.1% was prepared by dissolving in distilled water; the solution was filtered using a 0.45 μm syringe filter to remove any precipitates, and the solution was stored at 4° C.

Glucose Standard Curve

The DNSA method quantifies the quantity of glucose produced in a solution via colorimetric analysis. This method is used to identify the presence of a free carboxyl group (C=O) caused by reducing sugars such as glucose. An oxidation of the aldehyde functional group present in glucose causes a reaction with the DNSA, which is reduced to 3-amino-5-nitrosalicylic acid (ANSA) and, in turn, caused the solution to become a red-brown colour. Using a stock solution of 10 mg/ml of D-glucose in distilled water, a standard curve of 0, 0.1, 0.2, 0.3, 0.4, 0.5, 0.6, 0.7, 0.8, 0.9, 1, 2, 3, 4, 5, 6, 7, 8, 9, and 10 mg/ml was made. Using the DNSA reagent methods and the protocol from HIMEDIA, a standard curve of glucose production from the degradation of the cellulose-based dermal filler may be established. By diluting the stock solution of D-glucose to a concentration ranging from 0.1 mg/mL to 10 mg/mL, 200 μL of the standard was aliquoted. 0.5 mL of DNSA reagent was added to the standard and the samples were boiled (95° C.) for 15 minutes. Once completed, 0.5 mL of potassium sodium tartrate (40%) was added to the samples and mixed by vortexing. 150 μL of each standard were added to a 96-well plate, and the absorbance was taken at 540 nm using the Synergy Mx spectrometer.

Diluted Enzymatic Assay in Various Buffers

This assay was used to determine which buffers and enzymes were optimal for the degradation of the cellulose-based dermal filler on a smaller scale. Stock solutions of enzyme (1 mg/mL) were made in different buffers (PBS, sodium acetate, and sodium citrate), and then 50 μL of the stock solution was diluted in 950 μL of the same buffer. 1 mL of the cellulose-based dermal filler was added to the wells of a 24-well plate, and then the diluted enzyme solution was added to the wells. The plates were placed in a 37° C. incubator without agitation for three different time frames: 1 hour, 24 hours, and 48 hours. A 200 μL aliquot was taken for each time frame and was stored at 4° C. to inhibit enzyme activity until DNSA analysis. Glucose production estimation was done by the DNSA method.

Diluted Pectinase Cellulase Ratios Assay in Various Buffers

This assay was used to determine which buffers are optimal for the degradation of the cellulose-based dermal filler with different ratios of pectinase and cellulase. By using a stock solution of pectinase (1 mg/mL) and a stock solution of cellulase (1 mg/mL) in different buffers (PBS, sodium acetate, and sodium citrate), ratios of 100:0, 75:25, 50:50, 25:75 of pectinase:cellulase were made at a final volume of 50 μL. This solution was then diluted with 950 μL of the corresponding buffer. 1 mL of the cellulose-based dermal filler was added to the wells of a 24-well plate, and the diluted mixture of pectinase and cellulase was added to the wells. The plates were placed in a 37° C. incubator without agitation for 1 hour, 24 hours, and 48 hours. A 200 μl aliquot was taken for each time frame and was stored at 4° C. Glucose production estimation was done by the DNSA method.

Different Enzymatic Concentration Assay

This assay was used to determine the optimal concentration to totally degrade the cellulose-based dermal filler in optimal buffers tested in above. By using a stock solution of enzymes (1 mg/mL) in sodium acetate or sodium citrate, ratios of 100:0, 75:25, 50:50, 25:75, and 0:100 (enzyme: buffer) were made by diluting with the corresponding buffer to a final volume of 1.2 mL. A volume of 0.5 mL of the cellulose-based dermal filler was added to a 24-well plate, and the different enzyme concentration solutions were added to the appropriate wells. The plates were placed in a 37° C. incubator without agitation for 1 hour, 24 hours, and 48 hours. 200 μL aliquots were taken from each well after the specified incubation time and were stored at 4° C. to inhibit enzyme activity until DNSA analysis. Glucose production estimation was done by the DNSA method, and dermal filler particle degradation was visualized with fluorescence microscopy imaging at a magnification of 2.5× using a SZX16 stereo microscope with a Blue-Violet filter was done by Congo Red staining.

Different Pectinase and Cellulase Ratios Concentrations Assay

This assay was used to determine the optimal ratio of pectinase and cellulase mixture to totally degrade the cellulose-based dermal filler, and to visualize if any changes resulted from the addition of pectinase. The selection of buffers used in this assay were based on the results from experiments using the methods from section 2.4. By using a stock solution of pectinase (1 mg/mL) and a stock solution of cellulase (1 mg/mL) in sodium acetate or sodium citrate, ratios of 100:0, 75:25, 50:50, 25:75, and 0:100 (pectinase: cellulase) were made by combining the necessary amount of each stock solution for a final volume of 1.2 mL. A volume of 0.5 mL of the cellulose-based dermal filler was added to the wells of a 24-well plate, and the pectinase-cellulase solutions were added to the appropriate wells. The plates were placed in a 37° C. incubator without agitation for 1 hour, 24 hours, and 48 hours. 200 μL aliquots were taken from each well after the specified incubation time and were stored at 4° C. to inhibit enzyme activity until DNSA analysis. Glucose production estimation was done by the DNSA method, and dermal filler particle degradation was visualized with fluorescence microscopy imaging at a magnification of 2.5× using the SZX16 stereo microscope with a Blue-Violet filter was done by Congo Red staining.

Enzyme Degradation Efficacy at Different Times and Different Concentrations

This assay was used to determine if the efficiency of the enzyme solutions changed if made in advance and stored at different temperatures as compared to freshly-made enzymes. Higher concentrations of enzymes were also tested: 1, 1.5, 2, 2.5, and 3 mg/mL. In the above assays, the solutions were made in a 2-hour period and were placed in an ice bath to keep the enzyme solution fresh. Conversely, the experiment was repeated with solutions that were kept at 4° C. for a week. The enzymes that were used were cellulase from *Trichoderma* sp. and a mixture of cellulase from *Trichoderma* sp. and pectinase from *Aspergillus niger* at a ratio of 25:75 (Pectinase:Cellulase) in sodium acetate buffer. A volume of 1 mL of the cellulose-based dermal filler was added to the wells of a 24-well plate, and the enzyme solutions were added to the appropriate well. The plates were placed in a 37° C. incubator without agitation for 1 hour, 24 hours, and 48 hours. 200 μL aliquots were taken from each well after the specified incubation time and were stored at 4° C. to inhibit enzyme activity until DNSA analysis. Glucose production estimation was done by the DNSA method, and dermal filler particle degradation was visualized with fluorescence microscopy imaging at a magnification of 2.5× using the SZX16 stereo microscope with a Blue-Violet filter was done by Congo Red staining.

Microscopy Imaging

Remaining samples after enzymatic digestion were stained with a 0.1% Congo red solution and were used to assess whether particles were degraded. For image analysis, a 1/64 dilution to visualize single particles was performed. 1 mL of each sample was added to a 24-well plate and imaged at a magnification of 2.5× using the SZX16 stereo microscope with a Blue-Violet filter.

Statistical Analysis

Statistical analysis of the values obtained were performed with two-way ANOVA by using Origin 2021 software. All values presented are the mean±standard error (SE). For a value considered statistically significantly different, $p < 0.05$.

Results

Figure 79:
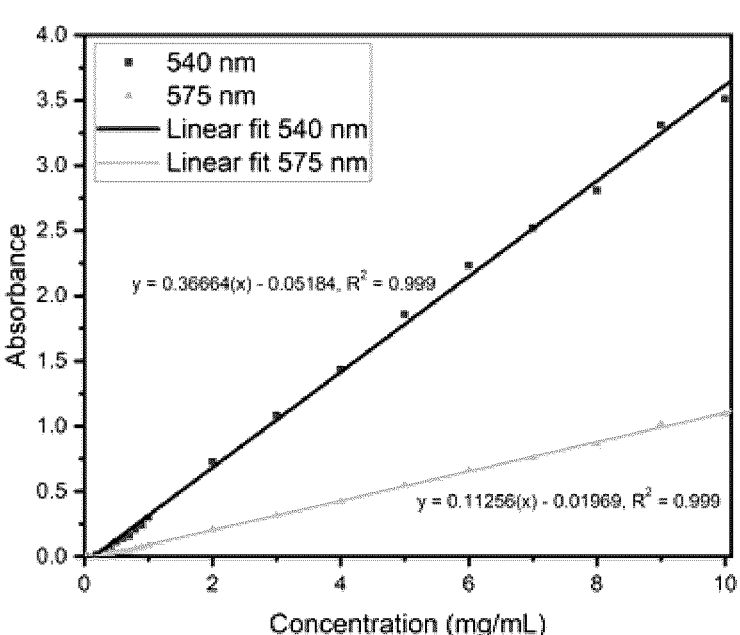
FIG. 79 shows standard absorbance-concentration curves at wavelengths of 540 nm and 570 nm for D-glucose produced from enzymatic activity on cellulose-based dermal fillers as described in Example 26.

Cellulose is a linear polysaccharide composed of multiple subunits of D-glucose that are attached together by β-1,4-glycosidic linkages. The cellulase enzyme will break this link to release the D-glucose subunits. For this reason, the DNSA method was used to acquire a standard curve of D-glucose that will be produced from enzymatic activity on the cellulose-based dermal filler. The standard curves shown in FIG. 79 were used to quantify the degradation of cellulose-based particles to D-glucose. With the equations obtained from the linear curve, the concentration of D-glucose produced can be calculated:[D-glucose]=(absorbance+0.05185)/0.36664 for wavelength of 540 nm and [D-glucose]=(absorbance+0.01969)/0.11256 for wavelength of 575 nm.

Figure 80:
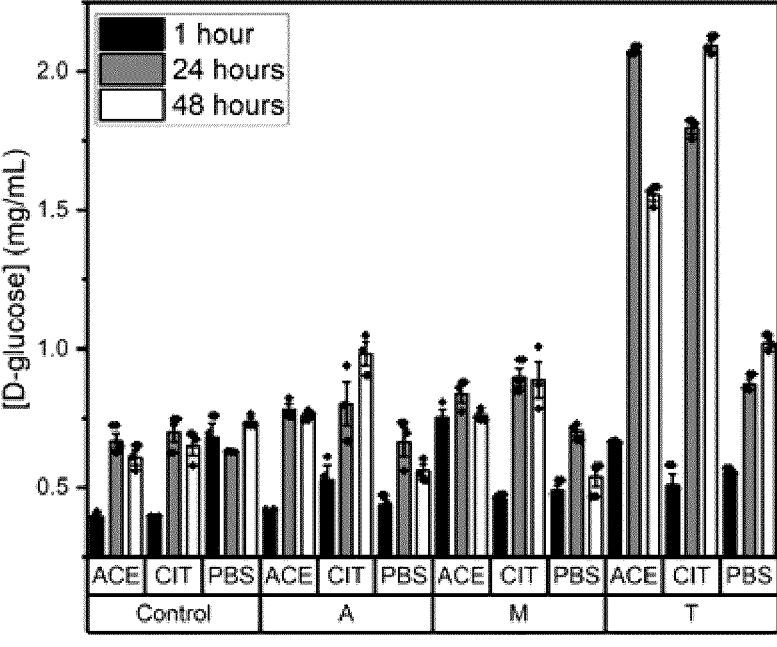
FIG. 80 shows the concentrations of D-glucose produced using diluted enzyme solutions in different buffers at 37° C. as described in Example 26.

Referring to FIG. 80, Cellulase from *Trichoderma* sp. (T) can be seen to have the best conversion of cellulose to glucose at an incubation temperature of 37° C. compared to cellulase from *Aspergillus niger* (A) and macerozyme R-10 (M). This may be explained by the optimal temperature of the enzymes, as macerozyme R-10 has an optimal temperature between 40° C. to 50° C.; cellulase from *Aspergillus niger* has an optimal temperature at 30° C., which may drastically drop the enzymatic activity thereof, and cellulase from *Trichoderma* sp. has an optimal temperature at 40° C., which may indicate why *Trichoderma* sp. is the only enzyme that had a larger production of glucose. Cellulase T performed better in sodium acetate (ACE) and sodium citrate (CIT) buffers. The control values that are represented in FIG. 80 show that in the buffer alone, a small quantity of D-glucose was present from the cellulose-based dermal filler. This may be caused by the mercerization process, which may break down the components of the apple cell wall such as lignin, cellulose, and hemicellulose into glucose.

Figure 81:
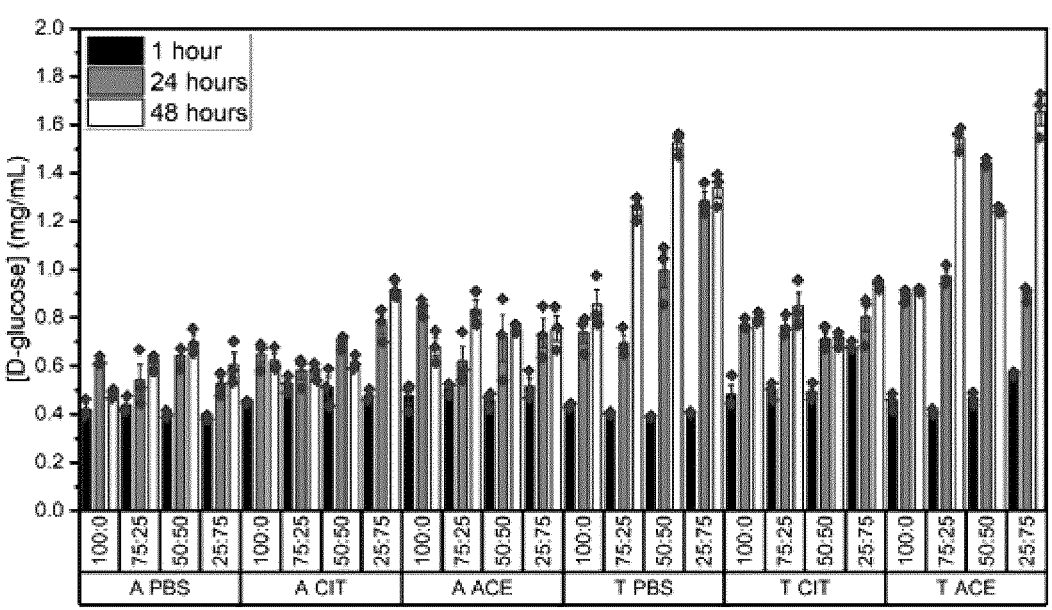
FIG. 81 shows the concentrations of D-glucose produced using diluted pectinase:cellulase ratios in different buffers at 37° C. as described in Example 26.

Next, various ratios of pectinase and cellulase were evaluated. FIG. 81 shows the assay of different pectinase:cellulase ratios in different buffers. As shown, pectinase alone at a ratio of 100:0 did not result in much degradation of the particles. When the pectinase was added to cellulase at a ratio of 25:75 with T ACE, the degradation was optimal compared to the other samples. Without being bound to any particular theory, it is thought that the addition of pectinase may help break down the hemicellulose polymers that are connected with cellulose microfibrils, which may, in turn, cause more cellulose to be liberated and available for hydrolysis with cellulase.

Figure 82:
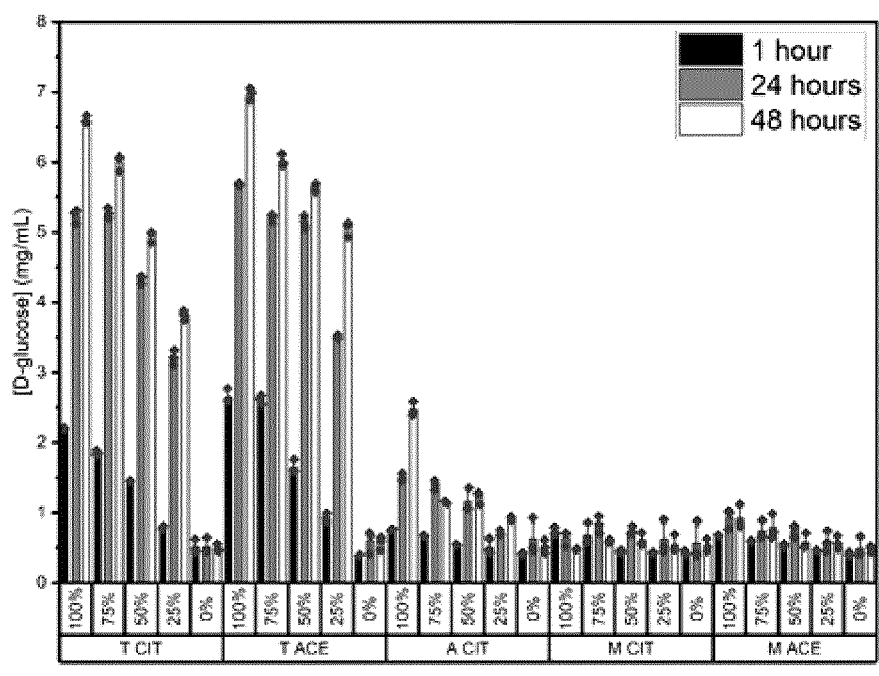
FIG. 82 shows the concentrations of D-glucose produced using different enzyme concentrations at 37° C. as described in Example 26.
Figure 83:
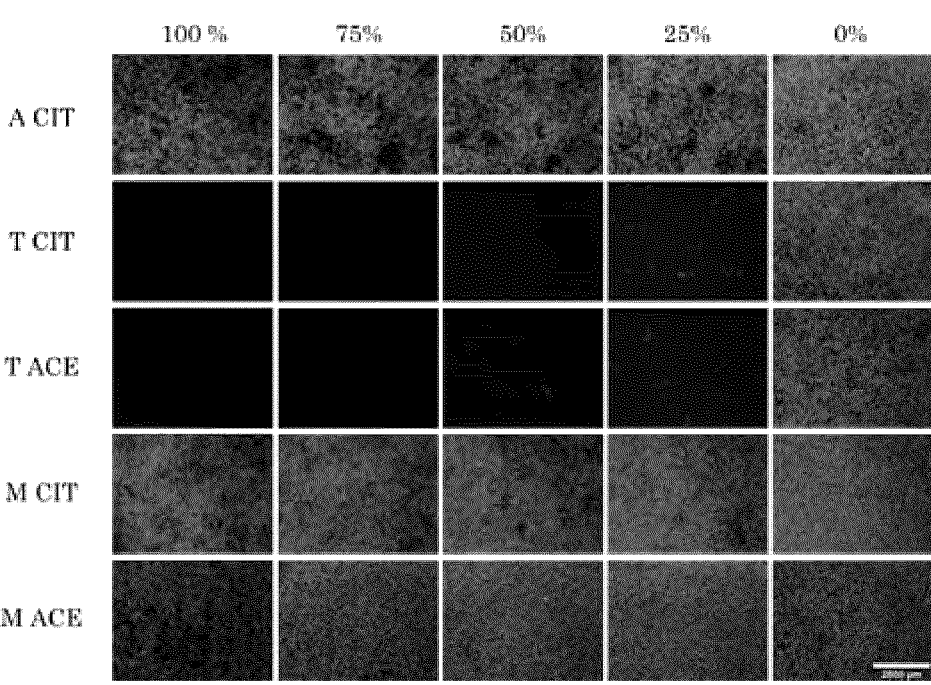
FIG. 83 shows microscopy images of cellulose-derived particles in different enzyme concentrations after 48 hours of incubation as described in Example 26.

Referring to FIG. 82, it is shown that cellulase T had a high glucose production even at a 25% concentration, and that the optimal buffer was ACE. For the other enzymes (A and M) there was barely any glucose produced when compared between different incubation times. FIG. 83 shows that concentrations of 100% to 50%, for both T CIT and T ACE, totally degraded the cellulose particles, and that there was a partial degradation for a concentration of 25%. This means that 1.2 mL of enzyme solution may be able de fully degrade cellulose particles of 0.5 mL of cellulose-based dermal filler from concentrations ranging from 100 to 50%.

Figure 84:
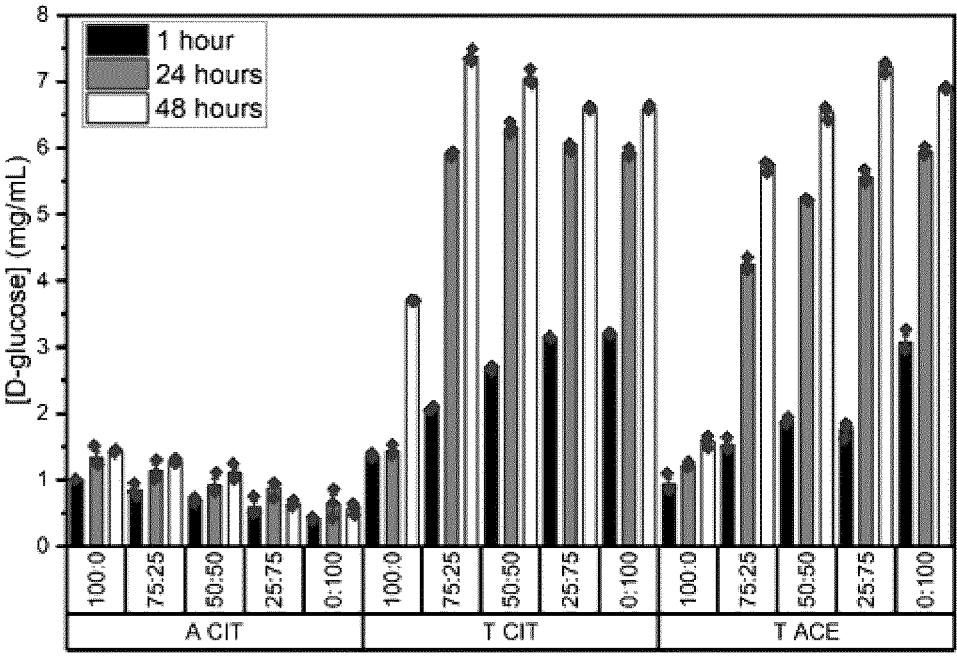
FIG. 84 shows the concentrations of D-glucose produced using different concentrations of pectinase:cellulase ratios at 37° C. as described in Example 26.
Figure 85:
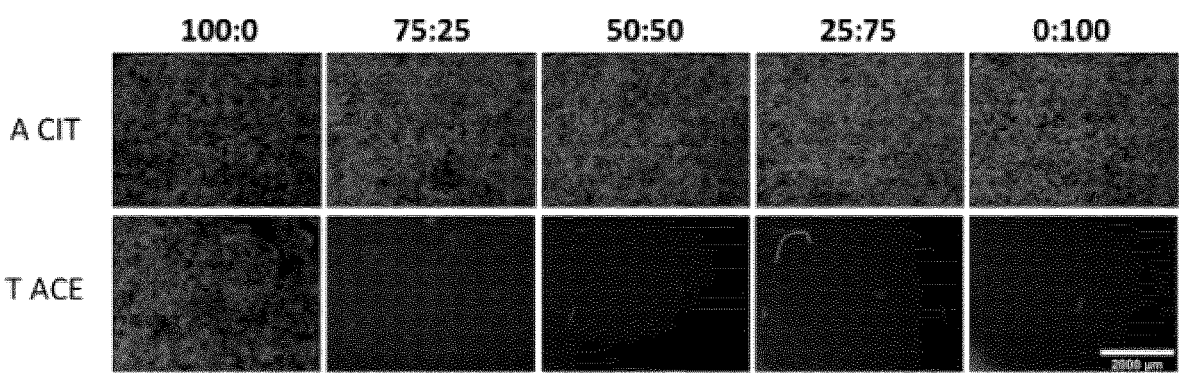
FIG. 85 shows microscopy images of cellulose-derived particles in different pectinase:cellulase ratios after 48 hours of incubation as described in Example 26.

The results of the different pectinase:cellulase ratios assay is shown in FIG. 84. As shown, cellulase T had a different optimal ratio depending on the buffer used. For T ACE, the optimal ratio of pectinase:cellulase was 25:75, and for T CIT the optimal ratio was 75:25. The stained microscopy images shown in FIG. 85 show a total degradation for ratios of pectinase:cellulase at 50:50, 25:75 and 0:100 for T ACE. The images for T CIT with pectinase were not accounted for because the cellulase enzyme was not added to the mixture.

Figure 86:
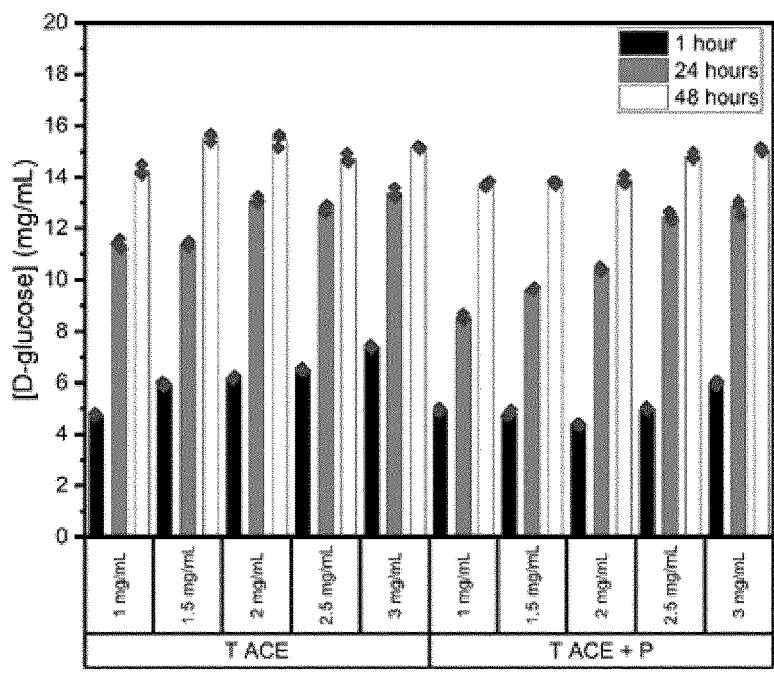
FIG. 86 shows the concentrations of D-glucose produced using different concentrations of fresh enzyme solutions as described in Example 26.
Figure 87:
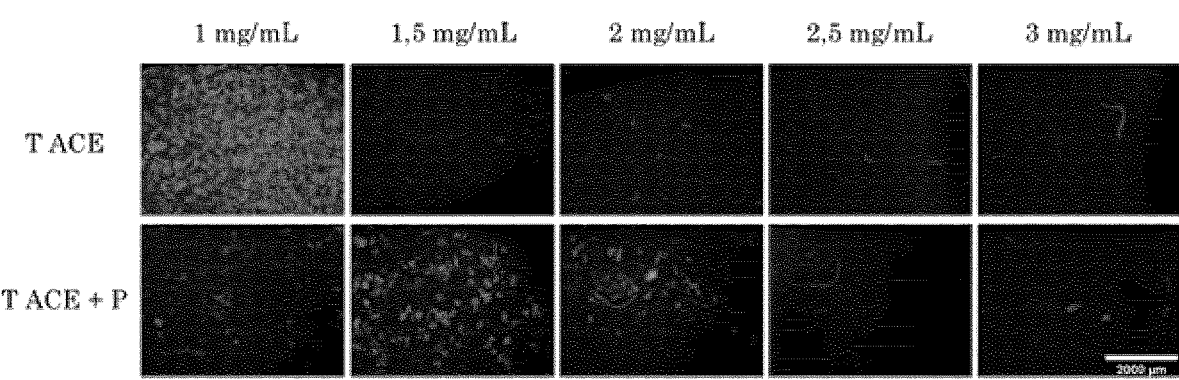
FIG. 87 shows microscopy images of cellulose-derived particles in different fresh enzyme solutions after 48 hours of incubation as described in Example 26.

As shown in FIG. 86, the different concentrations of fresh enzyme solution exhibited a plateau forming between concentrations of 12 mg/mL and 16 mg/mL of D-glucose produced for all the different cellulase concentrations with and without pectinase after 48 hours. The plateau may indicate that there were not enough enzymes for the quantity of substrate available. A total degradation of cellulose particles for concentrations at 2.5 mg/mL and 3 mg/mL with T ACE with and without pectinase was observed and is shown in FIG. 87. There was also a partial degradation of the particles at concentrations of 1.5 and 2 mg/ml for T ACE and concentrations of 1, 1.5, and 2 mg/mL for T ACE with pectinase.

Figure 88:
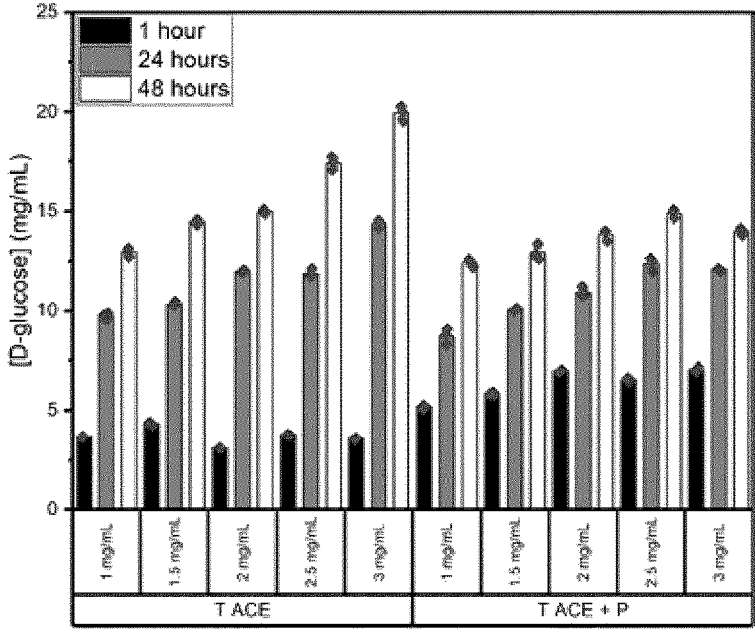
FIG. 88 shows the concentrations of D-glucose produced using different concentrations of pre-made enzyme solutions as described in Example 26.

As shown in FIG. 88, the different concentrations of pre-made enzyme solutions exhibited a gradual peak as the concentrations became higher, which is in contrast to the fresh enzyme solution that exhibited the plateau. The D-glucose production was higher with T ACE only, starting from 12.5 to 20 mg/mL, compared to 12.5 to 15 mg/mL with pectinase added. By comparing results from the fresh enzyme solution, it is clear that the enzymatic activity was not affected after being stored at 4° C. for a week. As cellulase can be stored at 4° C. for 7.5 months without the enzymatic activity dropping, this result was expected.

Thus, out of the tested enzymes, the optimal enzyme to degrade the cellulose-based dermal fillers of the present disclosure out of the various combinations assessed here is cellulase from *Trichoderma* sp, with or without pectinase.

Example 27—In Vivo Injection of Dermal Fillers of the Present Disclosure

This study sought to expand on the results obtained in Example 3. Further in vivo injections were preformed using the dermal fillers of the present disclosure.

Three dermal filler formulations were prepared—one with a saline carrier, one with a hyaluronic acid (HA) carrier, and one with a collagen carrier. The formulations were prepared using the procedure outlined in Example 3.

Each of the three formulations were subcutaneously injected into three rats. The injection procedure outlined in Example 3 was followed again here. Each of the rats were resected at 4 weeks and 8 weeks. After 12 weeks, two rats for each formulation were euthanized and the tissue collected therefrom. After 1 year, the remaining rats were euthanized and the tissues were collected therefrom.

Results

Figure 89:
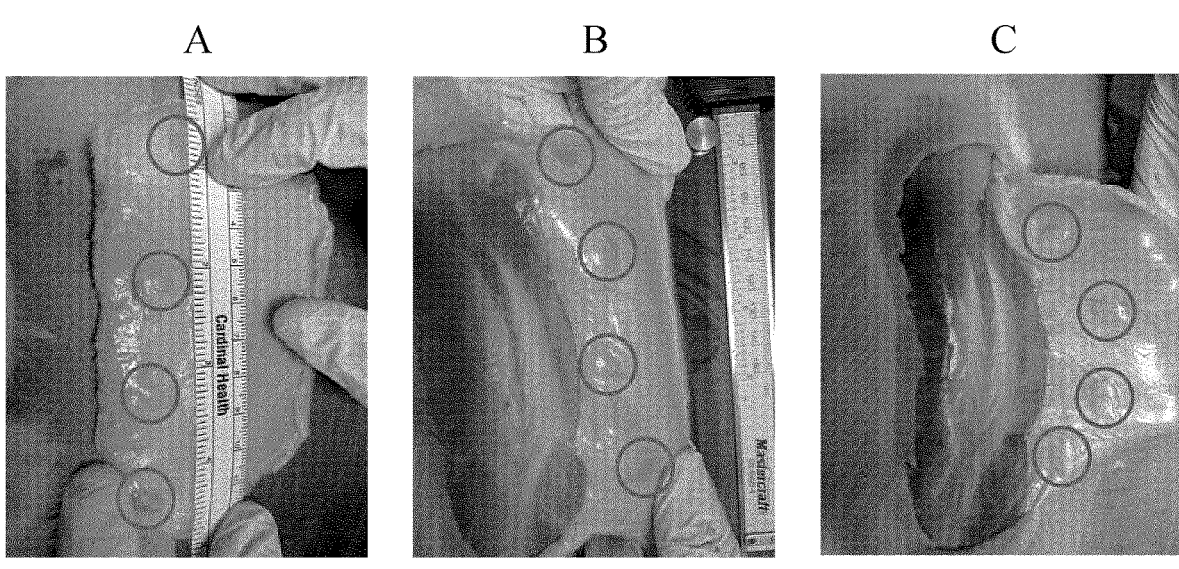

Examples of resections taken from one of the rats from each of the formulation trials are shown in FIG. 89, wherein FIG. 89A is a resection taken from a rat injected with the saline formulation, FIG. 89B is a resection taken from a rat injected with the HA formulation, and FIG. 89C is a resection taken from a rat injected with the collagen formulation.

The injected formulations were evaluated visually after resection. In general, the saline formulations were brown in colour. The HA formulations were similar in colour to the saline formulations, however, the morphology of the HA injections appeared to be "bumpy" or "fragmented" as compared to the saline formulations. The collagen fillers remained in compact ovals and were white in colour for the first 4 weeks and brown in colour at later time points, which may correspond to the time-frame for collagen resorption in the body of the rat.

Samples were taken from each of the injections at the various time points, stained with Masson's Trichrome (MT) or hematoxylin and eosin (HE) and imaged under a microscope. Microscopy images at the 12-week time point of each of the formulations are shown in FIG. 90 to FIG. 92.

Figure 90:
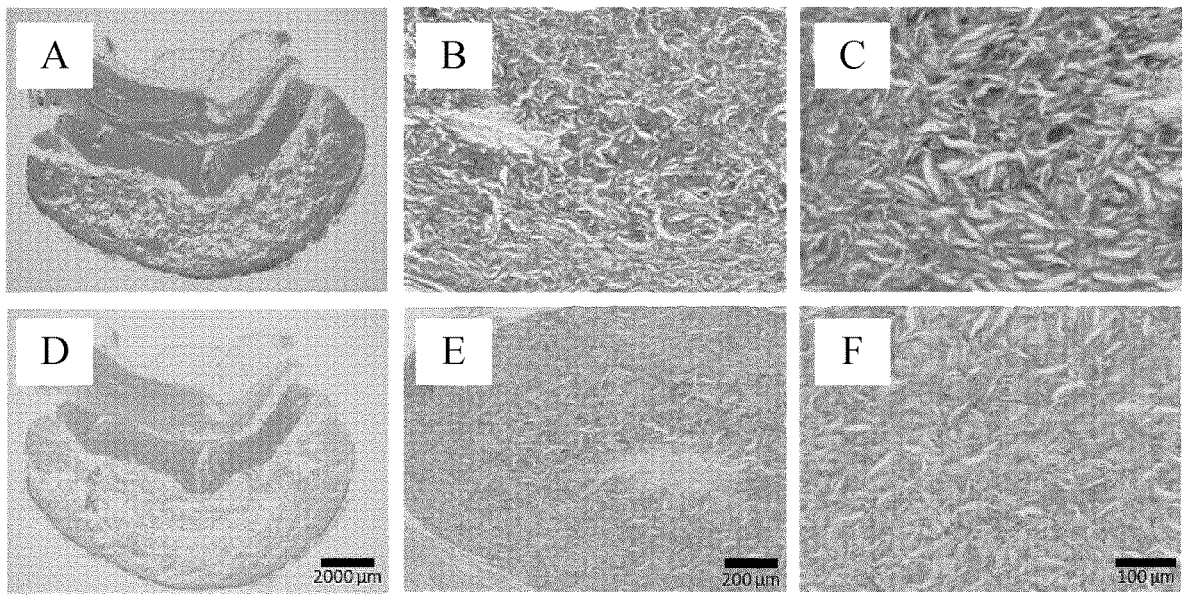

FIG. 90 shows microscopy images of a saline formulation injection at the 12-week point, wherein FIG. 90A shows a microscopy image of the injected saline formulation stained with MT at a magnification of 1×, FIG. 90B shows a microscopy image of the injected saline formulation stained with MT at a magnification of 10×, FIG. 90C shows a microscopy image of the injected saline formulation stained with MT at a magnification of 20×, FIG. 90D shows a microscopy image of the injected saline formulation stained with HE at a magnification of 1×, FIG. 90E shows a microscopy image of the injected saline formulation stained with HE at a magnification of 10×, and FIG. 90F shows a microscopy image of the injected saline formulation stained with HE at a magnification of 20×.

Figure 91:
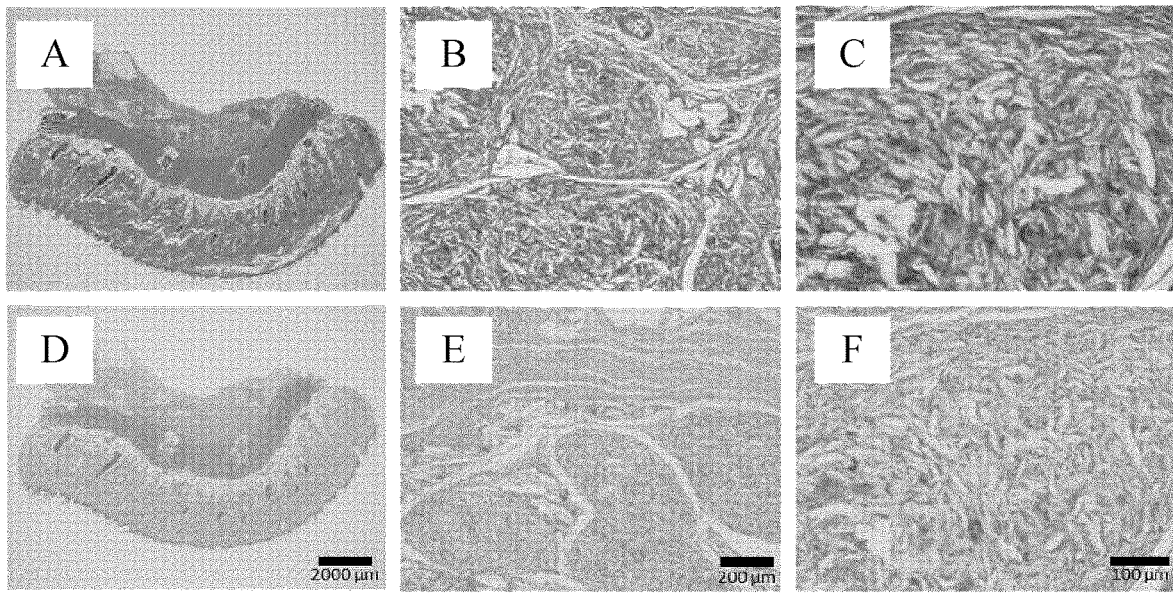

FIG. 91 shows microscopy images of a HA formulation injection at the 12-week point, wherein FIG. 91A shows a microscopy image of the injected HA formulation stained with MT at a magnification of 1×, FIG. 91B shows a microscopy image of the injected HA formulation stained with MT at a magnification of 10×, FIG. 91C shows a microscopy image of the injected HA formulation stained with MT at a magnification of 20×, FIG. 91D shows a microscopy image of the injected HA formulation stained with HE at a magnification of 1×, FIG. 91E shows a microscopy image of the injected HA formulation stained with HE at a magnification of 10×, and FIG. 91F shows a microscopy image of the injected HA formulation stained with HE at a magnification of 20×.

Figure 92:
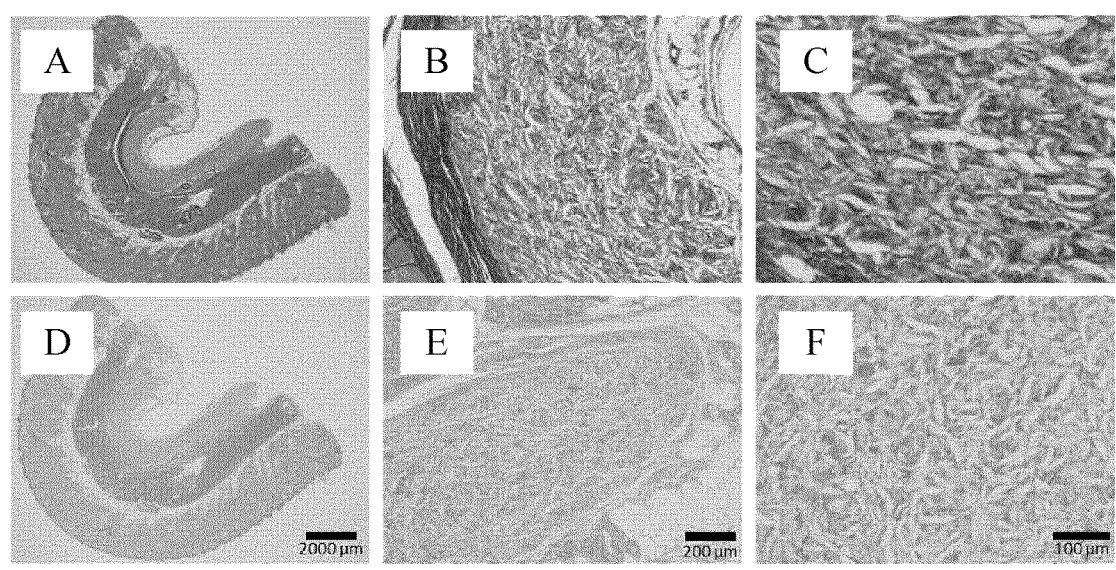

FIG. 92 shows microscopy images of a collagen formulation injection at the twelve-week point, wherein FIG. 92A shows a microscopy image of the injected collagen formulation stained with MT at a magnification of 1×, FIG. 92B shows a microscopy image of the injected collagen formulation stained with MR at a magnification of 10×, FIG. 92C shows a microscopy image of the injected collagen formulation stained with MT at a magnification of 20×, FIG. 92D shows a microscopy image of the injected collagen formulation stained with HE at a magnification of 1×, FIG. 92E shows a microscopy image of the injected collagen formulation stained with HE at a magnification of 10×, and FIG. 92F shows a microscopy image of the injected collagen formulation stained with HE at a magnification of 20×.

Samples of each of the injected formulations were also stained with Congo red and studied under microscope to investigate the extent that rat cells invaded the dermal fillers.

Figure 93:
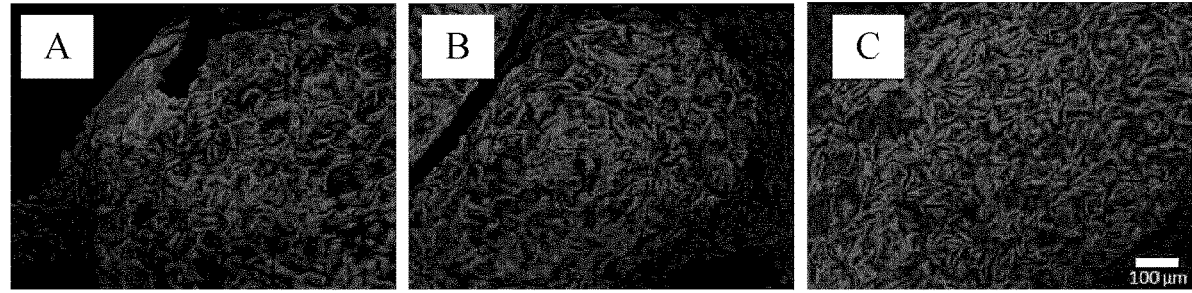

Invading rat cells were labeled with Hoechst 33342. The results are shown in FIG. 93, wherein FIG. 93A shows an injected saline formulation at a magnification of 10×, FIG. 93B shows an injected HA formulation at a magnification of 10×, and FIG. 93C shows an injected collagen formulation at a magnification of 10×. As shown, the three formulations experienced considerable rat cell invasion at the 12-week point.

Figure 94:
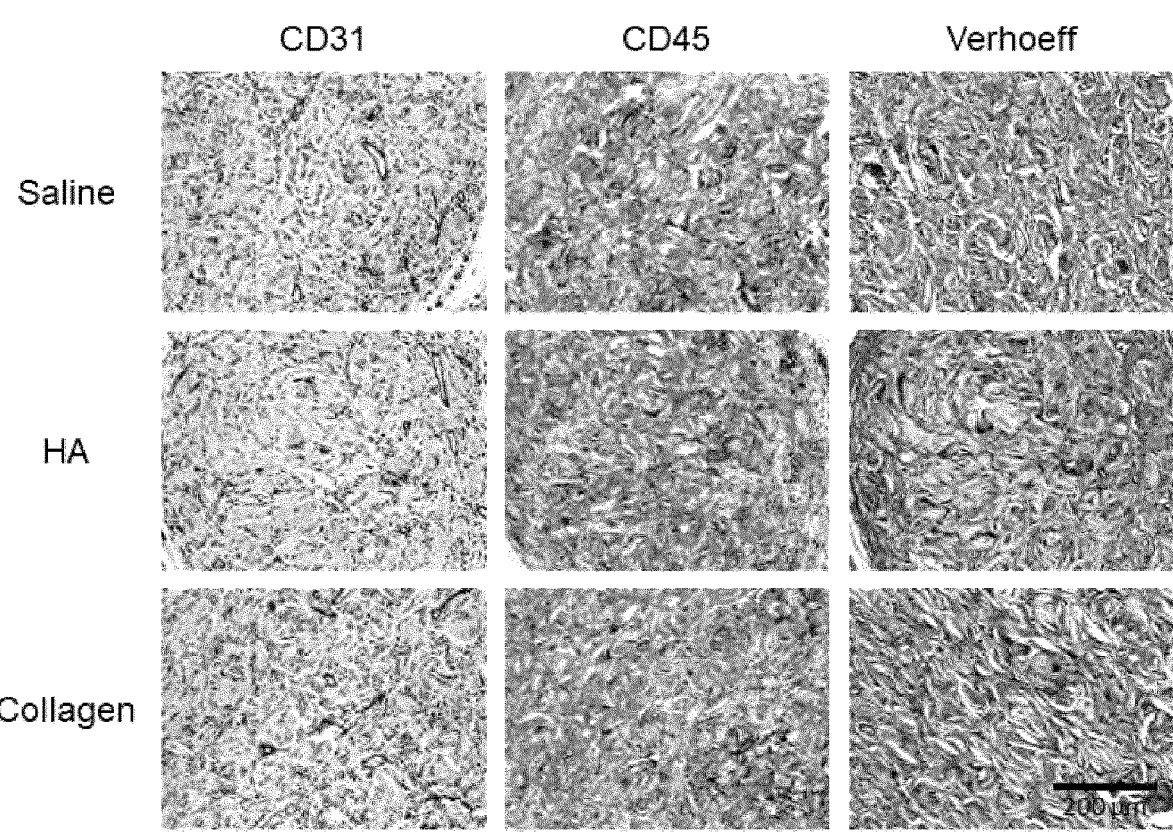
FIG. 94 shows microscopy images of the of injected dermal filler formulations as described in Example 27 after 12 weeks and stained with CD31, CD45, or a Verhoefff Van Gienson (Verhoeff) stain.

It was found that blood vessels and red blood cells could be seen in each of the injected formulations. To investigate the angiogenic interactions between the rat and the dermal filler formulations, CD31 staining was performed on the injected formulations at the 12-week point. As well, CD45 staining was used to assess the immune response of the rats, and a Verhoefff Van Gienson (Verhoeff) stain was used for elastin identification. The results of each of the stains are shown in FIG. 94. As shown, the CD31 staining confirmed the formation of blood vessel walls (the brown loop structures) and the CD45 staining showed an expected immune response to the injected foreign body (brown cytoplasm and blue nuclei). The Verhoeff staining did not show a significant amount of elastin fibres (black) but did, however, show that collagen fibres (red/pink) were present, as expected.

Histological Analysis

A histological analysis was also performed on the injected dermal filler formulations at the 12-week point and a commercially available BellaFill dermal filler. The injected formulations were evaluated according to the ISO 10993-6 guidelines, which are shown below in Table 39.

TABLE 39

| | | | | | |
|---|---|---|---|---|---|
| ISO 10993-6 Scoring Guidelines | | | | | |
| | | Score (*/hpf = per high powered (×400) field) | | | |
| Response | 0 | 1 | 2 | 3 | 4 |
| Polymorphonuclear cells | 0 | Rare. 1-5 hpf* | 6-10 hpf | Heavy infiltrate | Packed |
| Lymphocytes | 0 | Rare. 1-5 hpf | 6-10 hpf | Heavy infiltrate | Packed |
| Plasma cells | 0 | Rare. 1-5 hpf | 6-10 hpf | Heavy infiltrate | Packed |
| Macrophages | 0 | Rare. 1-5 hpf | 6-10 hpf | Heavy infiltrate | Packed |
| Giant cells | 0 | Rare. 1-2 hpf | 3-5 hpf | Heavy infiltrate | Packed |
| Necrosis | 0 | Minimal | Mild | Moderate | Marked |
| Neovascularization | 0 | Minimal capillary proliferation focal 1-3 buds | Groups of 4-7 capillaries with supporting fibroblastic structures | Broad band of capillaries with supporting structures | Extensive band of capillaries with supporting fibroblastic structures |
| Collagen deposition fibroconnective tissue | 0 | Minimal | Mild | Moderate | Marked |
| Fibrous encapsulation | 0 | Narrow band | Moderately thick band | Thick band | Extensive band |
| Fatty infiltrate | 0 | Minimal amount of fat associated with fibrosis | Several layers of fat and fibrosis | Elongated and broad accumulation of fat cells about the implant site | Extensive fat completely surrounding the implant |
| Fibrinous exudates | 0 | Minimal | Mild | Moderate | Marked |
| Mineralization | 0 | Minimal | Mild | Moderate | Marked |
| Granuloma | 0 | Minimal | Mild | Moderate | Marked |
| Hemorrhage | 0 | Minimal | Mild | Moderate | Marked |
| Foreign debris | 0 | Minimal | Mild | Moderate | Marked |

Table 40 details the samples selected for evaluation under ISO 10993-6.

TABLE 40

Injected Dermal Filler Formulation Samples

| Animal Identification Number | Group | Slide Identification Number | Stain | Description |
|---|---|---|---|---|
| VCUGC | 1 | HE VCUGC | HE | Test sample HE |
| | | MT VCUGC | MT | Test sample MT |
| | | CD31 VCUGC | CD31 | Test sample CD31 |
| | | CD45 VCUGC | CD45 | Test sample CD45 |
| | | Negative VCUGC | Negative control | Implanted in animal, no primary, slide stained with DAB as the chromogen and counterstained with Hematoxylin |
| XFYBE | 2 | HE XFYBE | HE | Test sample HE |
| | | MT XFYBE | MT | Test sample MT |
| | | CD31 XFYBE | CD31 | Test sample CD31 |
| | | CD45 XFYBE | CD45 | Test sample CD45 |
| | | Negative XFYBE | Negative control | Implanted in animal, no primary, slide stained with DAB as the chromogen and counterstained with Hematoxylin |
| UTNAP | 3 | HE UTNAP | HE | Test sample HE |
| | | MT UTNAP | MT | Test sample MT |
| | | CD31 UTNAP | CD31 | Test sample CD31 |
| | | CD45 UTNAP | CD45 | Test sample CD45 |
| | | Negative UTNAP | Negative control | Implanted in animal, no primary, slide stained with DAB as the chromogen and counterstained with Hematoxylin |
| LZNVU | 4 | HE LZNVU | HE | Test sample HE |
| | | MT LZNVU | MT | Test sample MT |
| | | CD31 LZNVU | CD31 | Test sample CD31 |
| | | CD45 LZNVU | CD45 | Test sample CD45 |
| | | Negative LZNVU | Negative centro1 | Implanted in animal, no primary, slide stained with DAB as the chromogen and counterstained with Hematoxylin |
| — | Negative control | Rb CD31 | CD31 | Powder, not implanted to animal, primary and secondary antibodies used in the staining (CD31) |
| | | Rb CD45 | CD45 | Powder. not implanted in animal. primary and secondary antibodies used in the staining (CD45) |

The results of the evaluation under ISO 10993-6 for each of the groups identified in Table 40 are shown below in Tables 41 to 43.

TABLE 41

ISO 10993-6 Analysis of Injected Collagen Formulation (Group 1)

| | Slide Identification VCUGC Section [a] | | | | |
|---|---|---|---|---|---|
| Parameters | 1 | 2 | Mean | SD | No. |
| Polymorphonuclear cells | 0 | 0 | 0.00 | 0.00 | 2 |
| Lymphocytes | 3 | 3 | 3.00 | 0.00 | 2 |
| Plasma cells | 1 | 1 | 1.00 | 0.00 | 2 |
| Macrophages | 3 | 3 | 3.00 | 0.00 | 2 |
| Giant cells | 4 | 4 | 4.00 | 0.00 | 2 |
| Necrosis | 0 | 0 | 0.00 | 0.00 | 2 |
| SUB TOTAL (X2) | 22 | 22 | 22.00 | 0.00 | 2 |
| Neovascularization | 3 | 3 | 3.00 | 0.00 | 2 |
| Collagen deposition/ fibroconnective tissue | 1 | 1 | 1.00 | 0.00 | 2 |
| Fatty infiltrate | 0 | 0 | 0.00 | 0.00 | 2 |
| SUB TOTAL | 4 | 4 | 4.00 | 0.00 | 2 |
| TOTAL | 26 | 26 | 26.00 | 0.00 | 2 |
| TOTAL BY GROUP | 52 | | — | — | — |
| AVERAGE BY GROUP[b] | 26.0 | | — | — | — |
| Fibrous encapsulation | 1 | 1 | 1.00 | 0.00 | 2 |
| Fibrinous exudates | 0 | 0 | 0.00 | 0.00 | 2 |
| Mineralization | 0 | 0 | 0.00 | 0.00 | 2 |
| Granuloma | 0 | 0 | 0.00 | 0.00 | 2 |
| Hemorrhage | 0 | 0 | 0.00 | 0.00 | 2 |

TABLE 41-continued

ISO 10993-6 Analysis of Injected Collagen Formulation (Group 1)

| | Slide Identification VCUGC Section [a] | | | | |
|---|---|---|---|---|---|
| Parameters | 1 | 2 | Mean | SD | No. |
| Foreign debris | 0 | 0 | 0.00 | 0.00 | 2 |
| No. of Sites Examined | 1 | 1 | — | — | 2 |

TABLE 42

ISO 10993-6 Analysis of Injected HA Formulation (Group 2)

| | Slide Identification XFYBE Section [a] | | | | |
|---|---|---|---|---|---|
| Parameters | 1 | 2 | Mean | SD | No. |
| Polymorphonuclear cells | 0 | 0 | 0.00 | 0.00 | 2 |
| Lymphocytes | 2 | 2 | 2.00 | 0.00 | 2 |
| Plasma cells | 1 | 1 | 1.00 | 0.00 | 2 |
| Macrophages | 2 | 3 | 2.50 | 0.71 | 2 |
| Giant cells | 3 | 3 | 3.00 | 0.00 | 2 |
| Necrosis | 0 | 0 | 0.00 | 0.00 | 2 |
| SUB TOTAL (X2) | 16 | 18 | 17.00 | 1.41 | 2 |
| Neovascularization | 2 | 2 | 2.00 | 0.00 | 2 |

TABLE 42-continued

ISO 10993-6 Analysis of Injected HA Formulation (Group 2)

| Parameters | Slide Identification XFYBE Section [a] 1 | 2 | Mean | SD | No. |
|---|---|---|---|---|---|
| Collagen deposition/fibroconnective tissue | 2 | 2 | 2.00 | 0.00 | 2 |
| Fatty infiltrate | 0 | 0 | 0.00 | 0.00 | 2 |
| SUB TOTAL | 4 | 4 | 4.00 | 0.00 | 2 |
| TOTAL | 20 | 22 | 21.00 | 1.41 | 2 |
| TOTAL BY GROUP | 42 | | — | — | — |
| AVERAGE BY GROUP [b] | 21.0 | | — | — | — |
| Fibrous encapsulation | 1 | 1 | 1.00 | 0.00 | 2 |
| Fibrinous exudates | 0 | 0 | 0.00 | 0.00 | 2 |
| Mineralization | 0 | 0 | 0.00 | 0.00 | 2 |
| Granuloma | 0 | 0 | 0.00 | 0.00 | 2 |
| Hemorrhage | 0 | 0 | 0.00 | 0.00 | 2 |
| Foreign debris | 0 | 0 | 0.00 | 0.00 | 2 |
| No. of Sites Examined | 1 | 1 | — | — | 2 |

TABLE 43

ISO 10993-6 Analysis of Injected Saline Formulation (Group 3)

| Parameters | Slide Identification UTNAP Section [a] 1 | 2 | Mean | SD | No. |
|---|---|---|---|---|---|
| Polymorphonuclear cells | 0 | 0 | 0.00 | 0.00 | 2 |
| Lymphocytes | 3 | 3 | 3.00 | 0.00 | 2 |
| Plasma cells | 1 | 1 | 1.00 | 0.00 | 2 |
| Macrophages | 2 | 3 | 2.50 | 0.71 | 2 |
| Giant cells | 4 | 4 | 4.00 | 0.00 | 2 |
| Necrosis | 0 | 0 | 0.00 | 0.00 | 2 |
| SUB TOTAL (X2) | 20 | 22 | 21.00 | 1.41 | 2 |
| Neovascularization | 3 | 3 | 3.00 | 0.00 | 2 |
| Collagen deposition/fibroconnective tissue | 1 | 1 | 1.00 | 0.00 | 2 |
| Fatty infiltrate | 0 | 0 | 0.00 | 0.00 | 2 |
| SUB TOTAL | 4 | 4 | 4.00 | 0.00 | 2 |
| TOTAL | 24 | 26 | 25.00 | 1.41 | 2 |
| TOTAL BY GROUP | 50 | | — | — | — |
| AVERAGE BY GROUP [b] | 25.0 | | — | — | — |

TABLE 43-continued

ISO 10993-6 Analysis of Injected Saline Formulation (Group 3)

| Parameters | Slide Identification UTNAP Section [a] 1 | 2 | Mean | SD | No. |
|---|---|---|---|---|---|
| Fibrous encapsulation | 1 | 1 | 1.00 | 0.00 | 2 |
| Fibrinous exudates | 0 | 0 | 0.00 | 0.00 | 2 |
| Mineralization | 0 | 0 | 0.00 | 0.00 | 2 |
| Granuloma | 0 | 0 | 0.00 | 0.00 | 2 |
| Hemorrhage | 0 | 0 | 0.00 | 0.00 | 2 |
| Foreign debris | 0 | 0 | 0.00 | 0.00 | 2 |
| No. of Sites Examined | 1 | 1 | — | — | 2 |

TABLE 44

ISO 10993-6 Analysis of Injected BellaFill Formulation (Group 4)

| Parameters | Slide Identification LZNVU Section a 1 | 2 | Mean | SD | No. |
|---|---|---|---|---|---|
| Polymorphonuclear cells | 0 | 0 | 0.00 | 0.00 | 2 |
| Lymphocytes | 3 | 3 | 3.00 | 0.00 | 2 |
| Plasma cells | 1 | 1 | 1.00 | 0.00 | 2 |
| Macrophages | 2 | 2 | 2.00 | 0.00 | 2 |
| Giant cells | 2 | 2 | 2.00 | 0.00 | 2 |
| Necrosis | 0 | 0 | 0.00 | 0.00 | 2 |
| SUB TOTAL (X2) | 16 | 16 | 16.00 | 0.00 | 2 |
| Neovascularization | 2 | 2 | 2.00 | 0.00 | 2 |
| Collagen deposition/fibroconnective tissue | 1 | 1 | 1.00 | 0.00 | 2 |
| Fatty infiltrate | 0 | 0 | 0.00 | 0.00 | 2 |
| SUB TOTAL | 3 | 3 | 3.00 | 0.00 | 2 |
| TOTAL | 19 | 19 | 19.00 | 0.00 | 2 |
| TOTAL BY GROUP | 38 | | — | — | — |
| AVERAGE BY GROUP [b] | 19.0 | | — | — | — |
| Fibrous encapsulation | 1 | 1 | 1.00 | 0.00 | 2 |
| Fibrinous exudates | 0 | 0 | 0.00 | 0.00 | 2 |
| Mineralization | 0 | 0 | 0.00 | 0.00 | 2 |
| Granuloma | 0 | 0 | 0.00 | 0.00 | 2 |
| Hemorrhage | 0 | 0 | 0.00 | 0.00 | 2 |
| Foreign debris | 0 | 0 | 0.00 | 0.00 | 2 |
| No. of Sites Examined | 1 | 1 | — | — | 2 |

A summary of the averages of various parameters of each sample group are shown below in Table 45.

TABLE 45

Summary of Group Averages based on ISO 10993-6 Scoring

| | | Group 1 n = 2 | Group 2 n = 2 | Group 3 n = 2 | Group 4 n = 2 |
|---|---|---|---|---|---|
| Lymphocytes | Mean ± SD | 3.00 ± 0.00 | 2.00 ± 0.00 | 3.00 ± 0.00 | 3.00 ± 0.00 |
| Plasma cells | Mean ± SD | 1.00 ± 0.00 | 1.00 ± 0.00 | 1.00 ± 0.00 | 1.00 ± 0.00 |
| Macrophages | Mean ± SD | 3.00 ± 0.00 | 2.50 ± 0.71 | 2.50 ± 0.71 | 2.00 ± 0.00 |
| Giant cells | Mean ± SD | 4.00 ± 0.00 | 3.00 ± 0.00 | 4.00 ± 0.00 | 2.00 ± 0.00 |
| Neovascularization | Mean ± SD | 3.00 ± 0.00 | 2.00 ± 0.00 | 3.00 ± 0.00 | 2.00 ± 0.00 |
| Collagen deposition/fibroconnective tissue | Mean ± SD | 1.00 ± 0.00 | 2.00 ± 0.00 | 1.00 ± 0.00 | 1.00 ± 0.00 |
| Fibrous encapsulation | Mean ± SD | 1.00 ± 0.00 | 1.00 ± 0.00 | 1.00 ± 0.00 | 1.00 ± 0.00 |

As shown, polymorphonuclear cells, necrosis, fatty infiltrate, fibrinous exudates, mineralization, granuloma, hemorrhage or foreign debris were not seen in any of the Group 1, 2, 3 and 4 implant sites.

The tissue reaction to the Group 1, Group 2, and Group 3 test implants was characterized by the infiltration of 6 to heavy infiltrates of lymphocytes and macrophages, 1 to 5 plasma cells, and heavy infiltrates to packed giant cells per high power field and minimal or mild collagen deposition/ fibroconnective tissue.

In the test groups, the resorbing/degrading test formulation particles was observed within the giant cells or surrounded by macrophages, while the lymphocytes and plasma cells were mostly seen at the periphery of the implants.

Minimal fibrous encapsulation, characterized by a narrow band of fibrous connective tissue, was observed surrounding the Groups 1, 2 and 3 test implant sites.

The tissue reaction in Group 4 control implant sites was characterized by the infiltration of 6 to heavy infiltrates of lymphocytes, 1 to 5 plasma cells, 6 to 10 macrophages and 3 to 5 giant cells per high power field and minimal collagen deposition/fibroconnective tissue. In the control group, the inflammatory cells were seen surrounding the control article microspheres.

Neovascularization characterized by groups of 4-7 capillaries with supporting fibroblastic structures was seen in Group 2 test and Group 4 control implant sites while broad bands of capillaries with supporting tissues was observed in Groups 1 and 3 test implant sites.

The inflammatory reaction appeared to be slightly higher in the Groups 1 and 3 test implants than the Group 2 test and Group 4 control implants. Although the inflammatory reaction was significant based on the ISO 10993-6 scoring, the Group 2 test implant was deemed to be non-irritant and the Groups 1 and 3 test implants were deemed slight irritants when compared to the Group 4 control. A summery of the irritancy of the formulations is shown below in Table 46.

TABLE 46

Summary of Irritancy of each Group

| Group | | Average | | Irritancy/ Reactivity Status |
|---|---|---|---|---|
| Test | Group 1 | 26.0 | 7.0 | Slight irritant |
| Test | Group 2 | 21.0 | 2.0 | Non-irritant |
| Test | Group 3 | 25.0 | 6.0 | Slight irritant |
| Control | Group 4 | 19.0 | — | — |

| Overall Irritancy Score | Irritancy/Reactivity Status |
|---|---|
| 0.0 to 2.9 | Minimal or no reaction (non-irritant) |
| 3.0 to 8.9 | Slight reaction (slight irritant) |
| 9.0 to 15.0 | Moderate reaction (moderate irritant) |
| >15.0 | Severe reaction (severe irritant) |

Overall, all of the groups resulted in inflammatory reactions (comprised mostly of giant cells, lymphocytes and macrophages) and no necrosis, fatty infiltrate, fibrinous exudates, mineralization, granuloma, hemorrhage or foreign debris. Based on the ISO 10993-6 scoring, the Group 2 test implant was deemed to be a non-irritant while the Groups 1 and 3 test implants were deemed slight irritants when compared to the Group 4 control implant.

Injection Size Measurements

The size of bumps formed by the volume of injected dermal filler were monitored for each of the formulations as well as for a trial using the commercially available BellaFill dermal filler. The generally ellipsoidal-shaped injections were monitored by recording the length of two perpendicular diameters and the height (perpendicular to the skin) using calipers. The measurements were used to calculate the in-plane area as well as an estimate for the ellipsoidal volume.

Figure 95:
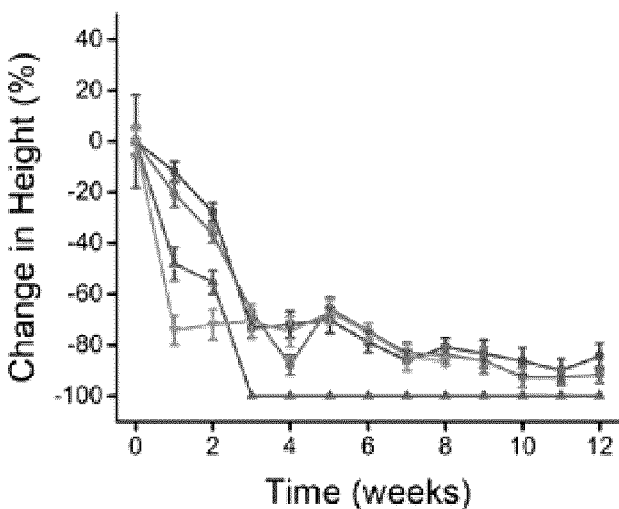
FIG. 95 shows the change in height of bumps formed by the injection of dermal filler formulations described in Example 27 over time.

The change in height of each injection bump represented as normalized percentage decreases for the formulations over time is shown in FIG. 95, wherein the collagen formulation is the black line, the HA formulation is the red line, the saline formulation is the blue line, and the BellaFill formulation is the purple line.

As shown, the collagen and HA formulations exhibited a gradual decrease in size that eventually plateaued while the saline formulation exhibited a rapid decrease in height, as expected. The height of BellaFill derma filler injection gradually decreased to a plateau, similar to the collagen and HA formulations.

It is noted that the decrease in size of the injection bumps does not indicate particle degradation. The histological evaluation above shows that the particles remained intact. Rather, the decrease in size may be attributed to the resorption of the carrier, the compaction of the material, the expansion of the formulation in the lateral directions, and/or the increase in mass of the rat over time.

Example 28—Further In Vivo Studies of the Dermal Fillers of the Present Disclosure A further in vivo trial was performed using dermal filler formulations of the present disclosure comprising mercerized apple material.

Four formulations were tested, namely a first formulation (Mer100) comprised only of mercerized apple, a second formulation (20Mer80Sal) comprising 20% mercerized apple in a 0.9% saline solution, a third formulation (20Mer80Col) comprising 20% mercerized apple in a 3.5% collagen solution, and a fourth formulation (20Mer80Reg) comprising 20% mercerized apple in dissolved regenerated cellulose. Each of the formulations also comprised 0.3% lidocaine.

The dissolved regenerated cellulose by dissolving decellularized apple material with a solution of LiCl and dimethyl acetamide (DMAc). The dissolved cellulose is then "regenerated" via solvent exchange and mixing with mercerized apple.

Each of the formulations were injected into two rats four times. For each formulation, one rat was resected after 12 weeks and the other after 1 year. Each of the injection volumes comprised 600 μL of formulation. The bumps formed after injection of the formulations were measured weekly for 12 weeks and monthly thereafter. The bump sizes were measured as previously described herein using calipers.

Results

Observationally, it was noted that the 20Mer80Sal and 20Mer80Col injection bumps were smaller than those of the Mer100 formulation. As well, the 20Mer80Reg injection bumps were the stiffest of the tested formulations.

Figure 96:
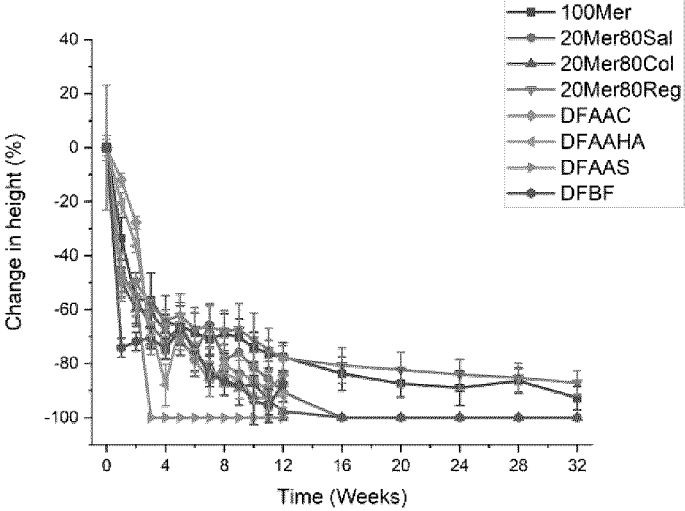
FIG. 96 shows the change in height of bumps formed by the injection of dermal filler formulations described in Examples 27 and 28 over time.

The changes in height of the injection bumps for each of the formulations over time are shown in FIG. 96. For comparison, the height change results of Example 27 are included, wherein DFAAC refers to the collagen formulation of Example 27, DFAAHA refers to the HA formulation of Example 27, DFAAS refers to the saline formulation of Example 27, and DFBF refers to the BellaFill dermal filler.

As shown, each of the formulations comprising mercerized apple generally exhibited a decrease in height until an eventual plateau.

Figure 97:
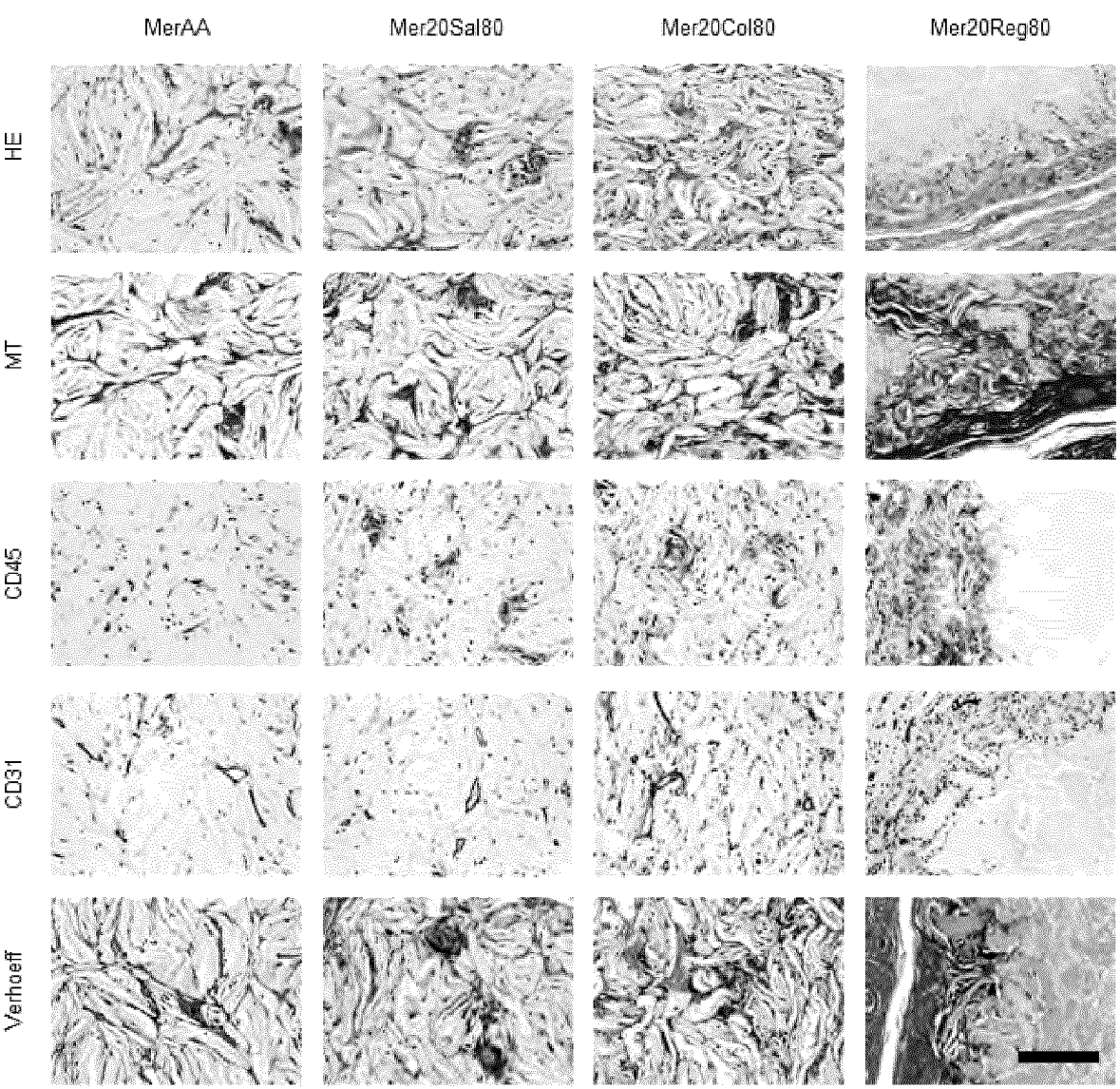
FIG. 97 shows microscopy images of the of injected dermal filler formulations as described in Example 28 after 12 weeks and stained with CD31, CD45, or a Verhoefff stain.

The injected formulations were also histologically analyzed. The injected formulations were stained with HE, MT, CD45, CD31, and Verhoeff stains as described above in Example 27 and analyzed under microscope. The results, at a scale of 200 µm, are shown in FIG. 97. Notes taken by the performer of histological analyses are shown below in Table 47.

In general, the histological analyses that the formulations using mercerized apple exhibited a reduced inflammatory response as compared to the formulations investigated in Example 27. As well, the formulations using mercerized apple proved to be biocompatible, presented blood vessel formulation, and had extracellular matrix deposition.

Further, it is noted that the 20Mer80Reg formulation had cell invasion localized to the periphery thereof. Without being bound to a particular theory, it is thought that the localization of the cell invasion to the periphery of the

TABLE 47

| | Histological Observations on Injected Mercerized Apple Formulations | | | | |
|---|---|---|---|---|---|
| Group | HE | MT | CD31 | CD45 | Verhoeff |
| MerAA | Filler material, few blood vessels, Giant cells scarce | Fine bands of collagen surrounding filler material | Few scattered well formed small BVs | cytoplasmic blush; no true staining | Noted around some BVs |
| MerAA | Filler material, more blood vessels, more giant cells compared to BRNBP | Fine bands of collagen surrounding filler material and some blood vessels | More well formed small BVs compared to BRNBP | cytoplasmic blush; ? Rare lymphocytes stain | Noted around some BVs |
| MerAA | Filler material, scattered blood vessels, scattered giant cells | Fine bands of collagen surrounding filler material and some blood vessels | Similar to JCFDE | cytoplasmic blush; no true staining | noted around some BVs |
| Mer20 Sa180 | Filler material with scattered blood vessels and occasional giant cells | Fine bands of collagen surrounding filler material and a few blood vessels | Scattered small well formed BVs noted | Cytoplasmic blush; no true staining | some elastin around BVs |
| Mer20 Sa180 | Filler material with scattered blood vessels and occasional giant cells | Fine bands of collagen surrounding filler material and a few blood vessels | scattered small well formed BVs noted | Cytoplasmic blush; no true staining | some elastin around BVs |
| Mer20 Sa180 | Filler material with scattered blood vessels and occasional giant cells | Fine bands of collagen surrounding filler material and a few blood vessels | Scattered small well formed BVs noted | Cytoplasmic blush; no true staining | some elastin around BVs |
| Mer20 Co180 | Filler material, scattered blood vessels, few giant cells | Thicker bands of collagen mostly at periphery, finer bands centrally within filler material and around some blood vessels | Well formed small BVs noted | Blush; no true staining of lymphocytes | Noted around some BVs |
| Mer20 Co180 | Dense collagen subepidermally | Subepidermal collagen | Too low power to see; ? A few BVs visible? | V low power; no staining | NA |
| Mer20 Co180 | Filler material, broad bands of collagen, scattered giant cells and blood vessels | Broad bands of collagen noted centrally within filler material | Several small blood BVs noted | Cytoplasmic blush; no true staining | Some genuine staining a few BVs |
| Mer20 Reg80 | Abundant central filler material, scattered blood vessels and giant cells at periphery | Fine bands of collagen noted mostly at periphery | Several small well formed BVs noted | Cytoplasmic blush; no true staining | Some elastin around BVs |
| Mer20 Reg80 | Abundant central filler material, scattered blood vessels and giant cells at periphery | Fine bands of collagen noted mostly at periphery | Scattered well formed small BVs at periphery | Cytoplasmic blush; no true staining | Some elastin around BVs |
| Mer20 Reg80 | Abundant central filler material, blood vessels and a few giant cells at periphery | Collagen mostly at periphery fine and narrow bands | Well formed blood vessels at the periphery noted | Cytoplasmic blush; no true staining | Some elastin around BVs |

20Mer80Reg formulation may be due to the small pore size of the entangled dissolved and regenerated cellulose polymers.

Example 29—Further Quantification of SDS Content in Dermal Fillers of the Present Disclosure This study sought to further characterize the amount of residual SDS in the dermal fillers of the present disclosure, building upon the results of Example 22.

Using, the standard curve developed and process outlined in Example 22, further samples were analyzed using spectrophotometry. The samples used had 5 apples worth of material (5AA), 10 apples worth of material (10AA), or 15 apples worth of material (15AA).

Table 48 shows the results of the SDS quantification of the beaker solutions (diluted 1:10) from the 5AA, 10AA, and 15AA samples after 72 hours of incubation in 0.1% SDS.

TABLE 48

SDS Quantification of Beaker Solutions of 5AA, 10AA, and 15AA Samples after 72 hours of Incubation in 0.1% SDS

| Reading (499 nm) | Blank | 0.01% SDS solution | 5AA sample | 10AA sample | 15AA sample |
|---|---|---|---|---|---|
| Sample 1 | 0.136 | 0.387 | 0.395 | 0.359 | 0.346 |
| Sample 2 | 0.128 | 0.391 | 0.390 | 0.361 | 0.348 |
| Sample 3 | 0.126 | 0.385 | 0.389 | 0.364 | 0.349 |
| Average | 0.130 ± 0.005 | 0.388 ± 0.003 | 0.391 ± 0.003 | 0.361 ± 0.003 | 0.348 ± 0.003 |
| Correction | 0.000 ± 0.007 | 0.258 ± 0.006 | 0.261 ± 0.006 | 0.231 ± 0.006 | 0.218 ± 0.006 |
| % SDS from standard curve | 0.000 | 0.011 | 0.011 | 0.010 | 0.009 |

Table 49 shows the SDS quantification of the liquid phase (undiluted) from the 5AA, 10AA, and 15AA samples after the decellularization process.

TABLE 49

SDS Quantification of Liquid Phase of the 5AA, 10AA, and 15AA Samples after Decellularizing

| Reading (499 nm) | Blank | 5AA sample | 10AA sample | 15AA sample |
|---|---|---|---|---|
| Sample 1 | 0.132 | 0.203 | 0.315 | 0.282 |
| Sample 2 | 0.134 | 0.196 | 0.314 | 0.28 |
| Sample 3 | 0.125 | 0.196 | 0.324 | 0.275 |
| Sample 4 | 0.137 | 0.195 | 0.306 | 0.269 |
| Sample 5 | 0.135 | 0.201 | 0.308 | 0.271 |
| Sample 6 | 0.141 | 0.197 | 0.309 | 0.261 |
| Average | 0.134 ± 0.005 | 0.198 ± 0.003 | 0.313 ± 0.007 | 0.273 ± 0.008 |
| Correction | 0.000 ± 0.008 | 0.064 ± 0.006 | 0.179 ± 0.008 | 0.139 ± 0.009 |
| % SDS from standard curve | 0.000 ± 0.001 | 0.003 ± 0.001 | 0.008 ± 0.001 | 0.006 ± 0.001 |

Thus, as shown, the SDS content of the samples was sufficiently low, which supports the findings of Example 22. As well, As well, the SDS content will further decrease during mercerization procedures due to the plurality of centrifugation and washing steps.

One or more illustrative embodiments have been described by way of example. It will be understood to persons skilled in the art that a number of variations and modifications can be made without departing from the scope of the invention as defined in the claims.

REFERENCES

1. Huh, J. B et al. Effects of PMMA and Cross-Linked Dextran Filler for Soft Tissue Augmentation in Rats. Int. J. Mol. Sci. 16, 28523 (2015).
2. Hillel, A. T. et al. Validation of a Small Animal Model for Soft Tissue Filler Characterization. Dermatologic Surg. 38, 471 (2012).
3. Cena, R. B. et al. Effects of Crosslinked Dextran in Hydroxylpropyl Methylcellulose on Soft Tissue Augmentation in Rats. J. Biomed. Mater. Res.—Part B Appl. Biomater. 102, 131 (2014).
4. Lee, Y. B. et al. Histology of a Novel Injectable Filler (Polymethylmethacrylate and Cross-Linked Dextran in Hydroxypropyl Methylcellulose) in a Rat Model. J. Cosmet. Laser Ther. 16, 191 (2014).
5. Lemperle, G.; Morhenn, V. B.; Pestonjamasp, V.; Gallo, R. L. Migration Studies and Histology of Injectable Microspheres of Different Sizes in Mice. Plast. Reconstr. Surg. 113, 1380 (2004).
6. Lemperle et al. ArteFill Permanent Injectable for Soft Tissue Augmentation: I. Mechanism of Action and Injection Techniques. Aesth Plast Surg. 34, 264 (2010).
7. Luebberding et al. Critical Appraisal of the Safety of Dermal Fillers: A Primer for Clinicians. Curr Derm Rep 2, 150 (2013).
8. Frazer, R. Q. et al. PMMA: An essential material in medicine and dentistry. J. Long Term Effect Med. Implants. 15, 629 (2005).
9. Hickey, R. et al. Customizing the Shape and Microenvironment Biochemistry of Biocompatible Macroscopic Plant-Derived Cellulose Scaffolds. ACS Biomater. Sci. Eng. 4, 3726 (2018).
10. WO2017/136950, entitled "Decellularised Cell Wall Structures from Plants and Fungus and Use Thereof as Scaffold Materials".
11. Nguyen et al. "Cosmetic Medicine: Facial Resurfacing and Injectables", Plast Reconstr Surg. 129, 142e (2012).
12. Luebberding et al. "Critical Appraisal of the Safety of Dermal Fillers: A Primer for Clinicians", Curr Derm Rep. 2, 150 (2013).

All reference cited herein and elsewhere in this specification are herein incorporated by reference in their entireties.

What is claimed is:

1. A non-resorbable dermal filler comprising decellularized plant or fungal tissue from which cellular materials and nucleic acids of the tissue are removed, wherein the decellularized plant or fungal tissue is disassembled into particles having a size, diameter, or minimum feret diameter of at least about 20 μm.

2. The dermal filler of claim 1, wherein the decellularized plant or fungal tissue is chitin-based, pectin-based, chitosan-based, lignocellulosic-based, or cellulose-based.

3. The dermal filler of claim 2, wherein the decellularized plant or fungal tissue is derived from leafy structure, root, flesh, hypanthium, lettuce, carrot, apple, or pear, pulp structures of a plant or a combination thereof.

4. The dermal filler of claim 3, wherein the decellularized plant or fungal tissue is homogenized or dried, subjected to grinding, and optionally reconstituted or rehydrated.

5. The dermal filler of claim 1, wherein the decellularized plant or fungal tissue is disassembled into particles the size of single structural cells, or smaller.

6. The dermal filler of claim 5, wherein the dermal filler further comprises a hydrogel, matrix, or carrier fluid for the decellularized plant or fungal tissue.

7. The dermal filler of claim 6, wherein the hydrogel, matrix, or carrier fluid comprises PBS, saline, hyaluronic acid (cross-linked or non-crosslinked), alginate, collagen, pluronic acid (e.g. pluronic F 127), agar, agarose, fibrin, calcium hydroxyapatite, Poly-L-lactic acid, autologous fat, silicone, dextran, methylcellulose, dissolved regenerated cellulose, or any combinations thereof.

8. The dermal filler of claim 7, wherein the dermal filler is dried, or hydrated.

9. The dermal filler of claim 8, wherein the dermal filler comprises lidocaine or other anesthetic.

10. The dermal filler of claim 9, wherein the decellularized plant or fungal tissue is disassembled into particles having irregular 3D shapes and/or which are non-spherical, thin, flake-like structures.

11. The dermal filler of claim 10, wherein the flake-like structures have a thickness of about 0.01 to about 100 μm, for example about 0.1 μm.

12. The dermal filler of claim 11, wherein the decellularized plant or fungal tissue is disassembled into particles having a size sufficiently large so as not to be phagocytosed by a cell or cells.

13. The dermal filler of claim 12, wherein the decellularized plant or fungal tissue is disassembled into particles having a size, diameter, or feret diameter within a range of about 20 μm to about 1000 μm, or about 20 μm to about 200 μm, or about 100 μm to about 300 μm.

14. The dermal filler of claim 13, wherein the decellularized plant or fungal tissue is disassembled into particles having a size, diameter, or maximum feret diameter of less than about 200 μm or less than about 300 μm.

15. The dermal filler of claim 14, wherein the decellularized plant or fungal tissue is disassembled into particles having a particle size, diameter, or feret diameter distribution having a peak within about 30 μm to about 100 μm, or within about 100 μm to about 300 μm.

16. The dermal filler of claim 15, wherein the decellularized plant or fungal tissue is disassembled into particles having a mean particle size, diameter, or feret diameter within a range of about 30 μm to about 100 μm or about 100 μm to about 300 μm.

17. The dermal filler of claim 16, wherein the decellularized plant or fungal tissue is disassembled into particles having an average projected particle area within a range of about 200 to about 3000 μm², or within a range of about 200 to about 300 μm²; wherein the decellularized plant or fungal tissue is disassembled into particles having a surface area to volume ratio of about 0.1 to 100 μm⁻¹; wherein the decellularized plant or fungal tissue is disassembled into particles having a packing density of about $4\times10^5$ particles/mL to about $7\times10^9$ particles/mL; or any combinations thereof.

18. The dermal filler of claim 7, having a viscosity of less than about 500,000 cp.

19. The dermal filler of claim 18, having a viscosity within a range of about 100,000 cp to about 200,000 cp.

20. The dermal filler of claim 19, wherein the decellularized plant, fungal tissue, or the dermal filler is sterilized.

21. The dermal filler of claim 20, wherein the sterilization comprises a plurality of sterilization steps and wherein the sterilization is conducted by one of heat treatment, gamma sterilization, autoclaving, or ethanol treatment.

22. The dermal filler of 21, wherein the decellularized plant or fungal tissue is treated by heating with sodium hydroxide and hydrogen peroxide.

23. The dermal filler of claim 22, wherein the treatment includes a step of mercerization.

24. The dermal filler of claim 23, wherein the decellularization further comprises size-reducing the plant or fungal tissue using a mechanical size reduction to provide the particles, optionally where the mechanical size reduction is performed on dried, lyophilized, or freeze-dried materials.

25. The dermal filler of claim 24, wherein the mechanical size reduction comprises crushing, extrusion, grinding, milling, ultrasonication, electrospinning, chemical dissolution, enzymatic breakdown, or shearing the plant or fungal tissue, before or after decellularizing, to provide the particles.

26. The dermal filler of claim 23, wherein the dermal filler is formulated for subdermal injection, deep dermal injection, subcutaneous injection (e.g. subcutaneous fat injection), or any combinations thereof.

27. The dermal filler of claim 26, wherein the dermal filler is degradable through the addition of one or more enzymes thereto.

28. The dermal filler of claim 27, wherein the plant or fungal tissue is cellulose-based, and the one or more enzymes comprise cellulase.

29. The dermal filler of claim 28, wherein the cellulase is cellulase from *Trichoderma* sp.

30. The dermal filler of claim 26, provided in a syringe or injection device.

31. A kit comprising the dermal filler as defined in claim 1 and any one or more of:

a hydrogel, matrix, or carrier fluid;

PBS, saline, hyaluronic acid (cross-linked or non-crosslinked), alginate, collagen, pluronic acid, agar, agarose, fibrin, calcium hydroxyapatite, Poly-L-lactic acid, autologous fat, silicone, dextran, methylcellulose, dissolved regenerated cellulose, or any combinations thereof;

lidocaine or other aesthetic;

one or more syringes, or another injection device;

a luer-lock fitting or coupler for two or more syringes;

instructions for use of the kit;

one or more decellularization reagents;

one or more containers, packages, or vessels;

one or more buffers, water, or saline for injection;

a reagent or enzyme for dissolving dermal filler at an undesirable region or location; or any combinations thereof.

\* \* \* \* \*